United States Patent [19]
Law et al.

[11] Patent Number: 5,866,780
[45] Date of Patent: Feb. 2, 1999

[54] MAIZE CHLOROTIC DWARF VIRUS GENOME AND USES THEREFOR

[75] Inventors: Marcus Law, Chapel Hill, N.C.; Bradford B. Reddick; Ledare Habera, both of Knoxville, Tenn.

[73] Assignee: Novartis Finance Corporation, New York, N.Y.

[21] Appl. No.: 416,603

[22] Filed: Apr. 4, 1995

[51] Int. Cl.⁶ .............................. A01H 5/00; C12N 15/82
[52] U.S. Cl. .................... 800/205; 536/23.72; 435/69.1; 435/172.3; 435/419
[58] Field of Search ......................... 800/205; 536/23.72; 435/69.1, 172.3, 240.4, 320.1, 419

[56] References Cited

FOREIGN PATENT DOCUMENTS 9421796  9/1994  WIPO .

OTHER PUBLICATIONS

Lopes, J.R.S. et al. (1994) "Leafhopper Transmission and host Plant Range of Maize Chlorotic Dwarf Waikavirus Strains" Phytopathology 84:876–882.

Gingery, R.E., L.R. Nault (1990) "Severe Maize Chlorotic Dwarf Disease Caused by Double Infection" Phytopathology 80:687–691.

Wilson, TMA (Apr. 1993) Proc. Natl Acad. Sci USA 90:3134–3141.

Nejidat et al (1990) Physiologia Plantanum 80: 662–668.

*Primary Examiner*—Elizabeth F. McElwain
*Attorney, Agent, or Firm*—Saliwanchik, Lloyd & Saliwanchik

[57] ABSTRACT

The present invention provides the nucleotide structure and organization of a novel maize chlorotic dwarf virus genome designated MCDV-Tn. Methods for using the complete or partial MCDV-Tn genomic sequence as a probe for diagnostic and other purposes are taught. Methods for inhibiting MCDV-Tn infection are also taught. These methods include the generation of transformed plants capable of expressing MCDV-Tn proteins, either in modified or unmodified form, and antisense sequences targeting MCDV-Tn genomic RNA. Recombinant production of MCDV-Tn proteins in appropriate host cells is also taught.

10 Claims, No Drawings

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 11832 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i x ) FEATURE:
        ( A ) NAME/KEY: CDS
        ( B ) LOCATION: 435..10763
        ( D ) OTHER INFORMATION: /note= "cDNA of MCDV-Tn genome"

(xi) SEQUENCE DESCRIPTION: SEQ ID NO:1:

```
NAAAAGGAGG TATATAGGAT ACCGTCTTTC ACACAAGCTC ATGGAGTTTT CTGGCTAAAC        60

AGCAATAGGC GCTCCCAAGG CTTAACAAAA ATGGTGTGGC AGAACCCGTA TGGGGGATCA       120

AGTCACTTCA GTTCATGAGA TAAATATACA GTCGTATTGG ACCCTTCTAG ATAGAACCCA       180

GTGGATTGAC AGGCCTGGCC TGGTAAGTTC CCAAGTGGTA AGAGACCCGG CACGAAGTGT       240

AGTAAGACGC CATTGGCGCA GTAAATCGCG ATGCGTAGCT TCGGGCTTTT ATCATTGAAG       300

ACGCCCGCCA GTAACTTGCG GCTCTAACGC TGAGTTGGTT TGAAGCTGGT AGTAAACTAT       360

TAGGGGATTC GTACGTCTCA CTGTACCACG AACACAGAGT ATGTTAATGC TGAGGGAACT       420

CCGTTTTAAA TTAC ATG ATG TCT TGT GAA CAA AGC AAA AAC AAC AAC AAT        470
              Met Met Ser Cys Glu Gln Ser Lys Asn Asn Asn Asn
                1               5                  10

CAA CAA TCA ACA GCT TTG GAA AAT TCG GAA ATC AGA TAC CCC GGA GGA         518
Gln Gln Ser Thr Ala Leu Glu Asn Ser Glu Ile Arg Tyr Pro Gly Gly
         15                  20                  25

TAC TAT ATC CCT CTG GGA GAC GGT GGC ATC CGG GTT CCA GTA GAG GCT         566
Tyr Tyr Ile Pro Leu Gly Asp Gly Gly Ile Arg Val Pro Val Glu Ala
     30                  35                  40

ATA TAC AGA CCC GGA GAA CCT CAG AAT TGG GTG CCA ATT TGT GGA AAC         614
Ile Tyr Arg Pro Gly Glu Pro Gln Asn Trp Val Pro Ile Cys Gly Asn
 45                  50                  55                  60

GAT TTC CAC CTA AGC CAG GAT GAC CCG TGC TCT GAA TGC GAC GCG ATT         662
Asp Phe His Leu Ser Gln Asp Asp Pro Cys Ser Glu Cys Asp Ala Ile
                 65                  70                  75

GAG GGA TCA TCA GAG AGA GCA GCT ATT GCA ATT TCA GAC TCA TAT GTG         710
Glu Gly Ser Ser Glu Arg Ala Ala Ile Ala Ile Ser Asp Ser Tyr Val
             80                  85                  90

GCA TCA GAT CCT CAT TTT ACT GTT GAT GCT CGT TCT TTG TCG AGG AGA         758
Ala Ser Asp Pro His Phe Thr Val Asp Ala Arg Ser Leu Ser Arg Arg
         95                 100                 105

GAC CAC ACT TGC ACT CAT AGG GGC TGC TTT TCT ATA TGT TCT AGT TAT         806
Asp His Thr Cys Thr His Arg Gly Cys Phe Ser Ile Cys Ser Ser Tyr
    110                 115                 120

AGA TTT TGT TCA TTT TGC TTA TTT TTG TTT AAT TTA GAT AAA TTT CAG         854
Arg Phe Cys Ser Phe Cys Leu Phe Leu Phe Asn Leu Asp Lys Phe Gln
125                 130                 135                 140

AAA AAC ACA AAA TAC TTT CAT AGT AAG AGA TCT TTA AGT AGA CTT GTG         902
Lys Asn Thr Lys Tyr Phe His Ser Lys Arg Ser Leu Ser Arg Leu Val
                145                 150                 155

CAC TGT TCT GCT GAA CAG TTA ATT AGT AAC GCT ATA TTG TTT TCT TCT         950
His Cys Ser Ala Glu Gln Leu Ile Ser Asn Ala Ile Leu Phe Ser Ser
            160                 165                 170

AAT AGA ATA ATA GAT GCA GAG GTG GTT GCT GAT AAT AGG GTT AGC TGT         998
Asn Arg Ile Ile Asp Ala Glu Val Val Ala Asp Asn Arg Val Ser Cys
        175                 180                 185

GAA TAT GCT AAG TTG CTT CTT TCA AAT GCT CGG GTT GGT GTT CAG GTT        1046
Glu Tyr Ala Lys Leu Leu Leu Ser Asn Ala Arg Val Gly Val Gln Val
    190                 195                 200

ACC CCT CCT GCT TGT GAT TGG GTT GTG TGT AAC AAT GTT GAA CAT CTT        1094
Thr Pro Pro Ala Cys Asp Trp Val Val Cys Asn Asn Val Glu His Leu
205                 210                 215                 220

TTT GAG TGT TTT GGC ATT AGT GAC GCG CAG CGA GGA CAC ATT ACT GGA        1142
Phe Glu Cys Phe Gly Ile Ser Asp Ala Gln Arg Gly His Ile Thr Gly
                225                 230                 235

TTT AAT GAC GAG AAT GCA TAT TGG AAC GCC TCG TGC GCA AAA TGT GGC        1190
Phe Asn Asp Glu Asn Ala Tyr Trp Asn Ala Ser Cys Ala Lys Cys Gly
            240                 245                 250
```

| | | | | | | | | | | | | | | | | |
|---|---|---|---|---|---|---|---|---|---|---|---|---|---|---|---|---|
| GCC | TGT | TGC | CAG | GGA | GCG | AAC | GCT | AGG | TCC | GCG | ATC | CCG | ATA | GTC | TTG | 1238 |
| Ala | Cys | Cys | Gln | Gly | Ala | Asn | Ala | Arg | Ser | Ala | Ile | Pro | Ile | Val | Leu | |
| | | 255 | | | | 260 | | | | | 265 | | | | | |
| CTA | TTG | AAA | TTC | ATA | ACG | ATT | AGA | AAA | GAG | CAA | GAT | ATT | TGG | CTA | GCT | 1286 |
| Leu | Leu | Lys | Phe | Ile | Thr | Ile | Arg | Lys | Glu | Gln | Asp | Ile | Trp | Leu | Ala | |
| 270 | | | | | 275 | | | | | 280 | | | | | | |
| TCA | CAC | ATG | CAT | CAT | GAC | AAT | GAC | TTT | GTG | GAG | ATT | AAC | AGC | ATC | ACA | 1334 |
| Ser | His | Met | His | His | Asp | Asn | Asp | Phe | Val | Glu | Ile | Asn | Ser | Ile | Thr | |
| 285 | | | | | 290 | | | | | 295 | | | | | 300 | |
| GCC | CAG | ATT | ATA | GCC | AAA | ATC | AAT | AAT | ATA | CCA | AAT | GTT | GAT | GAA | CCT | 1382 |
| Ala | Gln | Ile | Ile | Ala | Lys | Ile | Asn | Asn | Ile | Pro | Asn | Val | Asp | Glu | Pro | |
| | | | | 305 | | | | | 310 | | | | | 315 | | |
| GCA | GTA | GGA | TAC | ATG | GGA | TCT | AAA | CTT | GAA | AAT | TGG | ATT | TCC | TAC | CGC | 1430 |
| Ala | Val | Gly | Tyr | Met | Gly | Ser | Lys | Leu | Glu | Asn | Trp | Ile | Ser | Tyr | Arg | |
| | | 320 | | | | 325 | | | | | 330 | | | | | |
| GAC | ACA | GAC | TTC | ACA | GAA | GAA | GAT | TGG | ACT | CTG | AAG | CAC | CCG | TGC | TCA | 1478 |
| Asp | Thr | Asp | Phe | Thr | Glu | Glu | Asp | Trp | Thr | Leu | Lys | His | Pro | Cys | Ser | |
| 335 | | | | | 340 | | | | | 345 | | | | | | |
| GGA | CCT | TTA | GAA | AGC | GAA | GAA | TGT | GAT | CAC | GAC | TTC | ATC | ATC | AGA | AAT | 1526 |
| Gly | Pro | Leu | Glu | Ser | Glu | Glu | Cys | Asp | His | Asp | Phe | Ile | Ile | Arg | Asn | |
| 350 | | | | | 355 | | | | | 360 | | | | | | |
| CAA | TAT | GGG | TTT | GAG | CTA | TAT | TTG | AAT | CAT | GCA | ATG | CTT | CTA | AAT | TTT | 1574 |
| Gln | Tyr | Gly | Phe | Glu | Leu | Tyr | Leu | Asn | His | Ala | Met | Leu | Leu | Asn | Phe | |
| 365 | | | | | 370 | | | | | 375 | | | | | 380 | |
| GCT | GCA | TTG | TGT | CTT | TAT | CAT | GGC | AGA | TTG | TAT | AAC | TCT | GAC | AAA | TCA | 1622 |
| Ala | Ala | Leu | Cys | Leu | Tyr | His | Gly | Arg | Leu | Tyr | Asn | Ser | Asp | Lys | Ser | |
| | | | | 385 | | | | | 390 | | | | | 395 | | |
| GTT | GGA | ATA | CTG | GTC | ACC | TTT | GGA | GGA | ATG | ATA | GGG | GTG | AAC | ATT | GCA | 1670 |
| Val | Gly | Ile | Leu | Val | Thr | Phe | Gly | Gly | Met | Ile | Gly | Val | Asn | Ile | Ala | |
| | | | 400 | | | | | 405 | | | | | 410 | | | |
| TGC | AAT | GAG | GCA | TTT | ATG | GAA | TTC | CAC | AAA | CGT | TTC | TAT | AGC | GGC | ACT | 1718 |
| Cys | Asn | Glu | Ala | Phe | Met | Glu | Phe | His | Lys | Arg | Phe | Tyr | Ser | Gly | Thr | |
| | | 415 | | | | 420 | | | | | 425 | | | | | |
| CTC | AGA | ATA | AGT | CCA | ATG | AAT | ATG | TAT | TTG | AGG | AGA | GAG | AGA | TGC | CAA | 1766 |
| Leu | Arg | Ile | Ser | Pro | Met | Asn | Met | Tyr | Leu | Arg | Arg | Glu | Arg | Cys | Gln | |
| | 430 | | | | | 435 | | | | | 440 | | | | | |
| GCT | CAG | TCA | GAC | TTC | AAT | GAT | GAA | GAA | TTT | CAA | AGA | CTG | ATG | GCA | GAA | 1814 |
| Ala | Gln | Ser | Asp | Phe | Asn | Asp | Glu | Glu | Phe | Gln | Arg | Leu | Met | Ala | Glu | |
| 445 | | | | | 450 | | | | | 455 | | | | | 460 | |
| GAG | GGC | GAT | GCG | GAA | ATT | CAA | AGC | GTC | TCA | AAT | TGG | GTT | AGT | GAA | TAT | 1862 |
| Glu | Gly | Asp | Ala | Glu | Ile | Gln | Ser | Val | Ser | Asn | Trp | Val | Ser | Glu | Tyr | |
| | | | | 465 | | | | | 470 | | | | | 475 | | |
| CTT | GAG | ATA | GAA | GAC | GTC | ATT | GAC | ATA | GTG | GAT | GAA | GCT | GAA | AGC | AAG | 1910 |
| Leu | Glu | Ile | Glu | Asp | Val | Ile | Asp | Ile | Val | Asp | Glu | Ala | Glu | Ser | Lys | |
| | | | 480 | | | | | 485 | | | | | 490 | | | |
| AAA | ACT | CGA | GGA | TTA | GGT | TTG | AAT | CAG | GTT | TTG | GGA | GGA | TTG | CTC | AAA | 1958 |
| Lys | Thr | Arg | Gly | Leu | Gly | Leu | Asn | Gln | Val | Leu | Gly | Gly | Leu | Leu | Lys | |
| | | 495 | | | | 500 | | | | | 505 | | | | | |
| GGT | GTC | TCG | CAT | TGC | GTA | GAC | AGC | TTA | CAC | AAG | GTT | TTT | GAC | TGG | CCC | 2006 |
| Gly | Val | Ser | His | Cys | Val | Asp | Ser | Leu | His | Lys | Val | Phe | Asp | Trp | Pro | |
| 510 | | | | | 515 | | | | | 520 | | | | | | |
| ATT | GAT | CTT | GCA | ATT | GAT | GCG | GCA | AAA | GGC | ACA | GCT | GAT | TGG | CTT | GAA | 2054 |
| Ile | Asp | Leu | Ala | Ile | Asp | Ala | Ala | Lys | Gly | Thr | Ala | Asp | Trp | Leu | Glu | |
| 525 | | | | | 530 | | | | | 535 | | | | | 540 | |
| GGT | AAT | AAG | TCA | TCA | GTC | GAT | GAC | AGC | AAA | ATC | TGT | GCT | GGA | TGC | CCT | 2102 |
| Gly | Asn | Lys | Ser | Ser | Val | Asp | Asp | Ser | Lys | Ile | Cys | Ala | Gly | Cys | Pro | |
| | | | | 545 | | | | | 550 | | | | | 555 | | |
| GAA | ATT | CAG | AAA | GAT | ATG | CAA | GAT | TTC | CAG | AAA | GAA | ACG | AAG | ATG | GGA | 2150 |
| Glu | Ile | Gln | Lys | Asp | Met | Gln | Asp | Phe | Gln | Lys | Glu | Thr | Lys | Met | Gly | |
| | | | 560 | | | | | 565 | | | | | 570 | | | |

| | | | | | | | | | | | | | | | |
|---|---|---|---|---|---|---|---|---|---|---|---|---|---|---|---|
| ATA | GAG | ATC | CTG | AGA | GAT | TCG | ATC | AAG | AAA | TTA | TCA | GAA | GGG | ATT | GAC | 2198
| Ile | Glu | Ile | Leu | Arg | Asp | Ser | Ile | Lys | Lys | Leu | Ser | Glu | Gly | Ile | Asp |
|     |     | 575 |     |     |     |     | 580 |     |     |     |     | 585 |     |     |     |

| AAG | ATC | ACC | AGA | ATG | AAT | CAA | ACA | AAT | TTT | GAA | CGA | ATT | GTT | GAT | CGA | 2246
| Lys | Ile | Thr | Arg | Met | Asn | Gln | Thr | Asn | Phe | Glu | Arg | Ile | Val | Asp | Arg |
|     |     | 590 |     |     |     |     | 595 |     |     |     |     | 600 |     |     |     |

| ATT | AGA | CCC | ATC | GAG | AGC | AAA | CTC | AAA | GAA | CTT | GAA | AAG | ATT | AAA | CCT | 2294
| Ile | Arg | Pro | Ile | Glu | Ser | Lys | Leu | Lys | Glu | Leu | Glu | Lys | Ile | Lys | Pro |
| 605 |     |     |     |     | 610 |     |     |     |     | 615 |     |     |     |     | 620 |

| GAT | GCT | GGG | GGA | TCA | AAA | GAT | AGT | GAA | GCT | ATG | CGC | CAA | TTA | GTC | CAG | 2342
| Asp | Ala | Gly | Gly | Ser | Lys | Asp | Ser | Glu | Ala | Met | Arg | Gln | Leu | Val | Gln |
|     |     |     |     | 625 |     |     |     |     | 630 |     |     |     |     | 635 |     |

| GCC | ATC | AAA | GAT | ATT | AAG | CTT | ATT | AAA | CAA | GCG | ATG | ATG | GAA | CTT | AAT | 2390
| Ala | Ile | Lys | Asp | Ile | Lys | Leu | Ile | Lys | Gln | Ala | Met | Met | Glu | Leu | Asn |
|     |     |     | 640 |     |     |     |     | 645 |     |     |     |     | 650 |     |     |

| GAT | AGA | ATT | AAA | GAC | CTG | GAG | GAT | AGC | AAG | CAG | CAT | CAA | GAA | GAT | TCA | 2438
| Asp | Arg | Ile | Lys | Asp | Leu | Glu | Asp | Ser | Lys | Gln | His | Gln | Glu | Asp | Ser |
|     |     | 655 |     |     |     |     | 660 |     |     |     |     | 665 |     |     |     |

| AAG | CCA | GAT | GAT | GAT | ACA | GCA | GGT | GAG | CAA | AAA | CCC | ATT | CCA | AAA | ATC | 2486
| Lys | Pro | Asp | Asp | Asp | Thr | Ala | Gly | Glu | Gln | Lys | Pro | Ile | Pro | Lys | Ile |
| 670 |     |     |     |     | 675 |     |     |     |     | 680 |     |     |     |     |     |

| AAT | AAA | ATA | AGG | GTT | AAA | GCC | AAG | AGA | GTT | GAG | AAG | CAA | TCA | GGT | ACG | 2534
| Asn | Lys | Ile | Arg | Val | Lys | Ala | Lys | Arg | Val | Glu | Lys | Gln | Ser | Gly | Thr |
| 685 |     |     |     |     | 690 |     |     |     |     | 695 |     |     |     |     | 700 |

| AAC | ATA | GTG | AAC | AAT | GAG | ATA | GAA | CAG | GCT | TTT | CAA | GAT | GAA | GAA | AAG | 2582
| Asn | Ile | Val | Asn | Asn | Glu | Ile | Glu | Gln | Ala | Phe | Gln | Asp | Glu | Glu | Lys |
|     |     |     |     | 705 |     |     |     |     | 710 |     |     |     |     | 715 |     |

| AGA | ACT | GTT | GAT | CCA | AAT | ATC | AGT | GAT | ATG | TAC | AAC | GCT | ATC | AAA | AGT | 2630
| Arg | Thr | Val | Asp | Pro | Asn | Ile | Ser | Asp | Met | Tyr | Asn | Ala | Ile | Lys | Ser |
|     |     |     | 720 |     |     |     |     | 725 |     |     |     |     | 730 |     |     |

| GAG | TAT | TTG | GTT | AAA | AGC | TTT | TCT | TGG | AAA | GTC | TCA | GAT | GGA | CAA | GAT | 2678
| Glu | Tyr | Leu | Val | Lys | Ser | Phe | Ser | Trp | Lys | Val | Ser | Asp | Gly | Gln | Asp |
|     |     | 735 |     |     |     |     | 740 |     |     |     |     | 745 |     |     |     |

| AAA | GTT | CTA | TCT | AAT | ATT | AAT | ATA | CCT | GAG | GAT | TTG | TGG | AAT | ACA | AAC | 2726
| Lys | Val | Leu | Ser | Asn | Ile | Asn | Ile | Pro | Glu | Asp | Leu | Trp | Asn | Thr | Asn |
| 750 |     |     |     |     | 755 |     |     |     |     | 760 |     |     |     |     |     |

| TCC | CGG | CTG | AAC | GAC | ATA | ATG | AGC | TAT | TTC | CAG | TAC | TAC | AAG | GCT | ACA | 2774
| Ser | Arg | Leu | Asn | Asp | Ile | Met | Ser | Tyr | Phe | Gln | Tyr | Tyr | Lys | Ala | Thr |
| 765 |     |     |     |     | 770 |     |     |     |     | 775 |     |     |     |     | 780 |

| GGT | TTA | ACA | TTT | AGA | ATA | TCA | ACG | ACC | TGT | ATT | CCA | ATG | CAT | GGA | GGT | 2822
| Gly | Leu | Thr | Phe | Arg | Ile | Ser | Thr | Thr | Cys | Ile | Pro | Met | His | Gly | Gly |
|     |     |     |     | 785 |     |     |     |     | 790 |     |     |     |     | 795 |     |

| ACA | CTG | TTT | GCA | GCG | TGG | GAT | GCA | TGT | GGA | TGT | GCT | ACT | CGA | CAA | GGG | 2870
| Thr | Leu | Phe | Ala | Ala | Trp | Asp | Ala | Cys | Gly | Cys | Ala | Thr | Arg | Gln | Gly |
|     |     |     | 800 |     |     |     |     | 805 |     |     |     |     | 810 |     |     |

| ATA | GCT | ACG | GCT | GTG | CAA | CTG | ACA | GGG | CTT | CCT | GGA | ATC | ATG | ATA | GAA | 2918
| Ile | Ala | Thr | Ala | Val | Gln | Leu | Thr | Gly | Leu | Pro | Gly | Ile | Met | Ile | Glu |
|     |     | 815 |     |     |     |     | 820 |     |     |     |     | 825 |     |     |     |

| GCA | CAC | AGT | TCG | TCC | TTG | ACG | ACT | TTC | TCA | GTC | GAG | GAT | CCG | TTA | ACG | 2966
| Ala | His | Ser | Ser | Ser | Leu | Thr | Thr | Phe | Ser | Val | Glu | Asp | Pro | Leu | Thr |
|     | 830 |     |     |     |     | 835 |     |     |     |     | 840 |     |     |     |     |

| CAA | TCT | ACT | GTG | TGC | CTT | AGT | GGA | AGT | GAA | CAT | TCG | TTT | GGG | CGG | ATT | 3014
| Gln | Ser | Thr | Val | Cys | Leu | Ser | Gly | Ser | Glu | His | Ser | Phe | Gly | Arg | Ile |
| 845 |     |     |     |     | 850 |     |     |     |     | 855 |     |     |     |     | 860 |

| GGA | ATT | CTC | AAA | ATT | TGT | TGC | CTA | AAC | GTG | TTG | AAT | GCA | CCA | CAA | GCA | 3062
| Gly | Ile | Leu | Lys | Ile | Cys | Cys | Leu | Asn | Val | Leu | Asn | Ala | Pro | Gln | Ala |
|     |     |     |     | 865 |     |     |     |     | 870 |     |     |     |     | 875 |     |

| GCC | ACC | CAA | TCC | GTT | TCC | GTA | AAC | GTA | TGG | GTG | AAG | TTT | GAT | GGG | GTG | 3110
| Ala | Thr | Gln | Ser | Val | Ser | Val | Asn | Val | Trp | Val | Lys | Phe | Asp | Gly | Val |
|     |     |     | 880 |     |     |     |     | 885 |     |     |     |     | 890 |     |     |

| | | | | | | | | | | | | | | | | |
|---|---|---|---|---|---|---|---|---|---|---|---|---|---|---|---|---|
| AAA | TTT | CAT | TTC | TAC | TCC | CTC | AAA | AAG | CAA | CCC | GTG | GTC | TCC | CAA | ATG | 3158 |
| Lys | Phe | His 895 | Phe | Tyr | Ser | Leu | Lys 900 | Lys | Gln | Pro | Val | Val 905 | Ser | Gln | Met | |
| CTA | GTA | GAT | AAA | TTG | ACT | AAT | CTT | GGA | GAA | ATG | GGT | TGT | GTA | GTT | GCA | 3206 |
| Leu | Val | Asp 910 | Lys | Leu | Thr | Asn | Leu 915 | Gly | Glu | Met | Gly | Cys 920 | Val | Val | Ala | |
| ACT | GGA | ACA | TGG | TCA | ACG | ACT | TCA | AGT | TTG | AAT | TTG | TTG | CAG | CTA | AAC | 3254 |
| Thr | Gly | Thr 925 | Trp | Ser | Thr | Thr | Ser 930 | Ser | Leu | Asn | Leu | Leu 935 | Gln | Leu | Asn 940 | |
| GTG | CAT | CCA | ACA | GCT | TGC | TTT | ATA | AGT | GAT | GGC | CTG | GTT | ACT | CAG | ACC | 3302 |
| Val | His | Pro | Thr | Ala 945 | Cys | Phe | Ile | Ser | Asp 950 | Gly | Leu | Val | Thr | Gln 955 | Thr | |
| CCA | CTA | AGT | GTA | ATA | GCT | CAT | GCT | TTC | GCA | CGA | TGG | AGG | GGA | TCA | TTG | 3350 |
| Pro | Leu | Ser | Val | Ile 960 | Ala | His | Ala | Phe | Ala 965 | Arg | Trp | Arg | Gly | Ser 970 | Leu | |
| AAA | TTC | ACC | ATC | ACT | TTT | GGA | GCT | AGT | ATG | TTC | ACA | AGA | GGA | AGA | GTC | 3398 |
| Lys | Phe | Thr 975 | Ile | Thr | Phe | Gly | Ala 980 | Ser | Met | Phe | Thr | Arg 985 | Gly | Arg | Val | |
| CTG | GTA | GCA | GCT | ATA | CCT | GTG | GCG | AAG | CGA | AAA | GAG | ACT | CTC | ACA | ATT | 3446 |
| Leu | Val | Ala 990 | Ala | Ile | Pro | Val | Ala 995 | Lys | Arg | Lys | Glu | Thr 1000 | Leu | Thr | Ile | |
| GAA | GAG | ATT | AGT | GGA | TAT | CAC | AAT | GTA | ATG | TGC | CTG | CTC | AAT | GGA | GAA | 3494 |
| Glu | Glu 1005 | Ile | Ser | Gly | Tyr | His 1010 | Asn | Val | Met | Cys | Leu 1015 | Leu | Asn | Gly | Glu 1020 | |
| AGG | ACA | TCT | TTC | GAA | CTT | GAA | GTC | CCT | TAT | CAC | TCA | GTG | GGA | GAG | GAT | 3542 |
| Arg | Thr | Ser | Phe | Glu 1025 | Leu | Glu | Val | Pro | Tyr 1030 | His | Ser | Val | Gly | Glu 1035 | Asp | |
| TCT | TAT | GTT | TGT | AGG | GAT | GCC | CTA | TTT | GAT | GTT | TCG | TCA | TAC | GCA | CAG | 3590 |
| Ser | Tyr | Val | Cys | Arg 1040 | Asp | Ala | Leu | Phe | Asp 1045 | Val | Ser | Ser | Tyr | Ala 1050 | Gln | |
| AAC | TTT | ATG | ATC | ACC | AGA | TTA | CAC | ATG | GTA | GTT | ATA | GAC | ACA | TTG | GTG | 3638 |
| Asn | Phe | Met | Ile | Thr 1055 | Arg | Leu | His | Met | Val 1060 | Val | Ile | Asp | Thr | Leu 1065 | Val | |
| ATG | AGT | TCA | AAT | GCA | AGT | AAC | ACA | ATA | AGT | TAC | TGT | GTG | ATG | ATG | GGA | 3686 |
| Met | Ser | Ser 1070 | Asn | Ala | Ser | Asn | Thr 1075 | Ile | Ser | Tyr | Cys | Val 1080 | Met | Met | Gly | |
| CCA | GGC | AAA | GAT | CTT | GAA | TTG | AGA | TAT | CTA | AAT | GGT | GTC | CAT | GCT | CAG | 3734 |
| Pro | Gly 1085 | Lys | Asp | Leu | Glu | Leu 1090 | Arg | Tyr | Leu | Asn | Gly 1095 | Val | His | Ala | Gln 1100 | |
| AGA | AAT | GTG | AGA | GAA | TTA | AAA | GCT | CAG | GTA | AGC | CTT | GGT | TTT | TCC | TTA | 3782 |
| Arg | Asn | Val | Arg | Glu 1105 | Leu | Lys | Ala | Gln | Val 1110 | Ser | Leu | Gly | Phe | Ser 1115 | Leu | |
| CAA | TCT | GGA | AGG | AAC | ATT | GGA | GTG | GGT | TTC | AGT | GAT | TTG | CTC | AAA | AGA | 3830 |
| Gln | Ser | Gly | Arg 1120 | Asn | Ile | Gly | Val | Gly 1125 | Phe | Ser | Asp | Leu | Leu 1130 | Lys | Arg | |
| TGG | GCC | CAC | CTG | CTC | ACA | CTG | CAC | TTT | GAT | GAA | AAT | AAC | GAA | AAA | TCA | 3878 |
| Trp | Ala | His | Leu 1135 | Leu | Thr | Leu | His 1140 | Phe | Asp | Glu | Asn | Asn 1145 | Glu | Lys | Ser | |
| GAA | GAA | AAA | GTT | GGT | TCT | TAT | ATT | GTC | ACT | GTA | GCG | CCA | AGT | TAT | AGA | 3926 |
| Glu | Glu 1150 | Lys | Val | Gly | Ser | Tyr 1155 | Ile | Val | Thr | Val | Ala 1160 | Pro | Ser | Tyr | Arg | |
| GCT | TTT | CCG | CAG | CAC | AAC | ACT | TTA | TTG | AGT | TGG | TTT | TCA | CAA | CTA | TTC | 3974 |
| Ala | Phe | Pro 1165 | Gln | His | Asn | Thr | Leu 1170 | Leu | Ser | Trp | Phe | Ser 1175 | Gln | Leu | Phe 1180 | |
| GTG | CAA | TGG | CAA | GGC | TCT | TTG | TGC | TAC | AGG | TTA | CAC | GTG | GAC | TCA | CAA | 4022 |
| Val | Gln | Trp | Gln | Gly 1185 | Ser | Leu | Cys | Tyr | Arg 1190 | Leu | His | Val | Asp | Ser 1195 | Gln | |
| GAG | AGA | AGA | TAT | GGA | GGT | TAT | TTG | CGC | ATA | TGG | CAT | GAT | CCT | AAC | GGT | 4070 |
| Glu | Arg | Arg | Tyr | Gly 1200 | Gly | Tyr | Leu | Arg | Ile 1205 | Trp | His | Asp | Pro | Asn 1210 | Gly | |

| | | | | | | | | | | | | | | | | |
|---|---|---|---|---|---|---|---|---|---|---|---|---|---|---|---|---|
| TCA | TTA | GAT | GAA | GGA | GTC | GAA | TTC | GCT | ATG | TCA | ACA | AAC | TTA | GAG | CCA | 4118 |
| Ser | Leu | Asp | Glu | Gly | Val | Glu | Phe | Ala | Met | Ser | Thr | Asn | Leu | Glu | Pro | |
| | | 1215 | | | | 1220 | | | | 1225 | | | | | | |
| CCC | CCA | GGT | GCC | TTT | GTG | AAA | TAC | TGG | AAT | TAT | AAT | GAG | CAG | AGC | GAG | 4166 |
| Pro | Pro | Gly | Ala | Phe | Val | Lys | Tyr | Trp | Asn | Tyr | Asn | Glu | Gln | Ser | Glu | |
| | | 1230 | | | | 1235 | | | | 1240 | | | | | | |
| TTT | GAG | TTT | GTG | GTA | CCA | TAC | ACG | GCT | CGA | ACC | CCT | CGC | TTA | TTC | GTG | 4214 |
| Phe | Glu | Phe | Val | Val | Pro | Tyr | Thr | Ala | Arg | Thr | Pro | Arg | Leu | Phe | Val | |
| 1245 | | | | | 1250 | | | | | 1255 | | | | | 1260 | |
| CCA | AAG | GCA | ATG | ATT | CCG | ACA | GAT | TCG | AAG | TCA | TGG | ATA | TTG | AAT | TAT | 4262 |
| Pro | Lys | Ala | Met | Ile | Pro | Thr | Asp | Ser | Lys | Ser | Trp | Ile | Leu | Asn | Tyr | |
| | | | | 1265 | | | | 1270 | | | | | 1275 | | | |
| AAT | GGA | ACT | TTG | AAC | TTC | GAT | TAT | AGG | GGA | GTG | GAT | GAT | TTT | AAC | GTC | 4310 |
| Asn | Gly | Thr | Leu | Asn | Phe | Asp | Tyr | Arg | Gly | Val | Asp | Asp | Phe | Asn | Val | |
| | | | 1280 | | | | | 1285 | | | | | 1290 | | | |
| ACT | GTT | GAC | ATT | AGC | GCT | GGA | GAT | AAC | TTC | GAG | TTC | TCT | GTT | CGT | ACG | 4358 |
| Thr | Val | Asp | Ile | Ser | Ala | Gly | Asp | Asn | Phe | Glu | Phe | Ser | Val | Arg | Thr | |
| | | 1295 | | | | | 1300 | | | | 1305 | | | | | |
| GTA | GCT | CCC | AAA | GCT | GGA | AAA | GTG | AAT | GAA | TCG | TTT | ACA | AAG | CTA | TCG | 4406 |
| Val | Ala | Pro | Lys | Ala | Gly | Lys | Val | Asn | Glu | Ser | Phe | Thr | Lys | Leu | Ser | |
| | | 1310 | | | | 1315 | | | | | 1320 | | | | | |
| TAT | AGC | AAT | GAG | CTC | GTC | GAT | ATC | AAG | AAA | CCG | TTG | ACA | GCA | GCT | GGA | 4454 |
| Tyr | Ser | Asn | Glu | Leu | Val | Asp | Ile | Lys | Lys | Pro | Leu | Thr | Ala | Ala | Gly | |
| 1325 | | | | | 1330 | | | | | 1335 | | | | | 1340 | |
| AGA | CTC | AAA | GGA | CCG | TTC | AAT | TTG | AAC | ACT | TTG | AAA | ACT | GCT | GTC | CCT | 4502 |
| Arg | Leu | Lys | Gly | Pro | Phe | Asn | Leu | Asn | Thr | Leu | Lys | Thr | Ala | Val | Pro | |
| | | | | 1345 | | | | | 1350 | | | | | 1355 | | |
| AAA | GAA | ACG | CCC | AAA | GAA | AGC | TCT | GAT | GAT | AAG | GAT | AAA | TCA | AAT | CAG | 4550 |
| Lys | Glu | Thr | Pro | Lys | Glu | Ser | Ser | Asp | Asp | Lys | Asp | Lys | Ser | Asn | Gln | |
| | | | 1360 | | | | | 1365 | | | | | 1370 | | | |
| AAG | AGG | AAA | GGA | GCT | ATG | GAT | TCG | TTA | CTA | AAC | GCT | GTT | GCT | CAG | ATG | 4598 |
| Lys | Arg | Lys | Gly | Ala | Met | Asp | Ser | Leu | Leu | Asn | Ala | Val | Ala | Gln | Met | |
| | | 1375 | | | | | 1380 | | | | | 1385 | | | | |
| GAA | ACT | ATA | AAT | AGT | GAC | GCG | AAT | GGG | TGT | TTC | TCT | TTA | GGG | GGA | TTG | 4646 |
| Glu | Thr | Ile | Asn | Ser | Asp | Ala | Asn | Gly | Cys | Phe | Ser | Leu | Gly | Gly | Leu | |
| | | 1390 | | | | | 1395 | | | | | 1400 | | | | |
| AAG | TCT | ACT | GCC | AAA | ATG | CTG | GAC | TCA | AGA | AAA | ACG | TGC | GAG | AAA | TTT | 4694 |
| Lys | Ser | Thr | Ala | Lys | Met | Leu | Asp | Ser | Arg | Lys | Thr | Cys | Glu | Lys | Phe | |
| 1405 | | | | | 1410 | | | | | 1415 | | | | | 1420 | |
| GCT | GAC | ATC | ATG | GAT | TTC | ACT | CAT | GAT | ACT | CTT | GGT | GTC | AAA | GAT | GGA | 4742 |
| Ala | Asp | Ile | Met | Asp | Phe | Thr | His | Asp | Thr | Leu | Gly | Val | Lys | Asp | Gly | |
| | | | | 1425 | | | | | 1430 | | | | | 1435 | | |
| CCG | GCA | GCG | CAG | AGA | CTT | GCA | GCG | GCT | GTG | GCG | CAA | ATT | GCT | CCA | ATT | 4790 |
| Pro | Ala | Ala | Gln | Arg | Leu | Ala | Ala | Ala | Val | Ala | Gln | Ile | Ala | Pro | Ile | |
| | | | 1440 | | | | | 1445 | | | | | 1450 | | | |
| ATA | GAA | AGC | GTG | AGC | AGA | ACG | ACA | GAA | AGT | GTG | GAA | TCG | AAG | CTC | ACA | 4838 |
| Ile | Glu | Ser | Val | Ser | Arg | Thr | Thr | Glu | Ser | Val | Glu | Ser | Lys | Leu | Thr | |
| | | 1455 | | | | | 1460 | | | | | 1465 | | | | |
| TGC | CTG | GAT | AAG | TAC | AAG | GAT | GGA | ATT | CTT | GGG | ATA | TTA | CAA | AGC | TTA | 4886 |
| Cys | Leu | Asp | Lys | Tyr | Lys | Asp | Gly | Ile | Leu | Gly | Ile | Leu | Gln | Ser | Leu | |
| | | 1470 | | | | | 1475 | | | | | 1480 | | | | |
| TGC | AAA | GAG | ACA | ATC | CCA | GGA | CTT | GCC | ATT | GTG | GAC | TTC | AAG | AAG | GGC | 4934 |
| Cys | Lys | Glu | Thr | Ile | Pro | Gly | Leu | Ala | Ile | Val | Asp | Phe | Lys | Lys | Gly | |
| 1485 | | | | | 1490 | | | | | 1495 | | | | | 1500 | |
| AAG | TAC | ATG | TGG | GCA | ACC | CTC | CTC | ACG | CTG | ATA | GCA | GGA | GCA | GCT | CTC | 4982 |
| Lys | Tyr | Met | Trp | Ala | Thr | Leu | Leu | Thr | Leu | Ile | Ala | Gly | Ala | Ala | Leu | |
| | | | | 1505 | | | | | 1510 | | | | | 1515 | | |
| TTC | TGG | GCA | TGT | AAA | AGC | CAG | AAG | AGC | TTT | TTG | AAA | AGG | TTT | TCC | GTG | 5030 |
| Phe | Trp | Ala | Cys | Lys | Ser | Gln | Lys | Ser | Phe | Leu | Lys | Arg | Phe | Ser | Val | |
| | | | 1520 | | | | | 1525 | | | | | 1530 | | | |

| | | | | | | | | | | | | | | | | |
|---|---|---|---|---|---|---|---|---|---|---|---|---|---|---|---|---|
| GTT | GTA | ATG | ATC | ATT | TGG | AGT | CCT | TTT | CTT | GCT | GGA | AAA | GTA | TGG | AGC | 5078 |
| Val | Val | Met | Ile | Ile | Trp | Ser | Pro | Phe | Leu | Ala | Gly | Lys | Val | Trp | Ser | |
| | | 1535 | | | | 1540 | | | | | 1545 | | | | | |
| TTA | GGC | CAG | TGG | ATA | GTT | CAA | AAG | TGG | TGC | CAT | TTG | TGG | CCC | AAA | TCA | 5126 |
| Leu | Gly | Gln | Trp | Ile | Val | Gln | Lys | Trp | Cys | His | Leu | Trp | Pro | Lys | Ser | |
| | | 1550 | | | | 1555 | | | | | 1560 | | | | | |
| GAC | TCA | TGC | CGA | CAA | CAC | TCT | TTG | GCA | GGC | CTG | TTC | GAA | AGT | GCG | AAA | 5174 |
| Asp | Ser | Cys | Arg | Gln | His | Ser | Leu | Ala | Gly | Leu | Phe | Glu | Ser | Ala | Lys | |
| 1565 | | | | | 1570 | | | | | 1575 | | | | | 1580 | |
| ACG | AAG | GTT | CGT | GGT | TTC | CCA | GAT | TGG | TTT | CGA | TCC | GGG | GGC | ATG | AAC | 5222 |
| Thr | Lys | Val | Arg | Gly | Phe | Pro | Asp | Trp | Phe | Arg | Ser | Gly | Gly | Met | Asn | |
| | | | | 1585 | | | | | 1590 | | | | | 1595 | | |
| ATT | GTG | ACG | CAA | GTT | TGT | TCA | GTA | TTA | CTG | ACG | ATA | GTG | AGT | CTG | ATC | 5270 |
| Ile | Val | Thr | Gln | Val | Cys | Ser | Val | Leu | Leu | Thr | Ile | Val | Ser | Leu | Ile | |
| | | | 1600 | | | | | 1605 | | | | | 1610 | | | |
| ACG | TTA | GGG | ACA | ATC | CCC | AGT | GCA | AAG | AAA | AGC | AAA | TCA | CTG | GCC | GAT | 5318 |
| Thr | Leu | Gly | Thr | Ile | Pro | Ser | Ala | Lys | Lys | Ser | Lys | Ser | Leu | Ala | Asp | |
| | | 1615 | | | | 1620 | | | | | 1625 | | | | | |
| CGC | TTT | ATC | GAA | TTT | GGC | AAC | ATG | AAT | AGA | GCT | GCA | ACC | TCT | ATT | GCT | 5366 |
| Arg | Phe | Ile | Glu | Phe | Gly | Asn | Met | Asn | Arg | Ala | Ala | Thr | Ser | Ile | Ala | |
| | | 1630 | | | | 1635 | | | | | 1640 | | | | | |
| GCA | GGC | TAC | AAG | AGT | ATC | TCA | GAA | TTG | TGT | TCA | AAA | TTC | ACT | CAT | TTT | 5414 |
| Ala | Gly | Tyr | Lys | Ser | Ile | Ser | Glu | Leu | Cys | Ser | Lys | Phe | Thr | His | Phe | |
| 1645 | | | | | 1650 | | | | | 1655 | | | | | 1660 | |
| GTA | GCA | ACA | CAT | TTT | CTG | GGA | GCC | ACT | GTA | GAT | GAC | AAT | GTC | TTC | AAA | 5462 |
| Val | Ala | Thr | His | Phe | Leu | Gly | Ala | Thr | Val | Asp | Asp | Asn | Val | Phe | Lys | |
| | | | | 1665 | | | | | 1670 | | | | | 1675 | | |
| GAC | CTA | GTT | ACG | TTC | AAC | GTT | AAA | GAT | TGG | GTC | GAA | CAA | GTC | AAA | GTG | 5510 |
| Asp | Leu | Val | Thr | Phe | Asn | Val | Lys | Asp | Trp | Val | Glu | Gln | Val | Lys | Val | |
| | | | 1680 | | | | | 1685 | | | | | 1690 | | | |
| GCA | TCT | CTT | GAG | GAA | AAC | AAG | TTT | AAA | TCA | TTC | GGA | TCG | CCT | GAG | CAG | 5558 |
| Ala | Ser | Leu | Glu | Glu | Asn | Lys | Phe | Lys | Ser | Phe | Gly | Ser | Pro | Glu | Gln | |
| | | 1695 | | | | 1700 | | | | | 1705 | | | | | |
| CTA | ACG | CGA | GTA | AGA | CAC | ATG | TAT | GAC | AAG | AGC | CTG | GAA | ATA | ACC | AAC | 5606 |
| Leu | Thr | Arg | Val | Arg | His | Met | Tyr | Asp | Lys | Ser | Leu | Glu | Ile | Thr | Asn | |
| | | 1710 | | | | 1715 | | | | | 1720 | | | | | |
| AAA | CTT | CTG | GAT | AGA | AAC | AAA | GTG | CCC | GTA | GCG | ATG | CTC | CCG | GTT | ATC | 5654 |
| Lys | Leu | Leu | Asp | Arg | Asn | Lys | Val | Pro | Val | Ala | Met | Leu | Pro | Val | Ile | |
| 1725 | | | | | 1730 | | | | | 1735 | | | | | 1740 | |
| AGA | GAT | ACA | TGT | AAG | AAA | TGC | GAG | GAG | CTT | TTG | AAT | GAC | AGC | TAC | AGT | 5702 |
| Arg | Asp | Thr | Cys | Lys | Lys | Cys | Glu | Glu | Leu | Leu | Asn | Asp | Ser | Tyr | Ser | |
| | | | | 1745 | | | | | 1750 | | | | | 1755 | | |
| TAC | AAG | GGA | ATG | AAG | ACC | CCT | AGA | ATA | GAT | CCA | TTC | TAC | ATT | TGT | CTG | 5750 |
| Tyr | Lys | Gly | Met | Lys | Thr | Pro | Arg | Ile | Asp | Pro | Phe | Tyr | Ile | Cys | Leu | |
| | | | 1760 | | | | | 1765 | | | | | 1770 | | | |
| ACT | GGT | CCA | CCT | GGT | GTT | GGA | AAA | TCC | ACT | GTG | GCC | TCC | ATA | ATT | ATC | 5798 |
| Thr | Gly | Pro | Pro | Gly | Val | Gly | Lys | Ser | Thr | Val | Ala | Ser | Ile | Ile | Ile | |
| | | 1775 | | | | 1780 | | | | | 1785 | | | | | |
| AAT | GAT | CTT | TTG | GAT | TAT | ATG | GGA | GAG | CCT | AAG | ACT | GAT | AGA | ATA | TAC | 5846 |
| Asn | Asp | Leu | Leu | Asp | Tyr | Met | Gly | Glu | Pro | Lys | Thr | Asp | Arg | Ile | Tyr | |
| | | 1790 | | | | 1795 | | | | | 1800 | | | | | |
| ACC | AGA | TGT | TGC | GCC | GAT | TCA | TAT | TGG | AGC | AAC | TAC | CAC | CAT | GAA | CCA | 5894 |
| Thr | Arg | Cys | Cys | Ala | Asp | Ser | Tyr | Trp | Ser | Asn | Tyr | His | His | Glu | Pro | |
| 1805 | | | | | 1810 | | | | | 1815 | | | | | 1820 | |
| GTT | ATC | ATT | TAT | GAC | GAT | CTA | GGG | GCT | ATT | TCA | AAA | GTA | GCT | AGT | TTA | 5942 |
| Val | Ile | Ile | Tyr | Asp | Asp | Leu | Gly | Ala | Ile | Ser | Lys | Val | Ala | Ser | Leu | |
| | | | | 1825 | | | | | 1830 | | | | | 1835 | | |
| TCC | GAC | TAT | GCT | GAA | ATT | ATG | GGT | ATT | AAA | TCA | AAC | AGG | CCC | TAC | TCT | 5990 |
| Ser | Asp | Tyr | Ala | Glu | Ile | Met | Gly | Ile | Lys | Ser | Asn | Arg | Pro | Tyr | Ser | |
| | | | 1840 | | | | | 1845 | | | | | 1850 | | | |

```
TTG  CCG  ATG  GCT  GCT  GTT  GAG  GAA  AAA  GGA  AGG  CAT  TGC  TTA  TCA  AAG     6038
Leu  Pro  Met  Ala  Ala  Val  Glu  Glu  Lys  Gly  Arg  His  Cys  Leu  Ser  Lys
          1855                    1860                    1865

TAC  TTA  GTA  GCC  TGC  ACC  AAC  CTC  ACT  CAT  CTC  GAT  GAT  ACG  GGA  GAC     6086
Tyr  Leu  Val  Ala  Cys  Thr  Asn  Leu  Thr  His  Leu  Asp  Asp  Thr  Gly  Asp
     1870                    1875                    1880

GTC  AAA  ACG  AAG  GAA  GCT  TAT  TAC  AGA  AGA  ATT  AAT  CTT  CCC  GTA  ACC     6134
Val  Lys  Thr  Lys  Glu  Ala  Tyr  Tyr  Arg  Arg  Ile  Asn  Leu  Pro  Val  Thr
1885                    1890                    1895                    1900

GTC  GAG  AGA  GAT  TTG  GCT  ATG  CCA  ATG  AGC  CCT  GAG  GAT  CCC  GCT  AGT     6182
Val  Glu  Arg  Asp  Leu  Ala  Met  Pro  Met  Ser  Pro  Glu  Asp  Pro  Ala  Ser
               1905                    1910                    1915

GGT  TTA  CTG  TTC  ACT  ATT  GGG  GAT  ATT  CAT  GAG  AAT  GGC  AGG  AAT  GTG     6230
Gly  Leu  Leu  Phe  Thr  Ile  Gly  Asp  Ile  His  Glu  Asn  Gly  Arg  Asn  Val
                    1920                    1925                    1930

AGC  GTG  GTT  GAG  AGT  AGG  TTG  CTC  AAT  GGT  CGA  GTG  CCT  TTT  AGA  GCT     6278
Ser  Val  Val  Glu  Ser  Arg  Leu  Leu  Asn  Gly  Arg  Val  Pro  Phe  Arg  Ala
               1935                    1940                    1945

GGA  GAC  TTA  CGA  AAC  ATG  AGC  TAC  AAT  TAC  TTT  ATG  GAG  TTC  GTG  AGG     6326
Gly  Asp  Leu  Arg  Asn  Met  Ser  Tyr  Asn  Tyr  Phe  Met  Glu  Phe  Val  Arg
          1950                    1955                    1960

ATC  TAC  GCA  ACT  ATC  TAT  ATG  GAG  AAT  CAA  CAG  CAA  CTC  GTG  GCT  AAG     6374
Ile  Tyr  Ala  Thr  Ile  Tyr  Met  Glu  Asn  Gln  Gln  Gln  Leu  Val  Ala  Lys
1965                    1970                    1975                    1980

CTT  TCA  GGA  GAT  GAT  TAC  GAA  AGC  TCT  TCA  TCA  TCG  TTT  CCC  GAG  AAT     6422
Leu  Ser  Gly  Asp  Asp  Tyr  Glu  Ser  Ser  Ser  Ser  Ser  Phe  Pro  Glu  Asn
                    1985                    1990                    1995

GAG  GAA  TTG  GAA  TTT  GAC  TTC  CTA  GCC  CAA  GCA  CAC  AAT  GGT  GTG  TAC     6470
Glu  Glu  Leu  Glu  Phe  Asp  Phe  Leu  Ala  Gln  Ala  His  Asn  Gly  Val  Tyr
               2000                    2005                    2010

CTA  ACG  ATA  GAG  GAA  GTT  GTA  GCT  AAA  TTT  GAG  TCA  ATG  AAA  TTC  TCG     6518
Leu  Thr  Ile  Glu  Glu  Val  Val  Ala  Lys  Phe  Glu  Ser  Met  Lys  Phe  Ser
          2015                    2020                    2025

GGA  AAA  CAA  CTC  AAT  GCT  GAA  ATT  GAA  AAA  TTC  GAA  AGA  ATT  GGA  GTT     6566
Gly  Lys  Gln  Leu  Asn  Ala  Glu  Ile  Glu  Lys  Phe  Glu  Arg  Ile  Gly  Val
     2030                    2035                    2040

GAT  GGA  TGG  AGA  ACT  AAC  AAA  GCT  CTC  TCC  TTT  AAT  GAT  TTG  GTC  AAA     6614
Asp  Gly  Trp  Arg  Thr  Asn  Lys  Ala  Leu  Ser  Phe  Asn  Asp  Leu  Val  Lys
2045                    2050                    2055                    2060

AGG  TTT  TGT  GGA  TGC  TGC  TTA  GGT  GAT  GAC  TGT  AAC  TTT  GAT  TTC  CAC     6662
Arg  Phe  Cys  Gly  Cys  Cys  Leu  Gly  Asp  Asp  Cys  Asn  Phe  Asp  Phe  His
                    2065                    2070                    2075

TAT  CGA  ACT  TTA  TTC  AAA  GTG  CTA  ATA  GAG  AAT  AAG  CAA  ATC  CCA  GCC     6710
Tyr  Arg  Thr  Leu  Phe  Lys  Val  Leu  Ile  Glu  Asn  Lys  Gln  Ile  Pro  Ala
               2080                    2085                    2090

TAC  AAG  TGT  ATG  GTT  CTC  CAT  AAA  GTG  AAT  CCA  GAT  AGA  ATG  AAG  ACT     6758
Tyr  Lys  Cys  Met  Val  Leu  His  Lys  Val  Asn  Pro  Asp  Arg  Met  Lys  Thr
          2095                    2100                    2105

CAG  ATA  AAG  ATG  GTG  AAC  GGG  TAC  ACT  TTG  GAA  ACA  ATG  TTT  AAG  ACT     6806
Gln  Ile  Lys  Met  Val  Asn  Gly  Tyr  Thr  Leu  Glu  Thr  Met  Phe  Lys  Thr
     2110                    2115                    2120

TTG  AAC  CCT  CTC  ACC  ATT  TTC  TTA  TAT  CTG  GTT  TTT  GTG  CTG  AAA  TGT     6854
Leu  Asn  Pro  Leu  Thr  Ile  Phe  Leu  Tyr  Leu  Val  Phe  Val  Leu  Lys  Cys
2125                    2130                    2135                    2140

GGT  ATT  AGT  GCC  GAC  AAT  GTA  TGT  TTA  TCG  TAC  CAA  TTA  TTT  GCT  ATG     6902
Gly  Ile  Ser  Ala  Asp  Asn  Val  Cys  Leu  Ser  Tyr  Gln  Leu  Phe  Ala  Met
                    2145                    2150                    2155

AAT  GAC  GCA  GAG  CAA  GTT  GAA  TTT  GAA  ATT  GAA  GAT  TCT  TTG  CGT  CTG     6950
Asn  Asp  Ala  Glu  Gln  Val  Glu  Phe  Glu  Ile  Glu  Asp  Ser  Leu  Arg  Leu
               2160                    2165                    2170
```

```
GAT GAA CAG GTA CAA ATT GGT CAA TAC TCA TGC TAT GTT TGG CCT AGT      6998
Asp Glu Gln Val Gln Ile Gly Gln Tyr Ser Cys Tyr Val Trp Pro Ser
        2175                    2180                    2185

GTC GGA AAA TTC TAT CCG GAA ATT CTG GCG AAG AGA GGT TGC ATT GCT      7046
Val Gly Lys Phe Tyr Pro Glu Ile Leu Ala Lys Arg Gly Cys Ile Ala
2190                    2195                    2200

GTG AAT GAT GGA ACT ACA TTT TAT ATT TTC GTT TCA AGT TCA CAG ATA      7094
Val Asn Asp Gly Thr Thr Phe Tyr Ile Phe Val Ser Ser Ser Gln Ile
2205                    2210                    2215                    2220

GAT AAA ATT CAC CCA GAA GCA GCG TGG TCG GAT ATG CTA CAA GGA GTA      7142
Asp Lys Ile His Pro Glu Ala Ala Trp Ser Asp Met Leu Gln Gly Val
                2225                    2230                    2235

GGC AGA AGA GGA GTC GAT ATT TTA AGT ATA GCT GGT CCA ACA AAA ACC      7190
Gly Arg Arg Gly Val Asp Ile Leu Ser Ile Ala Gly Pro Thr Lys Thr
        2240                    2245                    2250

AAG TTT CTG ATA AAA CAT GTG GAA AGT TGT TAC GAA ACT CTT AAG AGT      7238
Lys Phe Leu Ile Lys His Val Glu Ser Cys Tyr Glu Thr Leu Lys Ser
        2255                    2260                    2265

CCG GAA GAT TGG AAA GCT AAA TGC AAA GAG TAC TAT GAG TCC ATA AGC      7286
Pro Glu Asp Trp Lys Ala Lys Cys Lys Glu Tyr Tyr Glu Ser Ile Ser
        2270                    2275                    2280

TTA TAT GAG TAC ATT CTC TTA CTG ATG GCA GTT GGG TCT CGA GCT GGA      7334
Leu Tyr Glu Tyr Ile Leu Leu Leu Met Ala Val Gly Ser Arg Ala Gly
2285                    2290                    2295                    2300

ATT GAA ACC CAG AGG ATG AGT AAA TAT CAG GCC CGA AAG AAC AAA ATT      7382
Ile Glu Thr Gln Arg Met Ser Lys Tyr Gln Ala Arg Lys Asn Lys Ile
                2305                    2310                    2315

AGA ATG CCA GAA GTG TTG GAG AAG TAC ATT GAA GTT GAG AAA GCG ACC      7430
Arg Met Pro Glu Val Leu Glu Lys Tyr Ile Glu Val Glu Lys Ala Thr
        2320                    2325                    2330

ATA GGA AAG CTG TCA AAA CCA GCC AAG ACC TGT CTA GCA ATT GGT GCC      7478
Ile Gly Lys Leu Ser Lys Pro Ala Lys Thr Cys Leu Ala Ile Gly Ala
        2335                    2340                    2345

GGA GTG GCT ATT TTT GGA GTT CTA GCG GGG CTA GGA GTC GGT CTA TAT      7526
Gly Val Ala Ile Phe Gly Val Leu Ala Gly Leu Gly Val Gly Leu Tyr
        2350                    2355                    2360

AAA TTG ATA ACT CAT TTT TCT AAG ACC GAC TCA GAA GAC AAT GAC ATT      7574
Lys Leu Ile Thr His Phe Ser Lys Thr Asp Ser Glu Asp Asn Asp Ile
2365                    2370                    2375                    2380

GAA ATA GAT GAT CTA GTC CCG GAG ATG AGT GGA GCT CAT GCT TCT GAT      7622
Glu Ile Asp Asp Leu Val Pro Glu Met Ser Gly Ala His Ala Ser Asp
                2385                    2390                    2395

GAG AAT GTT ACC ACA TAT GCT GTC AGG AGA CAA GTT CCA AAG GTG CGA      7670
Glu Asn Val Thr Thr Tyr Ala Val Arg Arg Gln Val Pro Lys Val Arg
        2400                    2405                    2410

CTA GCC AAA CAA TTC AAA GTT CGC TCG TCA CCA AGC CCA TCA GAC AAT      7718
Leu Ala Lys Gln Phe Lys Val Arg Ser Ser Pro Ser Pro Ser Asp Asn
        2415                    2420                    2425

GAA CAA CCA AAA GTA GAT ATT CTA GTG CCT GAA ATG ACA GGG TGC CAT      7766
Glu Gln Pro Lys Val Asp Ile Leu Val Pro Glu Met Thr Gly Cys His
        2430                    2435                    2440

GCC AGT GAT GAA CAC CTC ACC AAG CAT TTT ACA AAA AGG AGA GTC ACC      7814
Ala Ser Asp Glu His Leu Thr Lys His Phe Thr Lys Arg Arg Val Thr
2445                    2450                    2455                    2460

ATG AAG AGA GTT GGA GCT GTC AAG GAA TCA CAC ATT GTG ACA TAT GAC      7862
Met Lys Arg Val Gly Ala Val Lys Glu Ser His Ile Val Thr Tyr Asp
                2465                    2470                    2475

GAG AAT ACT CCA CAT GTG AGA CTC ATC AGA AAT CTG AGA AGA ACA CGC      7910
Glu Asn Thr Pro His Val Arg Leu Ile Arg Asn Leu Arg Arg Thr Arg
        2480                    2485                    2490
```

```
TTG GCG AGA GCT ATT AAG CAA ATG GCA CAA CTT GGA GAA CTA CCG GAC      7958
Leu Ala Arg Ala Ile Lys Gln Met Ala Gln Leu Gly Glu Leu Pro Asp
    2495                2500                2505

ACA TTG TCA GAA ATT CAA GTG TGG CAA CAA TAT GTA GTG GAC AAA GGT      8006
Thr Leu Ser Glu Ile Gln Val Trp Gln Gln Tyr Val Val Asp Lys Gly
2510                2515                2520

ATC AGA CCA GCT GAA CAT ACA ACA GAT TTT AGA CTC TTC TCA GCT ATA      8054
Ile Arg Pro Ala Glu His Thr Thr Asp Phe Arg Leu Phe Ser Ala Ile
2525                2530                2535                2540

GCT GAT CAG GAA CAA GAG GAT CCA GAA GAA ATC AAT ATG GCG AGT GGA      8102
Ala Asp Gln Glu Gln Glu Asp Pro Glu Glu Ile Asn Met Ala Ser Gly
            2545                2550                2555

GAA ACG ATG AAA TTT GAC GAA AAC AAG TAC AAT GAG ATA GTC CAA GTC      8150
Glu Thr Met Lys Phe Asp Glu Asn Lys Tyr Asn Glu Ile Val Gln Val
        2560                2565                2570

GTC AAA GGG ATA TCG CCA ACT AAA TCT GAC ATA GTG ACA ATG ACT ACT      8198
Val Lys Gly Ile Ser Pro Thr Lys Ser Asp Ile Val Thr Met Thr Thr
    2575                2580                2585

AAA GGA GCC CAC CAT ACG GCG ATC AAG CAG GTT CGA ATT GGA TAC AAA      8246
Lys Gly Ala His His Thr Ala Ile Lys Gln Val Arg Ile Gly Tyr Lys
2590                2595                2600

AGT TTA GAC AAG GAT CCG AAT ATG GTG AGC ATA CTT TCT AAC CAA CTA      8294
Ser Leu Asp Lys Asp Pro Asn Met Val Ser Ile Leu Ser Asn Gln Leu
2605                2610                2615                2620

ACC AAA ATT AGT TGT GTA ATT TTG AAC GTG ACT CCT GGT AGA ACG GCG      8342
Thr Lys Ile Ser Cys Val Ile Leu Asn Val Thr Pro Gly Arg Thr Ala
            2625                2630                2635

TAC CTA AAC GTC ATG AGG TTG TGT GGG ACA TTT GTT GTG TGC CCA GCC      8390
Tyr Leu Asn Val Met Arg Leu Cys Gly Thr Phe Val Val Cys Pro Ala
        2640                2645                2650

CAT TAT CTA GAA GCT CTA GAA GAG GAT GAC ACG ATT TAC TTC ATA TCC      8438
His Tyr Leu Glu Ala Leu Glu Glu Asp Asp Thr Ile Tyr Phe Ile Ser
    2655                2660                2665

TTT TCT GTC TGT ATT AAA CTC AGA TTT CAA CCA GAC AGA GTG ACA TTA      8486
Phe Ser Val Cys Ile Lys Leu Arg Phe Gln Pro Asp Arg Val Thr Leu
2670                2675                2680

GTC AAC ACT CAT CAA GAT CTT GTA GTG TGG GAT TTG GGT AAT TCA GTA      8534
Val Asn Thr His Gln Asp Leu Val Val Trp Asp Leu Gly Asn Ser Val
2685                2690                2695                2700

CCA CCG GCT ATT GAC GTT TTG AGC ATG ATA CCA ACC GTG GCA GAT TGG      8582
Pro Pro Ala Ile Asp Val Leu Ser Met Ile Pro Thr Val Ala Asp Trp
            2705                2710                2715

GAC AAG TTT CAA GAT GGC CCT GGT GCT TTT GGT GTG ACA AAG TAC AAT      8630
Asp Lys Phe Gln Asp Gly Pro Gly Ala Phe Gly Val Thr Lys Tyr Asn
        2720                2725                2730

GCT CGG TAT CCA ACA AAT TAC ATA AAT ACT CTT GAT ATG ATT GAG AGA      8678
Ala Arg Tyr Pro Thr Asn Tyr Ile Asn Thr Leu Asp Met Ile Glu Arg
    2735                2740                2745

ATC CGA GCC GAC ACT CAG AAC CCC ACG GGC ATA TAC AAA ATG CTC AAC      8726
Ile Arg Ala Asp Thr Gln Asn Pro Thr Gly Ile Tyr Lys Met Leu Asn
2750                2755                2760

TCC GAT CAC ACA ATC ACC ACA GGT CTT AGA TAT CAG ATG TAC TCA TTA      8774
Ser Asp His Thr Ile Thr Thr Gly Leu Arg Tyr Gln Met Tyr Ser Leu
2765                2770                2775                2780

GAA GGA TTC TGT GGT GGG CTG ATA CTA CGG GCT TGC ACT AGA ATG GTT      8822
Glu Gly Phe Cys Gly Gly Leu Ile Leu Arg Ala Cys Thr Arg Met Val
            2785                2790                2795

AGA AAG ATT GTG GGA CTT CAT GTA GCT GCT AGT GCA AAT CAC GCT ATG      8870
Arg Lys Ile Val Gly Leu His Val Ala Ala Ser Ala Asn His Ala Met
        2800                2805                2810
```

```
GGA  TAT  GCA  GAA  TGT  CTG  GTG  CAA  GAA  GAT  CTT  AAA  CAT  GCT  ATA  AAT        8918
Gly  Tyr  Ala  Glu  Cys  Leu  Val  Gln  Glu  Asp  Leu  Lys  His  Ala  Ile  Asn
          2815                    2820                    2825

AAG  CTG  TCA  CCA  GAT  GCA  AGG  AGT  TTA  ATT  ATC  GGA  CAT  CTC  AAT  CCC        8966
Lys  Leu  Ser  Pro  Asp  Ala  Arg  Ser  Leu  Ile  Ile  Gly  His  Leu  Asn  Pro
          2830                    2835                    2840

AAA  GTA  GAA  ACA  GCC  ACA  AAA  CAG  TGT  GGA  ATT  GTG  AGG  AGC  CTT  GGA        9014
Lys  Val  Glu  Thr  Ala  Thr  Lys  Gln  Cys  Gly  Ile  Val  Arg  Ser  Leu  Gly
2845                    2850                    2855                    2860

AGT  CTA  GGG  TGC  CAC  GGA  AAG  GTT  ACA  AGT  GAG  GAC  GTG  GCG  ATG  ACT        9062
Ser  Leu  Gly  Cys  His  Gly  Lys  Val  Thr  Ser  Glu  Asp  Val  Ala  Met  Thr
          2865                    2870                    2875

GCA  ACA  AAG  ACC  ACG  ATC  AGA  AAG  TCT  AGA  ATT  TAT  GGT  CTT  GTT  GGA        9110
Ala  Thr  Lys  Thr  Thr  Ile  Arg  Lys  Ser  Arg  Ile  Tyr  Gly  Leu  Val  Gly
          2880                    2885                    2890

GAT  ATC  AAA  ACA  GAA  CCC  TCA  ATT  TTA  CAT  GCT  CAT  GAC  CCA  CGT  CTC        9158
Asp  Ile  Lys  Thr  Glu  Pro  Ser  Ile  Leu  His  Ala  His  Asp  Pro  Arg  Leu
          2895                    2900                    2905

CCT  GAG  GAT  CAG  ATT  GGA  AAG  TGG  GAC  CCA  GTG  TTT  GAA  GCT  GCC  TTG        9206
Pro  Glu  Asp  Gln  Ile  Gly  Lys  Trp  Asp  Pro  Val  Phe  Glu  Ala  Ala  Leu
          2910                    2915                    2920

AAG  TAT  GGA  ACA  AGA  ATA  GAA  CCA  TTC  CCC  ATT  GAA  GAA  ATT  CTT  GAA        9254
Lys  Tyr  Gly  Thr  Arg  Ile  Glu  Pro  Phe  Pro  Ile  Glu  Glu  Ile  Leu  Glu
2925                    2930                    2935                    2940

GTG  GAA  GAT  CAT  TTA  TCT  ATT  ATA  CTT  AAA  GGC  ATG  GAC  AAT  ACT  CTC        9302
Val  Glu  Asp  His  Leu  Ser  Ile  Ile  Leu  Lys  Gly  Met  Asp  Asn  Thr  Leu
          2945                    2950                    2955

AAG  AAA  AGA  AAT  GTC  AAC  AAT  CTT  GAA  GTT  GGG  ATA  AAC  GGA  ATA  GAT        9350
Lys  Lys  Arg  Asn  Val  Asn  Asn  Leu  Glu  Val  Gly  Ile  Asn  Gly  Ile  Asp
          2960                    2965                    2970

CAA  TCA  GAT  TAT  TGG  CTT  CAG  ATA  GAG  ACA  AAT  ACT  TCT  CCT  GGG  TGG        9398
Gln  Ser  Asp  Tyr  Trp  Leu  Gln  Ile  Glu  Thr  Asn  Thr  Ser  Pro  Gly  Trp
          2975                    2980                    2985

CCC  TAC  ACA  AAA  AGA  AAA  CCG  AAG  GGA  GCT  GAA  GGA  AAG  AAA  TGG  TTG        9446
Pro  Tyr  Thr  Lys  Arg  Lys  Pro  Lys  Gly  Ala  Glu  Gly  Lys  Lys  Trp  Leu
          2990                    2995                    3000

TTC  AAA  GAG  GTT  GGG  AAC  TAC  CCC  TCC  GGG  AAA  CCC  ATT  CTA  GAA  ATG        9494
Phe  Lys  Glu  Val  Gly  Asn  Tyr  Pro  Ser  Gly  Lys  Pro  Ile  Leu  Glu  Met
3005                    3010                    3015                    3020

GAG  GAC  TCA  GGA  CTC  ATT  GAG  AGC  TAC  AAT  AAA  ATG  TTG  AGA  GAT  GCC        9542
Glu  Asp  Ser  Gly  Leu  Ile  Glu  Ser  Tyr  Asn  Lys  Met  Leu  Arg  Asp  Ala
          3025                    3030                    3035

AAA  CAG  GGT  GTA  GCT  CCC  ATT  GTG  GTT  ACT  GTG  GAG  TGC  CCA  AAA  GAT        9590
Lys  Gln  Gly  Val  Ala  Pro  Ile  Val  Val  Thr  Val  Glu  Cys  Pro  Lys  Asp
          3040                    3045                    3050

GAA  CGC  AGA  AAG  TTA  AGT  AAG  ATC  TAC  GAA  CAA  CCA  GCC  ACC  AGG  ACT        9638
Glu  Arg  Arg  Lys  Leu  Ser  Lys  Ile  Tyr  Glu  Gln  Pro  Ala  Thr  Arg  Thr
          3055                    3060                    3065

TTC  ACG  ATT  CTC  CCG  CCT  GAA  ATA  AAC  ATT  CTC  TTT  AGG  CAA  TAT  TTT        9686
Phe  Thr  Ile  Leu  Pro  Pro  Glu  Ile  Asn  Ile  Leu  Phe  Arg  Gln  Tyr  Phe
          3070                    3075                    3080

GGT  GAC  TTT  GCC  GCC  ATG  ATA  ATG  ACT  AAT  AGA  TCA  AAA  TTA  TTC  TGT        9734
Gly  Asp  Phe  Ala  Ala  Met  Ile  Met  Thr  Asn  Arg  Ser  Lys  Leu  Phe  Cys
3085                    3090                    3095                    3100

CAG  GTT  GGG  ATA  AAT  CCA  GAG  AAT  ATG  GAA  TGG  AGT  GAT  CTA  ATG  CAT        9782
Gln  Val  Gly  Ile  Asn  Pro  Glu  Asn  Met  Glu  Trp  Ser  Asp  Leu  Met  His
          3105                    3110                    3115

GAG  TTC  CTC  CAC  AAG  TCA  ACA  CAT  GGC  TTT  GCT  GGA  GAC  TAC  TCA  AAA        9830
Glu  Phe  Leu  His  Lys  Ser  Thr  His  Gly  Phe  Ala  Gly  Asp  Tyr  Ser  Lys
          3120                    3125                    3130
```

-continued

```
TTT GAT GGA ATT GGA GAT CCT CAG ATT TAT CAT TCC ATA ACT CAG GTG         9878
Phe Asp Gly Ile Gly Asp Pro Gln Ile Tyr His Ser Ile Thr Gln Val
        3135            3140                3145

GTA AAT AAC TGG TAC GAT GAT GGG GAA GAA AAT GCC AGG ACA CGT CAC         9926
Val Asn Asn Trp Tyr Asp Asp Gly Glu Glu Asn Ala Arg Thr Arg His
3150                3155                3160

GCA CTA ATT AGT AGT ATA ATA CAT AGA GAG GGT ATA GTT AAG GAG TAT         9974
Ala Leu Ile Ser Ser Ile Ile His Arg Glu Gly Ile Val Lys Glu Tyr
3165                3170                3175            3180

CTT TTC CAG TAT TGT CAG GGA ATG CCT TCT GGT TTT GCC ATG ACA GTC        10022
Leu Phe Gln Tyr Cys Gln Gly Met Pro Ser Gly Phe Ala Met Thr Val
                3185                3190                3195

ATT TTC AAC TCC TTC GTG AAT TAT TAC TAT TTA GCT ATG GCG TGG ATG        10070
Ile Phe Asn Ser Phe Val Asn Tyr Tyr Tyr Leu Ala Met Ala Trp Met
            3200                3205                3210

AAT TTA ATC TCA CAC TCA CCA TTG AGT CCC CAA TCC ACG GTT AGA GAT        10118
Asn Leu Ile Ser His Ser Pro Leu Ser Pro Gln Ser Thr Val Arg Asp
        3215                3220                3225

TTC GAC AAC TAT TGT AAG GTA GTA GTT TAT GGG GAC GAT AAC ATA GTT        10166
Phe Asp Asn Tyr Cys Lys Val Val Val Tyr Gly Asp Asp Asn Ile Val
3230                3235                3240

TCA GTA GAT TTG AAC TTT CTA GAA TAT TAC AAC CTT AGG ACT GTA GCA        10214
Ser Val Asp Leu Asn Phe Leu Glu Tyr Tyr Asn Leu Arg Thr Val Ala
3245                3250                3255            3260

GCT TAT TTG TCT CAA TTT GGA GTA ACG TAC ACA GAT GAC GCA AAG AAT        10262
Ala Tyr Leu Ser Gln Phe Gly Val Thr Tyr Thr Asp Asp Ala Lys Asn
                3265                3270                3275

CCG ATT GAG AAA AGT GTG CCT TTC GTA GAA ATA ACT TCT GTT TCA TTT        10310
Pro Ile Glu Lys Ser Val Pro Phe Val Glu Ile Thr Ser Val Ser Phe
            3280                3285                3290

CTT AAG CGT AGG TGG GTG CCC TTG GGT GGA AGA CTT TCA ACT ATT TAC        10358
Leu Lys Arg Arg Trp Val Pro Leu Gly Gly Arg Leu Ser Thr Ile Tyr
        3295                3300                3305

AAG GCA CCT TTG GAC AAA ACT AGC ATA GAG GAG CGC CTT CAT TGG ATA        10406
Lys Ala Pro Leu Asp Lys Thr Ser Ile Glu Glu Arg Leu His Trp Ile
    3310                3315                3320

AGG GAG TGC GAT AAT GAC ATC GAA GCT CTC AAT CAG AAT ATT GAA AGC        10454
Arg Glu Cys Asp Asn Asp Ile Glu Ala Leu Asn Gln Asn Ile Glu Ser
3325                3330                3335                3340

GCC CTA TAT GAA GCA AGC ATT CAT GGA AAG ATC TAC TTT GGT GAT CTC        10502
Ala Leu Tyr Glu Ala Ser Ile His Gly Lys Ile Tyr Phe Gly Asp Leu
                3345                3350                3355

CTT CAG AGG ATC CGG ATT GCT TGT GAC GCT GTG ATG ATC CCA GTT CCA        10550
Leu Gln Arg Ile Arg Ile Ala Cys Asp Ala Val Met Ile Pro Val Pro
            3360                3365                3370

TCA GTA ACA TTT AAG GAT TGT CAC AAA AGG TGG TGG GCT TCC ATG ACT        10598
Ser Val Thr Phe Lys Asp Cys His Lys Arg Trp Trp Ala Ser Met Thr
        3375                3380                3385

GGA GGA GCT TTA GAT CCA GCT AGT CTA AGT CGG TTG TAC TTG GCC GCC        10646
Gly Gly Ala Leu Asp Pro Ala Ser Leu Ser Arg Leu Tyr Leu Ala Ala
    3390                3395                3400

GAG AAC CAG TTG GTC GAC ACT CGG AAA GTG TGG AAA GAT CGC TTC CTT        10694
Glu Asn Gln Leu Val Asp Thr Arg Lys Val Trp Lys Asp Arg Phe Leu
3405                3410                3415            3420

GGT GAG GAT AGG TCT TTA ATA GAC ATG CTG AAG TCA GCT CGT GCT GTT        10742
Gly Glu Asp Arg Ser Leu Ile Asp Met Leu Lys Ser Ala Arg Ala Val
                3425                3430                3435

CCT CTA GCT GCC TAT CAT GTA TAAGCCTCAC GACTCTGTGC AGAGTATAAC           10793
Pro Leu Ala Ala Tyr His Val
        3440
```

```
AGCACGACCC  CAGGTTATCG  ATAAGTCATG  TTGGTAGTCG  TCAAGTAAGA  ATGGGACAGA    10853

AAAGAGATTG  GAACTTTTAG  GATGGAACAT  CAGTAAACCT  ACGGGAAACA  GAGCTATGGA    10913

ACTCCCAAGT  ACTGTAGGTC  CCTATTGGTA  GTTCACTAAA  AGTAACCTTC  TGTGTATGAT    10973

CCCTACCCTG  AGTGAACGAC  AGAAATATGA  TACACGAGTA  CTCTCATTAG  AGAGAACCGG    11033

ATTCCACATT  GTGGAATCTC  CCAGGAATTG  ACCTGGGTTC  CTCACGAAAG  TGAGGCGACA    11093

ACTTGGTCGA  AAAACAAGTT  CAGTTTAGTT  GAGACTGAAG  TACAAACTCA  ACATTTCATA    11153

GTGTGTGATT  TTTCCGATCC  CCATTTGGTG  TAACCCATAT  GTGCCACCTC  ATAATCCTTT    11213

TAAGGGTTAA  ATTTGGTAAG  TGTTGTGGGG  AGCCAAGAGG  GGTAGGGTCT  TTTTGTTACG    11273

TACTTTCTCA  TGTCAACATG  GTGTTGAGAT  GGGCGCTTGG  TCAGCGGAAG  AATAAAGCGA    11333

GACGTACATT  ATTATCTCGT  AGACTACGGC  AGGTGAGACA  CACCGTCGTC  CCTTGAGGGG    11393

GAAAGTAGCT  CCAGGCATTT  AATCCTGAAG  TGTTCAGATA  AGTCTCTGAT  CCTCCTCCGG    11453

GGGAAAAAGG  GGACTTAATC  TGTTAAGCCG  TATCAACGAC  TTGATGAAAC  AACCACCTGT    11513

TCTGGTGTAA  ACCCAGGATA  ATCACATAGG  TAGCTGTGTG  GTGTTTCAAC  CATTTGGATT    11573

CATCCGAGCA  CGGATTACCT  TGTGGTCAGA  GTCTCCGAAT  GTCCTGTACG  ATGTGGGTAA    11633

CTCCCTTTGG  CCAGGGCTAG  GCACACTTCT  CTACGGGTTG  GTGTCGCTAG  ATATGTTAAT    11693

ACTAGTGCCA  TATCGGAAAT  AGTTGTAAAT  CGTTGAACCA  AGTGACGATG  GGGTCCATTG    11753

TACACCCGAC  TTGGTTACGT  TTTCTATTTT  CCGTGTCAAT  ATGGATAATA  GTGGGGTAGT    11813

AAAAAAAAAA  AAAAAAAA                                                     11832
```

(2) INFORMATION FOR SEQ ID NO:2:

(i) SEQUENCE CHARACTERISTICS:
       (A) LENGTH: 3443 amino acids
       (B) TYPE: amino acid
       (D) TOPOLOGY: linear (ii) MOLECULE TYPE: protein (xi) SEQUENCE DESCRIPTION: SEQ ID NO:2:

```
Met  Met  Ser  Cys  Glu  Gln  Ser  Lys  Asn  Asn  Asn  Asn  Gln  Gln  Ser  Thr
 1              5                    10                       15

Ala  Leu  Glu  Asn  Ser  Glu  Ile  Arg  Tyr  Pro  Gly  Gly  Tyr  Tyr  Ile  Pro
            20                    25                       30

Leu  Gly  Asp  Gly  Gly  Ile  Arg  Val  Pro  Val  Glu  Ala  Ile  Tyr  Arg  Pro
            35                    40                       45

Gly  Glu  Pro  Gln  Asn  Trp  Val  Pro  Ile  Cys  Gly  Asn  Asp  Phe  His  Leu
      50                    55                       60

Ser  Gln  Asp  Asp  Pro  Cys  Ser  Glu  Cys  Asp  Ala  Ile  Glu  Gly  Ser  Ser
65                         70                       75                       80

Glu  Arg  Ala  Ala  Ile  Ala  Ile  Ser  Asp  Ser  Tyr  Val  Ala  Ser  Asp  Pro
                 85                    90                       95

His  Phe  Thr  Val  Asp  Ala  Arg  Ser  Leu  Ser  Arg  Arg  Asp  His  Thr  Cys
                100                   105                      110

Thr  His  Arg  Gly  Cys  Phe  Ser  Ile  Cys  Ser  Ser  Tyr  Arg  Phe  Cys  Ser
           115                   120                      125

Phe  Cys  Leu  Phe  Leu  Phe  Asn  Leu  Asp  Lys  Phe  Gln  Lys  Asn  Thr  Lys
     130                   135                      140

Tyr  Phe  His  Ser  Lys  Arg  Ser  Leu  Ser  Arg  Leu  Val  His  Cys  Ser  Ala
145            150                   155                      160

Glu  Gln  Leu  Ile  Ser  Asn  Ala  Ile  Leu  Phe  Ser  Ser  Asn  Arg  Ile  Ile
```

|   |   |   |   |   | 165 |   |   |   |   | 170 |   |   |   |   | 175 |   |   |
|---|---|---|---|---|---|---|---|---|---|---|---|---|---|---|---|---|---|
| Asp | Ala | Glu | Val | Val | Ala | Asp | Asn | Arg | Val | Ser | Cys | Glu | Tyr | Ala | Lys |
|   |   |   | 180 |   |   |   |   | 185 |   |   |   |   |   | 190 |   |
| Leu | Leu | Leu | Ser | Asn | Ala | Arg | Val | Gly | Val | Gln | Val | Thr | Pro | Pro | Ala |
|   |   |   | 195 |   |   |   | 200 |   |   |   |   | 205 |   |   |   |
| Cys | Asp | Trp | Val | Val | Cys | Asn | Asn | Val | Glu | His | Leu | Phe | Glu | Cys | Phe |
|   |   | 210 |   |   |   | 215 |   |   |   |   | 220 |   |   |   |   |
| Gly | Ile | Ser | Asp | Ala | Gln | Arg | Gly | His | Ile | Thr | Gly | Phe | Asn | Asp | Glu |
| 225 |   |   |   |   | 230 |   |   |   |   | 235 |   |   |   |   | 240 |
| Asn | Ala | Tyr | Trp | Asn | Ala | Ser | Cys | Ala | Lys | Cys | Gly | Ala | Cys | Cys | Gln |
|   |   |   |   | 245 |   |   |   |   | 250 |   |   |   |   | 255 |   |
| Gly | Ala | Asn | Ala | Arg | Ser | Ala | Ile | Pro | Ile | Val | Leu | Leu | Leu | Lys | Phe |
|   |   |   | 260 |   |   |   |   | 265 |   |   |   |   | 270 |   |   |
| Ile | Thr | Ile | Arg | Lys | Glu | Gln | Asp | Ile | Trp | Leu | Ala | Ser | His | Met | His |
|   |   | 275 |   |   |   |   | 280 |   |   |   |   | 285 |   |   |   |
| His | Asp | Asn | Asp | Phe | Val | Glu | Ile | Asn | Ser | Ile | Thr | Ala | Gln | Ile | Ile |
|   | 290 |   |   |   |   | 295 |   |   |   |   | 300 |   |   |   |   |
| Ala | Lys | Ile | Asn | Asn | Ile | Pro | Asn | Val | Asp | Glu | Pro | Ala | Val | Gly | Tyr |
| 305 |   |   |   |   | 310 |   |   |   |   | 315 |   |   |   |   | 320 |
| Met | Gly | Ser | Lys | Leu | Glu | Asn | Trp | Ile | Ser | Tyr | Arg | Asp | Thr | Asp | Phe |
|   |   |   |   | 325 |   |   |   |   | 330 |   |   |   |   | 335 |   |
| Thr | Glu | Glu | Asp | Trp | Thr | Leu | Lys | His | Pro | Cys | Ser | Gly | Pro | Leu | Glu |
|   |   |   | 340 |   |   |   |   | 345 |   |   |   |   | 350 |   |   |
| Ser | Glu | Glu | Cys | Asp | His | Asp | Phe | Ile | Ile | Arg | Asn | Gln | Tyr | Gly | Phe |
|   |   | 355 |   |   |   |   | 360 |   |   |   |   | 365 |   |   |   |
| Glu | Leu | Tyr | Leu | Asn | His | Ala | Met | Leu | Leu | Asn | Phe | Ala | Ala | Leu | Cys |
|   | 370 |   |   |   |   | 375 |   |   |   |   | 380 |   |   |   |   |
| Leu | Tyr | His | Gly | Arg | Leu | Tyr | Asn | Ser | Asp | Lys | Ser | Val | Gly | Ile | Leu |
| 385 |   |   |   |   | 390 |   |   |   |   | 395 |   |   |   |   | 400 |
| Val | Thr | Phe | Gly | Gly | Met | Ile | Gly | Val | Asn | Ile | Ala | Cys | Asn | Glu | Ala |
|   |   |   |   | 405 |   |   |   |   | 410 |   |   |   |   | 415 |   |
| Phe | Met | Glu | Phe | His | Lys | Arg | Phe | Tyr | Ser | Gly | Thr | Leu | Arg | Ile | Ser |
|   |   |   | 420 |   |   |   |   | 425 |   |   |   |   | 430 |   |   |
| Pro | Met | Asn | Met | Tyr | Leu | Arg | Arg | Glu | Arg | Cys | Gln | Ala | Gln | Ser | Asp |
|   |   |   | 435 |   |   |   |   | 440 |   |   |   |   | 445 |   |   |
| Phe | Asn | Asp | Glu | Glu | Phe | Gln | Arg | Leu | Met | Ala | Glu | Glu | Gly | Asp | Ala |
| 450 |   |   |   |   | 455 |   |   |   |   | 460 |   |   |   |   |   |
| Glu | Ile | Gln | Ser | Val | Ser | Asn | Trp | Val | Ser | Glu | Tyr | Leu | Glu | Ile | Glu |
| 465 |   |   |   |   | 470 |   |   |   |   | 475 |   |   |   |   | 480 |
| Asp | Val | Ile | Asp | Ile | Val | Asp | Glu | Ala | Glu | Ser | Lys | Lys | Thr | Arg | Gly |
|   |   |   | 485 |   |   |   |   | 490 |   |   |   |   | 495 |   |   |
| Leu | Gly | Leu | Asn | Gln | Val | Leu | Gly | Gly | Leu | Leu | Lys | Gly | Val | Ser | His |
|   |   |   | 500 |   |   |   | 505 |   |   |   |   | 510 |   |   |   |
| Cys | Val | Asp | Ser | Leu | His | Lys | Val | Phe | Asp | Trp | Pro | Ile | Asp | Leu | Ala |
|   |   | 515 |   |   |   | 520 |   |   |   |   | 525 |   |   |   |   |
| Ile | Asp | Ala | Ala | Lys | Gly | Thr | Ala | Asp | Trp | Leu | Glu | Gly | Asn | Lys | Ser |
|   | 530 |   |   |   |   | 535 |   |   |   |   | 540 |   |   |   |   |
| Ser | Val | Asp | Asp | Ser | Lys | Ile | Cys | Ala | Gly | Cys | Pro | Glu | Ile | Gln | Lys |
| 545 |   |   |   |   | 550 |   |   |   |   | 555 |   |   |   |   | 560 |
| Asp | Met | Gln | Asp | Phe | Gln | Lys | Glu | Thr | Lys | Met | Gly | Ile | Glu | Ile | Leu |
|   |   |   |   | 565 |   |   |   |   | 570 |   |   |   |   | 575 |   |
| Arg | Asp | Ser | Ile | Lys | Lys | Leu | Ser | Glu | Gly | Ile | Asp | Lys | Ile | Thr | Arg |
|   |   |   | 580 |   |   |   |   | 585 |   |   |   |   | 590 |   |   |

| | | | | | | | | | | | | | |
|---|---|---|---|---|---|---|---|---|---|---|---|---|---|
| Met | Asn | Gln 595 | Thr | Asn | Phe | Glu 600 | Arg | Ile | Val | Asp | Arg 605 | Ile | Pro | Ile |
| Glu | Ser 610 | Lys | Lys | Leu | Lys | Glu 615 | Leu | Glu | Lys | Ile | Lys 620 | Pro | Asp | Ala | Gly | Gly |
| Ser 625 | Lys | Asp | Ser | Glu | Ala 630 | Met | Arg | Gln | Leu | Gln 635 | Ala | Ile | Lys | Asp 640 |
| Ile | Lys | Leu | Ile | Lys 645 | Gln | Ala | Met | Met | Glu 650 | Leu | Asn | Asp | Arg | Ile 655 | Lys |
| Asp | Leu | Glu | Asp 660 | Ser | Lys | Gln | His | Gln 665 | Glu | Asp | Ser | Lys | Pro 670 | Asp | Asp |
| Asp | Thr | Ala 675 | Gly | Glu | Gln | Lys | Pro 680 | Ile | Pro | Lys | Ile | Asn 685 | Lys | Ile | Arg |
| Val | Lys 690 | Ala | Lys | Arg | Val | Glu 695 | Lys | Gln | Ser | Gly | Thr 700 | Asn | Ile | Val | Asn |
| Asn 705 | Glu | Ile | Glu | Gln | Ala 710 | Phe | Gln | Asp | Glu | Lys 715 | Arg | Thr | Val | Asp 720 |
| Pro | Asn | Ile | Ser | Asp 725 | Met | Tyr | Asn | Ala | Ile 730 | Lys | Ser | Glu | Tyr | Leu 735 | Val |
| Lys | Ser | Phe | Ser 740 | Trp | Lys | Val | Ser | Gly 745 | Gln | Asp | Lys | Val 750 | Leu | Ser |
| Asn | Ile | Asn 755 | Ile | Pro | Glu | Asp | Leu 760 | Trp | Asn | Thr | Asn | Ser 765 | Arg | Leu | Asn |
| Asp | Ile 770 | Met | Ser | Tyr | Phe | Gln 775 | Tyr | Tyr | Lys | Ala | Thr 780 | Gly | Leu | Thr | Phe |
| Arg 785 | Ile | Ser | Thr | Thr | Cys 790 | Ile | Pro | Met | His | Gly 795 | Thr | Leu | Phe | Ala 800 |
| Ala | Trp | Asp | Ala | Cys 805 | Gly | Cys | Ala | Thr | Arg 810 | Gln | Gly | Ile | Ala | Thr 815 | Ala |
| Val | Gln | Leu | Thr 820 | Gly | Leu | Pro | Gly | Ile 825 | Met | Ile | Glu | Ala | His 830 | Ser | Ser |
| Ser | Leu | Thr 835 | Thr | Phe | Ser | Val | Glu 840 | Asp | Pro | Leu | Thr | Gln 845 | Ser | Thr | Val |
| Cys | Leu 850 | Ser | Gly | Ser | Glu | His 855 | Ser | Phe | Gly | Arg | Ile 860 | Gly | Ile | Leu | Lys |
| Ile 865 | Cys | Cys | Leu | Asn | Val 870 | Leu | Asn | Ala | Pro | Gln 875 | Ala | Ala | Thr | Gln | Ser 880 |
| Val | Ser | Val | Asn | Val 885 | Trp | Val | Lys | Phe | Asp 890 | Gly | Val | Lys | Phe | His 895 | Phe |
| Tyr | Ser | Leu | Lys 900 | Lys | Gln | Pro | Val | Val 905 | Ser | Gln | Met | Leu | Val 910 | Asp | Lys |
| Leu | Thr | Asn 915 | Leu | Gly | Glu | Met | Gly 920 | Cys | Val | Val | Ala | Thr 925 | Gly | Thr | Trp |
| Ser | Thr 930 | Thr | Ser | Ser | Leu | Asn 935 | Leu | Leu | Gln | Leu | Asn 940 | Val | His | Pro | Thr |
| Ala 945 | Cys | Phe | Ile | Ser | Asp 950 | Gly | Leu | Val | Thr | Gln 955 | Thr | Pro | Leu | Ser | Val 960 |
| Ile | Ala | His | Ala | Phe 965 | Ala | Arg | Trp | Arg | Gly 970 | Ser | Leu | Lys | Phe | Thr 975 | Ile |
| Thr | Phe | Gly | Ala 980 | Ser | Met | Phe | Thr | Arg 985 | Gly | Arg | Val | Leu | Val 990 | Ala | Ala |
| Ile | Pro | Val 995 | Ala | Lys | Arg | Lys | Glu 1000 | Thr | Leu | Thr | Ile | Glu 1005 | Glu | Ile | Ser |
| Gly | Tyr | His 1010 | Asn | Val | Met | Cys 1015 | Leu | Leu | Asn | Gly | Glu 1020 | Arg | Thr | Ser | Phe |

```
Glu Leu Glu Val Pro Tyr His Ser Val Gly Glu Asp Ser Tyr Val Cys
1025                1030                1035                1040

Arg Asp Ala Leu Phe Asp Val Ser Ser Tyr Ala Gln Asn Phe Met Ile
                1045                1050                1055

Thr Arg Leu His Met Val Val Ile Asp Thr Leu Val Met Ser Ser Asn
            1060                1065                1070

Ala Ser Asn Thr Ile Ser Tyr Cys Val Met Met Gly Pro Gly Lys Asp
        1075                1080                1085

Leu Glu Leu Arg Tyr Leu Asn Gly Val His Ala Gln Arg Asn Val Arg
    1090                1095                1100

Glu Leu Lys Ala Gln Val Ser Leu Gly Phe Ser Leu Gln Ser Gly Arg
1105                1110                1115                1120

Asn Ile Gly Val Gly Phe Ser Asp Leu Leu Lys Arg Trp Ala His Leu
                1125                1130                1135

Leu Thr Leu His Phe Asp Glu Asn Asn Glu Lys Ser Glu Glu Lys Val
            1140                1145                1150

Gly Ser Tyr Ile Val Thr Val Ala Pro Ser Tyr Arg Ala Phe Pro Gln
        1155                1160                1165

His Asn Thr Leu Leu Ser Trp Phe Ser Gln Leu Phe Val Gln Trp Gln
    1170                1175                1180

Gly Ser Leu Cys Tyr Arg Leu His Val Asp Ser Gln Glu Arg Arg Tyr
1185                1190                1195                1200

Gly Gly Tyr Leu Arg Ile Trp His Asp Pro Asn Gly Ser Leu Asp Glu
                1205                1210                1215

Gly Val Glu Phe Ala Met Ser Thr Asn Leu Glu Pro Pro Pro Gly Ala
            1220                1225                1230

Phe Val Lys Tyr Trp Asn Tyr Asn Glu Gln Ser Glu Phe Glu Phe Val
        1235                1240                1245

Val Pro Tyr Thr Ala Arg Thr Pro Arg Leu Phe Val Pro Lys Ala Met
    1250                1255                1260

Ile Pro Thr Asp Ser Lys Ser Trp Ile Leu Asn Tyr Asn Gly Thr Leu
1265                1270                1275                1280

Asn Phe Asp Tyr Arg Gly Val Asp Asp Phe Asn Val Thr Val Asp Ile
                1285                1290                1295

Ser Ala Gly Asp Asn Phe Glu Phe Ser Val Arg Thr Val Ala Pro Lys
            1300                1305                1310

Ala Gly Lys Val Asn Glu Ser Phe Thr Lys Leu Ser Tyr Ser Asn Glu
        1315                1320                1325

Leu Val Asp Ile Lys Lys Pro Leu Thr Ala Ala Gly Arg Leu Lys Gly
    1330                1335                1340

Pro Phe Asn Leu Asn Thr Leu Lys Thr Ala Val Pro Lys Glu Thr Pro
1345                1350                1355                1360

Lys Glu Ser Ser Asp Asp Lys Asp Lys Ser Asn Gln Lys Arg Lys Gly
                1365                1370                1375

Ala Met Asp Ser Leu Leu Asn Ala Val Ala Gln Met Glu Thr Ile Asn
            1380                1385                1390

Ser Asp Ala Asn Gly Cys Phe Ser Leu Gly Gly Leu Lys Ser Thr Ala
        1395                1400                1405

Lys Met Leu Asp Ser Arg Lys Thr Cys Glu Lys Phe Ala Asp Ile Met
    1410                1415                1420

Asp Phe Thr His Asp Thr Leu Gly Val Lys Asp Gly Pro Ala Ala Gln
1425                1430                1435                1440

Arg Leu Ala Ala Ala Val Ala Gln Ile Ala Pro Ile Ile Glu Ser Val
```

-continued

```
                    1445                         1450                           1455
Ser  Arg  Thr  Thr  Glu  Ser  Val  Glu  Ser  Lys  Leu  Thr  Cys  Leu  Asp  Lys
                         1460                         1465                    1470
Tyr  Lys  Asp  Gly  Ile  Leu  Gly  Ile  Leu  Gln  Ser  Leu  Cys  Lys  Glu  Thr
               1475                         1480                    1485
Ile  Pro  Gly  Leu  Ala  Ile  Val  Asp  Phe  Lys  Lys  Gly  Lys  Tyr  Met  Trp
               1490                         1495                    1500
Ala  Thr  Leu  Leu  Thr  Leu  Ile  Ala  Gly  Ala  Ala  Leu  Phe  Trp  Ala  Cys
1505                         1510                    1515                    1520
Lys  Ser  Gln  Lys  Ser  Phe  Leu  Lys  Arg  Phe  Ser  Val  Val  Met  Ile
                    1525                         1530                    1535
Ile  Trp  Ser  Pro  Phe  Leu  Ala  Gly  Lys  Val  Trp  Ser  Leu  Gly  Gln  Trp
                    1540                         1545                    1550
Ile  Val  Gln  Lys  Trp  Cys  His  Leu  Trp  Pro  Lys  Ser  Asp  Ser  Cys  Arg
                    1555                         1560                    1565
Gln  His  Ser  Leu  Ala  Gly  Leu  Phe  Glu  Ser  Ala  Lys  Thr  Lys  Val  Arg
                    1570                         1575                    1580
Gly  Phe  Pro  Asp  Trp  Phe  Arg  Ser  Gly  Met  Asn  Ile  Val  Thr  Gln
1585                         1590                         1595                    1600
Val  Cys  Ser  Val  Leu  Leu  Thr  Ile  Val  Ser  Leu  Ile  Thr  Leu  Gly  Thr
                              1605                         1610                    1615
Ile  Pro  Ser  Ala  Lys  Lys  Ser  Lys  Ser  Leu  Ala  Asp  Arg  Phe  Ile  Glu
                    1620                         1625                    1630
Phe  Gly  Asn  Met  Asn  Arg  Ala  Ala  Thr  Ser  Ile  Ala  Ala  Gly  Tyr  Lys
                    1635                         1640                    1645
Ser  Ile  Ser  Glu  Leu  Cys  Ser  Lys  Phe  Thr  His  Phe  Val  Ala  Thr  His
                    1650                         1655                    1660
Phe  Leu  Gly  Ala  Thr  Val  Asp  Asp  Asn  Val  Phe  Lys  Asp  Leu  Val  Thr
1665                         1670                         1675                    1680
Phe  Asn  Val  Lys  Asp  Trp  Val  Glu  Gln  Val  Lys  Val  Ala  Ser  Leu  Glu
                              1685                         1690                    1695
Glu  Asn  Lys  Phe  Lys  Ser  Phe  Gly  Ser  Pro  Glu  Gln  Leu  Thr  Arg  Val
                    1700                         1705                    1710
Arg  His  Met  Tyr  Asp  Lys  Ser  Leu  Glu  Ile  Thr  Asn  Lys  Leu  Leu  Asp
                    1715                         1720                    1725
Arg  Asn  Lys  Val  Pro  Val  Ala  Met  Leu  Pro  Val  Ile  Arg  Asp  Thr  Cys
               1730                         1735                    1740
Lys  Lys  Cys  Glu  Glu  Leu  Leu  Asn  Asp  Ser  Tyr  Ser  Tyr  Lys  Gly  Met
1745                         1750                         1755                    1760
Lys  Thr  Pro  Arg  Ile  Asp  Pro  Phe  Tyr  Ile  Cys  Leu  Thr  Gly  Pro  Pro
                         1765                         1770                    1775
Gly  Val  Gly  Lys  Ser  Thr  Val  Ala  Ser  Ile  Ile  Ile  Asn  Asp  Leu  Leu
                              1780                         1785                    1790
Asp  Tyr  Met  Gly  Glu  Pro  Lys  Thr  Asp  Arg  Ile  Tyr  Thr  Arg  Cys  Cys
                    1795                         1800                    1805
Ala  Asp  Ser  Tyr  Trp  Ser  Asn  Tyr  His  His  Glu  Pro  Val  Ile  Ile  Tyr
                    1810                         1815                    1820
Asp  Asp  Leu  Gly  Ala  Ile  Ser  Lys  Val  Ala  Ser  Leu  Ser  Asp  Tyr  Ala
1825                         1830                         1835                    1840
Glu  Ile  Met  Gly  Ile  Lys  Ser  Asn  Arg  Pro  Tyr  Ser  Leu  Pro  Met  Ala
                              1845                         1850                    1855
Ala  Val  Glu  Glu  Lys  Gly  Arg  His  Cys  Leu  Ser  Lys  Tyr  Leu  Val  Ala
                    1860                         1865                    1870
```

```
Cys Thr Asn Leu Thr His Leu Asp Asp Thr Gly Asp Val Lys Thr Lys
        1875                    1880                    1885
Glu Ala Tyr Tyr Arg Arg Ile Asn Leu Pro Val Thr Val Glu Arg Asp
        1890                    1895                    1900
Leu Ala Met Pro Met Ser Pro Glu Asp Pro Ala Ser Gly Leu Leu Phe
1905                    1910                    1915                    1920
Thr Ile Gly Asp Ile His Glu Asn Gly Arg Asn Val Ser Val Val Glu
            1925                    1930                    1935
Ser Arg Leu Leu Asn Gly Arg Val Pro Phe Arg Ala Gly Asp Leu Arg
            1940                    1945                    1950
Asn Met Ser Tyr Asn Tyr Phe Met Glu Phe Val Arg Ile Tyr Ala Thr
            1955                    1960                    1965
Ile Tyr Met Glu Asn Gln Gln Gln Leu Val Ala Lys Leu Ser Gly Asp
        1970                    1975                    1980
Asp Tyr Glu Ser Ser Ser Ser Ser Phe Pro Glu Asn Glu Glu Leu Glu
1985                    1990                    1995                    2000
Phe Asp Phe Leu Ala Gln Ala His Asn Gly Val Tyr Leu Thr Ile Glu
            2005                    2010                    2015
Glu Val Val Ala Lys Phe Glu Ser Met Lys Phe Ser Gly Lys Gln Leu
            2020                    2025                    2030
Asn Ala Glu Ile Glu Lys Phe Glu Arg Ile Gly Val Asp Gly Trp Arg
        2035                    2040                    2045
Thr Asn Lys Ala Leu Ser Phe Asn Asp Leu Val Lys Arg Phe Cys Gly
        2050                    2055                    2060
Cys Cys Leu Gly Asp Asp Cys Asn Phe Asp Phe His Tyr Arg Thr Leu
2065                    2070                    2075                    2080
Phe Lys Val Leu Ile Glu Asn Lys Gln Ile Pro Ala Tyr Lys Cys Met
            2085                    2090                    2095
Val Leu His Lys Val Asn Pro Asp Arg Met Lys Thr Gln Ile Lys Met
                2100                    2105                    2110
Val Asn Gly Tyr Thr Leu Glu Thr Met Phe Lys Thr Leu Asn Pro Leu
            2115                    2120                    2125
Thr Ile Phe Leu Tyr Leu Val Phe Val Leu Lys Cys Gly Ile Ser Ala
    2130                    2135                    2140
Asp Asn Val Cys Leu Ser Tyr Gln Leu Phe Ala Met Asn Asp Ala Glu
2145                    2150                    2155                    2160
Gln Val Glu Phe Glu Ile Glu Asp Ser Leu Arg Leu Asp Glu Gln Val
            2165                    2170                    2175
Gln Ile Gly Gln Tyr Ser Cys Tyr Val Trp Pro Ser Val Gly Lys Phe
                2180                    2185                    2190
Tyr Pro Glu Ile Leu Ala Lys Arg Gly Cys Ile Ala Val Asn Asp Gly
        2195                    2200                    2205
Thr Thr Phe Tyr Ile Phe Val Ser Ser Gln Ile Asp Lys Ile His
    2210                    2215                    2220
Pro Glu Ala Ala Trp Ser Asp Met Leu Gln Gly Val Gly Arg Arg Gly
2225                    2230                    2235                    2240
Val Asp Ile Leu Ser Ile Ala Gly Pro Thr Lys Thr Lys Phe Leu Ile
                2245                    2250                    2255
Lys His Val Glu Ser Cys Tyr Glu Thr Leu Lys Ser Pro Glu Asp Trp
            2260                    2265                    2270
Lys Ala Lys Cys Lys Glu Tyr Tyr Glu Ser Ile Ser Leu Tyr Glu Tyr
        2275                    2280                    2285
Ile Leu Leu Leu Met Ala Val Gly Ser Arg Ala Gly Ile Glu Thr Gln
        2290                    2295                    2300
```

```
Arg  Met  Ser  Lys  Tyr  Gln  Ala  Arg  Lys  Asn  Lys  Ile  Arg  Met  Pro  Glu
2305                2310                2315                2320

Val  Leu  Glu  Lys  Tyr  Ile  Glu  Val  Glu  Lys  Ala  Thr  Ile  Gly  Lys  Leu
                    2325                2330                2335

Ser  Lys  Pro  Ala  Lys  Thr  Cys  Leu  Ala  Ile  Gly  Ala  Gly  Val  Ala  Ile
               2340                2345                2350

Phe  Gly  Val  Leu  Ala  Gly  Leu  Gly  Val  Gly  Leu  Tyr  Lys  Leu  Ile  Thr
          2355                2360                2365

His  Phe  Ser  Lys  Thr  Asp  Ser  Glu  Asp  Asn  Asp  Ile  Glu  Ile  Asp  Asp
2370                2375                2380

Leu  Val  Pro  Glu  Met  Ser  Gly  Ala  His  Ala  Ser  Asp  Glu  Asn  Val  Thr
2385                2390                2395                2400

Thr  Tyr  Ala  Val  Arg  Arg  Gln  Val  Pro  Lys  Val  Arg  Leu  Ala  Lys  Gln
                    2405                2410                2415

Phe  Lys  Val  Arg  Ser  Ser  Pro  Ser  Pro  Ser  Asp  Asn  Glu  Gln  Pro  Lys
               2420                2425                2430

Val  Asp  Ile  Leu  Val  Pro  Glu  Met  Thr  Gly  Cys  His  Ala  Ser  Asp  Glu
               2435                2440                2445

His  Leu  Thr  Lys  His  Phe  Thr  Lys  Arg  Arg  Val  Thr  Met  Lys  Arg  Val
2450                2455                2460

Gly  Ala  Val  Lys  Glu  Ser  His  Ile  Val  Thr  Tyr  Asp  Glu  Asn  Thr  Pro
2465                2470                2475                2480

His  Val  Arg  Leu  Ile  Arg  Asn  Leu  Arg  Arg  Thr  Arg  Leu  Ala  Arg  Ala
               2485                2490                2495

Ile  Lys  Gln  Met  Ala  Gln  Leu  Gly  Glu  Leu  Pro  Asp  Thr  Leu  Ser  Glu
                    2500                2505                2510

Ile  Gln  Val  Trp  Gln  Gln  Tyr  Val  Val  Asp  Lys  Gly  Ile  Arg  Pro  Ala
                    2515                2520                2525

Glu  His  Thr  Thr  Asp  Phe  Arg  Leu  Phe  Ser  Ala  Ile  Ala  Asp  Gln  Glu
               2530                2535                2540

Gln  Glu  Asp  Pro  Glu  Glu  Ile  Asn  Met  Ala  Ser  Gly  Glu  Thr  Met  Lys
2545                2550                2555                2560

Phe  Asp  Glu  Asn  Lys  Tyr  Asn  Glu  Ile  Val  Gln  Val  Val  Lys  Gly  Ile
                    2565                2570                2575

Ser  Pro  Thr  Lys  Ser  Asp  Ile  Val  Thr  Met  Thr  Thr  Lys  Gly  Ala  His
               2580                2585                2590

His  Thr  Ala  Ile  Lys  Gln  Val  Arg  Ile  Gly  Tyr  Lys  Ser  Leu  Asp  Lys
               2595                2600                2605

Asp  Pro  Asn  Met  Val  Ser  Ile  Leu  Ser  Asn  Gln  Leu  Thr  Lys  Ile  Ser
2610                2615                2620

Cys  Val  Ile  Leu  Asn  Val  Thr  Pro  Gly  Arg  Thr  Ala  Tyr  Leu  Asn  Val
2625                2630                2635                2640

Met  Arg  Leu  Cys  Gly  Thr  Phe  Val  Val  Cys  Pro  Ala  His  Tyr  Leu  Glu
               2645                2650                2655

Ala  Leu  Glu  Glu  Asp  Asp  Thr  Ile  Tyr  Phe  Ile  Ser  Phe  Ser  Val  Cys
               2660                2665                2670

Ile  Lys  Leu  Arg  Phe  Gln  Pro  Asp  Arg  Val  Thr  Leu  Val  Asn  Thr  His
               2675                2680                2685

Gln  Asp  Leu  Val  Val  Trp  Asp  Leu  Gly  Asn  Ser  Val  Pro  Pro  Ala  Ile
2690                2695                2700

Asp  Val  Leu  Ser  Met  Ile  Pro  Thr  Val  Ala  Asp  Trp  Asp  Lys  Phe  Gln
2705                2710                2715                2720

Asp  Gly  Pro  Gly  Ala  Phe  Gly  Val  Thr  Lys  Tyr  Asn  Ala  Arg  Tyr  Pro
```

|      |      |      |      |      | 2725 |      |      |      |      | 2730 |      |      |      |      | 2735 |
|------|------|------|------|------|------|------|------|------|------|------|------|------|------|------|------|

Thr Asn Tyr Ile Asn Thr Leu Asp Met Ile Glu Arg Ile Arg Ala Asp
                2740                    2745                    2750

Thr Gln Asn Pro Thr Gly Ile Tyr Lys Met Leu Asn Ser Asp His Thr
         2755                    2760                    2765

Ile Thr Thr Gly Leu Arg Tyr Gln Met Tyr Ser Leu Glu Gly Phe Cys
             2770                    2775                    2780

Gly Gly Leu Ile Leu Arg Ala Cys Thr Arg Met Val Arg Lys Ile Val
2785                    2790                    2795                    2800

Gly Leu His Val Ala Ala Ser Ala Asn His Ala Met Gly Tyr Ala Glu
                2805                    2810                    2815

Cys Leu Val Gln Glu Asp Leu Lys His Ala Ile Asn Lys Leu Ser Pro
                2820                    2825                    2830

Asp Ala Arg Ser Leu Ile Ile Gly His Leu Asn Pro Lys Val Glu Thr
             2835                    2840                    2845

Ala Thr Lys Gln Cys Gly Ile Val Arg Ser Leu Gly Ser Leu Gly Cys
         2850                    2855                    2860

His Gly Lys Val Thr Ser Glu Asp Val Ala Met Thr Ala Thr Lys Thr
2865                    2870                    2875                    2880

Thr Ile Arg Lys Ser Arg Ile Tyr Gly Leu Val Gly Asp Ile Lys Thr
             2885                    2890                    2895

Glu Pro Ser Ile Leu His Ala His Asp Pro Arg Leu Pro Glu Asp Gln
             2900                    2905                    2910

Ile Gly Lys Trp Asp Pro Val Phe Glu Ala Ala Leu Lys Tyr Gly Thr
         2915                    2920                    2925

Arg Ile Glu Pro Phe Pro Ile Glu Glu Ile Leu Glu Val Glu Asp His
2930                    2935                    2940

Leu Ser Ile Ile Leu Lys Gly Met Asp Asn Thr Leu Lys Lys Arg Asn
2945                    2950                    2955                    2960

Val Asn Asn Leu Glu Val Gly Ile Asn Gly Ile Asp Gln Ser Asp Tyr
                2965                    2970                    2975

Trp Leu Gln Ile Glu Thr Asn Thr Ser Pro Gly Trp Pro Tyr Thr Lys
             2980                    2985                    2990

Arg Lys Pro Lys Gly Ala Glu Gly Lys Lys Trp Leu Phe Lys Glu Val
         2995                    3000                    3005

Gly Asn Tyr Pro Ser Gly Lys Pro Ile Leu Glu Met Glu Asp Ser Gly
3010                    3015                    3020

Leu Ile Glu Ser Tyr Asn Lys Met Leu Arg Asp Ala Lys Gln Gly Val
3025                    3030                    3035                    3040

Ala Pro Ile Val Val Thr Val Glu Cys Pro Lys Asp Glu Arg Arg Lys
                3045                    3050                    3055

Leu Ser Lys Ile Tyr Glu Gln Pro Ala Thr Arg Thr Phe Thr Ile Leu
             3060                    3065                    3070

Pro Pro Glu Ile Asn Ile Leu Phe Arg Gln Tyr Phe Gly Asp Phe Ala
         3075                    3080                    3085

Ala Met Ile Met Thr Asn Arg Ser Lys Leu Phe Cys Gln Val Gly Ile
         3090                    3095                    3100

Asn Pro Glu Asn Met Glu Trp Ser Asp Leu Met His Glu Phe Leu His
3105                    3110                    3115                    3120

Lys Ser Thr His Gly Phe Ala Gly Asp Tyr Ser Lys Phe Asp Gly Ile
             3125                    3130                    3135

Gly Asp Pro Gln Ile Tyr His Ser Ile Thr Gln Val Val Asn Asn Trp
             3140                    3145                    3150

-continued

```
Tyr Asp Asp Gly Glu Glu Asn Ala Arg Thr Arg His Ala Leu Ile Ser
        3155                3160                3165

Ser Ile Ile His Arg Glu Gly Ile Val Lys Glu Tyr Leu Phe Gln Tyr
    3170                3175                3180

Cys Gln Gly Met Pro Ser Gly Phe Ala Met Thr Val Ile Phe Asn Ser
3185                3190                3195                3200

Phe Val Asn Tyr Tyr Tyr Leu Ala Met Ala Trp Met Asn Leu Ile Ser
                3205                3210                3215

His Ser Pro Leu Ser Pro Gln Ser Thr Val Arg Asp Phe Asp Asn Tyr
            3220                3225                3230

Cys Lys Val Val Val Tyr Gly Asp Asp Asn Ile Val Ser Val Asp Leu
        3235                3240                3245

Asn Phe Leu Glu Tyr Tyr Asn Leu Arg Thr Val Ala Ala Tyr Leu Ser
    3250                3255                3260

Gln Phe Gly Val Thr Tyr Thr Asp Asp Ala Lys Asn Pro Ile Glu Lys
3265                3270                3275                3280

Ser Val Pro Phe Val Glu Ile Thr Ser Val Ser Phe Leu Lys Arg Arg
                3285                3290                3295

Trp Val Pro Leu Gly Gly Arg Leu Ser Thr Ile Tyr Lys Ala Pro Leu
            3300                3305                3310

Asp Lys Thr Ser Ile Glu Glu Arg Leu His Trp Ile Arg Glu Cys Asp
        3315                3320                3325

Asn Asp Ile Glu Ala Leu Asn Gln Asn Ile Glu Ser Ala Leu Tyr Glu
    3330                3335                3340

Ala Ser Ile His Gly Lys Ile Tyr Phe Gly Asp Leu Leu Gln Arg Ile
3345                3350                3355                3360

Arg Ile Ala Cys Asp Ala Val Met Ile Pro Val Pro Ser Val Thr Phe
                3365                3370                3375

Lys Asp Cys His Lys Arg Trp Trp Ala Ser Met Thr Gly Gly Ala Leu
            3380                3385                3390

Asp Pro Ala Ser Leu Ser Arg Leu Tyr Leu Ala Ala Glu Asn Gln Leu
        3395                3400                3405

Val Asp Thr Arg Lys Val Trp Lys Asp Arg Phe Leu Gly Glu Asp Arg
    3410                3415                3420

Ser Leu Ile Asp Met Leu Lys Ser Ala Arg Ala Val Pro Leu Ala Ala
3425                3430                3435                3440

Tyr His Val
```

( 2 ) INFORMATION FOR SEQ ID NO:3:

( i ) SEQUENCE CHARACTERISTICS:
( A ) LENGTH: 11785 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i x ) FEATURE:
( A ) NAME/KEY: misc_feature
( B ) LOCATION: 1..11785
( D ) OTHER INFORMATION: /note= "cDNA sequence of MCDV-T genome as disclosed in WO 94/21796"

( i x ) FEATURE:
( A ) NAME/KEY: CDS
( B ) LOCATION: 456..10826

( x i ) SEQUENCE DESCRIPTION: SEQ ID NO:3:

```
NTGAAAAGGA  GGGTATAGAG  ATACCCTTCA  TATATTCTGC  GGATGGCGTG  CCGTGAGTAG      60

ACCTCGCGAC  GTTTCCCAGA  GGAAAATGGA  AATGGTCCAT  GTAACACCAG  ATATTTATCT     120

GGTTGAGGAA  CATGGTTTAG  TGGTAGAGAT  AAACTCAACT  TTGTGTTGGA  CCCCGATGCT     180

GTGAAAAGTA  AATAAAGACA  AGGCCACTTA  GCGAAGGATA  TTCGAAGTAG  TGATGAAAGG     240

AAGTGCAATA  AGTCATGCCG  TAAGTCGCAA  TGCGCTATAA  GTCATGCCGT  AAGCCGCGTC     300

GCCTGGATTT  GCTATTAGAA  TGTCCCTAGC  CGGTGATAAC  CTTGAGTCCC  CGTCATAGGA     360

CTACTTTTGT  TTGCTTAGTA  ATACATTGGG  ACCACCCGCA  TGGAGCTCTG  AGCCTACCAT     420

ACATAGTACA  TTTTCCGAGG  GATTGTCTTT  TGATA ATG ATG CAG ACA AAC AAC           473
                                         Met Met Gln Thr Asn Asn
                                             3445
```

| AAC | CAA | AAT | CCC | ACT | CAA | GGA | AGC | ATT | CCT | GAG | AAC | TCC | TCA | CAA | GAT | 521 |
|-----|-----|-----|-----|-----|-----|-----|-----|-----|-----|-----|-----|-----|-----|-----|-----|-----|
| Asn | Gln | Asn | Pro | Thr | Gln | Gly | Ser | Ile | Pro | Glu | Asn | Ser | Ser | Gln | Asp | |
| 3450 | | | | 3455 | | | | | 3460 | | | | | 3465 | | |

| CGC | AAC | TTA | GGA | GTG | CCC | GCT | GGA | TAT | TCT | TTA | AGC | GTT | GAG | GAC | CCC | 569 |
|-----|-----|-----|-----|-----|-----|-----|-----|-----|-----|-----|-----|-----|-----|-----|-----|-----|
| Arg | Asn | Leu | Gly | Val | Pro | Ala | Gly | Tyr | Ser | Leu | Ser | Val | Glu | Asp | Pro | |
| | | | | 3470 | | | | 3475 | | | | | 3480 | | | |

| TTC | GGG | AAC | CGG | TCT | GAC | TTT | CAT | ATC | CCA | GTG | CAC | CAA | ATC | ATT | CGG | 617 |
|-----|-----|-----|-----|-----|-----|-----|-----|-----|-----|-----|-----|-----|-----|-----|-----|-----|
| Phe | Gly | Asn | Arg | Ser | Asp | Phe | His | Ile | Pro | Val | His | Gln | Ile | Ile | Arg | |
| | | | | 3485 | | | | | 3490 | | | | | 3495 | | |

| GAA | GAG | ATT | GAT | CGT | CCA | AAT | TGG | GTT | CCT | ATA | TGT | TCA | AAC | GAT | TTT | 665 |
|-----|-----|-----|-----|-----|-----|-----|-----|-----|-----|-----|-----|-----|-----|-----|-----|-----|
| Glu | Glu | Ile | Asp | Arg | Pro | Asn | Trp | Val | Pro | Ile | Cys | Ser | Asn | Asp | Phe | |
| | | | | 3500 | | | | | 3505 | | | | | 3510 | | |

| CAT | CTT | AAC | AGT | GAG | GAT | TAT | TGT | GAG | GAG | TGC | GAA | TCT | GAA | CGG | ATC | 713 |
|-----|-----|-----|-----|-----|-----|-----|-----|-----|-----|-----|-----|-----|-----|-----|-----|-----|
| His | Leu | Asn | Ser | Glu | Asp | Tyr | Cys | Glu | Glu | Cys | Glu | Ser | Glu | Arg | Ile | |
| | | | 3515 | | | | | 3520 | | | | | 3525 | | | |

| AAA | AAT | TTC | GAA | ATA | TTC | AGA | TCA | CAG | AAT | TTG | ATT | GAC | CAA | CAC | CTA | 761 |
|-----|-----|-----|-----|-----|-----|-----|-----|-----|-----|-----|-----|-----|-----|-----|-----|-----|
| Lys | Asn | Phe | Glu | Ile | Phe | Arg | Ser | Gln | Asn | Leu | Ile | Asp | Gln | His | Leu | |
| 3530 | | | | | 3535 | | | | | 3540 | | | | | 3545 | |

| AAT | CTC | TGT | ACT | GAT | TCA | AAG | GAT | TGT | GAT | CAT | TTT | TCT | TGT | TTT | TCC | 809 |
|-----|-----|-----|-----|-----|-----|-----|-----|-----|-----|-----|-----|-----|-----|-----|-----|-----|
| Asn | Leu | Cys | Thr | Asp | Ser | Lys | Asp | Cys | Asp | His | Phe | Ser | Cys | Phe | Ser | |
| | | | | 3550 | | | | | 3555 | | | | | 3560 | | |

| ACG | AGT | ACA | AGT | TGC | AGA | TTT | TGC | CCT | TTT | TGC | TTA | TTC | ATT | TTT | AAT | 857 |
|-----|-----|-----|-----|-----|-----|-----|-----|-----|-----|-----|-----|-----|-----|-----|-----|-----|
| Thr | Ser | Thr | Ser | Cys | Arg | Phe | Cys | Pro | Phe | Cys | Leu | Phe | Ile | Phe | Asn | |
| | | | | 3565 | | | | | 3570 | | | | | 3575 | | |

| TTG | GAT | AAA | TTT | TAC | AAA | CAA | AAT | CTA | TAT | TTG | ATT | AGT | CGT | CAG | GCT | 905 |
|-----|-----|-----|-----|-----|-----|-----|-----|-----|-----|-----|-----|-----|-----|-----|-----|-----|
| Leu | Asp | Lys | Phe | Tyr | Lys | Gln | Asn | Leu | Tyr | Leu | Ile | Ser | Arg | Gln | Ala | |
| | | | 3580 | | | | | 3585 | | | | | 3590 | | | |

| CTA | GCT | AGA | TTG | TTC | CAC | GGA | AGC | GCC | GAA | GAG | TTA | CTC | AGT | AGA | GCG | 953 |
|-----|-----|-----|-----|-----|-----|-----|-----|-----|-----|-----|-----|-----|-----|-----|-----|-----|
| Leu | Ala | Arg | Leu | Phe | His | Gly | Ser | Ala | Glu | Glu | Leu | Leu | Ser | Arg | Ala | |
| | | 3595 | | | | | 3600 | | | | | 3605 | | | | |

| ATT | TTC | TTT | ACG | TAT | AAT | ATT | TGT | ATT | GAT | GCA | GAG | GTG | GTT | GCT | AAT | 1001 |
|-----|-----|-----|-----|-----|-----|-----|-----|-----|-----|-----|-----|-----|-----|-----|-----|------|
| Ile | Phe | Phe | Thr | Tyr | Asn | Ile | Cys | Ile | Asp | Ala | Glu | Val | Val | Ala | Asn | |
| 3610 | | | | | 3615 | | | | | 3620 | | | | | 3625 | |

| AAT | AGG | ATT | GGC | TGT | GAA | TAT | GTT | AAG | TTG | TTT | CAT | CCA | GAC | CTT | AGG | 1049 |
|-----|-----|-----|-----|-----|-----|-----|-----|-----|-----|-----|-----|-----|-----|-----|-----|------|
| Asn | Arg | Ile | Gly | Cys | Glu | Tyr | Val | Lys | Leu | Phe | His | Pro | Asp | Leu | Arg | |
| | | | | 3630 | | | | | 3635 | | | | | 3640 | | |

| CCT | AGT | ATT | ACG | TCT | CCC | CCT | TAT | GCT | AGT | GAT | TGG | GTT | ATG | TGT | GAT | 1097 |
|-----|-----|-----|-----|-----|-----|-----|-----|-----|-----|-----|-----|-----|-----|-----|-----|------|
| Pro | Ser | Ile | Thr | Ser | Pro | Pro | Tyr | Ala | Ser | Asp | Trp | Val | Met | Cys | Asp | |
| | | | 3645 | | | | | 3650 | | | | | 3655 | | | |

| AAT | GCT | AAA | CAT | CTT | TTT | GAG | TGT | CTT | GGC | CTT | GGT | GAC | ACG | ACC | AGA | 1145 |
|-----|-----|-----|-----|-----|-----|-----|-----|-----|-----|-----|-----|-----|-----|-----|-----|------|
| Asn | Ala | Lys | His | Leu | Phe | Glu | Cys | Leu | Gly | Leu | Gly | Asp | Thr | Thr | Arg | |
| | | | 3660 | | | | | 3665 | | | | | 3670 | | | |

| GGA | CAC | CTA | TAT | GGA | CTT | ATT | AGC | GAG | AAT | GCA | TAT | TGG | AAC | GCC | ACG | 1193 |
|-----|-----|-----|-----|-----|-----|-----|-----|-----|-----|-----|-----|-----|-----|-----|-----|------|
| Gly | His | Leu | Tyr | Gly | Leu | Ile | Ser | Glu | Asn | Ala | Tyr | Trp | Asn | Ala | Thr | |
| | | 3675 | | | | | 3680 | | | | | 3685 | | | | |

| TGC | TCA | AAA | TGC | GGA | GCC | TGT | TGT | CAG | GGA | GCA | AAT | GCC | CGT | ACG | GCG | 1241 |

```
Cys  Ser  Lys  Cys  Gly  Ala  Cys  Cys  Gln  Gly  Ala  Asn  Ala  Arg  Thr  Ala
3690           3695                3700                3705

ATA  CCG  ATA  GTG  ATG  GCG  TTG  CAG  TAC  TGC  AGG  GTG  GAT  GTG  TAT  TAT       1289
Ile  Pro  Ile  Val  Met  Ala  Leu  Gln  Tyr  Cys  Arg  Val  Asp  Val  Tyr  Tyr
               3710                3715                3720

AGT  GAG  TAC  TAT  TTA  TAC  CAC  ATC  TAC  GCT  CCG  GAA  GAG  AGA  ATG  AAG       1337
Ser  Glu  Tyr  Tyr  Leu  Tyr  His  Ile  Tyr  Ala  Pro  Glu  Glu  Arg  Met  Lys
               3725                3730                3735

ATT  GAT  CAA  CAG  ACA  GCA  CAC  TTG  CTA  CAC  AGT  ATA  ATC  CGA  GGA  GCA       1385
Ile  Asp  Gln  Gln  Thr  Ala  His  Leu  Leu  His  Ser  Ile  Ile  Arg  Gly  Ala
               3740                3745                3750

CCA  GCA  GTG  GAT  TGC  TCT  GAG  TTA  TCT  CAG  GAG  CCA  ATT  CAC  AGG  ATG       1433
Pro  Ala  Val  Asp  Cys  Ser  Glu  Leu  Ser  Gln  Glu  Pro  Ile  His  Arg  Met
               3755                3760                3765

GTA  ATG  GAT  AGC  TCA  AAG  TTA  GTG  GCA  CTG  GAT  TCG  ACA  ATC  AGG  CAT       1481
Val  Met  Asp  Ser  Ser  Lys  Leu  Val  Ala  Leu  Asp  Ser  Thr  Ile  Arg  His
3770           3775                3780                3785

CCT  AAG  AGC  CAA  GGA  AGT  TTG  CTC  GAT  TCA  GAA  TGC  GAT  CAT  GAG  TTT       1529
Pro  Lys  Ser  Gln  Gly  Ser  Leu  Leu  Asp  Ser  Glu  Cys  Asp  His  Glu  Phe
               3790                3795                3800

ATT  CTA  AGA  ACG  TCC  CAT  GGT  ATC  AAA  ATA  CCG  ATG  AGT  AAG  TCT  TTA       1577
Ile  Leu  Arg  Thr  Ser  His  Gly  Ile  Lys  Ile  Pro  Met  Ser  Lys  Ser  Leu
               3805                3810                3815

TTT  ATA  TCA  TTT  CTT  ACC  ATG  GGA  GCT  TAT  CAT  GGG  TAT  GCT  CAT  GAT       1625
Phe  Ile  Ser  Phe  Leu  Thr  Met  Gly  Ala  Tyr  His  Gly  Tyr  Ala  His  Asp
               3820                3825                3830

GAT  CAG  CAG  GAG  CAA  AAT  GCG  ATA  ATA  TCT  TTT  GGT  GGG  ATG  CCC  GGA       1673
Asp  Gln  Gln  Glu  Gln  Asn  Ala  Ile  Ile  Ser  Phe  Gly  Gly  Met  Pro  Gly
               3835                3840                3845

GTC  AAT  TTG  GCT  TGT  AAC  AAA  AAT  TTC  CTG  AGA  ATG  CAT  AAG  TTG  TTT       1721
Val  Asn  Leu  Ala  Cys  Asn  Lys  Asn  Phe  Leu  Arg  Met  His  Lys  Leu  Phe
3850           3855                3860                3865

TAT  TCT  GGA  AGT  TTT  AGG  CGC  AGA  CCC  CTG  TTT  ATG  AGC  CAA  ATT  CCC       1769
Tyr  Ser  Gly  Ser  Phe  Arg  Arg  Arg  Pro  Leu  Phe  Met  Ser  Gln  Ile  Pro
               3870                3875                3880

TCT  ACG  AAT  GCC  ACC  GCT  CAG  TCC  GGT  TTT  AAT  GAT  GAA  GAA  TTC  GAA       1817
Ser  Thr  Asn  Ala  Thr  Ala  Gln  Ser  Gly  Phe  Asn  Asp  Glu  Glu  Phe  Glu
               3885                3890                3895

AGA  TTG  ATG  GCT  GAA  GAG  GGT  GTG  CAT  GTC  AAA  GTC  GAG  CGT  CCA  ATA       1865
Arg  Leu  Met  Ala  Glu  Glu  Gly  Val  His  Val  Lys  Val  Glu  Arg  Pro  Ile
               3900                3905                3910

GCA  GAG  AGG  TTT  GAT  TAT  GAG  GAC  GTT  ATT  GAT  ATT  TAC  GAT  GAG  ACC       1913
Ala  Glu  Arg  Phe  Asp  Tyr  Glu  Asp  Val  Ile  Asp  Ile  Tyr  Asp  Glu  Thr
               3915                3920                3925

GAC  CAC  GAC  AGG  ACA  CGA  GCT  CTA  GGC  CTT  GGC  CAA  GTA  TTC  GGA  GGT       1961
Asp  His  Asp  Arg  Thr  Arg  Ala  Leu  Gly  Leu  Gly  Gln  Val  Phe  Gly  Gly
3930           3935                3940                3945

TTG  CTC  AAA  GGA  ATT  TCT  CAT  TGT  GTA  GAT  AGC  CTA  CAT  AAG  GTA  TTT       2009
Leu  Leu  Lys  Gly  Ile  Ser  His  Cys  Val  Asp  Ser  Leu  His  Lys  Val  Phe
               3950                3955                3960

GAT  TTC  CCT  CTG  GAC  CTG  GCC  ATA  GAA  GCA  GCT  CAG  AAA  ACT  GGT  GAT       2057
Asp  Phe  Pro  Leu  Asp  Leu  Ala  Ile  Glu  Ala  Ala  Gln  Lys  Thr  Gly  Asp
               3965                3970                3975

TGG  CTT  GAA  GGA  AAT  AAA  GCT  GCA  GTA  GAT  GAA  ACT  AAA  ATT  TGT  GTG       2105
Trp  Leu  Glu  Gly  Asn  Lys  Ala  Ala  Val  Asp  Glu  Thr  Lys  Ile  Cys  Val
               3980                3985                3990

GGC  TGT  CCC  GAG  ATT  CAA  AAA  GAT  ATG  ATC  AGT  TTC  CAG  AAT  GAA  ACA       2153
Gly  Cys  Pro  Glu  Ile  Gln  Lys  Asp  Met  Ile  Ser  Phe  Gln  Asn  Glu  Thr
               3995                4000                4005

AAA  GAA  GCT  TTT  GAA  TTA  ATA  CGA  TCA  AGT  ATA  AAG  AAG  CTT  TCC  GAG       2201
```

```
                    Lys Glu Ala Phe Glu Leu Ile Arg Ser Ser Ile Lys Lys Leu Ser Glu
                    4010                4015                4020                4025

GGC ATT GAC AAA ATC ACG AAG ATG AAT GCT ACG AAC TTT GAA CGA ATC              2249
Gly Ile Asp Lys Ile Thr Lys Met Asn Ala Thr Asn Phe Glu Arg Ile
                4030                4035                4040

CTA GAC GGG ATT AAA CCA ATC GAG AGC AGG TTG ACA GAA CTT GAG AAC              2297
Leu Asp Gly Ile Lys Pro Ile Glu Ser Arg Leu Thr Glu Leu Glu Asn
            4045                4050                4055

AAG GCA CCC GCT TCA GAC AGC AAA GCC ATG GAA GCT CTG GTC CAG GCC              2345
Lys Ala Pro Ala Ser Asp Ser Lys Ala Met Glu Ala Leu Val Gln Ala
        4060                4065                4070

GTG AAA GAC TTG AAA ATC ATG AAA GAG GCG ATG CTC GAT CTA AAT CGA              2393
Val Lys Asp Leu Lys Ile Met Lys Glu Ala Met Leu Asp Leu Asn Arg
    4075                4080                4085

AGA CTG AGC AAG CTG GAA GGA AAG AAA AGT GAT GGC CAG ACT ACT GAA              2441
Arg Leu Ser Lys Leu Glu Gly Lys Lys Ser Asp Gly Gln Thr Thr Glu
4090                4095                4100                4105

GGG ACA GCG GGA GAG CAA CAA CCG ATC CCT AAG ACT CCA ACT CGA GTG              2489
Gly Thr Ala Gly Glu Gln Gln Pro Ile Pro Lys Thr Pro Thr Arg Val
                4110                4115                4120

AAG GCA AGA CCA GTT GTG AAG CAA TCA GGA ACG ATA ATG GTA AAC GAA              2537
Lys Ala Arg Pro Val Val Lys Gln Ser Gly Thr Ile Met Val Asn Glu
            4125                4130                4135

GAG AGC ACA GAA ACT TTC AGG GAT AAT GAG AGT CGA GTG ACT GAC CCT              2585
Glu Ser Thr Glu Thr Phe Arg Asp Asn Glu Ser Arg Val Thr Asp Pro
        4140                4145                4150

AAC AGG AGC GAT ATG TTT GCT GCT GTT ACT GCA GAA TAC TTA GTT AAA              2633
Asn Arg Ser Asp Met Phe Ala Ala Val Thr Ala Glu Tyr Leu Val Lys
    4155                4160                4165

TCG TTT ACA TGG AAA GTT TCT GAT GGA CAA GAT AAA GTT TTG GCT GAC              2681
Ser Phe Thr Trp Lys Val Ser Asp Gly Gln Asp Lys Val Leu Ala Asp
4170                4175                4180                4185

CTT GAT TTA CCT CAA GAC TTA TGG AAA TCC AAT TCC CGA TTG AGT GAT              2729
Leu Asp Leu Pro Gln Asp Leu Trp Lys Ser Asn Ser Arg Leu Ser Asp
                4190                4195                4200

ATC ATG GGG TAT TTC CAA TAT TAT GAT GCA ACC GGA ATC ACT TTT CGC              2777
Ile Met Gly Tyr Phe Gln Tyr Tyr Asp Ala Thr Gly Ile Thr Phe Arg
            4205                4210                4215

ATA ACG ACA ACA TGT GTT CCT ATG CAC GGT GGT ACT TTA TGT GCT GCT              2825
Ile Thr Thr Thr Cys Val Pro Met His Gly Gly Thr Leu Cys Ala Ala
        4220                4225                4230

TGG GAT GCT AAT GGT TGC GCT ACA CGA CAA GGT ATA GCC ACA ACG GTT              2873
Trp Asp Ala Asn Gly Cys Ala Thr Arg Gln Gly Ile Ala Thr Thr Val
    4235                4240                4245

CAG CTG ACT GGT TTG CCC AAA ACA TTT ATT GAA GCT CAC AGC TCA TCA              2921
Gln Leu Thr Gly Leu Pro Lys Thr Phe Ile Glu Ala His Ser Ser Ser
4250                4255                4260                4265

GAA ACG ATA ATC GTG GTA AAG AAT TCC AAT ATA CAA TCC GCG ATT TGT              2969
Glu Thr Ile Ile Val Val Lys Asn Ser Asn Ile Gln Ser Ala Ile Cys
                4270                4275                4280

CTA AGT GGA AGT GAG CAC TCG TTT GGG AGA ATG GGA ATC CTG AAG ATC              3017
Leu Ser Gly Ser Glu His Ser Phe Gly Arg Met Gly Ile Leu Lys Ile
            4285                4290                4295

TGT TGC TTG AAT ACG TTG AAT GCG CCA AAG GAA GCT ACA CAG CAA GTG              3065
Cys Cys Leu Asn Thr Leu Asn Ala Pro Lys Glu Ala Thr Gln Gln Val
        4300                4305                4310

GCT GTG AAC GTC TGG ATT AAG TTT GAC GGA GTT AAA TTT CAC GTT TAT              3113
Ala Val Asn Val Trp Ile Lys Phe Asp Gly Val Lys Phe His Val Tyr
    4315                4320                4325

TCT TTA AGG AAA AAT CCA GTC GTT TCG CAA CTG CAG GTG GCA TCT CTT              3161
```

```
Ser Leu Arg Lys Asn Pro Val Val Ser Gln Leu Gln Val Ala Ser Leu
4330                4335                4340                4345

ACA GAC ATA GGA GAA TTG AGC AGT GTG GTT GCT ACT GGT TCT TGG TCT    3209
Thr Asp Ile Gly Glu Leu Ser Ser Val Val Ala Thr Gly Ser Trp Ser
                4350                4355                4360

ACT ACC TCG GCT ACT AAT TTG ATG GAA TTA AAC ATT CAT CCC ACC TCC    3257
Thr Thr Ser Ala Thr Asn Leu Met Glu Leu Asn Ile His Pro Thr Ser
            4365                4370                4375

TGT GCT ATT CAG AAC GGA TTG ATA ACA CAG ACA CCA TTG AGT GTT TTA    3305
Cys Ala Ile Gln Asn Gly Leu Ile Thr Gln Thr Pro Leu Ser Val Leu
                4380                4385                4390

GCT CAT GCT TTT GCA AGG TGG AGA GGA TCG TTG AAA ATT TCC ATC ATT    3353
Ala His Ala Phe Ala Arg Trp Arg Gly Ser Leu Lys Ile Ser Ile Ile
            4395                4400                4405

TTC GGA GCG AGT TTG TTT ACC CGA GGA CGA ATC TTA GCC GCT GCT GTG    3401
Phe Gly Ala Ser Leu Phe Thr Arg Gly Arg Ile Leu Ala Ala Ala Val
4410                4415                4420                4425

CCC GTT GCT AAG CGC AAA GGT ACC ATG AGC CTT GAC GAG ATT AGT GGG    3449
Pro Val Ala Lys Arg Lys Gly Thr Met Ser Leu Asp Glu Ile Ser Gly
                4430                4435                4440

TAT CAT AAT GTT TGC TGC TTA TTG AAT GGT CAG CAA ACT ACA TTT GAA    3497
Tyr His Asn Val Cys Cys Leu Leu Asn Gly Gln Gln Thr Thr Phe Glu
            4445                4450                4455

TTG GAA ATC CCA TAT TAT TCT GTG GGC CAA GAT TCT TTC GTG TAC CGT    3545
Leu Glu Ile Pro Tyr Tyr Ser Val Gly Gln Asp Ser Phe Val Tyr Arg
                4460                4465                4470

GAT GCT CTT TTT GAT ATC TCT GCG CAC GAT GGG AAT TTT ATG ATT ACT    3593
Asp Ala Leu Phe Asp Ile Ser Ala His Asp Gly Asn Phe Met Ile Thr
            4475                4480                4485

CGC TTG CAT CTC GTG ATA CTG GAT AAA TTG GTA ATG AGC GCT AAT GCG    3641
Arg Leu His Leu Val Ile Leu Asp Lys Leu Val Met Ser Ala Asn Ala
4490                4495                4500                4505

AGC AAC AGC ATA AAT TTT TCC GTG ACT CTT GGA CCA GGT TCT GAT TTG    3689
Ser Asn Ser Ile Asn Phe Ser Val Thr Leu Gly Pro Gly Ser Asp Leu
                4510                4515                4520

GAA TTG AAA TAT CTT GCA GGA GTA CAT GGG CAG CGC ATA GTC CGC GAG    3737
Glu Leu Lys Tyr Leu Ala Gly Val His Gly Gln Arg Ile Val Arg Glu
            4525                4530                4535

TTG AAG ATG CAG GTT TCA TTG GGT CGG TCA TTT GAG AAT GGA GTG CTT    3785
Leu Lys Met Gln Val Ser Leu Gly Arg Ser Phe Glu Asn Gly Val Leu
            4540                4545                4550

ATT GGT AGT GGC TTC GAC GAC TTG CTA CAA AGA TGG AGT CAT TTG GTG    3833
Ile Gly Ser Gly Phe Asp Asp Leu Leu Gln Arg Trp Ser His Leu Val
            4555                4560                4565

TCC ATG CCT TTT AAT GCA AAA GGA GAC AGC GAT GAG ATC CAA GTC TTT    3881
Ser Met Pro Phe Asn Ala Lys Gly Asp Ser Asp Glu Ile Gln Val Phe
4570                4575                4580                4585

GGC TAT ATC ATG ACT GTT GCC CCG GCG TAT CGT TCC CTT CCA GTC CAC    3929
Gly Tyr Ile Met Thr Val Ala Pro Ala Tyr Arg Ser Leu Pro Val His
                4590                4595                4600

TGC ACG CTG CTA AGT TGG TTT TCA CAA TTA TTC GTG CAG TGG AAA GGT    3977
Cys Thr Leu Leu Ser Trp Phe Ser Gln Leu Phe Val Gln Trp Lys Gly
            4605                4610                4615

GGT ATA AAG TAT AGA CTA CAC ATT GAT TCA GAA GAG CGC AGA TGG GGT    4025
Gly Ile Lys Tyr Arg Leu His Ile Asp Ser Glu Glu Arg Arg Trp Gly
            4620                4625                4630

GGA TTC ATC AAA GTT TGG CAT GAC CCA AAT GGC TCT TTG GAT GAA GGG    4073
Gly Phe Ile Lys Val Trp His Asp Pro Asn Gly Ser Leu Asp Glu Gly
            4635                4640                4645

AAA GAA TTT GCT AAA GCG GAT ATT CTA TCG CCA CCA GCC GGA GCT ATG    4121
```

|     |     |     |     |     |     |     |     |     |     |     |     |     |     |     |      |
|-----|-----|-----|-----|-----|-----|-----|-----|-----|-----|-----|-----|-----|-----|-----|------|
| Lys | Glu | Phe | Ala | Lys | Ala | Asp | Ile | Leu | Ser | Pro | Pro | Ala | Gly | Ala | Met  |
| 4650|     |     |     |     | 4655|     |     |     |     | 4660|     |     |     |     | 4665 |

```
GTT  CGT  TAT  TGG  AAC  TAT  TTA  AAT  GGA  GAC  TTG  GAG  TTT  ACA  GTA  CCA       4169
Val  Arg  Tyr  Trp  Asn  Tyr  Leu  Asn  Gly  Asp  Leu  Glu  Phe  Thr  Val  Pro
                    4670                4675                     4680

TTT  TGT  GCT  AGA  ACC  AGT  ACG  CTG  TTC  ATA  CCA  AAA  GCT  ATG  ATT  GCC       4217
Phe  Cys  Ala  Arg  Thr  Ser  Thr  Leu  Phe  Ile  Pro  Lys  Ala  Met  Ile  Ala
                    4685                4690                     4695

ACC  GAT  TCA  AAG  TCA  TGG  ATT  CTG  AAC  TAC  AAC  GGT  ACA  TTG  AAT  TTC       4265
Thr  Asp  Ser  Lys  Ser  Trp  Ile  Leu  Asn  Tyr  Asn  Gly  Thr  Leu  Asn  Phe
                    4700                4705                     4710

GCG  TAC  CAA  GGA  GTA  GAT  GAC  TTC  ACA  ATT  ACA  GTG  GAA  ACA  AGT  GCA       4313
Ala  Tyr  Gln  Gly  Val  Asp  Asp  Phe  Thr  Ile  Thr  Val  Glu  Thr  Ser  Ala
                    4715                4720                     4725

GCC  GAC  GAC  TTT  GAA  TTT  CAC  GTT  CGA  ACA  GTT  GCA  CCC  CGC  GCT  GGA       4361
Ala  Asp  Asp  Phe  Glu  Phe  His  Val  Arg  Thr  Val  Ala  Pro  Arg  Ala  Gly
4730                4735                4740                     4745

AAG  GTC  AAC  GAA  GCT  TTT  GCC  AAA  TTG  GAG  TAC  GCT  TCT  GAT  TTA  AAG       4409
Lys  Val  Asn  Glu  Ala  Phe  Ala  Lys  Leu  Glu  Tyr  Ala  Ser  Asp  Leu  Lys
                    4750                4755                     4760

GAT  ATC  AAA  GAA  TCT  CTG  ACA  TCT  TCC  ACT  CGT  TTG  AAA  GGG  CCT  CAT       4457
Asp  Ile  Lys  Glu  Ser  Leu  Thr  Ser  Ser  Thr  Arg  Leu  Lys  Gly  Pro  His
                    4765                4770                     4775

TAT  AAA  ACG  AAA  ATT  ACC  TCA  ATA  GAG  CCA  AAT  AAA  ATT  GAT  GAA  AAT       4505
Tyr  Lys  Thr  Lys  Ile  Thr  Ser  Ile  Glu  Pro  Asn  Lys  Ile  Asp  Glu  Asn
                    4780                4785                     4790

GAG  TCC  TCA  CGT  GGT  AAA  GAT  AAC  AAG  TCA  AAT  TCG  AAA  TTT  GAG  GAC       4553
Glu  Ser  Ser  Arg  Gly  Lys  Asp  Asn  Lys  Ser  Asn  Ser  Lys  Phe  Glu  Asp
                    4795                4800                     4805

TTA  CTC  AAT  GCA  ACA  GCT  CAG  ATG  GAT  TTT  GAT  CGA  GCC  ACA  GCG  AAC       4601
Leu  Leu  Asn  Ala  Thr  Ala  Gln  Met  Asp  Phe  Asp  Arg  Ala  Thr  Ala  Asn
4810                4815                4820                     4825

GTT  GGG  TGT  GTG  CCA  TTC  TCC  ATT  GCA  AAG  ACA  GCA  AAG  GTG  CTT  TCG       4649
Val  Gly  Cys  Val  Pro  Phe  Ser  Ile  Ala  Lys  Thr  Ala  Lys  Val  Leu  Ser
                    4830                4835                     4840

GAA  CGC  GAG  ACG  TGT  AAG  AAG  ATG  GCA  GAT  GTG  TTA  GAT  TTC  ACA  CAC       4697
Glu  Arg  Glu  Thr  Cys  Lys  Lys  Met  Ala  Asp  Val  Leu  Asp  Phe  Thr  His
                    4845                4850                     4855

TCA  TGT  TTG  AAC  TTA  GAC  AGT  CAA  CCT  GCG  GCG  GCA  AGA  TTA  GCA  GCG       4745
Ser  Cys  Leu  Asn  Leu  Asp  Ser  Gln  Pro  Ala  Ala  Ala  Arg  Leu  Ala  Ala
                    4860                4865                     4870

GCC  ATT  TCT  CAA  ATA  GCA  CCT  ATT  ATG  GAG  AGC  ATC  GGT  AGA  ACC  ACT       4793
Ala  Ile  Ser  Gln  Ile  Ala  Pro  Ile  Met  Glu  Ser  Ile  Gly  Arg  Thr  Thr
                    4875                4880                     4885

CAA  AGC  GTA  GAG  GAA  AAA  TTG  GCT  TCT  GTG  GAT  ACA  TTT  AGG  GAC  AAA       4841
Gln  Ser  Val  Glu  Glu  Lys  Leu  Ala  Ser  Val  Asp  Thr  Phe  Arg  Asp  Lys
4890                4895                4900                     4905

ATC  ATG  GCT  CTA  ATT  TCA  AAC  GTG  CTT  GGG  GAT  ACT  CTA  CCT  GGA  CTG       4889
Ile  Met  Ala  Leu  Ile  Ser  Asn  Val  Leu  Gly  Asp  Thr  Leu  Pro  Gly  Leu
                    4910                4915                     4920

GCC  ATT  GCT  GAC  TTC  AAA  AAA  GGA  AAA  TAT  GTG  TGG  GCC  TCG  TTC  CTG       4937
Ala  Ile  Ala  Asp  Phe  Lys  Lys  Gly  Lys  Tyr  Val  Trp  Ala  Ser  Phe  Leu
                    4925                4930                     4935

ACA  ATG  ATA  GCC  GCT  TGC  GTA  GTA  GCT  TGG  GCT  GCC  ACT  AGC  AAG  AAA       4985
Thr  Met  Ile  Ala  Ala  Cys  Val  Val  Ala  Trp  Ala  Ala  Thr  Ser  Lys  Lys
                    4940                4945                     4950

AGC  TTC  TTG  AAA  AGA  TTT  GCA  GTG  GTA  GCT  ATG  ATA  ATT  TGG  AGC  CCA       5033
Ser  Phe  Leu  Lys  Arg  Phe  Ala  Val  Val  Ala  Met  Ile  Ile  Trp  Ser  Pro
                    4955                4960                     4965

TTT  CTC  GCA  AGT  AAA  ATA  TGG  GCG  CTT  GGT  ACA  TGG  ATT  AGG  AAG  AGC       5081
```

-continued

| | | | | | | | | | | | | | | | | |
|---|---|---|---|---|---|---|---|---|---|---|---|---|---|---|---|---|
| Phe | Leu | Ala | Ser | Lys | Ile | Trp | Ala | Leu | Gly | Thr | Trp | Ile | Arg | Lys | Ser | |
| 4970 | | | | 4975 | | | | | 4980 | | | | | 4985 | | |

```
TGG  AGT  AAG  CTT  TGG  CCT  AAG  TCA  GAC  TCA  TGC  CGA  CAA  CAC  TCT  TTG       5129
Trp  Ser  Lys  Leu  Trp  Pro  Lys  Ser  Asp  Ser  Cys  Arg  Gln  His  Ser  Leu
               4990                    4995                         5000

GCA  GGC  CTG  TGT  GAA  AGT  GTG  TTC  ACA  TCA  TTC  AAG  GAT  TTC  CCT  GAC       5177
Ala  Gly  Leu  Cys  Glu  Ser  Val  Phe  Thr  Ser  Phe  Lys  Asp  Phe  Pro  Asp
                    5005                    5010                    5015

TGG  TTT  AAA  TCA  GGA  GGA  ATC  ACG  ATT  GTG  ACG  CAA  GTT  TGC  ACA  GTA       5225
Trp  Phe  Lys  Ser  Gly  Gly  Ile  Thr  Ile  Val  Thr  Gln  Val  Cys  Thr  Val
               5020                    5025                    5030

TTA  CTG  ACG  ATA  GTG  AGT  CTG  ATT  ACA  CTT  GGA  ACT  ATA  CCA  AGC  ACG       5273
Leu  Leu  Thr  Ile  Val  Ser  Leu  Ile  Thr  Leu  Gly  Thr  Ile  Pro  Ser  Thr
          5035                    5040                    5045

AAA  CAA  AAT  GCT  ACG  TTC  GCA  GAC  AAA  TTT  AAA  GAA  TTT  GGT  AAC  ATG       5321
Lys  Gln  Asn  Ala  Thr  Phe  Ala  Asp  Lys  Phe  Lys  Glu  Phe  Gly  Asn  Met
5050                    5055                    5060                    5065

AGC  AGA  GCT  ACA  ACG  TCA  ATA  GCT  GCA  GGT  TAC  AAG  ACG  ATA  TCA  GAG       5369
Ser  Arg  Ala  Thr  Thr  Ser  Ile  Ala  Ala  Gly  Tyr  Lys  Thr  Ile  Ser  Glu
               5070                    5075                    5080

CTG  TGT  TCG  AAA  TTC  ACC  AAT  TAC  TTG  GCT  GTA  ACC  TTC  TTT  GGG  GCG       5417
Leu  Cys  Ser  Lys  Phe  Thr  Asn  Tyr  Leu  Ala  Val  Thr  Phe  Phe  Gly  Ala
               5085                    5090                    5095

CAA  GTT  GAT  GAC  GAT  GCT  TTC  AAG  GGT  TTG  GTA  GCG  TTC  AAC  GTT  AAG       5465
Gln  Val  Asp  Asp  Asp  Ala  Phe  Lys  Gly  Leu  Val  Ala  Phe  Asn  Val  Lys
               5100                    5105                    5110

GAA  TGG  ATT  CTT  GAA  GTG  AAA  AAC  CTG  TCT  CTT  GAG  GAA  AAC  AAA  TTT       5513
Glu  Trp  Ile  Leu  Glu  Val  Lys  Asn  Leu  Ser  Leu  Glu  Glu  Asn  Lys  Phe
          5115                    5120                    5125

AGT  GGT  TTT  GGT  GGT  GAT  GAG  CAT  CTT  GTC  AAG  GTT  AGA  CAT  TTA  TAT       5561
Ser  Gly  Phe  Gly  Gly  Asp  Glu  His  Leu  Val  Lys  Val  Arg  His  Leu  Tyr
5130                    5135                    5140                    5145

GAT  AAA  TCT  GTG  GAA  ATA  ACC  TAT  AAG  TTG  CTC  CAG  AAA  AAT  CGA  GTT       5609
Asp  Lys  Ser  Val  Glu  Ile  Thr  Tyr  Lys  Leu  Leu  Gln  Lys  Asn  Arg  Val
               5150                    5155                    5160

CCC  ATT  GCT  ATG  CTT  CCT  ATC  ATC  CGA  GAC  ACG  TGT  AAG  AAG  TGC  GAG       5657
Pro  Ile  Ala  Met  Leu  Pro  Ile  Ile  Arg  Asp  Thr  Cys  Lys  Lys  Cys  Glu
               5165                    5170                    5175

GAT  TTG  CTA  AAC  GAG  AGT  TAT  ACT  TAC  AAA  GGT  ATG  AAA  ACT  CCG  CGC       5705
Asp  Leu  Leu  Asn  Glu  Ser  Tyr  Thr  Tyr  Lys  Gly  Met  Lys  Thr  Pro  Arg
               5180                    5185                    5190

GTG  GAC  CCA  TTC  TAT  ATA  TGC  CTT  TTT  GGA  GCA  CCT  GGA  GTT  GGC  AAG       5753
Val  Asp  Pro  Phe  Tyr  Ile  Cys  Leu  Phe  Gly  Ala  Pro  Gly  Val  Gly  Lys
          5195                    5200                    5205

TCC  ACA  GTG  GCA  TCG  ATG  ATT  GTT  GAC  GAT  TTG  TTG  GAT  GCT  ATG  GGC       5801
Ser  Thr  Val  Ala  Ser  Met  Ile  Val  Asp  Asp  Leu  Leu  Asp  Ala  Met  Gly
5210                    5215                    5220                    5225

GAA  CCT  AAG  GTT  GAT  AGG  ATC  TAT  ACT  CGA  TGC  TGT  TCT  GAT  CAA  TAT       5849
Glu  Pro  Lys  Val  Asp  Arg  Ile  Tyr  Thr  Arg  Cys  Cys  Ser  Asp  Gln  Tyr
               5230                    5235                    5240

TGG  AGC  AAT  TAT  CAC  CAC  GAG  CCA  GTT  ATT  TGT  TAT  GAC  GAC  TTG  GGG       5897
Trp  Ser  Asn  Tyr  His  His  Glu  Pro  Val  Ile  Cys  Tyr  Asp  Asp  Leu  Gly
               5245                    5250                    5255

GCA  ATC  AGC  AGA  CCA  GCG  AGT  TTA  TCA  GAC  TAT  GGG  GAG  ATA  ATG  GGA       5945
Ala  Ile  Ser  Arg  Pro  Ala  Ser  Leu  Ser  Asp  Tyr  Gly  Glu  Ile  Met  Gly
               5260                    5265                    5270

ATC  AAA  TCG  AAC  AGA  CCA  TAC  TCC  CTA  CCT  ATG  GCT  GCT  GTT  GAT  GAG       5993
Ile  Lys  Ser  Asn  Arg  Pro  Tyr  Ser  Leu  Pro  Met  Ala  Ala  Val  Asp  Glu
          5275                    5280                    5285

AAA  GGA  AGG  CAT  TGT  TTA  TCG  CGA  TAC  CTC  ATT  GCT  TGT  ACA  AAT  TTA       6041
```

```
Lys Gly Arg His Cys Leu Ser Arg Tyr Leu Ile Ala Cys Thr Asn Leu
5290                5295                5300                     5305

ACC CAT CTG GAC GAT ACG GGC GAT GTG AAA ACA AAG GAT GCC TAC TAT       6089
Thr His Leu Asp Asp Thr Gly Asp Val Lys Thr Lys Asp Ala Tyr Tyr
                5310                5315                5320

CGC AGA ATC AAT GTC CCA GTG ACA GTG ACG AGA GAA GTA ACC GCC ATG       6137
Arg Arg Ile Asn Val Pro Val Thr Val Thr Arg Glu Val Thr Ala Met
                5325                5330                5335

ATG AAC CCC GAG GAC CCA ACT GAT GGA CTA CGT TTC ACC GTG GAG CAA       6185
Met Asn Pro Glu Asp Pro Thr Asp Gly Leu Arg Phe Thr Val Glu Gln
                5340                5345                5350

GTG CTT GAT GGA GGT AGA TGG ATT AAT GTT ACT GAA AGC CGT CTC CTC       6233
Val Leu Asp Gly Gly Arg Trp Ile Asn Val Thr Glu Ser Arg Leu Leu
                5355                5360                5365

AAT GGA AGG ATG CCA TTC AGG GCT GAA GAT CTC ATG AAC ATG AAC TAC       6281
Asn Gly Arg Met Pro Phe Arg Ala Glu Asp Leu Met Asn Met Asn Tyr
5370                5375                5380                     5385

AGT TAC TTT ATG GAG TTT CTC AAG ATG TAT GCT GCT TTA TAT ATG GAA       6329
Ser Tyr Phe Met Glu Phe Leu Lys Met Tyr Ala Ala Leu Tyr Met Glu
                5390                5395                5400

AAT CAA AAC ATG TTG GTG GCA AAA TTG AGA GGA ACA GAG ATC CCA GAA       6377
Asn Gln Asn Met Leu Val Ala Lys Leu Arg Gly Thr Glu Ile Pro Glu
                5405                5410                5415

TCA CGT AGT TCA GAG AAT GAA GAA CTT GAA TTC GAT TAT TTG GCT ACA       6425
Ser Arg Ser Ser Glu Asn Glu Glu Leu Glu Phe Asp Tyr Leu Ala Thr
                5420                5425                5430

GCT CAG ATG GAC CAT ACA GTG ACA TTT GGG GAA CTA GTT ACC AAA TTC       6473
Ala Gln Met Asp His Thr Val Thr Phe Gly Glu Leu Val Thr Lys Phe
                5435                5440                5445

AAC TCG TAT AAG CTT ACT GGG AAA CAA TGG AAC AAG AGG CTC TGT GAA       6521
Asn Ser Tyr Lys Leu Thr Gly Lys Gln Trp Asn Lys Arg Leu Cys Glu
5450                5455                5460                     5465

CTT GGA TGG ACA TCT CTA GAC GGA TGG AAC ACG AAC AAG ATT ATG AGA       6569
Leu Gly Trp Thr Ser Leu Asp Gly Trp Asn Thr Asn Lys Ile Met Arg
                5470                5475                5480

TTC GAC GAT CTA GTT GCC GGA TTC TGT GGT TGC TCA AGG AAT GAG AAT       6617
Phe Asp Asp Leu Val Ala Gly Phe Cys Gly Cys Ser Arg Asn Glu Asn
                5485                5490                5495

TGC AAT TTT GAC TTC TAT CAT CAG AGA CTT CAA GCA TGT TTG AAC AAG       6665
Cys Asn Phe Asp Phe Tyr His Gln Arg Leu Gln Ala Cys Leu Asn Lys
                5500                5505                5510

AAA GGG TTT GCT CCC GCA TAT CAA TAT TTC AAC CTT CAC AAG TTG AAT       6713
Lys Gly Phe Ala Pro Ala Tyr Gln Tyr Phe Asn Leu His Lys Leu Asn
                5515                5520                5525

TCA GAC ACC CAG AAG ACA GAG CTC AAG CTT AAA TGC GGG ACA ACT GCT       6761
Ser Asp Thr Gln Lys Thr Glu Leu Lys Leu Lys Cys Gly Thr Thr Ala
5530                5535                5540                     5545

GAA GAT TTA TTC AGA CAA GCT GAC TTG ATG GTC ATA TTC TCC TAC CTC       6809
Glu Asp Leu Phe Arg Gln Ala Asp Leu Met Val Ile Phe Ser Tyr Leu
                5550                5555                5560

TTA TTT GTT GCG AGA ATT GGG GTG AGT GGA TCT CAT GTG TGT CTG TCA       6857
Leu Phe Val Ala Arg Ile Gly Val Ser Gly Ser His Val Cys Leu Ser
                5565                5570                5575

TAT AAC ATG TTG AAC GTC AAG GAT GTC AAG GAT TTT GAG ATA TGC AGG       6905
Tyr Asn Met Leu Asn Val Lys Asp Val Lys Asp Phe Glu Ile Cys Arg
                5580                5585                5590

GAG AAC GTT CTT GAT TTG TCC AGA AAA ACT ACA ATC GAC GGT GAA GAA       6953
Glu Asn Val Leu Asp Leu Ser Arg Lys Thr Thr Ile Asp Gly Glu Glu
                5595                5600                5605

TGC TAT ATC TGG AAT TTT ATT TCT GAT ATC TTC CCA CGC ATT GTG GCT       7001
```

```
Cys Tyr Ile Trp Asn Phe Ile Ser Asp Ile Phe Pro Arg Ile Val Ala
5610            5615            5620            5625

AAG TAC AAC TGT GTT GTG CTT AAC GAC GGA GAG AAG AGA TAC ATC TTC    7049
Lys Tyr Asn Cys Val Val Leu Asn Asp Gly Glu Lys Arg Tyr Ile Phe
            5630            5635            5640

GTG ACT GAC AGC GCG CCC ACT AGG ATC TTT CCC GAT TTG GCT TGG TCA    7097
Val Thr Asp Ser Ala Pro Thr Arg Ile Phe Pro Asp Leu Ala Trp Ser
            5645            5650            5655

GAT CTT ATT TCC GGC AAG CAA GTT GTG AGT CCA AAC ATT ATC AAA GTG    7145
Asp Leu Ile Ser Gly Lys Gln Val Val Ser Pro Asn Ile Ile Lys Val
            5660            5665            5670

GCT GGA GAA ACC AAG TCG AAA ACC ATT GCC CCT CTG CTA GCA GAT TCC    7193
Ala Gly Glu Thr Lys Ser Lys Thr Ile Ala Pro Leu Leu Ala Asp Ser
            5675            5680            5685

TAC AAG GTT TTC AAG GAT CCG AAG GCA TGG CTT GAG AGG AAC AAA GAA    7241
Tyr Lys Val Phe Lys Asp Pro Lys Ala Trp Leu Glu Arg Asn Lys Glu
5690            5695            5700            5705

TTG AAA GCA GCT CTA GAA ACA GAA GAA TAT ATC GCT CTC CTC TTT GCT    7289
Leu Lys Ala Ala Leu Glu Thr Glu Glu Tyr Ile Ala Leu Leu Phe Ala
            5710            5715            5720

GTT GCA TGT GAA GCT GGT AGA TTC ACT CAA ATT TTA GAC AAA CCT CCC    7337
Val Ala Cys Glu Ala Gly Arg Phe Thr Gln Ile Leu Asp Lys Pro Pro
            5725            5730            5735

AGT AGA CGC AAG ATT TTA AAT ATG TCC GAA AGG TAT AAT GCA TAT ATT    7385
Ser Arg Arg Lys Ile Leu Asn Met Ser Glu Arg Tyr Asn Ala Tyr Ile
            5740            5745            5750

GAA CAG GAA AAA GGG CTG ATT GGG AGA CTT TCT AAA CCA GCA AAG ATA    7433
Glu Gln Glu Lys Gly Leu Ile Gly Arg Leu Ser Lys Pro Ala Lys Ile
            5755            5760            5765

TGC TTA GCC ATA GGA ACT GGA GTT GCG ATC TTT GGG GCC CTA GCA GGC    7481
Cys Leu Ala Ile Gly Thr Gly Val Ala Ile Phe Gly Ala Leu Ala Gly
5770            5775            5780            5785

ATT GGA GTG GGT TTG TTT AAG CTG ATA GCT CAC TTC AAC AAA GAT GAA    7529
Ile Gly Val Gly Leu Phe Lys Leu Ile Ala His Phe Asn Lys Asp Glu
            5790            5795            5800

GAA GAG GTA GAC GAA ATT GAA TTT GAT ATA CTC TCC CCA GAG ATG AGC    7577
Glu Glu Val Asp Glu Ile Glu Phe Asp Ile Leu Ser Pro Glu Met Ser
            5805            5810            5815

GGT TCG CAC GAA TCC GGC CAA CAT ACC ACG AGG TAC GTC ACG AAG GAG    7625
Gly Ser His Glu Ser Gly Gln His Thr Thr Arg Tyr Val Thr Lys Glu
            5820            5825            5830

CGA GTT CCA TCC AAA CCA GCA AGG AGG CAA CAT GAA TTT GAT CTA ATG    7673
Arg Val Pro Ser Lys Pro Ala Arg Arg Gln His Glu Phe Asp Leu Met
            5835            5840            5845

TTC GAT AAT CTA CCC ACT CCA CAA GTT GAA GAG CTA AAG AGT GAG ATG    7721
Phe Asp Asn Leu Pro Thr Pro Gln Val Glu Glu Leu Lys Ser Glu Met
5850            5855            5860            5865

ACC TGC GCC AGT GCC AGT GAT GAG CAT AAG ACT CAG TAT GTT AAA AGA    7769
Thr Cys Ala Ser Ala Ser Asp Glu His Lys Thr Gln Tyr Val Lys Arg
            5870            5875            5880

AGA GTG GGA CCT GTA AGC AAA CGT AAG GAT GCT TCG GTA GCA GAA ATT    7817
Arg Val Gly Pro Val Ser Lys Arg Lys Asp Ala Ser Val Ala Glu Ile
            5885            5890            5895

AGT GGA GCT CAT GCG AGT GAT CAG CAT CAT ACA GAA TAC TTG AAA GCA    7865
Ser Gly Ala His Ala Ser Asp Gln His His Thr Glu Tyr Leu Lys Ala
            5900            5905            5910

CGC GTT CCA CTC ATG AAA AGA ATA GCT ACC AAA GAG AGC TAT GTT GTA    7913
Arg Val Pro Leu Met Lys Arg Ile Ala Thr Lys Glu Ser Tyr Val Val
            5915            5920            5925

ACT TAC GAT GAC GAA CCC AGC TCT CAT ATT TCC CTA GTT CGC AGG ATC    7961
```

| | | | | | | | | | | | | | | | | |
|---|---|---|---|---|---|---|---|---|---|---|---|---|---|---|---|---|
| Thr | Tyr | Asp | Asp | Glu | Pro | Ser | Ser | His | Ile | Ser | Leu | Val | Arg | Arg | Ile | |
| 5930 | | | | 5935 | | | | 5940 | | | | | | 5945 | | |

```
CGA CGT ACA CGA CTG GCA AGA GCC ATC AAG CAA ATG GCA GTC CTG GAG       8009
Arg Arg Thr Arg Leu Ala Arg Ala Ile Lys Gln Met Ala Val Leu Glu
         5950                5955                5960

GAC TTC CCA TCT ACC TTG GAA GAG ATA CGA CTT TGG AGA CAA AAC GCT       8057
Asp Phe Pro Ser Thr Leu Glu Glu Ile Arg Leu Trp Arg Gln Asn Ala
             5965                5970                5975

GCA AAT AAA GGG GTT ATT GTT CCG AAG TAC TCA ACA AGT GGG AAA TTC       8105
Ala Asn Lys Gly Val Ile Val Pro Lys Tyr Ser Thr Ser Gly Lys Phe
                 5980                5985                5990

TTC AGT GGC TTG TTG GAT GAT GAA GAA GAA GAA CCT CAG AAT GTG AAT       8153
Phe Ser Gly Leu Leu Asp Asp Glu Glu Glu Glu Pro Gln Asn Val Asn
         5995                6000                6005

ATG TTG AAC GAA GAG GAC ATT GAG GTA GAT AAG CGA ATG TTT GAG AAG       8201
Met Leu Asn Glu Glu Asp Ile Glu Val Asp Lys Arg Met Phe Glu Lys
6010                6015                6020                6025

ATT TCT GAG GTT ATA AGC GTG ATT CAA CCC AGA AAG AAT GAG CTG GAA       8249
Ile Ser Glu Val Ile Ser Val Ile Gln Pro Arg Lys Asn Glu Leu Glu
                 6030                6035                6040

AGA ATG ATT GAG GAA GGC GTA CAC CAC AAG GTC GTA AAG CAG GCA AGG       8297
Arg Met Ile Glu Glu Gly Val His His Lys Val Val Lys Gln Ala Arg
             6045                6050                6055

GTT AAC GAC AAG GGC TTA GCC AAA GAC CCC AAC ATG GTG ACT ATC TTG       8345
Val Asn Asp Lys Gly Leu Ala Lys Asp Pro Asn Met Val Thr Ile Leu
         6060                6065                6070

ACG GAC AAA TTA ATT AAT ATT AGT GCG GTG ATC GTC AAT TTA ACG CCG       8393
Thr Asp Lys Leu Ile Asn Ile Ser Ala Val Ile Val Asn Leu Thr Pro
     6075                6080                6085

ACA CGC CGG GCA TAC ATG AAC GTG GTA CGT CTT ATA GGC ACT ATA GTT       8441
Thr Arg Arg Ala Tyr Met Asn Val Val Arg Leu Ile Gly Thr Ile Val
6090                6095                6100                6105

GTT TGC CCA GCC CAC TAC TTG GAA GCT TTA GAG GAA GGA GAT GAG CTG       8489
Val Cys Pro Ala His Tyr Leu Glu Ala Leu Glu Glu Gly Asp Glu Leu
             6110                6115                6120

TAT TTC ATT TGC TTC TCA TTG GTT ATC AAG CTC ACT TTT GAT CCA AGT       8537
Tyr Phe Ile Cys Phe Ser Leu Val Ile Lys Leu Thr Phe Asp Pro Ser
         6125                6130                6135

AGA GTG ACT CTC GTG AAT AGC CAG CAG GAT TTG ATG GTT TGG GAT CTT       8585
Arg Val Thr Leu Val Asn Ser Gln Gln Asp Leu Met Val Trp Asp Leu
     6140                6145                6150

GGG AAC ATG GTA CCA CCC TCA ATT GAT ACT CTT AAA ATG ATA CCT ACG       8633
Gly Asn Met Val Pro Pro Ser Ile Asp Thr Leu Lys Met Ile Pro Thr
         6155                6160                6165

CTT GAA GAC TGG GAT CAC TTT CAG GAT GGA CCA GGA GCC TTT GCT GTT       8681
Leu Glu Asp Trp Asp His Phe Gln Asp Gly Pro Gly Ala Phe Ala Val
6170                6175                6180                6185

ACG AAA TAT AAC TCG AAA TTC CCA ACC AAT TAT ATC AAC ACA CTG ACT       8729
Thr Lys Tyr Asn Ser Lys Phe Pro Thr Asn Tyr Ile Asn Thr Leu Thr
             6190                6195                6200

ATG ATT GAG AGG ATT AGG GCA AAT ACT CAG AAT CCC ACG GGT TGT TAT       8777
Met Ile Glu Arg Ile Arg Ala Asn Thr Gln Asn Pro Thr Gly Cys Tyr
         6205                6210                6215

TCC ATG ATG GGC TCC CAA CAT ACA ATC ACC ACA GGA TTG CGA TAT CAA       8825
Ser Met Met Gly Ser Gln His Thr Ile Thr Thr Gly Leu Arg Tyr Gln
     6220                6225                6230

ATG TTC TCT CTT GAT GGA TTC TGC GGT GGG TTA ATC CTG AGA GCC AGC       8873
Met Phe Ser Leu Asp Gly Phe Cys Gly Gly Leu Ile Leu Arg Ala Ser
         6235                6240                6245

ACA AAC ATG GTG AGA AAG GTC GTC GGG ATC CAC GTT GCT GGA AGC CAG       8921
```

|  |  |
|---|---|
| Thr Asn Met Val Arg Lys Val Val Gly Ile His Val Ala Gly Ser Gln<br>6250                   6255                   6260                   6265 |  |
| AAT CAC GCT ATG GGA TAT GCA GAG TGC CTT ATT GCA GAA GAT TTA CGG<br>Asn His Ala Met Gly Tyr Ala Glu Cys Leu Ile Ala Glu Asp Leu Arg<br>                 6270                   6275                   6280 | 8969 |
| GCT GCA GTG GCG AGA TTG GCG CTA GAT CCT AGA AGC ACC ATC CAG GCA<br>Ala Ala Val Ala Arg Leu Ala Leu Asp Pro Arg Ser Thr Ile Gln Ala<br>                 6285                   6290                   6295 | 9017 |
| AGT CTG AAA GGT AGG ATT GAT GCT GTT TCT AAA CAA TGT GGT TTA GAC<br>Ser Leu Lys Gly Arg Ile Asp Ala Val Ser Lys Gln Cys Gly Leu Asp<br>          6300                   6305                   6310 | 9065 |
| AGA GCT CTG GGT ACG ATA GGA TGT CAC GGG AAA GTT GCC TCT GAA GAT<br>Arg Ala Leu Gly Thr Ile Gly Cys His Gly Lys Val Ala Ser Glu Asp<br>          6315                   6320                   6325 | 9113 |
| ATT ACA AGT GCC GCC ACG AAA ACT TCC ATA AGA AAG TCA AGA ATA CAT<br>Ile Thr Ser Ala Ala Thr Lys Thr Ser Ile Arg Lys Ser Arg Ile His<br>6330                   6335                   6340                   6345 | 9161 |
| GGT CTA GTG GGT GAG ATT AGA ACT GAG CCT TCA ATT TTA CAC GCT CAT<br>Gly Leu Val Gly Glu Ile Arg Thr Glu Pro Ser Ile Leu His Ala His<br>                 6350                   6355                   6360 | 9209 |
| GAT CCC CGA CTG CCT AAA GAC AAG ATT GGG AAA TGG GAC CCG GTT ATT<br>Asp Pro Arg Leu Pro Lys Asp Lys Ile Gly Lys Trp Asp Pro Val Ile<br>          6365                   6370                   6375 | 9257 |
| GAG GCA TCA ATG AAG TAT GGT TCG AGA ATC ACA CCG TTC CCT GTA GAC<br>Glu Ala Ser Met Lys Tyr Gly Ser Arg Ile Thr Pro Phe Pro Val Asp<br>                 6380                   6385                   6390 | 9305 |
| CAA ATT CTG GAA GTG GAG GAT CAT CTT TCT AAA ATG TTG GCC AAT TGT<br>Gln Ile Leu Glu Val Glu Asp His Leu Ser Lys Met Leu Ala Asn Cys<br>          6395                   6400                   6405 | 9353 |
| GAG AAT TCA AAA AAC AAG CGG CAG GTT AAT AAT CTA GAA ATA GGG ATT<br>Glu Asn Ser Lys Asn Lys Arg Gln Val Asn Asn Leu Glu Ile Gly Ile<br>6410                   6415                   6420                   6425 | 9401 |
| AAT GGA ATT GAC CAG TCG GAT TAT TGG CAA CAG ATA GAA ATG GAT ACT<br>Asn Gly Ile Asp Gln Ser Asp Tyr Trp Gln Gln Ile Glu Met Asp Thr<br>                 6430                   6435                   6440 | 9449 |
| TCA AGT GGT TGG CCA TAC GCT AAG CGT AAA CCT GTT GGG GCA GCT GGA<br>Ser Ser Gly Trp Pro Tyr Ala Lys Arg Lys Pro Val Gly Ala Ala Gly<br>          6445                   6450                   6455 | 9497 |
| AAG AAA TGG CTA TTC GAG CAA GAC GGC ACA TAT CCC TCC GGA AAA CCT<br>Lys Lys Trp Leu Phe Glu Gln Asp Gly Thr Tyr Pro Ser Gly Lys Pro<br>          6460                   6465                   6470 | 9545 |
| CGA TAT GTA TTT GGA GAT GCC GGG TTG ATT GAG AGC TAT AAC TCG ATG<br>Arg Tyr Val Phe Gly Asp Ala Gly Leu Ile Glu Ser Tyr Asn Ser Met<br>          6475                   6480                   6485 | 9593 |
| CTT GGT GAG GCG AAG CAA GGC ATT AGT CCC ACT GTC GTC ACA ATT GAG<br>Leu Gly Glu Ala Lys Gln Gly Ile Ser Pro Thr Val Val Thr Ile Glu<br>6490                   6495                   6500                   6505 | 9641 |
| TGC GCA AAA GAT GAG AGG CGG AAG CTT AAT AAG ATA TAT GAG AAA CCC<br>Cys Ala Lys Asp Glu Arg Arg Lys Leu Asn Lys Ile Tyr Glu Lys Pro<br>                 6510                   6515                   6520 | 9689 |
| GCC ACT CGG ACG TTC ACC ATA CTG CCA CCT GAG ATT AAT ATT TTA TTC<br>Ala Thr Arg Thr Phe Thr Ile Leu Pro Pro Glu Ile Asn Ile Leu Phe<br>          6525                   6530                   6535 | 9737 |
| AGG CAG TAT TTC GGA GAT TTT GCA GCG ATG GTA ATG ACA TGT AGA GCC<br>Arg Gln Tyr Phe Gly Asp Phe Ala Ala Met Val Met Thr Cys Arg Ala<br>          6540                   6545                   6550 | 9785 |
| AAG CTT TTC TGT CAA GTT GGC ATC AAC CCA GAG TCA ATG GAG TGG GGT<br>Lys Leu Phe Cys Gln Val Gly Ile Asn Pro Glu Ser Met Glu Trp Gly<br>          6555                   6560                   6565 | 9833 |
| GAT CTC ATG CTA GGT CTA AAG GAG AAA TCA ACT AAG GGA TTT GCA GGA | 9881 |

```
Asp  Leu  Met  Leu  Gly  Leu  Lys  Glu  Lys  Ser  Thr  Lys  Gly  Phe  Ala  Gly
6570                6575                6580                          6585

GAT  TAT  TCG  AAG  TTC  GAT  GGA  ATC  GGA  GAC  CCC  CAG  ATT  TAT  CAT  TCA      9929
Asp  Tyr  Ser  Lys  Phe  Asp  Gly  Ile  Gly  Asp  Pro  Gln  Ile  Tyr  His  Ser
               6590                6595                          6600

ATT  ACC  CAA  GTA  GTC  AAC  AAC  TGG  TAT  AAC  GAT  GGG  GAA  GAA  AAT  GCG      9977
Ile  Thr  Gln  Val  Val  Asn  Asn  Trp  Tyr  Asn  Asp  Gly  Glu  Glu  Asn  Ala
                    6605                6610                     6615

ACT  ATC  AGG  CAT  GCT  CTG  ATA  AGT  AGC  ATT  ATA  CAC  AGG  CGG  GGC  ATT      10025
Thr  Ile  Arg  His  Ala  Leu  Ile  Ser  Ser  Ile  Ile  His  Arg  Arg  Gly  Ile
               6620                6625                          6630

GTG  AAA  GAA  TAT  TTG  TTC  CAG  TAT  TGC  CAG  GGT  ATG  CCA  TCA  GGG  TTC      10073
Val  Lys  Glu  Tyr  Leu  Phe  Gln  Tyr  Cys  Gln  Gly  Met  Pro  Ser  Gly  Phe
               6635                6640                          6645

GCC  ATG  ACA  GTG  ATA  TTC  AAT  TCG  TTT  ATG  AAC  TAT  TAT  TAT  CTG  TCT      10121
Ala  Met  Thr  Val  Ile  Phe  Asn  Ser  Phe  Met  Asn  Tyr  Tyr  Tyr  Leu  Ser
6650                6655                6660                          6665

TTG  GCC  TGG  ATG  AAT  CTG  ATA  AGT  GCA  TCC  CCC  CTT  AGT  CCA  CAA  GCT      10169
Leu  Ala  Trp  Met  Asn  Leu  Ile  Ser  Ala  Ser  Pro  Leu  Ser  Pro  Gln  Ala
               6670                6675                          6680

TCT  TTG  AGA  TAT  TTT  GAT  GAG  TAT  TGT  AAG  GTC  ATT  GTT  TAC  GGT  GAT      10217
Ser  Leu  Arg  Tyr  Phe  Asp  Glu  Tyr  Cys  Lys  Val  Ile  Val  Tyr  Gly  Asp
               6685                6690                          6695

GAT  AAT  ATT  GTT  GCC  GTC  AAC  GAA  GAA  TTC  TTA  GAG  TAC  TAT  AAC  TTG      10265
Asp  Asn  Ile  Val  Ala  Val  Asn  Glu  Glu  Phe  Leu  Glu  Tyr  Tyr  Asn  Leu
               6700                6705                          6710

AGG  CTT  GTG  GCA  GGC  TAT  CTT  AGT  CAA  TTT  GGA  GTA  AGC  TAC  ACT  GAT      10313
Arg  Leu  Val  Ala  Gly  Tyr  Leu  Ser  Gln  Phe  Gly  Val  Ser  Tyr  Thr  Asp
               6715                6720                          6725

GAC  GCC  AAG  AAC  CCA  ATA  GAG  AAG  AGC  GAA  CGA  TAT  GTG  AAG  ATA  GAA      10361
Asp  Ala  Lys  Asn  Pro  Ile  Glu  Lys  Ser  Glu  Arg  Tyr  Val  Lys  Ile  Glu
6730                6735                6740                          6745

GAC  GTT  ACG  TTC  TTA  AAA  CGG  CGA  TGG  GTG  AGT  CTT  GGC  GGT  AGA  GCT      10409
Asp  Val  Thr  Phe  Leu  Lys  Arg  Arg  Trp  Val  Ser  Leu  Gly  Gly  Arg  Ala
               6750                6755                          6760

TCG  ATG  CTG  TAC  AAA  GCT  CCG  CTT  GAC  AAG  GTT  AGC  ATT  GAG  GAA  AGG      10457
Ser  Met  Leu  Tyr  Lys  Ala  Pro  Leu  Asp  Lys  Val  Ser  Ile  Glu  Glu  Arg
               6765                6770                          6775

CTT  AAC  TGG  ATC  AGA  GAG  TGT  GAC  GAT  GGG  GAA  CTA  GCT  CTG  GTG  CAG      10505
Leu  Asn  Trp  Ile  Arg  Glu  Cys  Asp  Asp  Gly  Glu  Leu  Ala  Leu  Val  Gln
               6780                6785                          6790

AAC  ATT  GAA  AGT  GCT  CTG  TAC  GAA  GCT  AGT  ATT  CAT  GGC  CAC  ACA  TAT      10553
Asn  Ile  Glu  Ser  Ala  Leu  Tyr  Glu  Ala  Ser  Ile  His  Gly  His  Thr  Tyr
6795                6800                6805

TTT  GGA  GAG  CTT  AAA  GAT  AAA  ATT  GCT  AAA  GCC  TGT  GAT  GCA  GTC  ATG      10601
Phe  Gly  Glu  Leu  Lys  Asp  Lys  Ile  Ala  Lys  Ala  Cys  Asp  Ala  Val  Met
6810                6815                6820                          6825

ATA  ACT  ATG  CCA  AAT  ATA  AGA  TAT  ATT  GAC  TGC  CAG  AGA  CGA  TGG  TGG      10649
Ile  Thr  Met  Pro  Asn  Ile  Arg  Tyr  Ile  Asp  Cys  Gln  Arg  Arg  Trp  Trp
               6830                6835                          6840

ACC  TCC  ATG  ACT  GGT  GGG  TAT  CTT  GAG  CCG  TCT  GAT  GTC  ACC  AAA  CTT      10697
Thr  Ser  Met  Thr  Gly  Gly  Tyr  Leu  Glu  Pro  Ser  Asp  Val  Thr  Lys  Leu
               6845                6850                          6855

GTA  AGG  CTT  GTT  GAG  AAA  GGA  CTA  CTA  GAC  CCG  AAA  TCA  GTA  TGG  AAA      10745
Val  Arg  Leu  Val  Glu  Lys  Gly  Leu  Leu  Asp  Pro  Lys  Ser  Val  Trp  Lys
               6860                6865                          6870

GAC  CCA  TTG  TAC  AGA  ACC  AAC  AAG  TTG  CTA  TTC  GAC  CTA  TTG  AGG  GAG      10793
Asp  Pro  Leu  Tyr  Arg  Thr  Asn  Lys  Leu  Leu  Phe  Asp  Leu  Leu  Arg  Glu
               6875                6880                          6885

GTT  AAG  GCA  GCA  CCC  CTG  GCC  GCA  TTT  GTG  GTC  TAAGTTACCC  TTCTGACAAA      10846
```

| | | | | | | | | | |
|---|---|---|---|---|---|---|---|---|---|
| Val | Lys | Ala | Ala | Pro | Leu | Ala | Ala | Phe | Val | Val |
| 6890 | | | | 6895 | | | | | 6900 |

```
AGGGCCTTGA ACGGTTATGG TTGAACAGAA CTGTAAAAGG TGAGGACTAT ATAAGTTGTA    10906
GTACGGATGA GATTGAAAGA AAATTGGGTC ACTCCCATTC CTTTATTAGG AAGGAGTGAT    10966
ACCTTTTGTG TAGATCTCTA CCCCGAAACT CTTGAACCCT CACACGTTTT GGAGTAACCA    11026
GTACACCCTT TTAGGTGGAC CCTCGACTAT AGATCGAGAC CAAGTATTGA CTTGGTGTTC    11086
ACGTCTTGCC GGACGCAAAA TGGCACCCTT GTTAGTGAT ATCAAGGTTA CAAATGTCAC    11146
GCCCCACTAG TAAAAGTTTT GGTATATACG CATTCGAACC GCCAATGTAT ACGTGTTTTC    11206
CCTTTTACTT TTTGTATGTC GTCGTGGTGA CGAGATGCAC GCCTGGTCAG CGGGGAATAA    11266
GTTCACTATA TGAACAGACT CCGGCGAGCG AGACACGCTG TCGGCCTCGG GAGAGGGAAC    11326
TAGCTCCAGG CACTTAAATC CTGAAGTGTT AGAACTAAGC GTTTGATCCT CCTCCGGGGG    11386
AAAGAGAACG CCAGTTCTTT AAGCCATAAC TCTAGTGAGT TGAATCCTAT TCATCCTTCT    11446
TAGGATTAAG GATTTCTGAA GTCTATCATG AAAAGTAGAT AGAAAGCAAC ACGTCAATAA    11506
CGTGGAACCT TTTCCGAGGA AGTAGGGTGC TTGTTCGAAA ATCATGGTAG ATTCGGAAAC    11566
AATTTGCTTA GAGTGTGTCT TTTCGCGTTG GTAGTTCAAC CGTTAGGGCT AGGCACACTT    11626
CTCCACGGGT TTGTGCTGCA GTATTAAATA TCATTAAGGT ACTGTGCTAT AGCGGAGAAA    11686
TTACAAAGCG TTGAACACAT TGACGATGGG GCCCAATGCG CACCCGGATG TGTTACGCAC    11746
CGTTTTCTC TGTGTCACTA TAGATAAAAG TGGGGTAGC                           11785
```

( 2 ) INFORMATION FOR SEQ ID NO:4:

( i ) SEQUENCE CHARACTERISTICS:
        ( A ) LENGTH: 3457 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| | | | | | | | | | | | | | | |
|---|---|---|---|---|---|---|---|---|---|---|---|---|---|---|
| Met | Met | Gln | Thr | Asn | Asn | Asn | Gln | Asn | Pro | Thr | Gln | Gly | Ser | Ile | Pro |
| 1 | | | | 5 | | | | | 10 | | | | | 15 | |
| Glu | Asn | Ser | Ser | Gln | Asp | Arg | Asn | Leu | Gly | Val | Pro | Ala | Gly | Tyr | Ser |
| | | | 20 | | | | | 25 | | | | | 30 | | |
| Leu | Ser | Val | Glu | Asp | Pro | Phe | Gly | Asn | Arg | Ser | Asp | Phe | His | Ile | Pro |
| | | | 35 | | | | | 40 | | | | | 45 | | |
| Val | His | Gln | Ile | Ile | Arg | Glu | Ile | Asp | Arg | Pro | Asn | Trp | Val | Pro |
| | | 50 | | | | | 55 | | | | | 60 | | | |
| Ile | Cys | Ser | Asn | Asp | Phe | His | Leu | Asn | Ser | Glu | Asp | Tyr | Cys | Glu | Glu |
| 65 | | | | | 70 | | | | | 75 | | | | | 80 |
| Cys | Glu | Ser | Glu | Arg | Ile | Lys | Asn | Phe | Glu | Ile | Phe | Arg | Ser | Gln | Asn |
| | | | | 85 | | | | | 90 | | | | | 95 | |
| Leu | Ile | Asp | Gln | His | Leu | Asn | Leu | Cys | Thr | Asp | Ser | Lys | Asp | Cys | Asp |
| | | | 100 | | | | | 105 | | | | | 110 | | |
| His | Phe | Ser | Cys | Phe | Ser | Thr | Ser | Thr | Ser | Cys | Arg | Phe | Cys | Pro | Phe |
| | | 115 | | | | | 120 | | | | | 125 | | | |
| Cys | Leu | Phe | Ile | Phe | Asn | Leu | Asp | Lys | Phe | Tyr | Lys | Gln | Asn | Leu | Tyr |
| | 130 | | | | | 135 | | | | | 140 | | | | |
| Leu | Ile | Ser | Arg | Gln | Ala | Leu | Ala | Arg | Leu | Phe | His | Gly | Ser | Ala | Glu |
| 145 | | | | | 150 | | | | | 155 | | | | | 160 |
| Glu | Leu | Leu | Ser | Arg | Ala | Ile | Phe | Phe | Thr | Tyr | Asn | Ile | Cys | Ile | Asp |
| | | | | 165 | | | | | 170 | | | | | 175 | |

-continued

| | | | | | | | | | | | | | | |
|---|---|---|---|---|---|---|---|---|---|---|---|---|---|---|
| Ala | Glu | Val | Val<br>180 | Ala | Asn | Asn | Arg | Ile<br>185 | Gly | Cys | Glu | Tyr | Val<br>190 | Lys | Leu |
| Phe | His | Pro<br>195 | Asp | Leu | Arg | Pro | Ser<br>200 | Ile | Thr | Ser | Pro | Pro<br>205 | Tyr | Ala | Ser |
| Asp | Trp<br>210 | Val | Met | Cys | Asp | Asn<br>215 | Ala | Lys | His | Leu | Phe<br>220 | Glu | Cys | Leu | Gly |
| Leu<br>225 | Gly | Asp | Thr | Thr | Arg<br>230 | Gly | His | Leu | Tyr | Gly<br>235 | Leu | Ile | Ser | Glu | Asn<br>240 |
| Ala | Tyr | Trp | Asn | Ala<br>245 | Thr | Cys | Ser | Lys | Cys<br>250 | Gly | Ala | Cys | Cys | Gln<br>255 | Gly |
| Ala | Asn | Ala | Arg<br>260 | Thr | Ala | Ile | Pro | Ile<br>265 | Val | Met | Ala | Leu | Gln<br>270 | Tyr | Cys |
| Arg | Val | Asp<br>275 | Val | Tyr | Tyr | Ser | Glu<br>280 | Tyr | Tyr | Leu | Tyr | His<br>285 | Ile | Tyr | Ala |
| Pro | Glu<br>290 | Glu | Arg | Met | Lys | Ile<br>295 | Asp | Gln | Gln | Thr | Ala<br>300 | His | Leu | Leu | His |
| Ser<br>305 | Ile | Ile | Arg | Gly | Ala<br>310 | Pro | Ala | Val | Asp | Cys<br>315 | Ser | Glu | Leu | Ser | Gln<br>320 |
| Glu | Pro | Ile | His | Arg<br>325 | Met | Val | Met | Asp | Ser<br>330 | Lys | Leu | Val | Ala<br>335 | Leu |
| Asp | Ser | Thr | Ile<br>340 | Arg | His | Pro | Lys | Ser<br>345 | Gln | Gly | Ser | Leu | Leu<br>350 | Asp | Ser |
| Glu | Cys | Asp<br>355 | His | Glu | Phe | Ile | Leu<br>360 | Arg | Thr | Ser | His | Gly<br>365 | Ile | Lys | Ile |
| Pro | Met<br>370 | Ser | Lys | Ser | Leu | Phe<br>375 | Ile | Ser | Phe | Leu | Thr<br>380 | Met | Gly | Ala | Tyr |
| His<br>385 | Gly | Tyr | Ala | His | Asp<br>390 | Asp | Gln | Gln | Glu | Gln<br>395 | Asn | Ala | Ile | Ile | Ser<br>400 |
| Phe | Gly | Gly | Met | Pro<br>405 | Gly | Val | Asn | Leu | Ala<br>410 | Cys | Asn | Lys | Asn | Phe<br>415 | Leu |
| Arg | Met | His | Lys<br>420 | Leu | Phe | Tyr | Ser | Gly<br>425 | Ser | Phe | Arg | Arg | Pro<br>430 | Leu |
| Phe | Met | Ser<br>435 | Gln | Ile | Pro | Ser | Thr<br>440 | Asn | Ala | Thr | Ala | Gln<br>445 | Ser | Gly | Phe |
| Asn | Asp<br>450 | Glu | Glu | Phe | Glu | Arg<br>455 | Leu | Met | Ala | Glu | Gly<br>460 | Val | His | Val |
| Lys<br>465 | Val | Glu | Arg | Pro | Ile<br>470 | Ala | Glu | Arg | Phe | Asp<br>475 | Tyr | Glu | Asp | Val | Ile<br>480 |
| Asp | Ile | Tyr | Asp | Glu<br>485 | Thr | Asp | His | Asp | Arg<br>490 | Thr | Arg | Ala | Leu | Gly<br>495 | Leu |
| Gly | Gln | Val | Phe<br>500 | Gly | Gly | Leu | Leu | Lys<br>505 | Gly | Ile | Ser | His | Cys<br>510 | Val | Asp |
| Ser | Leu | His<br>515 | Lys | Val | Phe | Asp | Phe<br>520 | Pro | Leu | Asp | Leu | Ala<br>525 | Ile | Glu | Ala |
| Ala | Gln | Lys<br>530 | Thr | Gly | Asp | Trp | Leu<br>535 | Glu | Gly | Asn | Lys | Ala<br>540 | Ala | Val | Asp |
| Glu<br>545 | Thr | Lys | Ile | Cys | Val<br>550 | Gly | Cys | Pro | Glu | Ile<br>555 | Gln | Lys | Asp | Met | Ile<br>560 |
| Ser | Phe | Gln | Asn | Glu<br>565 | Thr | Lys | Glu | Ala | Phe<br>570 | Glu | Leu | Ile | Arg | Ser<br>575 | Ser |
| Ile | Lys | Lys | Leu<br>580 | Ser | Glu | Gly | Ile<br>585 | Asp | Lys | Ile | Thr | Lys<br>590 | Met | Asn | Ala |
| Thr | Asn | Phe<br>595 | Glu | Arg | Ile | Leu | Asp<br>600 | Gly | Ile | Lys | Pro | Ile<br>605 | Glu | Ser | Arg |

```
Leu  Thr  Glu  Leu  Glu  Asn  Lys  Ala  Pro  Ala  Ser  Asp  Ser  Lys  Ala  Met
     610                 615                 620

Glu  Ala  Leu  Val  Gln  Ala  Val  Lys  Asp  Leu  Lys  Ile  Met  Lys  Glu  Ala
625                      630                 635                           640

Met  Leu  Asp  Leu  Asn  Arg  Arg  Leu  Ser  Lys  Leu  Glu  Gly  Lys  Lys  Ser
               645                      650                           655

Asp  Gly  Gln  Thr  Thr  Glu  Gly  Thr  Ala  Gly  Glu  Gln  Gln  Pro  Ile  Pro
               660                 665                      670

Lys  Thr  Pro  Thr  Arg  Val  Lys  Ala  Arg  Pro  Val  Val  Lys  Gln  Ser  Gly
          675                 680                      685

Thr  Ile  Met  Val  Asn  Glu  Glu  Ser  Thr  Glu  Thr  Phe  Arg  Asp  Asn  Glu
     690                 695                      700

Ser  Arg  Val  Thr  Asp  Pro  Asn  Arg  Ser  Asp  Met  Phe  Ala  Ala  Val  Thr
705                      710                 715                           720

Ala  Glu  Tyr  Leu  Val  Lys  Ser  Phe  Thr  Trp  Lys  Val  Ser  Asp  Gly  Gln
                    725                 730                      735

Asp  Lys  Val  Leu  Ala  Asp  Leu  Asp  Leu  Pro  Gln  Asp  Leu  Trp  Lys  Ser
               740                 745                      750

Asn  Ser  Arg  Leu  Ser  Asp  Ile  Met  Gly  Tyr  Phe  Gln  Tyr  Tyr  Asp  Ala
          755                 760                      765

Thr  Gly  Ile  Thr  Phe  Arg  Ile  Thr  Thr  Thr  Cys  Val  Pro  Met  His  Gly
770                           775                 780

Gly  Thr  Leu  Cys  Ala  Ala  Trp  Asp  Ala  Asn  Gly  Cys  Ala  Thr  Arg  Gln
785                      790                 795                           800

Gly  Ile  Ala  Thr  Thr  Val  Gln  Leu  Thr  Gly  Leu  Pro  Lys  Thr  Phe  Ile
               805                 810                      815

Glu  Ala  His  Ser  Ser  Ser  Glu  Thr  Ile  Ile  Val  Val  Lys  Asn  Ser  Asn
               820                 825                      830

Ile  Gln  Ser  Ala  Ile  Cys  Leu  Ser  Gly  Ser  Glu  His  Ser  Phe  Gly  Arg
               835                 840                      845

Met  Gly  Ile  Leu  Lys  Ile  Cys  Cys  Leu  Asn  Thr  Leu  Asn  Ala  Pro  Lys
     850                 855                      860

Glu  Ala  Thr  Gln  Gln  Val  Ala  Val  Asn  Val  Trp  Ile  Lys  Phe  Asp  Gly
865                      870                 875                           880

Val  Lys  Phe  His  Val  Tyr  Ser  Leu  Arg  Lys  Asn  Pro  Val  Val  Ser  Gln
               885                      890                      895

Leu  Gln  Val  Ala  Ser  Leu  Thr  Asp  Ile  Gly  Glu  Leu  Ser  Ser  Val  Val
               900                 905                      910

Ala  Thr  Gly  Ser  Trp  Ser  Thr  Thr  Ser  Ala  Thr  Asn  Leu  Met  Glu  Leu
               915                 920                      925

Asn  Ile  His  Pro  Thr  Ser  Cys  Ala  Ile  Gln  Asn  Gly  Leu  Ile  Thr  Gln
930                           935                 940

Thr  Pro  Leu  Ser  Val  Leu  Ala  His  Ala  Phe  Ala  Arg  Trp  Arg  Gly  Ser
945                      950                 955                           960

Leu  Lys  Ile  Ser  Ile  Ile  Phe  Gly  Ala  Ser  Leu  Phe  Thr  Arg  Gly  Arg
               965                 970                      975

Ile  Leu  Ala  Ala  Ala  Val  Pro  Val  Ala  Lys  Arg  Lys  Gly  Thr  Met  Ser
               980                 985                      990

Leu  Asp  Glu  Ile  Ser  Gly  Tyr  His  Asn  Val  Cys  Cys  Leu  Leu  Asn  Gly
          995                 1000                     1005

Gln  Gln  Thr  Thr  Phe  Glu  Leu  Glu  Ile  Pro  Tyr  Tyr  Ser  Val  Gly  Gln
     1010                     1015                     1020

Asp  Ser  Phe  Val  Tyr  Arg  Asp  Ala  Leu  Phe  Asp  Ile  Ser  Ala  His  Asp
```

-continued

```
   1025                1030                1035                1040
Gly  Asn  Phe  Met  Ile  Thr  Arg  Leu  His  Leu  Val  Ile  Leu  Asp  Lys  Leu
                    1045                1050                1055
Val  Met  Ser  Ala  Asn  Ala  Ser  Asn  Ser  Ile  Asn  Phe  Ser  Val  Thr  Leu
                    1060                1065                1070
Gly  Pro  Gly  Ser  Asp  Leu  Glu  Leu  Lys  Tyr  Leu  Ala  Gly  Val  His  Gly
                    1075                1080                1085
Gln  Arg  Ile  Val  Arg  Glu  Leu  Lys  Met  Gln  Val  Ser  Leu  Gly  Arg  Ser
                    1090                1095                1100
Phe  Glu  Asn  Gly  Val  Leu  Ile  Gly  Ser  Gly  Phe  Asp  Asp  Leu  Leu  Gln
1105                     1110                1115                     1120
Arg  Trp  Ser  His  Leu  Val  Ser  Met  Pro  Phe  Asn  Ala  Lys  Gly  Asp  Ser
                    1125                1130                1135
Asp  Glu  Ile  Gln  Val  Phe  Gly  Tyr  Ile  Met  Thr  Val  Ala  Pro  Ala  Tyr
                    1140                1145                1150
Arg  Ser  Leu  Pro  Val  His  Cys  Thr  Leu  Leu  Ser  Trp  Phe  Ser  Gln  Leu
                    1155                1160                1165
Phe  Val  Gln  Trp  Lys  Gly  Gly  Ile  Lys  Tyr  Arg  Leu  His  Ile  Asp  Ser
                    1170                1175                1180
Glu  Glu  Arg  Arg  Trp  Gly  Gly  Phe  Ile  Lys  Val  Trp  His  Asp  Pro  Asn
1185                     1190                1195                     1200
Gly  Ser  Leu  Asp  Glu  Gly  Lys  Glu  Phe  Ala  Lys  Ala  Asp  Ile  Leu  Ser
                    1205                1210                1215
Pro  Pro  Ala  Gly  Ala  Met  Val  Arg  Tyr  Trp  Asn  Tyr  Leu  Asn  Gly  Asp
                    1220                1225                1230
Leu  Glu  Phe  Thr  Val  Pro  Phe  Cys  Ala  Arg  Thr  Ser  Thr  Leu  Phe  Ile
                    1235                1240                1245
Pro  Lys  Ala  Met  Ile  Ala  Thr  Asp  Ser  Lys  Ser  Trp  Ile  Leu  Asn  Tyr
                    1250                1255                1260
Asn  Gly  Thr  Leu  Asn  Phe  Ala  Tyr  Gln  Gly  Val  Asp  Asp  Phe  Thr  Ile
1265                     1270                1275                     1280
Thr  Val  Glu  Thr  Ser  Ala  Ala  Asp  Asp  Phe  Glu  Phe  His  Val  Arg  Thr
                    1285                1290                1295
Val  Ala  Pro  Arg  Ala  Gly  Lys  Val  Asn  Glu  Ala  Phe  Ala  Lys  Leu  Glu
                    1300                1305                1310
Tyr  Ala  Ser  Asp  Leu  Lys  Asp  Ile  Lys  Glu  Ser  Leu  Thr  Ser  Ser  Thr
                    1315                1320                1325
Arg  Leu  Lys  Gly  Pro  His  Tyr  Lys  Thr  Lys  Ile  Thr  Ser  Ile  Glu  Pro
                    1330                1335                1340
Asn  Lys  Ile  Asp  Glu  Asn  Glu  Ser  Ser  Arg  Gly  Lys  Asp  Asn  Lys  Ser
1345                     1350                1355                     1360
Asn  Ser  Lys  Phe  Glu  Asp  Leu  Leu  Asn  Ala  Thr  Ala  Gln  Met  Asp  Phe
                    1365                1370                1375
Asp  Arg  Ala  Thr  Ala  Asn  Val  Gly  Cys  Val  Pro  Phe  Ser  Ile  Ala  Lys
                    1380                1385                1390
Thr  Ala  Lys  Val  Leu  Ser  Glu  Arg  Glu  Thr  Cys  Lys  Lys  Met  Ala  Asp
                    1395                1400                1405
Val  Leu  Asp  Phe  Thr  His  Ser  Cys  Leu  Asn  Leu  Asp  Ser  Gln  Pro  Ala
                    1410                1415                1420
Ala  Ala  Arg  Leu  Ala  Ala  Ala  Ile  Ser  Gln  Ile  Ala  Pro  Ile  Met  Glu
1425                     1430                1435                     1440
Ser  Ile  Gly  Arg  Thr  Thr  Gln  Ser  Val  Glu  Glu  Lys  Leu  Ala  Ser  Val
                    1445                1450                1455
```

```
Asp Thr Phe Arg Asp Lys Ile Met Ala Leu Ile Ser Asn Val Leu Gly
            1460                1465                1470
Asp Thr Leu Pro Gly Leu Ala Ile Ala Asp Phe Lys Lys Gly Lys Tyr
            1475                1480                1485
Val Trp Ala Ser Phe Leu Thr Met Ile Ala Ala Cys Val Val Ala Trp
            1490                1495                1500
Ala Ala Thr Ser Lys Lys Ser Phe Leu Lys Arg Phe Ala Val Val Ala
1505                1510                1515                1520
Met Ile Ile Trp Ser Pro Phe Leu Ala Ser Lys Ile Trp Ala Leu Gly
            1525                1530                1535
Thr Trp Ile Arg Lys Ser Trp Ser Lys Leu Trp Pro Lys Ser Asp Ser
            1540                1545                1550
Cys Arg Gln His Ser Leu Ala Gly Leu Cys Glu Ser Val Phe Thr Ser
            1555                1560                1565
Phe Lys Asp Phe Pro Asp Trp Phe Lys Ser Gly Gly Ile Thr Ile Val
            1570                1575                1580
Thr Gln Val Cys Thr Val Leu Leu Thr Ile Val Ser Leu Ile Thr Leu
1585                1590                1595                1600
Gly Thr Ile Pro Ser Thr Lys Gln Asn Ala Thr Phe Ala Asp Lys Phe
            1605                1610                1615
Lys Glu Phe Gly Asn Met Ser Arg Ala Thr Thr Ser Ile Ala Ala Gly
            1620                1625                1630
Tyr Lys Thr Ile Ser Glu Leu Cys Ser Lys Phe Thr Asn Tyr Leu Ala
            1635                1640                1645
Val Thr Phe Phe Gly Ala Gln Val Asp Asp Ala Phe Lys Gly Leu
            1650                1655                1660
Val Ala Phe Asn Val Lys Glu Trp Ile Leu Glu Val Lys Asn Leu Ser
1665                1670                1675                1680
Leu Glu Glu Asn Lys Phe Ser Gly Phe Gly Gly Asp Glu His Leu Val
            1685                1690                1695
Lys Val Arg His Leu Tyr Asp Lys Ser Val Glu Ile Thr Tyr Lys Leu
            1700                1705                1710
Leu Gln Lys Asn Arg Val Pro Ile Ala Met Leu Pro Ile Ile Arg Asp
            1715                1720                1725
Thr Cys Lys Lys Cys Glu Asp Leu Leu Asn Glu Ser Tyr Thr Tyr Lys
            1730                1735                1740
Gly Met Lys Thr Pro Arg Val Asp Pro Phe Tyr Ile Cys Leu Phe Gly
1745                1750                1755                1760
Ala Pro Gly Val Gly Lys Ser Thr Val Ala Ser Met Ile Val Asp Asp
                        1765                1770                1775
Leu Leu Asp Ala Met Gly Glu Pro Lys Val Asp Arg Ile Tyr Thr Arg
            1780                1785                1790
Cys Cys Ser Asp Gln Tyr Trp Ser Asn Tyr His His Glu Pro Val Ile
            1795                1800                1805
Cys Tyr Asp Asp Leu Gly Ala Ile Ser Arg Pro Ala Ser Leu Ser Asp
            1810                1815                1820
Tyr Gly Glu Ile Met Gly Ile Lys Ser Asn Arg Pro Tyr Ser Leu Pro
1825                1830                1835                1840
Met Ala Ala Val Asp Glu Lys Gly Arg His Cys Leu Ser Arg Tyr Leu
            1845                1850                1855
Ile Ala Cys Thr Asn Leu Thr His Leu Asp Asp Thr Gly Asp Val Lys
            1860                1865                1870
Thr Lys Asp Ala Tyr Tyr Arg Arg Ile Asn Val Pro Val Thr Val Thr
            1875                1880                1885
```

Arg Glu Val Thr Ala Met Met Asn Pro Glu Asp Pro Thr Asp Gly Leu
          1890                1895                1900

Arg Phe Thr Val Glu Gln Val Leu Asp Gly Gly Arg Trp Ile Asn Val
          1905                1910                1915                1920

Thr Glu Ser Arg Leu Leu Asn Gly Arg Met Pro Phe Arg Ala Glu Asp
                1925                1930                1935

Leu Met Asn Met Asn Tyr Ser Tyr Phe Met Glu Phe Leu Lys Met Tyr
          1940                1945                1950

Ala Ala Leu Tyr Met Glu Asn Gln Asn Met Leu Val Ala Lys Leu Arg
          1955                1960                1965

Gly Thr Glu Ile Pro Glu Ser Arg Ser Ser Glu Asn Glu Glu Leu Glu
          1970                1975                1980

Phe Asp Tyr Leu Ala Thr Ala Gln Met Asp His Thr Val Thr Phe Gly
1985                1990                1995                2000

Glu Leu Val Thr Lys Phe Asn Ser Tyr Lys Leu Thr Gly Lys Gln Trp
                2005                2010                2015

Asn Lys Arg Leu Cys Glu Leu Gly Trp Thr Ser Leu Asp Gly Trp Asn
                2020                2025                2030

Thr Asn Lys Ile Met Arg Phe Asp Asp Leu Val Ala Gly Phe Cys Gly
          2035                2040                2045

Cys Ser Arg Asn Glu Asn Cys Asn Phe Asp Phe Tyr His Gln Arg Leu
2050                2055                2060

Gln Ala Cys Leu Asn Lys Lys Gly Phe Ala Pro Ala Tyr Gln Tyr Phe
2065                2070                2075                2080

Asn Leu His Lys Leu Asn Ser Asp Thr Gln Lys Thr Glu Leu Lys Leu
                2085                2090                2095

Lys Cys Gly Thr Thr Ala Glu Asp Leu Phe Arg Gln Ala Asp Leu Met
                2100                2105                2110

Val Ile Phe Ser Tyr Leu Leu Phe Val Ala Arg Ile Gly Val Ser Gly
          2115                2120                2125

Ser His Val Cys Leu Ser Tyr Asn Met Leu Asn Val Lys Asp Val Lys
          2130                2135                2140

Asp Phe Glu Ile Cys Arg Glu Asn Val Leu Asp Leu Ser Arg Lys Thr
2145                2150                2155                2160

Thr Ile Asp Gly Glu Glu Cys Tyr Ile Trp Asn Phe Ile Ser Asp Ile
                2165                2170                2175

Phe Pro Arg Ile Val Ala Lys Tyr Asn Cys Val Val Leu Asn Asp Gly
                2180                2185                2190

Glu Lys Arg Tyr Ile Phe Val Thr Asp Ser Ala Pro Thr Arg Ile Phe
          2195                2200                2205

Pro Asp Leu Ala Trp Ser Asp Leu Ile Ser Gly Lys Gln Val Val Ser
          2210                2215                2220

Pro Asn Ile Ile Lys Val Ala Gly Glu Thr Lys Ser Lys Thr Ile Ala
2225                2230                2235                2240

Pro Leu Leu Ala Asp Ser Tyr Lys Val Phe Lys Asp Pro Lys Ala Trp
                2245                2250                2255

Leu Glu Arg Asn Lys Glu Leu Lys Ala Ala Leu Glu Thr Glu Glu Tyr
                2260                2265                2270

Ile Ala Leu Leu Phe Ala Val Ala Cys Glu Ala Gly Arg Phe Thr Gln
          2275                2280                2285

Ile Leu Asp Lys Pro Pro Ser Arg Arg Lys Ile Leu Asn Met Ser Glu
          2290                2295                2300

Arg Tyr Asn Ala Tyr Ile Glu Gln Glu Lys Gly Leu Ile Gly Arg Leu

-continued

```
              2305                    2310                    2315                    2320
Ser  Lys  Pro  Ala  Lys  Ile  Cys  Leu  Ala  Ile  Gly  Thr  Gly  Val  Ala  Ile
                         2325                    2330                    2335
Phe  Gly  Ala  Leu  Ala  Gly  Ile  Gly  Val  Gly  Leu  Phe  Lys  Leu  Ile  Ala
                         2340                    2345                    2350
His  Phe  Asn  Lys  Asp  Glu  Glu  Val  Asp  Glu  Ile  Glu  Phe  Asp  Ile
                         2355                    2360                    2365
Leu  Ser  Pro  Glu  Met  Ser  Gly  Ser  His  Glu  Ser  Gly  Gln  His  Thr  Thr
                         2370                    2375                    2380
Arg  Tyr  Val  Thr  Lys  Glu  Arg  Val  Pro  Ser  Lys  Pro  Ala  Arg  Arg  Gln
2385                     2390                    2395                    2400
His  Glu  Phe  Asp  Leu  Met  Phe  Asp  Asn  Leu  Pro  Thr  Pro  Gln  Val  Glu
                         2405                    2410                    2415
Glu  Leu  Lys  Ser  Glu  Met  Thr  Cys  Ala  Ser  Ala  Ser  Asp  Glu  His  Lys
                         2420                    2425                    2430
Thr  Gln  Tyr  Val  Lys  Arg  Arg  Val  Gly  Pro  Val  Ser  Lys  Arg  Lys  Asp
                         2435                    2440                    2445
Ala  Ser  Val  Ala  Glu  Ile  Ser  Gly  Ala  His  Ala  Ser  Asp  Gln  His  His
                         2450                    2455                    2460
Thr  Glu  Tyr  Leu  Lys  Ala  Arg  Val  Pro  Leu  Met  Lys  Arg  Ile  Ala  Thr
2465                     2470                    2475                    2480
Lys  Glu  Ser  Tyr  Val  Val  Thr  Tyr  Asp  Asp  Glu  Pro  Ser  Ser  His  Ile
                         2485                    2490                    2495
Ser  Leu  Val  Arg  Arg  Ile  Arg  Arg  Thr  Arg  Leu  Ala  Arg  Ala  Ile  Lys
                         2500                    2505                    2510
Gln  Met  Ala  Val  Leu  Glu  Asp  Phe  Pro  Ser  Thr  Leu  Glu  Glu  Ile  Arg
                         2515                    2520                    2525
Leu  Trp  Arg  Gln  Asn  Ala  Ala  Asn  Lys  Gly  Val  Ile  Val  Pro  Lys  Tyr
                         2530                    2535                    2540
Ser  Thr  Ser  Gly  Lys  Phe  Phe  Ser  Gly  Leu  Leu  Asp  Asp  Glu  Glu  Glu
2545                     2550                    2555                    2560
Glu  Pro  Gln  Asn  Val  Asn  Met  Leu  Asn  Glu  Glu  Asp  Ile  Glu  Val  Asp
                         2565                    2570                    2575
Lys  Arg  Met  Phe  Glu  Lys  Ile  Ser  Glu  Val  Ile  Ser  Val  Ile  Gln  Pro
                         2580                    2585                    2590
Arg  Lys  Asn  Glu  Leu  Glu  Arg  Met  Ile  Glu  Glu  Gly  Val  His  His  Lys
                         2595                    2600                    2605
Val  Val  Lys  Gln  Ala  Arg  Val  Asn  Asp  Lys  Gly  Leu  Ala  Lys  Asp  Pro
                         2610                    2615                    2620
Asn  Met  Val  Thr  Ile  Leu  Thr  Asp  Lys  Leu  Ile  Asn  Ile  Ser  Ala  Val
2625                     2630                    2635                    2640
Ile  Val  Asn  Leu  Thr  Pro  Thr  Arg  Arg  Ala  Tyr  Met  Asn  Val  Val  Arg
                         2645                    2650                    2655
Leu  Ile  Gly  Thr  Ile  Val  Val  Cys  Pro  Ala  His  Tyr  Leu  Glu  Ala  Leu
                         2660                    2665                    2670
Glu  Glu  Gly  Asp  Glu  Leu  Tyr  Phe  Ile  Cys  Phe  Ser  Leu  Val  Ile  Lys
                         2675                    2680                    2685
Leu  Thr  Phe  Asp  Pro  Ser  Arg  Val  Thr  Leu  Val  Asn  Ser  Gln  Gln  Asp
                         2690                    2695                    2700
Leu  Met  Val  Trp  Asp  Leu  Gly  Asn  Met  Val  Pro  Pro  Ser  Ile  Asp  Thr
                         2705                    2710                    2715                    2720
Leu  Lys  Met  Ile  Pro  Thr  Leu  Glu  Asp  Trp  Asp  His  Phe  Gln  Asp  Gly
                         2725                    2730                    2735
```

```
Pro Gly Ala Phe Ala Val Thr Lys Tyr Asn Ser Lys Phe Pro Thr Asn
            2740                    2745                    2750

Tyr Ile Asn Thr Leu Thr Met Ile Glu Arg Ile Arg Ala Asn Thr Gln
            2755                    2760                    2765

Asn Pro Thr Gly Cys Tyr Ser Met Met Gly Ser Gln His Thr Ile Thr
            2770                    2775                    2780

Thr Gly Leu Arg Tyr Gln Met Phe Ser Leu Asp Gly Phe Cys Gly Gly
2785                    2790                    2795                2800

Leu Ile Leu Arg Ala Ser Thr Asn Met Val Arg Lys Val Val Gly Ile
                2805                    2810                    2815

His Val Ala Gly Ser Gln Asn His Ala Met Gly Tyr Ala Glu Cys Leu
            2820                    2825                    2830

Ile Ala Glu Asp Leu Arg Ala Ala Val Ala Arg Leu Ala Leu Asp Pro
            2835                    2840                    2845

Arg Ser Thr Ile Gln Ala Ser Leu Lys Gly Arg Ile Asp Ala Val Ser
            2850                    2855                    2860

Lys Gln Cys Gly Leu Asp Arg Ala Leu Gly Thr Ile Gly Cys His Gly
2865                    2870                    2875                2880

Lys Val Ala Ser Glu Asp Ile Thr Ser Ala Ala Thr Lys Thr Ser Ile
            2885                    2890                    2895

Arg Lys Ser Arg Ile His Gly Leu Val Gly Glu Ile Arg Thr Glu Pro
            2900                    2905                    2910

Ser Ile Leu His Ala His Asp Pro Arg Leu Pro Lys Asp Lys Ile Gly
            2915                    2920                    2925

Lys Trp Asp Pro Val Ile Glu Ala Ser Met Lys Tyr Gly Ser Arg Ile
            2930                    2935                    2940

Thr Pro Phe Pro Val Asp Gln Ile Leu Glu Val Glu Asp His Leu Ser
2945                    2950                    2955                2960

Lys Met Leu Ala Asn Cys Glu Asn Ser Lys Asn Lys Arg Gln Val Asn
            2965                    2970                    2975

Asn Leu Glu Ile Gly Ile Asn Gly Ile Asp Gln Ser Asp Tyr Trp Gln
            2980                    2985                    2990

Gln Ile Glu Met Asp Thr Ser Ser Gly Trp Pro Tyr Ala Lys Arg Lys
            2995                    3000                    3005

Pro Val Gly Ala Ala Gly Lys Lys Trp Leu Phe Glu Gln Asp Gly Thr
3010                    3015                    3020

Tyr Pro Ser Gly Lys Pro Arg Tyr Val Phe Gly Asp Ala Gly Leu Ile
3025                    3030                    3035                3040

Glu Ser Tyr Asn Ser Met Leu Gly Glu Ala Lys Gln Gly Ile Ser Pro
            3045                    3050                    3055

Thr Val Val Thr Ile Glu Cys Ala Lys Asp Glu Arg Arg Lys Leu Asn
            3060                    3065                    3070

Lys Ile Tyr Glu Lys Pro Ala Thr Arg Thr Phe Thr Ile Leu Pro Pro
            3075                    3080                    3085

Glu Ile Asn Ile Leu Phe Arg Gln Tyr Phe Gly Asp Phe Ala Ala Met
            3090                    3095                    3100

Val Met Thr Cys Arg Ala Lys Leu Phe Cys Gln Val Gly Ile Asn Pro
3105                    3110                    3115                3120

Glu Ser Met Glu Trp Gly Asp Leu Met Leu Gly Leu Lys Glu Lys Ser
            3125                    3130                    3135

Thr Lys Gly Phe Ala Gly Asp Tyr Ser Lys Phe Asp Gly Ile Gly Asp
                3140                    3145                    3150

Pro Gln Ile Tyr His Ser Ile Thr Gln Val Val Asn Asn Trp Tyr Asn
            3155                    3160                    3165
```

| | | | | | | | | | | | | | | |
|---|---|---|---|---|---|---|---|---|---|---|---|---|---|---|
| Asp | Gly | Glu | Glu | Asn | Ala | Thr | Ile | Arg | His | Ala | Leu | Ile | Ser | Ser | Ile |
| | | 3170 | | | | 3175 | | | | 3180 | | | | |
| Ile | His | Arg | Arg | Gly | Ile | Val | Lys | Glu | Tyr | Leu | Phe | Gln | Tyr | Cys | Gln |
| 3185 | | | | | 3190 | | | | | 3195 | | | | | 3200 |
| Gly | Met | Pro | Ser | Gly | Phe | Ala | Met | Thr | Val | Ile | Phe | Asn | Ser | Phe | Met |
| | | | | 3205 | | | | 3210 | | | | | | 3215 | |
| Asn | Tyr | Tyr | Tyr | Leu | Ser | Leu | Ala | Trp | Met | Asn | Leu | Ile | Ser | Ala | Ser |
| | | | 3220 | | | | | 3225 | | | | | 3230 | | |
| Pro | Leu | Ser | Pro | Gln | Ala | Ser | Leu | Arg | Tyr | Phe | Asp | Glu | Tyr | Cys | Lys |
| | | | 3235 | | | | | 3240 | | | | | 3245 | | |
| Val | Ile | Val | Tyr | Gly | Asp | Asp | Asn | Ile | Val | Ala | Val | Asn | Glu | Glu | Phe |
| | | | 3250 | | | | 3255 | | | | | 3260 | | | |
| Leu | Glu | Tyr | Tyr | Asn | Leu | Arg | Leu | Val | Ala | Gly | Tyr | Leu | Ser | Gln | Phe |
| 3265 | | | | | 3270 | | | | | 3275 | | | | | 3280 |
| Gly | Val | Ser | Tyr | Thr | Asp | Asp | Ala | Lys | Asn | Pro | Ile | Glu | Lys | Ser | Glu |
| | | | | 3285 | | | | | 3290 | | | | | 3295 | |
| Arg | Tyr | Val | Lys | Ile | Glu | Asp | Val | Thr | Phe | Leu | Lys | Arg | Arg | Trp | Val |
| | | | | 3300 | | | | | 3305 | | | | | 3310 | |
| Ser | Leu | Gly | Gly | Arg | Ala | Ser | Met | Leu | Tyr | Lys | Ala | Pro | Leu | Asp | Lys |
| | | | 3315 | | | | | 3320 | | | | | 3325 | | |
| Val | Ser | Ile | Glu | Glu | Arg | Leu | Asn | Trp | Ile | Arg | Glu | Cys | Asp | Asp | Gly |
| | | | 3330 | | | | | 3335 | | | | | 3340 | | |
| Glu | Leu | Ala | Leu | Val | Gln | Asn | Ile | Glu | Ser | Ala | Leu | Tyr | Glu | Ala | Ser |
| 3345 | | | | | | 3350 | | | | | 3355 | | | | 3360 |
| Ile | His | Gly | His | Thr | Tyr | Phe | Gly | Glu | Leu | Lys | Asp | Lys | Ile | Ala | Lys |
| | | | | 3365 | | | | | 3370 | | | | | 3375 | |
| Ala | Cys | Asp | Ala | Val | Met | Ile | Thr | Met | Pro | Asn | Ile | Arg | Tyr | Ile | Asp |
| | | | 3380 | | | | | 3385 | | | | | 3390 | | |
| Cys | Gln | Arg | Arg | Trp | Trp | Thr | Ser | Met | Thr | Gly | Gly | Tyr | Leu | Glu | Pro |
| | | 3395 | | | | | 3400 | | | | | 3405 | | | |
| Ser | Asp | Val | Thr | Lys | Leu | Val | Arg | Leu | Val | Glu | Lys | Gly | Leu | Leu | Asp |
| | | 3410 | | | | | 3415 | | | | | 3420 | | | |
| Pro | Lys | Ser | Val | Trp | Lys | Asp | Pro | Leu | Tyr | Arg | Thr | Asn | Lys | Leu | Leu |
| 3425 | | | | | 3430 | | | | | 3435 | | | | | 3440 |
| Phe | Asp | Leu | Leu | Arg | Glu | Val | Lys | Ala | Ala | Pro | Leu | Ala | Ala | Phe | Val |
| | | | | 3445 | | | | | 3450 | | | | | 3455 | |
| Val | | | | | | | | | | | | | | | |

( 2 ) INFORMATION FOR SEQ ID NO:5:

( i ) SEQUENCE CHARACTERISTICS:
        ( A ) LENGTH: 834 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i x ) FEATURE:
        ( A ) NAME/KEY: CDS
        ( B ) LOCATION: 1..834
        ( D ) OTHER INFORMATION: /note= "This corresponds to
        nucleotides 3762 to 4595 of SEQ ID NO:1"

( x i ) SEQUENCE DESCRIPTION: SEQ ID NO:5:

| | | | | | | | | | | | | | | | | |
|---|---|---|---|---|---|---|---|---|---|---|---|---|---|---|---|---|
| GTA | AGC | CTT | GGT | TTT | TCC | TTA | CAA | TCT | GGA | AGG | AAC | ATT | GGA | GTG | GGT | 48 |
| Val | Ser | Leu | Gly | Phe | Ser | Leu | Gln | Ser | Gly | Arg | Asn | Ile | Gly | Val | Gly | |

|  |  |  |  |  |  |  |  |  |  |  |  |  |  |  |  |
|---|---|---|---|---|---|---|---|---|---|---|---|---|---|---|---|
|  |  | 3460 |  |  |  | 3465 |  |  |  |  | 3470 |  |  |  |  |
| TTC | AGT | GAT | TTG | CTC | AAA | AGA | TGG | GCC | CAC | CTG | CTC | ACA | CTG | CAC | TTT | 96 |
| Phe | Ser | Asp | Leu | Leu | Lys | Arg | Trp | Ala | His | Leu | Leu | Thr | Leu | His | Phe |
|  | 3475 |  |  |  | 3480 |  |  |  |  | 3485 |  |  |  |  |  |
| GAT | GAA | AAT | AAC | GAA | AAA | TCA | GAA | GAA | AAA | GTT | GGT | TCT | TAT | ATT | GTC | 144 |
| Asp | Glu | Asn | Asn | Glu | Lys | Ser | Glu | Glu | Lys | Val | Gly | Ser | Tyr | Ile | Val |
| 3490 |  |  |  | 3495 |  |  |  |  | 3500 |  |  |  |  | 3505 |  |
| ACT | GTA | GCG | CCA | AGT | TAT | AGA | GCT | TTT | CCG | CAG | CAC | AAC | ACT | TTA | TTG | 192 |
| Thr | Val | Ala | Pro | Ser | Tyr | Arg | Ala | Phe | Pro | Gln | His | Asn | Thr | Leu | Leu |
|  |  |  | 3510 |  |  |  |  | 3515 |  |  |  |  | 3520 |  |  |
| AGT | TGG | TTT | TCA | CAA | CTA | TTC | GTG | CAA | TGG | CAA | GGC | TCT | TTG | TGC | TAC | 240 |
| Ser | Trp | Phe | Ser | Gln | Leu | Phe | Val | Gln | Trp | Gln | Gly | Ser | Leu | Cys | Tyr |
|  |  |  | 3525 |  |  |  |  | 3530 |  |  |  |  | 3535 |  |  |
| AGG | TTA | CAC | GTG | GAC | TCA | CAA | GAG | AGA | AGA | TAT | GGA | GGT | TAT | TTG | CGC | 288 |
| Arg | Leu | His | Val | Asp | Ser | Gln | Glu | Arg | Arg | Tyr | Gly | Gly | Tyr | Leu | Arg |
|  |  | 3540 |  |  |  |  | 3545 |  |  |  |  | 3550 |  |  |  |
| ATA | TGG | CAT | GAT | CCT | AAC | GGT | TCA | TTA | GAT | GAA | GGA | GTC | GAA | TTC | GCT | 336 |
| Ile | Trp | His | Asp | Pro | Asn | Gly | Ser | Leu | Asp | Glu | Gly | Val | Glu | Phe | Ala |
|  | 3555 |  |  |  |  | 3560 |  |  |  |  | 3565 |  |  |  |  |
| ATG | TCA | ACA | AAC | TTA | GAG | CCA | CCC | CCA | GGT | GCC | TTT | GTG | AAA | TAC | TGG | 384 |
| Met | Ser | Thr | Asn | Leu | Glu | Pro | Pro | Pro | Gly | Ala | Phe | Val | Lys | Tyr | Trp |
| 3570 |  |  |  |  | 3575 |  |  |  |  | 3580 |  |  |  |  | 3585 |
| AAT | TAT | AAT | GAG | CAG | AGC | GAG | TTT | GAG | TTT | GTG | GTA | CCA | TAC | ACG | GCT | 432 |
| Asn | Tyr | Asn | Glu | Gln | Ser | Glu | Phe | Glu | Phe | Val | Val | Pro | Tyr | Thr | Ala |
|  |  |  |  | 3590 |  |  |  |  | 3595 |  |  |  |  | 3600 |  |
| CGA | ACC | CCT | CGC | TTA | TTC | GTG | CCA | AAG | GCA | ATG | ATT | CCG | ACA | GAT | TCG | 480 |
| Arg | Thr | Pro | Arg | Leu | Phe | Val | Pro | Lys | Ala | Met | Ile | Pro | Thr | Asp | Ser |
|  |  |  | 3605 |  |  |  |  | 3610 |  |  |  |  | 3615 |  |  |
| AAG | TCA | TGG | ATA | TTG | AAT | TAT | AAT | GGA | ACT | TTG | AAC | TTC | GAT | TAT | AGG | 528 |
| Lys | Ser | Trp | Ile | Leu | Asn | Tyr | Asn | Gly | Thr | Leu | Asn | Phe | Asp | Tyr | Arg |
|  |  | 3620 |  |  |  |  | 3625 |  |  |  |  | 3630 |  |  |  |
| GGA | GTG | GAT | GAT | TTT | AAC | GTC | ACT | GTT | GAC | ATT | AGC | GCT | GGA | GAT | AAC | 576 |
| Gly | Val | Asp | Asp | Phe | Asn | Val | Thr | Val | Asp | Ile | Ser | Ala | Gly | Asp | Asn |
|  |  | 3635 |  |  |  |  | 3640 |  |  |  |  | 3645 |  |  |  |
| TTC | GAG | TTC | TCT | GTT | CGT | ACG | GTA | GCT | CCC | AAA | GCT | GGA | AAA | GTG | AAT | 624 |
| Phe | Glu | Phe | Ser | Val | Arg | Thr | Val | Ala | Pro | Lys | Ala | Gly | Lys | Val | Asn |
| 3650 |  |  |  |  | 3655 |  |  |  |  | 3660 |  |  |  |  | 3665 |
| GAA | TCG | TTT | ACA | AAG | CTA | TCG | TAT | AGC | AAT | GAG | CTC | GTC | GAT | ATC | AAG | 672 |
| Glu | Ser | Phe | Thr | Lys | Leu | Ser | Tyr | Ser | Asn | Glu | Leu | Val | Asp | Ile | Lys |
|  |  |  | 3670 |  |  |  |  | 3675 |  |  |  |  | 3680 |  |  |
| AAA | CCG | TTG | ACA | GCA | GCT | GGA | AGA | CTC | AAA | GGA | CCG | TTC | AAT | TTG | AAC | 720 |
| Lys | Pro | Leu | Thr | Ala | Ala | Gly | Arg | Leu | Lys | Gly | Pro | Phe | Asn | Leu | Asn |
|  |  |  | 3685 |  |  |  |  | 3690 |  |  |  |  | 3695 |  |  |
| ACT | TTG | AAA | ACT | GCT | GTC | CCT | AAA | GAA | ACG | CCC | AAA | GAA | AGC | TCT | GAT | 768 |
| Thr | Leu | Lys | Thr | Ala | Val | Pro | Lys | Glu | Thr | Pro | Lys | Glu | Ser | Ser | Asp |
|  |  | 3700 |  |  |  |  | 3705 |  |  |  |  | 3710 |  |  |  |
| GAT | AAG | GAT | AAA | TCA | AAT | CAG | AAG | AGG | AAA | GGA | GCT | ATG | GAT | TCG | TTA | 816 |
| Asp | Lys | Asp | Lys | Ser | Asn | Gln | Lys | Arg | Lys | Gly | Ala | Met | Asp | Ser | Leu |
|  | 3715 |  |  |  |  | 3720 |  |  |  |  | 3725 |  |  |  |  |
| CTA | AAC | GCT | GTT | GCT | CAG |  |  |  |  |  |  |  |  |  |  | 834 |
| Leu | Asn | Ala | Val | Ala | Gln |  |  |  |  |  |  |  |  |  |  |
| 3730 |  |  |  |  | 3735 |  |  |  |  |  |  |  |  |  |  |

( 2 ) INFORMATION FOR SEQ ID NO:6:

( i ) SEQUENCE CHARACTERISTICS:
        ( A ) LENGTH: 278 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| Val | Ser | Leu | Gly | Phe | Ser | Leu | Gln | Ser | Gly | Arg | Asn | Ile | Gly | Val | Gly |
| 1 | | | | 5 | | | | | 10 | | | | | 15 | |

| Phe | Ser | Asp | Leu | Leu | Lys | Arg | Trp | Ala | His | Leu | Leu | Thr | Leu | His | Phe |
| | | | 20 | | | | | 25 | | | | | 30 | | |

| Asp | Glu | Asn | Asn | Glu | Lys | Ser | Glu | Glu | Lys | Val | Gly | Ser | Tyr | Ile | Val |
| | | 35 | | | | | 40 | | | | | 45 | | | |

| Thr | Val | Ala | Pro | Ser | Tyr | Arg | Ala | Phe | Pro | Gln | His | Asn | Thr | Leu | Leu |
| | 50 | | | | | 55 | | | | | 60 | | | | |

| Ser | Trp | Phe | Ser | Gln | Leu | Phe | Val | Gln | Trp | Gln | Gly | Ser | Leu | Cys | Tyr |
| 65 | | | | | 70 | | | | 75 | | | | | | 80 |

| Arg | Leu | His | Val | Asp | Ser | Gln | Glu | Arg | Arg | Tyr | Gly | Gly | Tyr | Leu | Arg |
| | | | | 85 | | | | | 90 | | | | | 95 | |

| Ile | Trp | His | Asp | Pro | Asn | Gly | Ser | Leu | Asp | Glu | Gly | Val | Glu | Phe | Ala |
| | | | 100 | | | | | 105 | | | | | 110 | | |

| Met | Ser | Thr | Asn | Leu | Glu | Pro | Pro | Pro | Gly | Ala | Phe | Val | Lys | Tyr | Trp |
| | | 115 | | | | | 120 | | | | | 125 | | | |

| Asn | Tyr | Asn | Glu | Gln | Ser | Glu | Phe | Glu | Phe | Val | Val | Pro | Tyr | Thr | Ala |
| | 130 | | | | | 135 | | | | | 140 | | | | |

| Arg | Thr | Pro | Arg | Leu | Phe | Val | Pro | Lys | Ala | Met | Ile | Pro | Thr | Asp | Ser |
| 145 | | | | | 150 | | | | | 155 | | | | | 160 |

| Lys | Ser | Trp | Ile | Leu | Asn | Tyr | Asn | Gly | Thr | Leu | Asn | Phe | Asp | Tyr | Arg |
| | | | | 165 | | | | | 170 | | | | | 175 | |

| Gly | Val | Asp | Asp | Phe | Asn | Val | Thr | Val | Asp | Ile | Ser | Ala | Gly | Asp | Asn |
| | | | 180 | | | | | 185 | | | | | 190 | | |

| Phe | Glu | Phe | Ser | Val | Arg | Thr | Val | Ala | Pro | Lys | Ala | Gly | Lys | Val | Asn |
| | | 195 | | | | | 200 | | | | | 205 | | | |

| Glu | Ser | Phe | Thr | Lys | Leu | Ser | Tyr | Ser | Asn | Glu | Leu | Val | Asp | Ile | Lys |
| | 210 | | | | | 215 | | | | | 220 | | | | |

| Lys | Pro | Leu | Thr | Ala | Ala | Gly | Arg | Leu | Lys | Gly | Pro | Phe | Asn | Leu | Asn |
| 225 | | | | | 230 | | | | | 235 | | | | | 240 |

| Thr | Leu | Lys | Thr | Ala | Val | Pro | Lys | Glu | Thr | Pro | Lys | Glu | Ser | Ser | Asp |
| | | | | 245 | | | | | 250 | | | | | 255 | |

| Asp | Lys | Asp | Lys | Ser | Asn | Gln | Lys | Arg | Lys | Gly | Ala | Met | Asp | Ser | Leu |
| | | | 260 | | | | | 265 | | | | | 270 | | |

| Leu | Asn | Ala | Val | Ala | Gln |
| | | | 275 | | |

( 2 ) INFORMATION FOR SEQ ID NO:7:

( i ) SEQUENCE CHARACTERISTICS:
        ( A ) LENGTH: 630 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i x ) FEATURE:
        ( A ) NAME/KEY: CDS
        ( B ) LOCATION: 1..630
        ( D ) OTHER INFORMATION: /note= "This corresponds to
        nucleotides 2526 to 3155 of SEQ ID NO:1"

( x i ) SEQUENCE DESCRIPTION: SEQ ID NO:7:

| TCA | GGT | ACG | AAC | ATA | GTG | AAC | AAT | GAG | ATA | GAA | CAG | GCT | TTT | CAA | GAT | 48 |
| Ser | Gly | Thr | Asn | Ile | Val | Asn | Asn | Glu | Ile | Glu | Gln | Ala | Phe | Gln | Asp | |
| 280 | | | | | 285 | | | | | 290 | | | | | | |

```
GAA  GAA  AAG  AGA  ACT  GTT  GAT  CCA  AAT  ATC  AGT  GAT  ATG  TAC  AAC  GCT     96
Glu  Glu  Lys  Arg  Thr  Val  Asp  Pro  Asn  Ile  Ser  Asp  Met  Tyr  Asn  Ala
295                      300                 305                      310

ATC  AAA  AGT  GAG  TAT  TTG  GTT  AAA  AGC  TTT  TCT  TGG  AAA  GTC  TCA  GAT    144
Ile  Lys  Ser  Glu  Tyr  Leu  Val  Lys  Ser  Phe  Ser  Trp  Lys  Val  Ser  Asp
                    315                 320                      325

GGA  CAA  GAT  AAA  GTT  CTA  TCT  AAT  ATT  AAT  ATA  CCT  GAG  GAT  TTG  TGG    192
Gly  Gln  Asp  Lys  Val  Leu  Ser  Asn  Ile  Asn  Ile  Pro  Glu  Asp  Leu  Trp
               330                 335                      340

AAT  ACA  AAC  TCC  CGG  CTG  AAC  GAC  ATA  ATG  AGC  TAT  TTC  CAG  TAC  TAC    240
Asn  Thr  Asn  Ser  Arg  Leu  Asn  Asp  Ile  Met  Ser  Tyr  Phe  Gln  Tyr  Tyr
               345                 350                      355

AAG  GCT  ACA  GGT  TTA  ACA  TTT  AGA  ATA  TCA  ACG  ACC  TGT  ATT  CCA  ATG    288
Lys  Ala  Thr  Gly  Leu  Thr  Phe  Arg  Ile  Ser  Thr  Thr  Cys  Ile  Pro  Met
360                      365                 370

CAT  GGA  GGT  ACA  CTG  TTT  GCA  GCG  TGG  GAT  GCA  TGT  GGA  TGT  GCT  ACT    336
His  Gly  Gly  Thr  Leu  Phe  Ala  Ala  Trp  Asp  Ala  Cys  Gly  Cys  Ala  Thr
375                      380                 385                      390

CGA  CAA  GGG  ATA  GCT  ACG  GCT  GTG  CAA  CTG  ACA  GGG  CTT  CCT  GGA  ATC    384
Arg  Gln  Gly  Ile  Ala  Thr  Ala  Val  Gln  Leu  Thr  Gly  Leu  Pro  Gly  Ile
                    395                 400                      405

ATG  ATA  GAA  GCA  CAC  AGT  TCG  TCC  TTG  ACG  ACT  TTC  TCA  GTC  GAG  GAT    432
Met  Ile  Glu  Ala  His  Ser  Ser  Ser  Leu  Thr  Thr  Phe  Ser  Val  Glu  Asp
               410                 415                      420

CCG  TTA  ACG  CAA  TCT  ACT  GTG  TGC  CTT  AGT  GGA  AGT  GAA  CAT  TCG  TTT    480
Pro  Leu  Thr  Gln  Ser  Thr  Val  Cys  Leu  Ser  Gly  Ser  Glu  His  Ser  Phe
          425                 430                      435

GGG  CGG  ATT  GGA  ATT  CTC  AAA  ATT  TGT  TGC  CTA  AAC  GTG  TTG  AAT  GCA    528
Gly  Arg  Ile  Gly  Ile  Leu  Lys  Ile  Cys  Cys  Leu  Asn  Val  Leu  Asn  Ala
     440                 445                      450

CCA  CAA  GCA  GCC  ACC  CAA  TCC  GTT  TCC  GTA  AAC  GTA  TGG  GTG  AAG  TTT    576
Pro  Gln  Ala  Ala  Thr  Gln  Ser  Val  Ser  Val  Asn  Val  Trp  Val  Lys  Phe
455                      460                 465                      470

GAT  GGG  GTG  AAA  TTT  CAT  TTC  TAC  TCC  CTC  AAA  AAG  CAA  CCC  GTG  GTC    624
Asp  Gly  Val  Lys  Phe  His  Phe  Tyr  Ser  Leu  Lys  Lys  Gln  Pro  Val  Val
               475                 480                      485

TCC  CAA                                                                           630
Ser  Gln
```

( 2 ) INFORMATION FOR SEQ ID NO:8:

( i ) SEQUENCE CHARACTERISTICS:
        ( A ) LENGTH: 210 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Ser  Gly  Thr  Asn  Ile  Val  Asn  Asn  Glu  Ile  Glu  Gln  Ala  Phe  Gln  Asp
  1                 5                     10                      15

Glu  Glu  Lys  Arg  Thr  Val  Asp  Pro  Asn  Ile  Ser  Asp  Met  Tyr  Asn  Ala
                20                     25                      30

Ile  Lys  Ser  Glu  Tyr  Leu  Val  Lys  Ser  Phe  Ser  Trp  Lys  Val  Ser  Asp
               35                     40                      45

Gly  Gln  Asp  Lys  Val  Leu  Ser  Asn  Ile  Asn  Ile  Pro  Glu  Asp  Leu  Trp
          50                     55                      60

Asn  Thr  Asn  Ser  Arg  Leu  Asn  Asp  Ile  Met  Ser  Tyr  Phe  Gln  Tyr  Tyr
 65                     70                     75                       80

Lys  Ala  Thr  Gly  Leu  Thr  Phe  Arg  Ile  Ser  Thr  Thr  Cys  Ile  Pro  Met
```

|  | 85 |  |  |  |  |  |  | 90 |  |  |  |  |  |  | 95 |  |
|---|---|---|---|---|---|---|---|---|---|---|---|---|---|---|---|---|
| His | Gly | Gly | Thr<br>100 | Leu | Phe | Ala | Ala | Trp<br>105 | Asp | Ala | Cys | Gly | Cys<br>110 | Ala | Thr |  |
| Arg | Gln | Gly<br>115 | Ile | Ala | Thr | Ala | Val<br>120 | Gln | Leu | Thr | Gly | Leu<br>125 | Pro | Gly | Ile |  |
| Met | Ile<br>130 | Glu | Ala | His | Ser<br>135 | Ser | Ser | Leu | Thr | Thr | Phe<br>140 | Ser | Val | Glu | Asp |  |
| Pro<br>145 | Leu | Thr | Gln | Ser<br>150 | Thr | Val | Cys | Leu | Ser | Gly<br>155 | Ser | Glu | His | Ser | Phe<br>160 |  |
| Gly | Arg | Ile | Gly | Ile<br>165 | Leu | Lys | Ile | Cys | Cys<br>170 | Leu | Asn | Val | Leu | Asn<br>175 | Ala |  |
| Pro | Gln | Ala | Ala<br>180 | Thr | Gln | Ser | Val | Ser<br>185 | Val | Asn | Val | Trp | Val<br>190 | Lys | Phe |  |
| Asp | Gly | Val<br>195 | Lys | Phe | His | Phe | Tyr<br>200 | Ser | Leu | Lys | Lys | Gln<br>205 | Pro | Val | Val |  |
| Ser | Gln<br>210 |  |  |  |  |  |  |  |  |  |  |  |  |  |  |  |

( 2 ) INFORMATION FOR SEQ ID NO:9:

( i ) SEQUENCE CHARACTERISTICS:
        ( A ) LENGTH: 606 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i x ) FEATURE:
        ( A ) NAME/KEY: CDS
        ( B ) LOCATION: 1..606
        ( D ) OTHER INFORMATION: /note= "This corresponds to
            nucleotides 3156 to 3761 of SEQ ID NO:1"

( x i ) SEQUENCE DESCRIPTION: SEQ ID NO:9:

| ATG | CTA | GTA | GAT | AAA | TTG | ACT | AAT | CTT | GGA | GAA | ATG | GGT | TGT | GTA | GTT | 48 |
|---|---|---|---|---|---|---|---|---|---|---|---|---|---|---|---|---|
| Met | Leu | Val | Asp<br>215 | Lys | Leu | Thr | Asn | Leu | Gly<br>220 | Glu | Met | Gly | Cys | Val<br>225 | Val |  |
| GCA | ACT | GGA | ACA | TGG | TCA | ACG | ACT | TCA | AGT | TTG | AAT | TTG | TTG | CAG | CTA | 96 |
| Ala | Thr | Gly | Thr<br>230 | Trp | Ser | Thr | Thr | Ser<br>235 | Ser | Leu | Asn | Leu | Leu<br>240 | Gln | Leu |  |
| AAC | GTG | CAT | CCA | ACA | GCT | TGC | TTT | ATA | AGT | GAT | GGC | CTG | GTT | ACT | CAG | 144 |
| Asn | Val | His<br>245 | Pro | Thr | Ala | Cys | Phe<br>250 | Ile | Ser | Asp | Gly | Leu<br>255 | Val | Thr | Gln |  |
| ACC | CCA | CTA | AGT | GTA | ATA | GCT | CAT | GCT | TTC | GCA | CGA | TGG | AGG | GGA | TCA | 192 |
| Thr | Pro<br>260 | Leu | Ser | Val | Ile | Ala<br>265 | His | Ala | Phe | Ala | Arg<br>270 | Trp | Arg | Gly | Ser |  |
| TTG | AAA | TTC | ACC | ATC | ACT | TTT | GGA | GCT | AGT | ATG | TTC | ACA | AGA | GGA | AGA | 240 |
| Leu<br>275 | Lys | Phe | Thr | Ile | Thr<br>280 | Phe | Gly | Ala | Ser | Met<br>285 | Phe | Thr | Arg | Gly | Arg<br>290 |  |
| GTC | CTG | GTA | GCA | GCT | ATA | CCT | GTG | GCG | AAG | CGA | AAA | GAG | ACT | CTC | ACA | 288 |
| Val | Leu | Val | Ala | Ala<br>295 | Ile | Pro | Val | Ala | Lys<br>300 | Arg | Lys | Glu | Thr | Leu<br>305 | Thr |  |
| ATT | GAA | GAG | ATT | AGT | GGA | TAT | CAC | AAT | GTA | ATG | TGC | CTG | CTC | AAT | GGA | 336 |
| Ile | Glu | Glu | Ile<br>310 | Ser | Gly | Tyr | His | Asn<br>315 | Val | Met | Cys | Leu | Leu<br>320 | Asn | Gly |  |
| GAA | AGG | ACA | TCT | TTC | GAA | CTT | GAA | GTC | CCT | TAT | CAC | TCA | GTG | GGA | GAG | 384 |
| Glu | Arg | Thr<br>325 | Ser | Phe | Glu | Leu | Glu<br>330 | Val | Pro | Tyr | His | Ser<br>335 | Val | Gly | Glu |  |
| GAT | TCT | TAT | GTT | TGT | AGG | GAT | GCC | CTA | TTT | GAT | GTT | TCG | TCA | TAC | GCA | 432 |

| | | | | | | | | | | | | | | | |
|---|---|---|---|---|---|---|---|---|---|---|---|---|---|---|---|
| Asp | Ser | Tyr | Val | Cys | Arg | Asp | Ala | Leu | Phe | Asp | Val | Ser | Ser | Tyr | Ala |
| 340 | | | | | 345 | | | | | 350 | | | | | |

| | | | | | | | | | | | | | | | |
|---|---|---|---|---|---|---|---|---|---|---|---|---|---|---|---|
| CAG | AAC | TTT | ATG | ATC | ACC | AGA | TTA | CAC | ATG | GTA | GTT | ATA | GAC | ACA | TTG | 480
| Gln | Asn | Phe | Met | Ile | Thr | Arg | Leu | His | Met | Val | Val | Ile | Asp | Thr | Leu |
| 355 | | | | | 360 | | | | | 365 | | | | | 370 |

| GTG | ATG | AGT | TCA | AAT | GCA | AGT | AAC | ACA | ATA | AGT | TAC | TGT | GTG | ATG | ATG | 528 |
|---|---|---|---|---|---|---|---|---|---|---|---|---|---|---|---|---|
| Val | Met | Ser | Ser | Asn | Ala | Ser | Asn | Thr | Ile | Ser | Tyr | Cys | Val | Met | Met | |
| | | | | 375 | | | | 380 | | | | | 385 | | | |

| GGA | CCA | GGC | AAA | GAT | CTT | GAA | TTG | AGA | TAT | CTA | AAT | GGT | GTC | CAT | GCT | 576 |
|---|---|---|---|---|---|---|---|---|---|---|---|---|---|---|---|---|
| Gly | Pro | Gly | Lys | Asp | Leu | Glu | Leu | Arg | Tyr | Leu | Asn | Gly | Val | His | Ala | |
| | | | 390 | | | | | 395 | | | | | 400 | | | |

| CAG | AGA | AAT | GTG | AGA | GAA | TTA | AAA | GCT | CAG | | | | | | | 606 |
|---|---|---|---|---|---|---|---|---|---|---|---|---|---|---|---|---|
| Gln | Arg | Asn | Val | Arg | Glu | Leu | Lys | Ala | Gln | | | | | | | |
| | | 405 | | | | | 410 | | | | | | | | | |

( 2 ) INFORMATION FOR SEQ ID NO:10:

( i ) SEQUENCE CHARACTERISTICS:
        ( A ) LENGTH: 202 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

| Met | Leu | Val | Asp | Lys | Leu | Thr | Asn | Leu | Gly | Glu | Met | Gly | Cys | Val | Val |
|---|---|---|---|---|---|---|---|---|---|---|---|---|---|---|---|
| 1 | | | | 5 | | | | | 10 | | | | | 15 | |

| Ala | Thr | Gly | Thr | Trp | Ser | Thr | Thr | Ser | Ser | Leu | Asn | Leu | Leu | Gln | Leu |
|---|---|---|---|---|---|---|---|---|---|---|---|---|---|---|---|
| | | | 20 | | | | | 25 | | | | | 30 | | |

| Asn | Val | His | Pro | Thr | Ala | Cys | Phe | Ile | Ser | Asp | Gly | Leu | Val | Thr | Gln |
|---|---|---|---|---|---|---|---|---|---|---|---|---|---|---|---|
| | | | 35 | | | | 40 | | | | | 45 | | | |

| Thr | Pro | Leu | Ser | Val | Ile | Ala | His | Ala | Phe | Ala | Arg | Trp | Arg | Gly | Ser |
|---|---|---|---|---|---|---|---|---|---|---|---|---|---|---|---|
| | 50 | | | | | 55 | | | | | 60 | | | | |

| Leu | Lys | Phe | Thr | Ile | Thr | Phe | Gly | Ala | Ser | Met | Phe | Thr | Arg | Gly | Arg |
|---|---|---|---|---|---|---|---|---|---|---|---|---|---|---|---|
| 65 | | | | | 70 | | | | | 75 | | | | | 80 |

| Val | Leu | Val | Ala | Ala | Ile | Pro | Val | Ala | Lys | Arg | Lys | Glu | Thr | Leu | Thr |
|---|---|---|---|---|---|---|---|---|---|---|---|---|---|---|---|
| | | | | 85 | | | | | 90 | | | | | 95 | |

| Ile | Glu | Glu | Ile | Ser | Gly | Tyr | His | Asn | Val | Met | Cys | Leu | Leu | Asn | Gly |
|---|---|---|---|---|---|---|---|---|---|---|---|---|---|---|---|
| | | | 100 | | | | | 105 | | | | | 110 | | |

| Glu | Arg | Thr | Ser | Phe | Glu | Leu | Glu | Val | Pro | Tyr | His | Ser | Val | Gly | Glu |
|---|---|---|---|---|---|---|---|---|---|---|---|---|---|---|---|
| | | 115 | | | | | 120 | | | | | 125 | | | |

| Asp | Ser | Tyr | Val | Cys | Arg | Asp | Ala | Leu | Phe | Asp | Val | Ser | Ser | Tyr | Ala |
|---|---|---|---|---|---|---|---|---|---|---|---|---|---|---|---|
| | 130 | | | | | 135 | | | | | 140 | | | | |

| Gln | Asn | Phe | Met | Ile | Thr | Arg | Leu | His | Met | Val | Val | Ile | Asp | Thr | Leu |
|---|---|---|---|---|---|---|---|---|---|---|---|---|---|---|---|
| 145 | | | | | 150 | | | | | 155 | | | | | 160 |

| Val | Met | Ser | Ser | Asn | Ala | Ser | Asn | Thr | Ile | Ser | Tyr | Cys | Val | Met | Met |
|---|---|---|---|---|---|---|---|---|---|---|---|---|---|---|---|
| | | | | 165 | | | | 170 | | | | | 175 | | |

| Gly | Pro | Gly | Lys | Asp | Leu | Glu | Leu | Arg | Tyr | Leu | Asn | Gly | Val | His | Ala |
|---|---|---|---|---|---|---|---|---|---|---|---|---|---|---|---|
| | | | 180 | | | | | 185 | | | | | 190 | | |

| Gln | Arg | Asn | Val | Arg | Glu | Leu | Lys | Ala | Gln |
|---|---|---|---|---|---|---|---|---|---|
| | | 195 | | | | | 200 | | |

( 2 ) INFORMATION FOR SEQ ID NO:11:

( i ) SEQUENCE CHARACTERISTICS:
        ( A ) LENGTH: 800 base pairs
        ( B ) TYPE: nucleic acid
        ( C ) STRANDEDNESS: single
        ( D ) TOPOLOGY: linear ( i i ) MOLECULE TYPE: cDNA (  i i i  ) HYPOTHETICAL: NO (  i x  ) FEATURE:
(  A  ) NAME/KEY: misc_feature
(  B  ) LOCATION: 1..800
(  D  ) OTHER INFORMATION: /note= "Sequence of three prime
terminus of M1 isolate of MCDV; see Ngazimibi dissertatio
reference in specification"

(  x i  ) SEQUENCE DESCRIPTION: SEQ ID NO:11:

| | | | | | | |
|---|---|---|---|---|---|---|
| TTGAACTCTC | ACGAGTCGAG | AAGGCAGTGG | TAGTTCCATA | GAACGACCCT | TTGTGGTGTG | 60 |
| ACTAGGCATT | GACCTAGTTG | GTGGTGTGAT | GAGCCATAAA | TCATCAGCTA | GTTAAGGTAC | 120 |
| ATCTAGTTTA | CAAAGTACCC | CCCACTCACA | AAGTTTTTGT | GATGGTCTCT | GGTTGAAGTC | 180 |
| AAGCTACTGG | CATTCGTTCA | TCCTTTTATA | GGATTTGAGT | CAGTACGGGT | CTTGATGGGG | 240 |
| AACCAGAACC | TAGCGTCTTT | TTGTTTTGTG | TTTTCTCACG | TCAACTTGGT | GTTGAGGTGG | 300 |
| GCGCTTGGTC | AGCAGCGGGA | AATAAAAGTG | TGACGTACAT | TATTGTCACA | CAGACTACGG | 360 |
| CAGGCGAGAC | ACGCCTCGTC | TCCTGAGGGG | GAAAGTAGCT | CCAGGCATTG | AATCCTGAAG | 420 |
| TGTTCAGTAG | TTATCTCTGA | TCCTCTCCGG | GGGAAAAATG | GGATACTATC | TGTTTGGTCA | 480 |
| TATTTCATTG | GCAGAGTAGA | TAGAAAGCGA | CTTTGTTGGT | CTTCTTTATA | TAGCGGCTGC | 540 |
| TTGCGAGAGA | TCAGCGAAGA | CTATCTGAGA | TGTAGGCGCG | TTGTTCGAAA | ATCTCATGAA | 600 |
| AGGCTCACAT | GGTGCGAGTA | ACATCCGTAC | ACTGTGGGTA | GGCACACTTC | TCCACGGGTT | 660 |
| TGTGTCGCTT | AGTATATTAA | TACGAGTGCT | ATATCGGAGA | CAGTTGTAAG | ACGTTGAACT | 720 |
| AAATGTCGAT | GGGGCCCAGT | GAGCACCCGG | TTTAGTTACG | CTTTCTGTTT | CTGTGTCAAT | 780 |
| AGAGATAAAA | GTGGGGTAAC | | | | | 800 |

MAIZE CHLOROTIC DWARF VIRUS GENOME AND USES THEREFOR

FIELD OF THE INVENTION

The invention relates generally to the characterization of plant virus genomes, particularly within the maize chlorotic dwarf virus family and to the application of various plant virus diagnostic and resistance strategies to a particular viral genome.

BACKGROUND OF THE INVENTION

Maize Chlorotic Dwarf Virus (MCDV) is a plant virus which has been classified as a member of a group of plant viruses known as Machloviruses based upon its semi-persistent relationship with its leafhopper vector and its 30 nm isometric nonenveloped particles (Brunt, A. et al., "Viruses of Tropical Plants," pub. by Redwood Press Ltd., Melksham, U.K. (1990)). MCDV has a genome composed of a single strand positive sense RNA molecule which is transcribed and translated as one polyprotein that is subsequently cleaved into its component parts.

MCDV is a major crop pest in maize where it can cause mosaic or yellow streaking, stunting and ultimately reduced crop yields (Gingery, R. E. et al., pages 19–32 of "Handbook of Plant Virus Infection and Comparative Diagnosis," ed. by E. Kurstak, pub. by Elsevier/North Holland Biomedical Press, Amsterdam (1981); Gordon, D. T. et al., *Phytopathology* 67: 27–36 (1977). When found in combination with other viruses such as maize dwarf mosaic virus, MCDV may cause even more severe crop damage.

The economic impact of yield losses due to MCDV has generated considerable interest in developing strategies to combat this virus. To date, however, only limited success has been achieved in reducing the adverse impact of this virus. Thus there remains a need to identify additional effective means for protecting host plants from MCDV.

Recently, a number of approaches for combatting plant viruses have been developed which are based upon the transformation of susceptible plant species with chimeric genes which express transcripts or proteins that inhibit viral infection. These approaches include genetically engineering plants to express plant viral coat protein or coat protein transcripts, viral replicases in unmodified or modified form, and antisense genes or ribozymes targeting viral genomic RNA or transcripts. To apply any of these approaches, knowledge of the structure and organization of the genome of the target virus is necessary.

Recently, the nucleotide sequence of the maize chlorotic dwarf virus genome was reported in international patent publication WO 94/21796 published Sep. 29, 1994. This sequence was reported as representing the genome of MCDV in general, reflecting the viewpoint in the field that MCDV is composed of a single viral strain. However, some evidence exists which suggests that MCDV might actually consist of two strains, designated MCDV-T and MCDV-M1 (Lopes, J. R. S. et al., *Phytopathology* 84(9): 876–882 (1994); Gingery, R. E. et al., *Phytopathology* 80: 687–691 (1990)).

BRIEF SUMMARY OF THE INVENTION

The present invention is based upon the characterization of the genomic structure and organization of a maize chlorotic dwarf virus (MCDV) isolate which revealed that this isolate represents a novel MCDV strain, designated herein as strain Tennessee (MCDV-Tn), distinct from the previously known MCDV-T and MCDV-M1 isolates.

Accordingly, in one aspect the present invention provides oligonucleotides unique to the MCDV-Tn genome which may be used to detect the presence of MCDV-Tn in plants.

In another aspect the present invention provides the coding sequences for three MCDV-Tn coat proteins. These coding sequences may be used to express MCDV-Tn coat protein in transgenic plants to confer resistance to MCDV-Tn infection. These coding sequences may also be used to recombinantly produce MCDV-Tn coat protein.

In yet another aspect the present invention provides antibodies to the MCDV-Tn coat proteins. These antibodies may be used to detect the presence of MCDV-Tn in plants.

In yet another aspect the present invention provides coding sequences for the MCDV-Tn replicase protein. These sequences may be used to express MCDV-Tn replicase in transgenic plants to confer resistance to MCDV-Tn infection. Alternatively, modified replicase proteins may be designed from these coding sequences which can be expressed in plants to confer resistance to MCDV-Tn infection. These sequences may also be used to recombinantly express and purify large amounts of MCDV-Tn replicase in a suitable microbial host.

In yet another aspect the present invention provides chimeric genes designed for expression of single chain antibodies to MCDV-Tn gene products in susceptible target plants to confer resistance to MCDV-Tn infection.

In yet another aspect the present invention provides antisense and ribozyme molecules which may be expressed in transgenic plants to confer resistance to MCDV-Tn.

In yet another aspect the present invention provides methods for inhibiting MCDV-Tn infection in susceptible plants which comprise expressing in such plants various inhibitory transcripts or proteins derived from the MCDV-Tn genome.

In yet another aspect of the present invention, resistant forms of plants normally susceptible to MCDV-Tn infection are provided. These resistant plants contain chimeric DNA molecules which allow them to express various inhibitory transcripts or proteins derived from the MCDV-Tn genome.

BRIEF DESCRIPTION OF THE SEQUENCES

SEQ ID NO. 1 is the entire nucleotide sequence of the MCDV-Tn positive strand RNA genome.

SEQ ID NO. 2 is the polyprotein amino acid sequence encoded by the MCDV-Tn positive strand RNA genome.

SEQ ID NO. 3 is the entire nucleotide sequence of the MCDV-T positive strand RNA genome.

SEQ ID NO. 4 is the polyprotein amino acid sequence encoded by the MCDV-T positive strand RNA genome.

SEQ ID NO. 5 is the coding sequence for the coat protein designated CP1 in the polyprotein encoded by the MCDV-Tn genome.

SEQ ID NO. 6 is the amino acid sequence of the coat protein designated CP1 in the polyprotein encoded by the MCDV-Tn genome.

SEQ ID NO. 7 is the coding sequence for the coat protein designated CP2 in the polyprotein encoded by the MCDV-Tn genome.

SEQ ID NO. 8 is the amino acid sequence of the coat protein designated CP2 in the polyprotein encoded by the MCDV-Tn genome.

SEQ ID NO. 9 is the coding sequence for the coat protein designated CP3 in the polyprotein encoded by the MCDV-Tn genome.

SEQ ID NO. 10 is the amino acid sequence of the coat protein designated CP3 in the polyprotein encoded by the MCDV-Tn genome.

SEQ ID NO. 11 is a portion of the nucleotide sequence of the 3' terminus of MCDV-M1.

DETAILED DISCLOSURE OF THE INVENTION

The present invention is based upon the discovery of a novel plant virus. Based upon host range, phenotype of host plants, vector transmissibility and reaction to MCDV-specific antibodies, this plant virus has been classified herein as a member of the maize chlorotic dwarf virus (MCDV) family. This classification was further supported by comparison of genomic sequence information taught herein for this virus with known plant viral sequences. This comparison revealed limited homology with rice tungro spherical virus, a proposed member of the machlovirus group, and members of the comovirus group. This is similar to the homology reported for MCDV-T in international patent publication WO 94/21796 published Sep. 29, 1994. This virus has been designated herein as variant Tennessee (MCDV-Tn) due to its original site of isolation from johnsongrass rhizomes.

The entire nucleotide sequence of the MCDV-Tn positive strand RNA genome is 11,813 bases in length and is shown in SEQ ID NO: 1. The polyprotein amino acid sequence encoded by this viral genome is provided in SEQ ID NO: 2. With the sequence information provided, this viral genome can be isolated and cloned using a variety of standard genetic engineering techniques well known to those of skill in the art. Five DNA fragments covering the entire MCDV-Tn genome except for 69 nucleotides at the 5' terminus have been cloned into a Bluescript II KS plasmid backbone (Stratagene), transformed and propagated in the *E. coli* cell line DH5a, and deposited on Feb. 8, 1995 with the Midwest Area National Center for Agricultural Utilization Research (formerly known as the National Regional Research Lab and still referred to by the corresponding acronym "NRRL"). One of the plasmids designated "26-7" contains nucleotides 70-3391 of the MCDV-Tn genome (NRRL No. B-21402). Another plasmid designated "53-37" contains nucleotides 2264–5181 of the MCDV-Tn genome (NRRL No. B-21405). Yet another plasmid designated "15-10" contains nucleotides 4649–8156 of the MCDV-Tn genome (NRRL No. B-21401). Yet another plasmid designated "52-30" contains nucleotides 7973–9450 of the MCDV-Tn genome (NRRL No. B-21404). Yet another plasmid designated "52" contains nucleotides 9436–11,813 of the MCDV-Tn genome (NRRL No. B-21403).

The MCDV-Tn strain of the present invention is readily distinguished from the MCDV strain previously characterized in international patent application no. PCT/US94/03028, pub. no. WO 94/21796 (Sep. 29, 1994) by comparing the nucleotide and amino acid sequences of these viruses. Such a comparison is set forth in Table 1(nucleotide comparison) and Table 2(amino acid comparison) below with the MCDV-Tn sequence shown as the top strand and the MCDV sequence disclosed in WO 94/21796, designated as MCDV-T, shown as the lower strand (nucleotide sequence=SEQ ID No. 3; amino acid sequence=SEQ ID No: 4). The GAP program (Needleman and Wunsch, *J. Mol. Biol.* 48: 443–453 (1970); Smith and Waterman, *Adv. Appl. Math.* 2:482–489 (1981); see also Devereux, J., Haeberli, P., and Smithies, O. *Nucleic Acids Research* 12: 387–395) was used for both comparisons.

TABLE 1

Comparison of MCDV-Tn and MCDV-T genomic nucleotide sequences

```
  1 . . NAAAAGGAGGTATATAGGATACCGTCTTTCACACAAGCTCATGGAGTT  48   (SEQ ID NO: 1)
      : | | | | | | | | |     | | | | | | |    |          | |   | | | |  | |
  1 NTGAAAAGGAGGGTATAGAGATACCCTTCATATATTCTGCGGATGGCGTG  50   (SEQ ID NO: 3)

49 TTCTGGCTAAACAGCAATAGGCGCTCCCAAGGCTTAACAAAAATGGTGTG  98
     | |   | | | |   |    | |      | |  | | |     | | |    |
 51 CCGTGAGTAGACCTCGCGACGTTTCCCAGAGGAAAATGGAAATGGTCCAT 100

99 GCAGAACCCG. . . . . . . TATGGGGGATCAAGTCACTTCAGTTCATGAGAT 141
    | |    | | | |         | | | |   | |  | |       | |  | | |       | | | | |
101 GTAACACCAGATATTTATCTGGTTGAGGAACATGGTTTAGTGGTAGAGAT 150

142 AAATATACAGTCGTATTGGACCCTTCTAGATAGAACCCAGTGGATTGACA 191
    | | |       |       |  | |  | | | | | | | | |    |           | | |           |   | | | |
151 AAACTCAACTTTGTGTTGGACCCCGATGCTGTGAAAAGTAAATAAAGACA 200

192 GGCCTGGCCTGGTAA. . . . . . . . . . . . . . . . . .GTTCCCAAGTGGTAAG 222
    | |       |   | |         |                              |       | | | | |    |
201 AGGCCACTTAGCGAAGGATATTCGAAGTAGTGATGAAAGGAAGTGCAATA 250

223 AGACCCGGCACGAAGTGTAGTAAGACGCCATTGGCGCAGTAAATCGCGAT 272
    | |  |    | |    |       | | | |    |       | |     | | | | |     | | | |
251 AGTCATGCCGTAAGTCGCAATGCGCTATAAGTCATGCCGTAAGCCGCGTC 300

273 GCGTAGCTTCGGGCTTTTATCATTGAAGACGCCCGCCAGTAACTTGCGGC 322
    | |  |   |  | |     | | |  | | |    | |             | | |  |    |   | | | | |  | |
301 GCCTGGATT. . TGCTATTAGAATGTCCCTAGCCGGTGATAACCTTGAGTC 348
```

TABLE 1-continued

```
 323 TCTAACGCTGAGTTGGTTTGAAGCTGGTAGTAAACTATTAGG. GGATTCG  371
        |    |    |    |  |||       ||||||   |||  ||    |   ||
 349 CCCGTCATAGGACTACTTTTGTTTGCTTAGTAATACATTGGGACCACCCG  398

372 TACGTCTCACTGTACCACGAACACAGAGTATGTTAATGCTGAGGGAACTC  421
       | |       |  |||   ||      |  ||| ||||  ||  |  |||   ||
 399 CATGGAGCTCTGAGCCTACCATACATAGTACATT. TTCCGAGGGATTGTC  447

422 CGTTTTAAATTACATGATGTCTTGTGAACAAAGCAAAAACAACAACAATC  471
        ||    |||  |             ||| ||      ||    |  |||  |
 448 TTTTGATAATGATGCAGACAAACAACAACCAAAATCCCACTCAAGGAAGC  497

472 AACAATCAACAGCTTTGGAAAATTCGGAAATCA. GATACCCCGGAGGATA  520
        |     |  |       |      ||     |||   ||  |  |  | | |   ||||    |||||
 498 ATTCCTGAGAACTCCTCACAAGATCGCAACTTAGGAGTGCCCGCTGGATA  547

521 CTAT.............ATCCCTCTGGGAGACGG..TGGCATCCGGGTTC  555
        | |                        |  ||||   ||||    |||   ||  |||||     |
 548 TTCTTTAAGCGTTGAGGACCCCTTCGGGAACCGGTCTGACTTTCATATCC  597

556 CAGTAGAGGCTATATACAG...ACCCGGAGAACCTCAGAATTGGGTGCCA  602
       ||||    |      ||         |     |      ||  |  ||     ||||||||  ||
 598 CAGTGCACCAAATCATTCGGGAAGAGATTGATCGTCCAAATTGGGTTCCT  647

603 ATTTGTGGAAACGATTTCCACCTAAGCCAGGATGACCCGTGCTCTGAATG  652
       ||  |||    ||||||||||  ||  ||  |  |       |||| ||      ||      ||  ||
 648 ATATGTTCAAACGATTTTCATCTTAACAGTGAGGATTATTGTGAGGAGTG  697

653 CGACGCGATTGAGGGATCATCAGAGAGAGCAGCTATTGCAATTTCAGACT  702
       |||                       |||      |   ||      |  |  |    ||||    |
 698 CGA............ATCTGAACGGATCAAAAATTTCGAAATATTCAGAT  735

703 CATATGTGGCATCAGATCCTCATTTTACTGTTGATGCTCGTTCTTTGTCG  752
       ||  |                ||   |   ||    |  |  | |       |  ||    ||||
 736 CACAGAATTTGATTGACCAACACCTAAATCTCTGTACTGATTC.......  778

753 AGGAGAGACCACACTTGCACTCATAGGGGCTGCTTTTCTATATGTTCTAG  802
                   |    |||    ||||       ||   ||||||   |      ||  |  ||
 779 ........AAAGGATTGTGATCATTTTCTTGTTTTTCCACGAGTACAAG  820

803 TTATAGATTTTGTTCATTTTGCTTATTTTTGTTTAATTTAGATAAATTTC  852
       ||    |||||||||  |   ||||||||||||  |  |||||||||||   |||||||||||
 821 TTGCAGATTTTGCCCTTTTTGCTTATTCATTTTTAATTTGGATAAATTTT  870

853 AGAAAAACACAAAATACTTTCATAGTAAGAGATCTTTAAGTAGACTTGTG  902
       |  |||  | |     |||  ||     ||||             ||  ||    |||| |      |
 871 ACAAACAAAATCTATATTTGATTAGTCGTCAGGCTCTAGCTAGATTGTTC  920

903 CACTGTTCTGCTGAACAGTTAATTAGTAACGCTATATTGTTTTCTTCTAA  952
       |||  |       || |||  ||||||  |  ||||    ||  ||  ||  |||   |||
 921 CACGGAAGCGCCGAAGAGTTACTCAGTAGAGCGATTTTCTTTACGTATAA  970

953 TAGAATAATAGATGCAGAGGTGGTTGCTGATAATAGGGTTAGCTGTGAAT 1002
       ||             ||  |||||||||||||||||||||| ||||||||||  ||   |||||||||
 971 TATTTGTATTGATGCAGAGGTGGTTGCTAATAATAGGATTGGCTGTGAAT 1020

1003 ATGCTAAGTTGCTTCTTTCAAATGCTCGGGTTGGTGTTCAGGTTACCCCT 1052
       |||  ||||||||   |||   ||  |    | ||   | ||   ||    |   ||||||
1021 ATGTTAAGTTGTTTCATCCAGACCTTAGGCCTAGTATTACGTCTCCCCCT 1070

1053 CCTGCTTGTGATTGGGTTGTGTGTAACAATGTTGAACATCTTTTTGAGTG 1102
       ||||  ||||||||||||| |||||  | |||| |  |||||||||||||||||||
1071 TATGCTAGTGATTGGGTTATGTGTGATAATGCTAAACATCTTTTTGAGTG 1120

1103 TTTTGGCATTAGTGACGCGCAGCGAGGACACATTACTGGATTTAATGACG 1152
       |  ||||   ||  ||||| |||          |||||||||  |      ||||  |||      ||
1121 TCTTGGCCTTGGTGACACGACCAGAGGACACCTATATGGACTTATTAGCG 1170

1153 AGAATGCATATTGGAACGCCTCGTGCGCAAAATGTGGCGCCTGTTGCCAG 1202
       |||||||||||||||||||||  |||||  |||||||  ||  |||||||||  |  |||||||||  |||
1171 AGAATGCATATTGGAACGCCACGTGCTCAAAATGCGGAGCCTGTTGTCAG 1220
```

TABLE 1-continued

```
1203 GGAGCGAACGCTAGGTCCGCGATCCCGATAGTCTTGCTATTGAAATTCAT 1252
     |||||  || ||     |   ||||||  ||||||||   ||    ||| | |||
1221 GGAGCAAATGCCCGTACGGCGATACCGATAGTGATGGCGTTGCAGTACTG 1270

1253 AACGATTAGAAAAGAGCAAGATATTTGGCTAGCTTCACACATGCATCATG 1302
        | | |        || ||||||  |       |  ||||||  |
1271 CAGGGTGGATGTGTATTATAGTGAGTACTATTTATACCACATCTACGCTC 1320

1303 ACAATGACTTTGTGGAGATTAACAGCATCACAGCCCAGATTATAGCCAAA 1352
       |  ||        || ||||||  |       |||||  ||   |   ||   ||
1321 CGGAAGAGAGAATGAAGATTGATCAACAGACAGCACTTGCTACACAGT 1370

1353 ATCAATAATATACCAAATGTTGATGAACCTGCAGTAGGATACATGGGATC 1402
     || |       ||| |  |  ||    || |      ||    ||   |
1371 ATAATCCGAGGAGCACCAGCAGTGGATTGCTCTGAGTTATCTCAGGAGCC 1420

1403 TAAACTTGAAAATTGGATTTCCTACCGCGACACAGACTTCACAGAAGAAG 1452
        | |        |   ||||      |  |||||||    ||  ||
1421 AATTC......ACAGGATGGTAATGGATAGCTCAAAGTTAGTGGCACTGG 1464

1453 ATTGGACTCTGAAGCACCC...GTGCTCAGGACCTTTAGAAAGCGAAGAA 1499
     ||| |||    | | |||  ||    | ||  ||||  |||         ||||
1465 ATTCGACAATCAGGCATCCTAAGAGCCAAGGAAGTTTGCTCGATTCAGAA 1514

1500 TGTGATCACGACTTCATCATCAGAAATCAATATGGGTTTGAGCTATATTT 1549
     || ||||||  || || ||   | ||||       ||||   |   ||      |
1515 TGCGATCATGAGTTTATTCTAAGAACGTCCCATGGTATCAAAATACCGAT 1564

1550 GAATCATGCAATGCTTCTAAATTTTGCTGCATTGTGTCTTTATCATGGCA 1599
     || | |     |     || | |||     ||| || |    || ||||||||
1565 GAGTAAGTCTTTATTTATATCATTTCTTACCATGGGAGCTTATCATGGGT 1614

1600 GATTGTATAACTCTGACAAATCAGTTGGAATACTGGTCACCTTTGGAGGA 1649
                ||  |     |||  |            |     |     | |||||  ||
1615 ATGCTCATGATGATCAGCAGGAGCAAAATGCGATAATATCTTTTGGTGGG 1664

1650 ATGATAGGGGTGAACATTGCATGCAATGAGGCATTTATGGAATTCCACAA 1699
     |||    || || || | || || ||   ||  ||   || || || ||
1665 ATGCCCGGAGTCAATTTGGCTTGTAACAAAAATTTCCTGAGAATGCATAA 1714

1700 ACGTTTCTATAGCGGCACTCTCAGAATAAGTCCAATGAATATG...TATT 1746
      || |||   || || || | || ||  || ||  ||  ||||    |
1715 GTTGTTTTATTCTGGAAGTTTTAGGCGCAGACCCCTGTTTATGAGCCAAA 1764

1747 TGAGGAGAGAGAGATGCCAAGCTCAGTCAGACTTCAATGATGAAGAATTT 1796
     |            ||       |    ||||||||| |  ||  |||||||||||||
1765 TTCCCTCTACGAATGCCACCGCTCAGTCCGGTTTTAATGATGAAGAATTC 1814

1797 CAAAGACTGATGGCAGAAGAGGGCGATGCGGAAATTCAAAGCGTCTCAAA 1846
     |||||  ||||||||  ||||||||                |     |     |  |||
1815 GAAAGATTGATGGCTGAAGAGGG......TGTGCATGTCAAAGTCGAGCG 1858

1847 TTGGGTTAGTGAATATCTTGAGATAGAAGACGTCATTGACATAGTGGATG 1896
       |     |     ||        ||||       ||  |||||  |||||  ||            ||||
1859 TCCAATAGCAGAGAGGTTTGATTATGAGGACGTTATTGATATTTACGATG 1908

1897 AAGCTGAAAGCAAGAAAACTCGAGGATTAGGTTTGAATCAGGTTTTGGGA 1946
      |  ||   |  |    ||  ||||    ||||     |    || || || |||
1909 AGACCGACCACGACAGGACACGAGCTCTAGGCCTTGGCCAAGTATTCGGA 1958

1947 GGATTGCTCAAAGGTGTCTCGCATTGCGTAGACAGCTTACACAAGGTTTT 1996
     ||  |||||||||||    |  || ||||| |||||  |||  ||||   ||||||  ||
1959 GGTTTGCTCAAAGGAATTTCTCATTGTGTAGATAGCCTACATAAGGTATT 2008

1997 TGACTGGCCCATTGATCTTGCAATTGATGCGGCAAAAGGCACAGCTGATT 2046
     |||  |   ||    | ||  || ||  || ||  ||   || |         || | ||||||
2009 TGATTTCCCTCTGGACCTGGCCATAGAAGCAGCTCAGAAAACTGGTGATT 2058

2047 GGCTTGAAGGTAATAAGTCATCAGTCGATGACAGCAAAATCTGTGCTGGA 2096
     |||||||| |||||   |||     |  |||| ||||||  |||||  |||| ||
2059 GGCTTGAAGGAAATAAAGCTGCAGTAGATGAAACTAAAATTTGTGTGGGC 2108
```

TABLE 1-continued

```
2097 TGCCCTGAAATTCAGAAAGATATGCAAGATTTCCAGAAAGAAACGAAGAT 2146
     || || || ||||| ||||||||    |||||||||| ||||| ||
2109 TGTCCCGAGATTCAAAAAGATATGATCAGTTTCCAGAATGAAACAAAAGA 2158

2147 GGGAATAGAGATCCTGAGAGATTCGATCAAGAAATTATCAGAAGGGATTG 2196
     |   |  ||   ||   ||    || |||||  | || || || ||||
2159 AGCTTTTGAATTAATACGATCAAGTATAAAGAAGCTTTCCGAGGGCATTG 2208

2197 ACAAGATCACCAGAATGAATCAAACAAATTTTGAACGAATTGTTGATCGA 2246
     ||||  |||||  |  |||||||   || ||  |||||||||||  | ||   |
2209 ACAAAATCACGAAGATGAATGCTACGAACTTTGAACGAATCCTAGACGGG 2258

2247 ATTAGACCCATCGAGAGCAAACTCAAAGAACTTGAAAAGATTAAACCTGA 2296
     ||||  |||  ||||||||||       | |  |||||||||  || |    ||| |
2259 ATTAAACCAATCGAGAGCAGGTTGACAGAACTTGAGAACAAGGCACCCGC 2308

2297 TGCTGGGGGATCAAAAGATAGTGAAGCTATGCGCCAATTAGTCCAGGCCA 2346
     | |              ||| ||  |||| |||      |  ||||||||||
2309 TTC...........AGACAGCAAAGCCATGGAAGCTCTGGTCCAGGCCG 2346

2347 TCAAAGATATTAAGCTTATTAAACAAGCGATGATGGAACTTAATGATAGA 2396
     | ||||| | ||  | ||  | ||| | |||||| | ||  || |||  |||
2347 TGAAAGACTTGAAAATCATGAAAGAGGCGATGCTCGATCTAAATCGAAGA 2396

2397 ATTAAAGACCTGGAGGATAGCAAGCAGCATCAAGAAGATTCAAAGCCAGA 2446
     | |    |  ||||| | |                  | ||  |||        ||| |
2397 CTGAGCAAGCTGGAAGGAA.........AGAAAGTGATGGCCAGACTAC 2437

2447 TGATGATACAGCAGGTGAGCAAAAACCCATTCCAAAAATCAATAAAATAA 2496
     ||| |  |||||  || ||||||| |||| || || ||      | | ||
2438 TGAAGGGACAGCGGGAGAGCAACAACCGATCCCTAA...GACTCCAACTC 2484

2497 GGGTTAAAGCCAAGAGAGTTGAGAAGCAATCAGGTACGAACATAGTGAAC 2546
     |  || || ||     |||| ||||||||||||| ||||  || || |||
2485 GAGTGAAGGCAAGACCAGTTGTGAAGCAATCAGGAACGATAATGGTAAAC 2534

2547 AATGAGATAGAACAGGCTTTTCAAGATGAAGAAAAGAGAACTGTTGATCC 2596
     |  ||||      ||  |  ||||     |||  | ||   ||    ||| ||
2535 GAAGAGAGCACAGAAACTTTCAGGGATAATGAGAGTCGAGTGACTGACCC 2584

2597 AAATATCAGTGATATGTACAACGCTATCAAAAGTGAGTATTTGGTTAAAA 2646
     ||  |  ||  ||||||||          |||  |   |      || || || ||
2585 TAACAGGAGCGATATGTTTGCTGCTGTTACTGCAGAATACTTAGTTAAAT 2634

2647 GCTTTTCTTGGAAAGTCTCAGATGGACAAGATAAAGTTCTATCTAATATT 2696
     |||  |  |||||||| ||  ||||||||||||||||||  |    |  ||
2635 CGTTTACATGGAAAGTTTCTGATGGACAAGATAAAGTTTGGCTGACCTT 2684

2697 AATATACCTGAGGATTTGTGGAATACAAACTCCCGGCTGAACGACATAAT 2746
     || ||||  |  ||  |||   |  |  |||| |||    ||| || ||| |
2685 GATTTACCTCAAGACTTATGGAAATCCAATTCCCGATTGAGTGATATCAT 2734

2747 GAGCTATTTCCAGTACTACAAGGCTACAGGTTTAACATTTAGAATATCAA 2796
     |   ||||||||| || ||   | || || ||   | || ||| ||| |
2735 GGGGTATTTCCAATATTATGATGCAACCGGAATCACTTTTCGCATAACGA 2784

2797 CGACCTGTATTCCAATGCATGGAGGTACACTGTTTGCAGCGTGGGATGCA 2846
     | || ||| |||| ||||| |||||| | |  | ||| || ||||||||
2785 CAACATGTGTTCCTATGCACGGTGGTACTTTATGTGCTGCTTGGGATGCT 2834

2847 TGTGGATGTGCTACTCGACAAGGGGATAGCTACGGCTGTGCAACTGACAGG 2896
     |||  || ||||| ||||||||| ||||||| || ||  |  |  | ||||| ||
2835 AATGGTTGCGCTACACGACAAGGTATAGCCACAACGGTTCAGCTGACTGG 2884

2897 GCTTCCTGGAATCATGATAGAAGCACACAGTTCGTCCTTGACGACTTTCT 2946
     |||  ||  ||| |||||| |||||| |||| ||  ||
2885 TTTGCCCAAAACATTTATTGAAGCTCACAGCTCATCAGAAACGATAATCG 2934
```

TABLE 1-continued

```
2947 CAGTCGAGGATCCGTTAACGCAATCTACTGTGTGCCTTAGTGGAAGTGAA 2996
     ||  || || |     |   |||||   |   | || || ||||||||||||
2935 TGGTAAAGAATTCCAATATACAATCCGCGATTTGTCTAAGTGGAAGTGAG 2984

2997 CATTCGTTTGGGCGGATTGGAATTCTCAAAATTTGTTGCCTAAACGTGTT 3046
     ||  |||||||||  | || ||||| ||  || |||||| | ||    |||
2985 CACTCGTTTGGGAGAATGGGAATCCTGAAGATCTGTTGCTTGAATACGTT 3034

3047 GAATGCACCACAAGCAGCCACCCAATCCGTTTCCGTAAACGTATGGGTGA 3096
     ||||||  |||  | |  ||| || ||       ||   | || ||||||  ||| |  |
3035 GAATGCGCCAAAGGAAGCTACACAGCAAGTGGCTGTGAACGTCTGGATTA 3084

3097 AGTTTGATGGGGTGAAATTTCATTTCTACTCCCTCAAAAAGCAACCCGTG 3146
     ||||||| ||  ||  |||||||||    |  || ||   |  ||   |  | ||  ||
3085 AGTTTGACGGAGTTAAATTTCACGTTTATTCTTTAAGGAAAAATCCAGTC 3134

3147 GTCTCCCAAATGCTAGTAGATAAATTGACTAATCTTGGAGAAATGGGTTG 3196
     ||  ||  ||| |||   |||    |   |   |  || |   ||| |||
3135 GTTTCGCAACTGCAGGTGGCATCTCTTACAGACATAGGAGAATTGAGCAG 3184

3197 TGTAGTTGCAACTGGAACATGGTCAACGACTTCAAGTTTGAATTTGTTGC 3246
     ||| ||||| |||||    |  ||||| || ||  ||     ||||||| ||
3185 TGTGGTTGCTACTGGTTCTTGGTCTACTACCTCGGCTACTAATTTGATGG 3234

3247 AGCTAAACGTGCATCCAACAGCTTGCTTTATAAGTGATGGCCTGGTTACT 3296
     |     |||||| |  ||||||| ||   | ||     | ||   || || ||
3235 AATTAAACATTCATCCCACCTCCTGTGCTATTCAGAACGGATTGATAACA 3284

3297 CAGACCCCACTAAGTGTAATAGCTCATGCTTTCGCACGATGGAGGGGATC 3346
     ||||| |||   | |||||| |||||||||||| |||   | |||||  ||||||
3285 CAGACACCATTGAGTGTTTTAGCTCATGCTTTTGCAAGGTGGAGAGGATC 3334

3347 ATTGAAATTCACCATCACTTTTGGAGCTAGTATGTTCACAAGAGGAAGAG 3396
     ||||||  |     |||||| |||  |||||  |||  ||||  | ||||| ||
3335 GTTGAAAATTTCCATCATTTTCGGAGCGAGTTTGTTTACCCGAGGACGAA 3384

3397 TCCTGGTAGCAGCTATACCTGTGGCGAAGCGAAAAGAGACTCTCACAATT 3446
     || |  |   ||  |||  |  | || || ||  ||||||  |||| ||   ||  ||
3385 TCTTAGCCGCTGCTGTGCCCGTTGCTAAGCGCAAAGGTACCATGAGCCTT 3434

3447 GAAGAGATTAGTGGATATCACAATGTAATGTGCCTGCTCAATGGAGAAAG 3496
     ||  |||||||||||| |||||  ||||| ||||||     ||| || |  || ||||||    |
3435 GACGAGATTAGTGGGTATCATAATGTTTGCTGCTTATTGAATGGTCAGCA 3484

3497 GACATCTTTCGAACTTGAAGTCCCTTATCACTCAGTGGGAGAGGATTCTT 3546
     ||   | ||  |||  |  |||   ||||   ||| |  |  || ||||||   |  |||||||
3485 AACTACATTTGAATTGGAAATCCCATATTATTCTGTGGGCCAAGATTCTT 3534

3547 ATGTTTGTAGGGATGCCCTATTTGATGTTTCGTCATACGCACAGAACTTT 3596
     ||  |      |  ||||| ||  |||||| |  || |   |||        ||| |||
3535 TCGTGTACCGTGATGCTCTTTTTGATATCTCTGCGCACGATGGGAATTTT 3584

3597 ATGATCACCAGATTACACATGGTAGTTATAGACACATTGGTGATGAGTTC 3646
     |||||  ||   |  || ||  |   | |    |   |  | ||||| ||||| |||||       |
3585 ATGATTACTCGCTTGCATCTCGTGATACTGGATAAATTGGTAATGAGCGC 3634

3647 AAATGCAAGTAACACAATAAGTTACTGTGTGATGATGGGACCAGGCAAAG 3696
     |||||  || ||||   |||| ||  |    ||||    | |||||||||       |
3635 TAATGCGAGCAACAGCATAAATTTTTCCGTGACTCTTGGACCAGGTTCTG 3684

3697 ATCTTGAATTGAGATATCTAAATGGTGTCCATGCTCAGAGAAATGTGAGA 3746
     ||  |  ||||||||| ||||||    ||  || |||| |||  ||  |||  |   ||  ||
3685 ATTTGGAATTGAAATATCTTGCAGGAGTACATGGGCAGCGCATAGTCCGC 3734

3747 GAATTAAAAGCTCAGGTAAGCCTTGGTTTTTCCTTACAATCTGGAAGGAA 3796
     ||  || || |||||   |   |||   ||||  ||    |  |||| ||     |
3735 GAGTTGAAGATGCAGGTTTCATTGGGTCGGTCATTTGAGAATGGAGTGCT 3784

3797 CATTGGAGTGGGTTTCAGTGATTTGCTCAAAAGATGGGCCCACCTGCTCA 3846
     |||||      ||  ||||   ||  ||||||   ||||||||||     ||  |||
3785 TATTGGTAGTGGCTTCGACGACTTGCTACAAAGATGGAGTCATTTGGTGT 3834
```

TABLE 1-continued

```
3847 CACTGCACTTTGATGAAAATAACGAAAAATCAGAAGAAAAAGTTGGTTCT 3896
      |  |||  |||  |||  |||     ||  |       ||     |||||   |
3835 CCATGCCTTTTAATGCAAAAGGAGACAGCGATGAGATCCAAGTCTTTGGC 3884

3897 TATATTGTCACTGTAGCGCCAAGTTATAGAGCTTTTCCGCAGCACAACAC 3946
     |||||    |  ||||| || ||      ||| |  ||||     |||   |||
3885 TATATCATGACTGTTGCCCCGGCGTATCGTTCCCTTCCAGTCCACTGCAC 3934

3947 TTTATTGAGTTGGTTTTCACAACTATTCGTGCAATGGCAAGGCTCTTTGT 3996
     |    |  |||||||||||||||| ||||||||||| |||  ||||   || |
3935 GCTGCTAAGTTGGTTTTCACAATTATTCGTGCAGTGGAAAGGTGGTATAA 3984

3997 GCTACAGGTTACACGTGGACTCACAAGAGAGAAGATATGGAGGTTATTTG 4046
     ||  ||  |||||| | ||  |||  ||||||| |  ||||  ||  ||  |
3985 AGTATAGACTACACATTGATTCAGAAGAGCGCAGATGGGGTGGATTCATC 4034

4047 CGCATATGGCATGATCCTAACGGTTCATTAGATGAAGGAGTCGAATTCGC 4096
     |  |||||||||  || ||  || || |||  ||||||||||     |||||| ||
4035 AAAGTTTGGCATGACCCAAATGGCTCTTTGGATGAAGGGAAAGAATTTGC 4084

4097 TAT   TCAACAAACTTAGAGCCACCCCCAGGTGCCTTTGTGAAATACTGGA 4146
     ||    |      |    ||   ||||||   |  ||  ||   ||     ||  ||||
4085 TAAAGCGGATATTCTATCGCCACCAGCCGGAGCTATGGTTCGTTATTGGA 4134

4147 ATTATAATGAGCAGAGCGAGTTTGAGTTTGTGGTACCATACACGGCTCGA 4196
     | |   ||     |   | || ||  ||||||     |||||||        |||  ||
4135 ACT...ATTTAAATGGAGACTTGGAGTTTACAGTACCATTTGTGCTAGA 4181

4197 ACCCCTCGCTTATTCGTGCCAAAGGCAATGATTCCGACAGATTCGAAGTC 4246
     |||   |      |  |||  |  ||||||  ||  ||||||||  |  ||  |||||  |||||
4182 ACCAGTACGCTGTTCATACCAAAAGCTATGATTGCCACCGATTCAAAGTC 4231

4247 ATGGATATTGAATTATAATGGAACTTTGAACTTCGATTATAGGGGAGTGG 4296
     ||||||    ||||   |||  ||  || ||   ||||  ||||   ||       ||||||  |
4232 ATGGATTCTGAACTACAACGGTACATTGAATTTCGCGTACCAAGGAGTAG 4281

4297 ATGATTTTAACGTCACTGTTGACATTAGCGCTGGAGATAACTTCGAGTTC 4346
     ||||  || |     |  || ||  || |     ||  ||  |     ||      |||||  ||  ||
4282 ATGACTTCACAATTACAGTGGAAACAAGTGCAGCCGACGACTTTGAATTT 4331

4347 TCTGTTCGTACGGTAGCTCCCAAAGCTGGAAAAGTGAATGAATCGTTTAC 4396
     |||||  ||  || || ||||      ||||||||       |||    ||   |
4332 CACGTTCGAACAGTTGCACCCCGCGCTGGAAAGGTCAACGAAGCTTTTGC 4381

4397 AAAGCTATCGTATAGCAATGAGCTCGTCGATATCAAGAAACCGTTGACAG 4446
     ||   |      |||         |||    |    |||||||||   || |    |||||
4382 CAAATTGGAGTACGCTTCTGATTTAAAGGATATCAAAGAATCTCTGACAT 4431

4447 CAGCTGGAAGACTCAAAGGACCGTTCAATTTGAACACTTTGAAAACTGCT 4496
     |   |   |  ||||||| ||    ||    ||  ||      |  |||       |
4432 CTTCCACTCGTTTGAAAGGGCCTCATTATAAAACGAAAATTACCTCAATA 4481

4497 GTCCCTAA.AGAAACGCCCAAAGAAAGCTCTGATGATAAGGATAAATCAA 4545
     |   ||  ||  ||| |    |||  ||  ||  |        ||||  |||
4482 GAGCCAAATAAAATTGATGAAAATGAGTCCTCACGTGGTAAAGATAACAA 4531

4546 ATCAGAAGAGGAAAGGAGCTATGGATTCGTTACTAAACGCTGTTGCTCAG 4595
     ||| |    ||||         | ||  ||||||||| ||      ||||||
4532 GTCAAATTCGAAA.......TTTGAGGACTTACTCAATGCAACAGCTCAG 4574

4596 ATGGAAACTATAAATAGTGACGCGAATGGGTGTTTCTCTTTAGGGGGATT 4645
     |||||    |          |||||  |   ||        |      |
4575 ATGGATTTTGATCGAGCCACAGCGAACGTTGGGTGTGTGCCATTCTCCAT 4624

4646 GAAGTCTACTGCCAAAATGCTGGACTCAAGAAAAACGTGCGAGAAATTTG 4695
     ||  ||  ||| ||||        |  |  |  ||||||  ||||  | |
4625 TGCAAAGACAGCAAAGGTGCTTTCGGAACGCGAGACGTGTAAGAAGATGG 4674
```

TABLE 1-continued

```
4696 CTGACATCATGGATTTCACTCATGATACTCTTGGTGTCAAAGATGGACCG 4745
     |  ||   |   |  ||||||||  ||       |  |     |     |   |||
4675 CAGATGTGTTAGATTTCACACACTCATGTTTGAACTTAGACAGTCAACCT 4724

4746 GCAGCGCAGAGACTTGCAGCGGCTGTGGCGCAAATTGCTCCAATTATAGA 4795
     ||  |||   |||  ||||||||| |    |   ||  ||  |||||  |||
4725 GCGGCGGCAAGATTAGCAGCGGCCATTTCTCAAATAGCACCTATTATGGA 4774

4796 AAGCGTGAGCAGAACGACAGAAAGTGTGGAATCGAAGCTCACATGCCTGG 4845
     |||  |    |  ||||||  ||  ||||  || ||      ||   |  |  |  |||
4775 GAGCATCGGTAGAACCACTCAAAGCGTAGAGGAAAAATTGGCTTCTGTGG 4824

4846 ATAAGTACAAGGATGGAATTCTTGGGATATTACAAAGCTTATGCAAAGAG 4895
     |||   |   |  |||   |||    |  |    ||  |      |||  |            ||
4825 ATACATTTAGGGACAAAATCATGGCTCTAATTTCAAACGTGCTTGGGGAT 4874

4896 ACAATCCCAGGACTTGCCATTGTGGACTTCAAGAAGGGCAAGTACATGTG 4945
     ||   |  ||  |||||  ||||||             |||||||||| |||||||||     ||
4875 ACTCTACCTGGACTGGCCATTGCTGACTTCAAAAAAGGAAAATATGTGTG 4924

4946 GGCAACCCTCCTCACGCTGATAGCAGGAGCAGCTCTCTTCTGGGCATGTA 4995
     |||    |   ||||  ||   ||||||||  |       |       |||||    |
4925 GGCCTCGTTCCTGACAATGATAGCCGCTTGCGTAGTAGCTTGGGCTGCCA 4974

4996 AAAGCCAGAAGAGCTTTTTGAAAAGGTTTTCCGTGGTTGTAATGATCATT 5045
     |||  ||||   |||||   ||||||||||  |||  |   ||||||   |  ||||||  |||
4975 CTAGCAAGAAAAGCTTCTTGAAAAGATTTGCAGTGGTAGCTATGATAATT 5024

5046 TGGAGTCCTTTTCTTGCTGGAAAAGTATGGAGCTTAGGCCAGTGGATAGT 5095
     |||||  ||  |||||   |    |||  ||||   |  ||   |||||
5025 TGGAGCCCATTTCTCGCAAGTAAAATATGGGCGCTTGGTACATGGATTAG 5074

5096 TCAAAAGTGGTGCCATTTGTGGCCCAAATCAGACTCATGCCGACAACACT 5145
     |  |   |||  |     |   ||||||  ||  ||||||||||||||||||||||||
5075 GAAGAGCTGGAGTAAGCTTTGGCCTAAGTCAGACTCATGCCGACAACACT 5124

5146 CTTTGGCAGGCCTGTTCGAAAGTGCGAAAACGAAGGTTCGTGGTTTCCCA 5195
     ||||||||||||||   |||||||  |   ||     |    | ||||||
5125 CTTTGGCAGGCCTGTGTGAAAGTGTGTTCACATCATTCAAGGATTTCCCT 5174

5196 GATTGGTTTCGATCCGGGGGCATGAACATTGTGACGCAAGTTTGTTCAGT 5245
     ||  ||||||    |||  || ||  ||   |||||||||||||||||    ||||
5175 GACTGGTTTAAATCAGGAGGAATCACGATTGTGACGCAAGTTTGCACAGT 5224

5246 ATTACTGACGATAGTGAGTCTGATCACGTTAGGGACAATCCCCAGTGCAA 5295
     ||||||||||||||||||||||||  |  | || || || || || ||  | |
5225 ATTACTGACGATAGTGAGTCTGATTACACTTGGAACTATACCAAGCACGA 5274

5296 AGAAAAGCAAATCACTGGCCGATCGCTTTATCGAATTTGGCAACATGAAT 5345
     |  |||        |   |  ||| ||    ||||  ||||||||  |||||||
5275 AACAAAATGCTACGTTCGCAGACAAATTTAAAGAATTTGGTAACATGAGC 5324

5346 AGAGCTGCAACCTCTATTGCTGCAGGCTACAAGAGTATCTCAGAATTGTG 5395
     ||||||  ||||  ||  ||  |||||||| |||||||   || |||||    ||||
5325 AGAGCTACAACGTCAATAGCTGCAGGTTACAAGACGATATCAGAGCTGTG 5374

5396 TTCAAAATTCACTCATTTTGTAGCAACACATTTTCTGGGAGCCACTGTAG 5445
     |||  |||||||| |||      |  ||   |    ||   ||  ||  |||   |
5375 TTCGAAATTCACCAATTACTTGGCTGTAACCTTCTTTGGGGCGCAAGTTG 5424

5446 ATGACAATGTCTTCAAAGACCTAGTTACGTTCAACGTTAAAGATTGGGTC 5495
     |||||  |||     ||||||  |    ||   ||||||||||||||  ||  ||||
5425 ATGACGATGCTTTCAAGGGTTTGGTAGCGTTCAACGTTAAGGAATGGATT 5474

5496 GAACAAGTCAAAGTGGCATCTCTTGAGGAAAACAAGTTTAAATCATTCGG 5545
     ||||  |||          ||||||||||||||||  ||||       ||  ||
5475 CTTGAAGTGAAAAACCTGTCTCTTGAGGAAAACAAATTTAGTGGTTTTGG 5524

5546 ATCGCCTGAGCAGCTAACGCGAGTAAGACACATGTATGACAAGAGCCTGG 5595
       ||||||  ||      ||  ||||||  |  ||||| ||          |||
5525 TGGTGATGAGCATCTTGTCAAGGTTAGACATTTATATGATAAATCTGTGG 5574
```

TABLE 1-continued

```
5596 AAATAACCAACAAACTTCTGGATAGAAACAAAGTGCCCGTAGCGATGCTC 5645
     ||||||||   ||   ||   |   |||   |||  |||  |  ||  |||||
5575 AAATAACCTATAAGTTGCTCCAGAAAAATCGAGTTCCCATTGCTATGCTT 5624

5646 CCGGTTATCAGAGATACATGTAAGAAATGCGAGGAGCTTTTGAATGACAG 5695
     ||   ||   |||  ||||  ||  |||||||||  ||||||||    ||   ||   ||  ||
5625 CCTATCATCCGAGACACGTGTAAGAAGTGCGAGGATTTGCTAAACGAGAG 5674

5696 CTACAGTTACAAGGGAATGAAGACCCCTAGAATAGATCCATTCTACATTT 5745
     ||  |   |||||||   ||   |||||  || ||    |   |||  |||||||||  || |
5675 TTATACTTACAAAGGTATGAAAACTCCGCGCGTGGACCCATTCTATATAT 5724

5746 GTCTGACTGGTCCACCTGGTGTTGGAAAATCCACTGTGGCCTCCATAATT 5795
     |  ||      |||    ||||||||  |||||   ||   ||||||  |||||  ||  ||  |||
5725 GCCTTTTTGGAGCACCTGGAGTTGGCAAGTCCACAGTGGCATCGATGATT 5774

5796 ATCAATGATCTTTTGGATTATATGGGAGAGCCTAAGACTGATAGAATATA 5845
     |   |   |||   |   |||||||     ||||||  ||  ||||||     ||||||  ||  ||
5775 GTTGACGTTTGTTTGGATGCTATGGGCGAACCTAAGGTTGATAGGATCTA 5824

5846 CACCAGATGTTGCGCCGATTCATATTGGAGCAACTACCACCATGAACCAG 5895
     ||   ||||  ||   |   |||   ||||||||||||||  ||   ||||||   ||  ||||
5825 TACTCGATGCTGTTCTGATCAATATTGGAGCAATTATCACCACGAGCCAG 5874

5896 TTATCATTTATGACGATCTAGGGGCTATTTCAAAAGTAGCTAGTTTATCC 5945
     ||||       |||||||||||   |   ||||||   ||       |   |    |||  |||||||||
5875 TTATTTGTTATGACGACTTGGGGGCAATCAGCAGACCAGCGAGTTTATCA 5924

5946 GACTATGCTGAAATTATGGGTATTAAATCAAACAGGCCCTACTCTTTGCC 5995
     |||||||    ||  ||  |||||   ||  |||||  |||||  ||  |||||   |  ||
5925 GACTATGGGGAGATAATGGGAATCAAATCGAACAGACCATACTCCCTACC 5974

5996 GATGGCTGCTGTTGAGGAAAAAGGAAGGCATTGCTTATCAAAGTACTTAG 6045
     ||||||||||||||  ||  |||||||||||||||||  |||||    |||   ||||
5975 TATGGCTGCTGTTGATGAGAAAGGAAGGCATTGTTTATCGCGATACCTCA 6024

6046 TAGCCTGCACCAACCTCACTCATCTCGATGATACGGGAGACGTCAAAACG 6095
     |  ||  ||  ||  ||    |  ||  |||||  ||  |||||||||||  ||  ||  |||||
6025 TTGCTTGTACAAATTTAACCCATCTGGACGATACGGGCGATGTGAAAACA 6074

6096 AAGGAAGCTTATTACAGAAGAATTAATCTTCCCGTAACCGTCGAGAGAGA 6145
     |||||  ||  ||   |  ||||||  |||  ||| ||  ||  ||  ||   ||||||
6075 AAGGATGCCTACTATCGCAGAATCAATGTCCCAGTGACAGTGACGAGAGA 6124

6146 TTTGGCTATGCCAATGAGCCCTGAGGATCCCGCTAGTGGTTTACTGTTCA 6195
     |   |    ||||  |||  ||||| ||   |||   |||   |||  ||||
6125 AGTAACCGCCATGATGAACCCCGAGGACCCAACTGATGGACTACGTTTCA 6174

6196 CTATTGGGGATATTCATGAGAATGGCAGGAATGTGAGCGTGGTTGAGAGT 6245
     |   |   |  ||       |||||||  ||  ||  ||||   |||  |||   |||  |||
6175 CCGTGGAGCAAGTGCTTGATGGAGGTAGATGGATTAATGTTACTGAAAGC 6224

6246 AGGTTGCTCAATGGTCGAGTGCCTTTTAGAGCTGGAGACTTACGAAACAT 6295
     |  |  |||||||||   |   ||||  ||  ||  ||||  |||    |   |||||
6225 CGTCTCCTCAATGGAAGGATGCCATTCAGGGCTGAAGATCTCATGAACAT 6274

6296 GAGCTACAATTACTTTATGGAGTTCGTGAGGATCTACGCAACTATCTATA 6345
     ||  |||||  ||||||||||||||  |   ||| ||  ||   ||   ||  ||||
6275 GAACTACAGTTACTTTATGGAGTTTCTCAAGATGTATGCTGCTTTATATA 6324

6346 TGGAGAATCAACAGCAACTCGTGGCTAAGCTTTCAGGAGATGATTACGAA 6395
     ||||  ||||||| |     |  |||||| ||    |||||       ||
6325 TGGAAAATCAAAACATGTTGGTGGCAAAATTGAGAGGA......ACAGAG 6368

6396 AGCTCTTCATCATCGTTTCCCGAGAATGAGGAATTGGAATTTGACTTCCT 6445
     |  |    ||||     |  |  |||||||||  |||  ||||||  ||   |     |
6369 ATCCCAGAATCACGTAGTTCAGAGAATGAAGAACTTGAATTCGATTATTT 6418
```

TABLE 1-continued

```
6446 AGCCCAAGCACACAATGGTGTGTACCTAACGATAGAGGAAGTTGTAGCTA 6495
     ||  ||| || |  |        | ||  | |||| | ||   | |
6419 GGCTACAGCTCAGATGGACCATACAGTGACATTTGGGGAACTAGTTACCA 6468

6496 AATTTGAGTCAATGAAATTCTCGGGAAAACAACTCAATGCTGAAATTGAA 6545
     ||||   | ||    ||    ||   ||||||  ||         |
6469 AATTCAACTCGTATAAGCTTACTGGGAAACAATGGAACAAGAGGCTCTGT 6518

6546 AAATTCGAAAGAATTGGAGTTGATGGATGGAGAACTAACAAAGCTCTCTC 6595
     ||  |  | | |       |  || ||||||||   ||  |||||    ||
6519 GAACTTGGATGGACATCTCTAGACGGATGGAACACGAACAAGATTATGAG 6568

6596 CTTTAATGATTTGGTCAAAAGGTTTTGTGGATGCTGCTTAGGTGATGACT 6645
     ||   |||  |  ||       | ||  ||||| ||||       ||| ||
6569 ATTCGACGATCTAGTTGCCGGATTCTGTGGTTGCTCAAGGAATGAGAATT 6618

6646 GTAACTTTGATTTCCACTATCGAACTTTATTCAAAGTGCTAATAGAGAAT 6695
     | ||  ||||| ||| |||   |||     |      |  ||  | ||||
6619 GCAATTTTGACTTCTATCATCAGAGACTTCAAGCATGTTTGAACAAGAAA 6668

6696 AAGCAAATCCCAGCCTACAAGTGTATGGTTCTCCATAAAGTGAATCCAGA 6745
     |        ||  || ||  |   | ||| || ||  || |||||  ||||
6669 GGGTTTGCTCCCGCATATCAATATTTCAACCTTCACAAGTTGAATTCAGA 6718

6746 TAGAATGAAGACTCAGATAAAGATGGTGAACGGGTACACTTTGGAAACAA 6795
     |     ||||||  || | ||| |        ||||   |||    |||
6719 CACCCAGAAGACAGAGCTCAAGCTTAAATGCGGGACAACTGCTGAAGATT 6768

6796 TGTTTAAGACTTTGAACCCTCTCACCATTTTCTTATATCTGGTTTTTGTG 6845
     | ||| |              ||     ||| ||||    ||   | ||||||
6769 TATTCAGACAAGCTGACTTGATGGTCATATTCTCCTACCTCTTATTTGTT 6818

6846 CTGAAATGTGGTATTAGTGCCGACAATGTATGTTTATCGTACCAATTATT 6895
     || |   |||    | ||||    |||| ||| | || ||   |    | ||
6819 GCGAGAATTGGGGTGAGTGGATCTCATGTGTGTCTGTCATATAACATGTT 6868

6896 TGCTATGAATGACGCAGAGCAAGTTGAATTTGAAATTGAAGATTCTTTGC 6945
          | || || |    ||| |   ||||  |      |  ||   | ||
6869 GAACGTCAAGGATGTCAAGGATTTTGAGATATGCAGGGAGAACGTTCTTG 6918

6946 GTCTGGATGAACAGGTACAAATTGGTCAATACTCATGCTATGTTTGGCCT 6995
     | |||    | ||       |||  |       | |||||||| ||| |
6919 ATTTGTCCAGAAAAACTACAATCGACGGTGAAGAATGCTATATCTGGAAT 6968

6996 AGTGTCGGAAAATTCTATCCGGAAATTCTGGCGAAGAGAGGTTGCATTGC 7045
     | |        |   |||  ||     ||| |||| |||       || |||
6969 TTTATTTCTGATATCTTCCCACGCATTGTGGCTAAGTACAACTGTGTTGT 7018

7046 TGTGAATGATGGAACTACATTTTATATTTTCGTTTCAAGTTCACAGATAG 7095
     | ||  || |||      |       || ||  ||||| |            |
7019 GCTTAACGACGGAGAGAAGAGATACATCTTCGTGACTGACAGCGCGCCCA 7068

7096 ATAAAATTCACCCAGAAGCAGCGTGGTCGGATATGCTACAAGGAGTAGGC 7145
     || ||      || ||      ||  |||| |||  |   |     ||
7069 CTAGGATCTTTCCCGATTTGGCTTGGTCAGATCTTATTTCCGGCAAGCAA 7118

7146 AGAAGAGGAGTCGATATTTTAAGTATAGCTGGTCCAACAAAAACCAAGTT 7195
               |  |||| | |    | |||||   ||| ||  | ||
7119 GTTGTGAGTCCAAACATTATCAAAGTGGCTGGAGAAACCAAGTCGAAAAC 7168

7196 TCTGATAAAACATGTGGAAAGTTGTTACGAAACTCTTAAGAGTCCGGAAG 7245
     |      |     | | |||   || |||  |   | |||   |||| | |
7169 CATTGCCCCTCTGCTAGCAGATTCCTACAAGGTTTTCAAGGATCCGAAGG 7218

7246 ATTGGAAAGCTAAATGCAAAGAGTACTATGAGTCCATAAGCTTATATGAG 7295
     |||   |   | |      ||||||| |   |   | ||   ||||| |||
7219 CATGGCTTGAGAGGAACAAAGAATTGAAAGCAGCTCTAGAAACAGAAGAA 7268

7296 TACATTCTCTTACTGATGGCAGTTGGGTCTCGAGCTGGAATTGAAACCCA 7345
     || ||   |||  ||| || ||||     | ||||||      || ||
7269 TATATCGCTCTCCTCTTTGCTGTTGCATGTGAAGCTGGTAGATTCACTCA 7318
```

TABLE 1-continued

```
7346 GAGGATGAGTAAATATCAGGCCCGAAAGAACAAAATTAGAATGCCAGAAG 7395
      |    |   |||  ||     ||    ||  ||   |  |   |||  | |||
7319 AATTTTAGACAAACCTCCCAGTAGACGCAAGATTTTAAATATGTCCGAAA 7368

7396 TGTTGGAGAAGTACATTGAAGTTGAGAAAGCGACCATAGGAAAGCTGTCA 7445
      ||    |    ||  |||||||   ||  ||||  |   || || |   || ||
7369 GGTATAATGCATATATTGAACAGGAAAAAGGGCTGATTGGGAGACTTTCT 7418

7446 AAACCAGCCAAGACCTGTCTAGCAATTGGTGCCGGAGTGGCTATTTTTGG 7495
     ||||||||  ||||   ||   ||||  ||  ||    |  |||||| || || |||||
7419 AAACCAGCAAAGATATGCTTAGCCATAGGAACTGGAGTTGCGATCTTTGG 7468

7496 AGTTCTAGCGGGGCTAGGAGTCGGTCTATATAAATTGATAACTCATTTTT 7545
      |    |||||  ||   |   |||||| |||   |  |  |||    |||||  |||| ||
7469 GGCCCTAGCAGGCATTGGAGTGGGTTTGTTTAAGCTGATAGCTCACTTCA 7518

7546 CTAAGACCGACTCAGAAGACAATGACATTGAAATAGATGATCTAGTCCCG 7595
      ||       ||      |||  |        |  ||  ||||||||   | |||    ||         |||
7519 ACAAAGATGAAGAAGAGGTAGACGAAATTGAATTTGATATACTCTCCCCA 7568

7596 GAGATGAGTGGAGCTCATGCTTCTGATGAGAATGTTACCACATATGCTGT 7645
     ||||||||  ||    |  |||    |||     |   |    |  ||    |||  |    || |
7569 GAGATGAGCGGTTCGCACGAATCCGGCCAACATACCACGAGGTACGTCAC 7618

7646 CAGGAGACAAGTTCCA............AAGGTGCGACTAGCCAAACAATT 7684
      | |    |  ||||||||           ||||  |   |    |  |
7619 GAAGGAGCGAGTTCCATCCAAACCAGCAAGGAGGCAACATGAATTTGATC 7668

7685 CAAAGTTCGCTCGTC.ACCAAGCCCATCAGACAATGAC............ 7722
      || ||||||  |   || |||  |   |||  ||  |    ||| |
7669 TAATGTTCGATAATCTACCCACTCCACAAGTTGAAGAGCTAAAGAGTGAG 7718

7723...............AACCAAAAGTA..GATATTCTAGTGCCTGAAATGA 7755
                     || ||||  |||    |||   |    ||   |  |||||| |
7769 AAGAGTGGGACCTGTAAGCAAACGTAAGGATGCTTCGGTAGCAGAAATTA 7818

7756 CAGGGTGCCATGCCAGTGATGAACACCTCACCAAGCATTTTACAAAAAGG 7805
      ||     |||||| ||||||| | |||    ||   |   |  | ||    | |
7819 GTGGAGCTCATGCGAGTGATCAGCATCATACAGAATACTTGAAAGCACGC 7868

7806 AGAGTCACCATGAAGAGAGTTGGAGCTGTCAAGGAATCACACATTGTGAC 7855
      ||||||  |||  |     |     ||  |          |
7869 GTTCCACTCATGAAAAGAATAGCTACCAAAGAGAGCTATGTTGTAACTTA 7918

7856 ATATGACGAGAATACTCCACATGTGAGACTCATCAGAAATCTGAGAAGAA 7905
     |||||||     |    |||       ||   ||    ||    | ||||
7919 CGATGACGAACCCAGCTCTCATATTTCCCTAGTTCGCAGGATCCGACGTA 7968

7906 CACGCTTGGCGAGAGCTATTAAGCAAATGGCACAACTTGGAGAACTACCG 7955
     ||||    ||||     |||||  ||  ||||||||||||  ||  |   ||  | ||
7969 CACGACTGGCAAGAGCCATCAAGCAAATGGCAGTCCTGGAGGACTTCCCA 8018

7956 GACACATTGTCAGAAATTCAAGTGTGGCAACAATATGTAGTGGACAAAGG 8005
      ||  |||    |||  ||  |  |    |||    ||||  |  |       |   |||||
8019 TCTACCTTGGAAGAGATACGACTTTGGAGACAAAACGCTGCAAATAAAGG 8068

8006 TATCAGACCAGCTGAACATACAACAGATTTTAGACTCTTCTCAGCTATAG 8055
      | ||         ||       ||||    |||||||      |  |||||||      |    |   |
8069 GGTTATTGTTCCGAAGTACTCAACAAGTGGGAAATTCTTCAGTGGCTTGT 8118

8056 CTGATCAGGAACAAGAGGATCCAGAAGAAATCAATATGGCGAGTGGAGAA 8105
      ||| |  |||  ||||  || ||    |    |  ||||||   || || |  |||
8119 TGGATGATGAAGAAGAAGAACCTCAGAATGTGAATATGTTGAACGAAGAG 8168
```

```
-continued
8106 ACGATGAAATTTGACGAAAACAAGTACAATGAGATAGTCCAAGTCGTCAA 8155
     ||  |   |  ||    |  ||     |   ||||     |||
8169 GACATTGAGGTAGATAAGCGAATGTTTGAGAAGATTTCTGAGGTTATAAG 8218

8156 AGGGATATCGCCAACTAAATCTGACATAGTGACAATGACTACTAAAGGAG 8205
     | |||    ||  |  ||    |||    | |   | ||||||   ||||  |
8219 CGTGATTCAACCCAGAAAGAATGAGCTGGAAAGAATGATTGAGGAAGGCG 8268

8206 CCCACCATACGGCGATCAAGCAGGTTCGAATTGGATACAAAAGTTTAGAC 8255
       |||||  |  ||     | ||||||||     |  ||    ||||   | ||||  |
8269 TACACCACAAGGTCGTAAAGCAGGCAAGGGTTAACGACAAGGGCTTAGCC 8318

8256 AAGGATCCGAATATGGTGAGCATACTTTCTAACCAACTAACCAAAATTAG 8305
     ||  ||  ||  ||  ||||||||   |  |  |||||||  || ||  ||||
8319 AAAGACCCCAACATGGTGACTATCTTGACGGACAAATTAATTAATATTAG 8368

8306 TTGTGTAATTTTGAACGTGACTCCTGGTAGAACGGCGTACCTAAACGTCA 8355
     |   || ||   |  |||    |  |||    ||     ||| |||  | |||||
8369 TGCGGTGATCGTCAATTTAACGCCGACACGCCGGGCATACATGAACGTGG 8418

8356 TGAGGTTGTGTGGGACATTTGTTGTGTGCCCAGCCCATTATCTAGAAGCT 8405
     |  |   |     ||  ||   ||||| ||||||||||||  ||    ||||||
8419 TACGTCTTATAGGCACTATAGTTGTTTGCCCAGCCCACTACTTGGAAGCT 8468

8406 CTAGAAGAGGATGACACGATTTACTTCATATCCTTTTCTGTCTGTATTAA 8455
     ||||  || |  ||     |  || |||||| | ||| ||    |||  ||
8469 TTAGAGGAAGGAGATGAGCTGTATTTCATTTGCTTCTCATTGGTTATCAA 8518

8456 ACTCAGATTTCAACCAGACAGAGTGACATTAGTCAACACTCATCAAGATC 8505
     ||||    |||  | ||||    ||||||||   |  || ||    || || |||
8519 GCTCACTTTTGATCCAAGTAGAGTGACTCTCGTGAATAGCCAGCAGGATT 8568

8506 TTGTAGTGTGGGATTTGGGTAATTCAGTACCACCGGCTATTGACGTTTTG 8555
     | | ||  ||||||  | ||  ||   |||||||||  |  |||||   ||  |
8569 TGATGGTTTGGGATCTTGGGAACATGGTACCACCCTCAATTGATACTCTT 8618

8556 AGCATGATACCAACCGTGGCAGATTGGGACAAGTTTCAAGATGGCCCTGG 8605
     |  ||||||||  ||   |  |   |||||  |  |||||  ||||| ||  ||
8619 AAAATGATACCTACGCTTGAAGACTGGGATCACTTTCAGGATGGACCAGG 8668

8606 TGCTTTTGGTGTGACAAAGTACAATGCTCGGTATCCAACAAATTACATAA 8655
     |  ||||  |||  |||    |  |  |       |  ||||  ||||  ||  |
8669 AGCCTTTGCTGTTACGAAATATAACTCGAAATTCCCAACCAATTATATCA 8718

8656 ATACTCTTGATATGATTGAGAGAATCCGAGCCGACACTCAGAACCCCACG 8705
     | || ||  |||||||||||| || |   ||| | ||||||||| ||||||
8719 ACACACTGACTATGATTGAGAGGATTAGGGCAAATACTCAGAATCCCACG 8768

8706 GGCATATACAAAATGCTCAACTCCGATCACACAATCACCACAGGTCTTAG 8755
     ||     |||      |||   |||| ||||||||||||||||||  |   |
8769 GGTTGTTATTCCATGATGGGCTCCCAACATACAATCACCACAGGATTGCG 8818

8756 ATATCAGATGTACTCATTAGAAGGATTCTGTGGTGGGCTGATACTACGGG 8805
     ||||||  ||||  |||    |   || |||||||| ||||||  |   ||  ||
8819 ATATCAAATGTTCTCTCTTGATGGATTCTGCGGTGGGTTAATCCTGAGAG 8868

8806 CTTGCACTAGAATGGTTAGAAAGATTGTGGGACTTCATGTAGCTGCTAGT 8855
     |  ||||   |||||| ||||||     | |   | ||   |||| ||
8869 CCAGCACAAACATGGTGAGAAAGGTCGTCGGGATCCACGTTGCTGGAAGC 8918

8856 GCAAATCACGCTATGGGATATGCAGAATGTCTGGTGCAAGAAGATCTTAA 8905
     |||||||||||||||||||||||||| ||  |      |||||||| |
8919 CAGAATCACGCTATGGGATATGCAGAGTGCCTTATTGCAGAAGATTTACG 8968

8906 ACATGCTATAAATAAGCTGTCACCAGATGCAAGGAGTTTAATTATCGGAC 8955
     |||   |      ||| |||||  || ||     ||     | |
8969 GGCTGCAGTGGCGAGATTGGCGCTAGATCCTAGAAGCACCATCCAGGCAA 9018

8956 ATCTCAATCCCAAAGTAGAAACAGCCACAAAACAGTGTGGAATTGTGAGG 9005
     |||  ||    |    |||   |  |        |  |||||| |||||   || ||
9019 GTCTGAAAGGTAGGATTGATGCTGTTTCTAAACAATGTGGTTTAGACAGA 9068
```

```
9006 AGCCTTGGAAGTCTAGGGTGCCACGGAAAGGTTACAAGTGAGGACGTGGC 9055
     ||  ||  |    ||||  ||    |||  ||  |||  |   ||  |
9069 GCTCTGGGTACGATAGGATGTCACGGGAAAGTTGCCTCTGAAGATATTAC 9118

9056 GATGACTGCAACAAAGACCACGATCAGAAAGTCTAGAATTTATGGTCTTG 9105
     |    |  ||  ||  ||   |  ||  |||||||||  |||||    ||||||| |
9119 AAGTGCCGCCACGAAAACTTCCATAAGAAAGTCAAGAATACATGGTCTAG 9168

9106 TTGGAGATATCAAAACAGAACCCTCAATTTTACATGCTCATGACCCACGT 9155
     | || || ||  |  ||| ||  ||  ||||||||||||  |||||||||  ||  ||
9169 TGGGTGAGATTAGAACTGAGCCTTCAATTTTACACGCTCATGATCCCCGA 9218

9156 CTCCCTGAGGATCAGATTGGAAAGTGGGACCCAGTGTTTGAAGCTGCCTT 9205
     ||  ||| ||  ||  ||||||||| ||  ||||||||| ||         |    |
9219 CTGCCTAAAGACAAGATTGGGAAATGGGACCCGGTTATTGAGGCATCAAT 9268

9206 GAAGTATGGAACAAGAATAGAACCATTCCCCATTGAAGAAATTCTTGAAG 9255
     |||||||||   |  |||||   |||  ||||||  |  ||    ||||||||  ||||
9269 GAAGTATGGTTCGAGAATCACACCGTTCCCTGTAGACCAAATTCTGGAAG 9318

9256 TGGAAGATCATTTATCTATTATACTTAAAGGCATGGACAATACTCTCAAG 9305
     ||||  ||||||| |  ||||  ||  |          ||  |||   ||
9319 TGGAGGATCATCTTTCTAAAATGTTGGCCAATTGTGAGAATTCAAAAAAC 9368

9306 AAAAGAAATGTCAACAATCTTGAAGTTGGGATAAACGGAATAGATCAATC 9355
     ||   |    |  ||  ||  |||||  |||   |  |||||  ||||||  ||  ||  ||
9369 AAGCGGCAGGTTAATAATCTAGAAATAGGGATTAATGGAATTGACCAGTC 9418

9356 AGATTATTGGCTTCAGATAGAGACAAATACTTCTCCTGGGTGGCCCTACA 9405
     |||||||||   ||||||| |    ||||||||    |||  ||||| |||
9419 GGATTATTGGCAACAGATAGAAATGGATACTTCAAGTGGTTGGCCATACG 9468

9406 CAAAAAGAAAACCGAAGGGAGCTGAAGGAAAGAAATGGTTGTTCAAAGAG 9455
     |  ||   |  ||||||    ||  ||  |    |||||||||||||| |  |||  |    |
9469 CTAAGCGTAAACCTGTTGGGGCAGCTGGAAAGAAATGGCTATTCGAGCAA 9518

9456 GTTGGGAACTACCCCTCCGGGAAACCCATTCTAGAAATGGAGGACTCAGG 9505
     |   ||   ||  ||||||| |||||             |    |    |    ||   |  ||
9519 GACGGCACATATCCCTCCGGAAAACCTCGATATGTATTTGGAGATGCCGG 9568

9506 ACTCATTGAGAGCTACAATAAAATGTTGAGAGATGCCAAACAGGGTGTAG 9555
     |  |||||||||||||  ||          |||  |   |  ||   || |
9569 GTTGATTGAGAGCTATAACTCGATGCTTGGTGAGGCGAAGCAAGGCATTA 9618

9556 CTCCCATTGTGGTTACTGTGGAGTGCCCAAAAGATGAACGCAGAAAGTTA 9605
     |||||  |||  ||  ||  |  |||||| ||||||||||     |    | || |
9619 GTCCCACTGTCGTCACAATTGAGTGCGCAAAAGATGAGAGGCGGAAGCTT 9668

9606 AGTAAGATCTACGAACAACCAGCCACCAGGACTTTCACGATTCTCCCGCC 9655
     |  |||||| |  ||  ||   ||||  |||||  ||   || ||  |||
9669 AATAAGATATATGAGAAACCCGCCACTCGGACGTTCACCATACTGCCACC 9718

9656 TGAAATAAACATTCTCTTTAGGCAATATTTTGGTGACTTTGCCGCCATGA 9705
     |||  ||  ||   |||  | ||  ||||| |||||| || || || |||
9719 TGAGATTAATATTTTATTCAGGCAGTATTTCGGAGATTTTGCAGCGATGG 9768

9706 TAATGACTAATAGATCAAAATTATTCTGTCAGGTTGGGATAAATCCAGAG 9755
     |||||||    ||||  | ||   |||||||| |||||  ||  ||||||
9769 TAATGACATGTAGAGCCAAGCTTTTCTGTCAAGTTGGCATCAACCCAGAG 9818

9756 AATATGGAATGGAGTGATCTAATGCATGAGTTCCTCCACAAGTCAACACA 9805
     |||||  |||  |||||||| ||||  |             |  || ||||||   |
9819 TCAATGGAGTGGGGTGATCTCATGCTAGGTCTAAAGGAGAAATCAACTAA 9868

9806 TGGCTTTGCTGGAGACTACTCAAAATTTGATGGAATTGGAGATCCTCAGA 9855
     ||  ||||| |||||  ||  || || || |||||||||| |||  ||||
9869 GGGATTTGCAGGAGATTATTCGAAGTTCGATGGAATCGGAGACCCCCAGA 9918

9856 TTTATCATTCCATAACTCAGGTGGTAAATAACTGGTACGATGATGGGGAA 9905
     |||||||||  ||   ||  ||  ||  ||  |  |||||||| | ||||||||
9919 TTTATCATTCAATTACCCAAGTAGTCAACAACTGGTATAACGATGGGGAA 9968
```

```
                                                  -continued
 9906 GAAAATGCCAGGACACGTCACGCACTAATTAGTAGTATAATACATAGAGA  9955
      ||||||||  |    |  | ||  || || |||||||  ||  ||||| |
 9969 GAAAATGCGACTATCAGGCATGCTCTGATAAGTAGCATTATACACAGGCG 10018

9956 GGGTATAGTTAAGGAGTATCTTTTCCAGTATTGTCAGGGAATGCCTTCTG 10005
      ||| || ||  || ||  ||  |||  |||||||||||  ||||| ||||  || |
10019 GGGCATTGTGAAAGAATATTTGTTCCAGTATTGCCAGGGTATGCCATCAG 10068

10006 GTTTTGCCATGACAGTCATTTTCAACTCCTTCGTGAATTATTACTATTTA 10055
      | ||  |||||||||||| || ||||| || ||  ||||  |||||  |||  |
10069 GGTTCGCCATGACAGTGATATTCAATTCGTTTATGAACTATTATTATCTG 10118

10056 GCTATGGCGTGGATGAATTTAATCTCACACTCACCATTGAGTCCCCAATC 10105
      ||  ||||| |||||||||| ||         || ||  ||| |||||| |
10119 TCTTTGGCCTGGATGAATCTGATAAGTGCATCCCCCCTTAGTCCACAAGC 10168

10106 CACGGTTAGAGATTTCGACAACTATTGTAAGGTAGTAGTTTATGGGGACG 10155
      |   |  ||| |||| ||  | |||||||||||||  |  |||||| || || |
10169 TTCTTTGAGATATTTTGATGAGTATTGTAAGGTCATTGTTTACGGTGATG 10218

10156 ATAACATAGTTTCAGTAGATTTGAACTTTCTAGAATATTACAACCTTAGG 10205
      ||||  || ||| || ||      |  ||  ||||  ||  ||  ||| |||
10219 ATAATATTGTTGCCGTCAACGAAGAATTCTTAGAGTACTATAACTTGAGG 10268

10206 ACTGTAGCAGCTTATTTGTCTCAATTTGGAGTAACGTACACAGATGACGC 10255
      |||  ||||     |||  |  |||||||||||||||  |||||  ||||||||||
10269 CTTGTGGCAGGCTATCTTAGTCAATTTGGAGTAAGCTACACTGATGACGC 10318

10256 AAAGAATCCGATTGAGAAAAGTGTGCCTTTCGTAGAAATAACTTCTGTTT 10305
      |||||  ||  ||  |||||| ||   |   |  ||  | |||         |||
10319 CAAGAACCCAATAGAGAAGAGCGAACGATATGTGAAGATAGAAGACGTTA 10368

10306 CATTTCTTAAGCGTAGGTGGGTGCCCTTGGGTGGAAGACTTTCAACTATT 10355
      | ||    | ||  ||   | ||||||    | ||  |||   |||| |           |
10369 CGTTCTTAAAACGGCGATGGGTGAGTCTTGGCGG  AGAGCTTCGATGCTG 10418

10356 TACAAGGCACCTTTGGACAAAACTAGCATAGAGGAGCGCCTTCATTGGAT 10405
      |||||  ||  ||   |  ||||||   |||||| ||||||   | |||   |||||
10419 TACAAAGCTCCGCTTGACAAGGTTAGCATTGAGGAAAGGCTTAACTGGAT 10468

10406 AAGGGAGTGCGATAATGACATCGAAGCTCTCAATCAGAATATTGAAAGCG 10455
      |  | ||||||  ||  |||      ||||||     |||||  ||||||||||| |
10469 CAGAGAGTGTGACGATGGGGAACTAGCTCTGGTGCAGAACATTGAAAGTG 10518

10456 CCCTATATGAAGCAAGCATTCATGGAAAGATCTACTTTGGTGATCTCCTT 10505
      | ||| ||  |||||| || |||||||||  |  | || || || ||| ||
10519 CTCTGTACGAAGCTAGTATTCATGGCCACACATATTTTGGAGAGCTTAAA 10568

10506 CAGAGGATCCGGATTGCTTGTGACGCTGTGATGATCCCAGTTCCATCAGT 10555
      | |   ||    || || ||||| |||||| ||||||  | ||   |  |||
10569 GATAAAATTGCTAAAGCCTGTGATGCAGTCATGATAACTATGCCAAATAT 10618

10556 AACATTTAAGGATTGTCACAAAAGGTGGTGGGCTTCCATGACTGGAGGAG 10605
      || || ||   ||| || || ||  |  ||||||  | |||||||||||| ||
10619 AAGATATATTGACTGCCAGAGACGATGGTGGACCTCCATGACTGGTGGGT 10668

10606 CTTTAGATCCAGCTAGTCTAAGTCGGTTGTACTTGGCCGCCGAGAACCAG 10655
      |  | || ||  ||   | |||   |     |    |    |    |||||
10669 ATCTTGAGCCGTCTGATGTCACCAAACTTGTAAGGCTTGTTGAGAAAGGA 10718

10656 TTGGTCGACACTCGGAAAGTGTGGAAAGATCGCTTCCTTGGTGAGGATAG 10705
      |  |  |||  |       ||| |||||||||| |  ||  |       |  |
10719 CTACTAGACCCGAAATCAGTATGGAAAGACCCATTGTACAGAACCAACAA 10768

10706 GTCTTTAATAGACATGCTGAAGTCAGCTCGTGCTGTTCCTCTAGCTGCCT 10755
      ||    || |||  ||| |||  | ||    |||| || |  || ||| |
10769 GTTGCTATTCGACCTATTGAGGGAGGTTAAGGCAGCACCCCTGGCCGCAT 10818

10756 ATCATGTATAAGCCTCACGACTCTGTGCAGAGTATAACAGCACGACCCCA 10805
      |   || ||||  || ||  ||                         |||  |
10819 TTGTGGTCTAAGTTACCCTTCT..................GACAAAA 10847
```

```
10806 GGTTATCGATAAGTCATGTTGGTAGTCGTCAAGTAAGAATGGGACAGAAA 10855
        ||  | ||      ||  |||       |  |  | ||  | |
10848 GGGCCTTGAACGGTTATGGT...............TGAACAGAACTGTAA 10882

10856 AGAGATTGGAACTTTTAGGATGGAACATCAGTAAACCTACGGGAAACAGA 10905
        |  |   |||    | ||| || |      |  |    |    ||||
10883 AAGGTGAGGACTATATAAGTTGTAGTACGGATGAGATTGAAAGAAA.... 10928

10906 GCTATGGAACTCCCAAGTACTGTAGGTCCCTATTGGTAGTTCACTAAAAG 10955
                                      |  | ||||| |
10929................................ATTGGGTCACTCCCAT 10944

10956 TAACCTTCTGTGTATGATCCCTACCCTGAGTGAACGACAGAAATATGATA 11005
        |    |   | | |||       |||| |||| |    |      || |
10945 TCCTTTATTAGGAAGGAGTGATACCTTTTGTGTAGATCTCTACCCCGAAA 10994

11006 CACGAGTACTCTCATTAGAGAGAACCGGATTCCACATTGTGGAATCTCCC 11055
        | |   | ||  ||||             ||| || |||| |   ||
10995 CTCTTGAACCCTCA.................CACGTTTTGGAGTAACCA 11026

11056 AGGAATTGACCTGGGTTCCTCACGAAAGTGAGGCGACAACTTGGTCGAAA 11105
            |    | |||   |      |                 |  | |||| |
11027 GTACACCCTTTTAGGTGGACCCTCGA...........CTATAGATCGAGA 11065

11106 AACAAGTTCAGTTTAGTTGAGACTGAAGTACAAACTCAACATTTCATAGT 11155
          |     ||  ||   ||    |     | ||  ||| ||  |
11066 CCAAGTATTGACTTGGTGTTCACGTCTTGCCGGACGCAAAATGGCA.... 11111

11156 GTGTGATTTTTCCGATCCCCATTTGGTGTAACCCATATGTGCCACCTCAT 11205
                      ||| | |   ||  |        | || ||  |
11112..................CCCTTGTTTAGTGATATCAAGGTTACAAATGTC 11144

11206 AATCCTTTTAAGGGTTAAATTTGGTAAGTGTTGTGGGGAGCCAAGAGGGG 11255
          |  ||        ||      |  |||||||  |           || ||     |   |
11145 ACGCCCCACTAGTAAAAGTTTTGGTATATACGCATTCGAACCGCCAATGT 11194

11256 TAGGGTCTTTTTGTTACGTACTTTCTCATGTCAACATGGTGTTGAGATGG 11305
           ||  ||||    |        |||   |||||  |  ||||||      ||||||
11195 ATACGTGTTTTCCCTTTTACTTTTTGTATGTCGTCGTGGTGACGAGATGC 11244

11306 GCGCTTGGTCAGCGGAAGAATAAAGCGAGACGTACATTATTATCTCGTAG 11355
         |||  ||||||||||||     |    |     |    |    |       ||
11245 ACGCCTGGTCAGCGGGGAATAAGTTCACTATATGAA...........CAG 11283

11356 ACTACGGCAGGTGAGACACACCGTCGTCCCTTGAGGGGGAAAGTAGCTCC 11405
        |||   ||||     |  ||||||||| |||| ||    |    |  ||  ||  ||||||||
11284 ACTCCGGCGAGCGAGACACGCTGTCGGCCTCGGGAGAGGGAACTAGCTCC 11333

11406 AGGCA.TTTAATCCTGAAGTGTT.CAGATAAGTCTCTGATCCTCCTCCGG 11453
       ||||| ||  ||||||||||||||   |     |||||  ||||||||||||||||
11334 AGGCACTTAAATCCTGAAGTGTTAGAACTAAGCGTTTGATCCTCCTCCGG 11383

11454 GGGAAAAAGGGGACTTAATCTGTTAAGCCGTATC...AACGACTTGATGA 11500
       ||||||  ||       |    ||||  ||||||| ||  |      |    | |  ||||
11384 GGGAAAGAGAACGCCAGTTCT.TTAAGCCATAACTCTAGTGAGTTGAATC 11432

11501 AACAACCACCTGTTCTGGTGTAAACCCAGGATAATCACATAGGTAGCTGT 11550
              |||   |     || |||               ||      ||     |
11433 CTATTCATCCTTCTTAGGATTAAGGATTTCTGAAGTCTATCATGAAAAGT 11482

11551 GTGGTGTTTCAACCATTTGGAT...........TCATCCAGCACGGATT 11589
            |   | || |  ||            |  ||||||  |  | |||
11483 AGATAGAAAGCAACACGTCAATAACGTGGAACCTTTTCCGAGGAAGTAGG 11532

11590 ACCTTGTGGTCAGAGTCTCCGAATGTCCTGTACGATGTGGGTAACTCCCT 11639
         |         |  |||   ||  |  | |     |  |  |   |  ||||     |
11533 GTGCTTGTTCGAAAATCATGGTAGATTCGGAAACAATTTGCTTAGAGTGT 11582

11640 TT.....................GGCCAGGGCTAGGCACACTTCTCTAC 11667
       |                       | ||||||||||||||||||||| ||
11583 GTCTTTTCGCGTTGGTAGTTCAACCGTTAGGGCTAGGCACACTTCTCCAC 11632
```

-continued

```
11668 GGGTTGGTGTCGCTAGATATGTTAATACTA.......GTGCCATATCGGA 11710
      |||||  |||   ||    ||      ||    ||   ||||  |||  ||||
11633 GGGTTTGTGCTGCAGTATTAAATATCATTAAGGTACTGTGCTATAGCGGA 11682

11711 AATAGTTGTAAATCGTTGAACCAAGTGACGATGGGGTCCATTGTACACCC 11760
      |  |  ||   |||  ||||||||||  | |||||||||||  ||  |||||
11683 GA..AATTACAAAGCGTTGAACACATTGACGATGGGGCCCAATGCGCACCC 11731

11761 GACTTGGTTACGTTTTCTATTT.TCCGTGTCAATATGGATAATAGTGGGG 11809
      |  |   ||||||      ||||  ||  ||||||  |||  |||||| ||||||||
11732 GGATGTGTTACGCACCGTTTTCTCTGTGTCACTATAGATAAAAGTGGGG 11781

11761 TAGTAAAAAAAAAAAAAAAAAA 11832
      |||
11782 TAGC.................. 11785
```

TABLE 2

Comparison of MCDV-Tn and MCDV-T amino acid sequences

```
  1 MMS CE QS KNNNNQQS TALENS....EI RYPGGYYI PLGD.....GGI RVP  41 (SEQ ID NO: 2)
    ||  :  ..|.|   |:.  |||    ::   |:||  :.::|   :::::|
  1 MM..QTNNNQNP TQGSI PENSS QDRNLGVP AGYS LS VEDP FGNRS DF HI P  48 (SEQ ID NO: 4)

42 VEAI YRPG.EPQNWVPI CGNDFHLSQDDP CSECDAI EGSSERAAI AI SDS  90
    |..|.|.:  :..|||||||:|||||. :|  |.||:     |||    |.:
 49 VHQI I REEI DRPNWVPI CSNDFHLNSEDYCEECE.....SER....I KNF  89

91 YVASDPHFTVDARSLSRRDHTCTHRGCFSI CSSYRFCSFCLFLFNLDKFQ  140
    :  ....::.   .|.|   ...|.|  :|||..:.|:|||.|||||:||||||
 90 EI FRSQNLI DQHLNLCTDSKDCDHFSCFSTSTSCRFCPFCLFI FNLDKFY  139

141 KNTKYFHSKRSLSRLVHCSAEQLI SNAI LFSSNRI I DAEVVADNRVSCEY  190
    |..  |:  |:..|.||.|.|||:|.||:|.|    .||||||||:||::|||
140 KQNLYLI SRQALARLFHGSAEELLSRAI FFTYNI CI DAEVVANNRI GCEY  189

191 AKLLLSNARVGVQVTPPACDWVVCNNVEHLFECFGI SDAQRGHI TGFNDE  240
    .||  .:  |..:   .|  |:|||:|:|..|||||||:|::|  |||.|:..|
190 VKLFHPDLRPSI TSPPYASDWVMCDNAKHLFECLGLGDTTRGHLYGLI SE  239

241 NAYWNASCAKCGACCQGANARSAI PI VLLLKFI TI RKEQDI WLASHMHHD  290
    ||||||.|.||||||||||||||.||||| |.:. :   . ::  |:. .
240 NAYWNATCSKCGACCQGANARTAI PI VMALQYCRVDVYYSEYYLYHI YAP  289

291 NDFVEI NSI TAQI I AKI NNI PNVDEPAVGY..MGSKLENWI SYRDTDFTE  338
    :: :.|:  ||||::.   .|  .     :.|||::   ::    :::      |:
290 EERMKI DQQTAHLLHSI I R....GAPAVDCSELSQEPI HRMVDSSKLVA  335

339 EDWTLKHPCS.GPLESEECDHDFI I RNQYGFELYLNHAMLLNFAALCLYH  387
    |.|::||  |.|  ||||   ..||||  ..|:   .|::     |    ||
336 LDSTI RHPKSQGSLLDSECDHEFI LRTSHGI KI PMSKSLFI SFLTMGAYH  385

388 GRLYNSDKSVGI LVTFGGMI GVNI ACNEAFMEFHKRFYSGTLRI SPMNMY  437
    |  .:.:..  ::.|||| |||:|||..|:   :||   ||||.:|  .|:  |
386 GYAHDDQQEQNAI I SFGGMPGVNLACNKNFLRMHKLFYSGSFRRRPLFMS  435

438 .LRRERCQAQSDFNDEEFQRLMAEEGDAEI QSVSNWVSEYLEI EDVI DI V  486
    : . . . . |||:|||||||:||||||||    .|. .  :|  :: :|||||
436 QI PSTNATAQSGFNDEEFERLMAEEGVH..VKVERPI AERFDYEDVI DI Y  483

487 DEAESKKTRGLGLNQVLGGLLKGVSHCVDSLHKVFDWPI DLAI DAAKGTA  536
    ||..:  ..:.||||||||:||||||||:||||||||||||||:|||.|.|
484 DETDHDRTRALGLGQVFGGLLKGI SHCVDSLHKVFDFPLDLAI EAAQKTG  533

537 DWLEGNKSSVDDSKI CAGCPEI QKDMQDFQKETKMGI EI LRDSI KKLSEG  586
    |||||||..||:.|||.|||||||||||  .||.|||  ::::|.||||||||
534 DWLEGNKAAVDETKI CVGCPEI QKDMI SFQNETKEAFELI RSSI KKLSEG  583
```

TABLE 2-continued

Comparison of MCDV-Tn and MCDV-T amino acid sequences

```
 587  I DKI T RMNQT NF ERI  VDRI  RPI ES KLKELEKI  KP DAGGS KDS EAMRQL VQ   636
      | | | | | : | | . | | | | | : |   | : | | | | | : . | | |   | . .       | | . | |  . | | |
 584  I DKI T KMNAT NF ERI  LDGI  KPI ES RLTELENKAP AS . . . . DS KAMEAL VQ   629

637  AI KDI KLI KQAMME LNDRI  KDLEDS KQHQEDS KP DDDT AGE QKPI P KI NK        686
      |  | | |  : | : : |  : | | | : : | |    | : . . | | : . |          . | : . . : : | | | | | . | | | |   . .
 630  AVKDL KI MKEAML DLNRRLS KLEGKK. . .  SDGQT T E GT AGE QQPI P K.  T P   675

687  I RVKAKR VE KQS GT NI  VNNEI  EQAF QDEE KRT VDP NI  SDMYNAI KS E YL V  736
      . | | | | : . |   | | | : |   . : : . | | |   | | | | | |   | | | : . | : . . | | | |
 676  T RVKARP VVKQS GT I  MVNEES T ET F RDNES RVT DP NRS DMF AAVT AE YL V   725

737  KS F S WKVS DGQDKVLS NI  NI  P EDLWNT NS RLNDI  MS YF QYYKAT GLT F RI  786
      | | | . | | | | | | | | | | | . : : : | : | | | . . | | | | . | | | : | | | | | . | | | : | | | |
 726  KS F T WKVS DGQDKVLADL DL P QDLWKS NS RLS DI  MGYF QYYDAT GI  T F RI   775

787  S T T CI  P MHGGT LF AAWDACGCAT RQGI  AT AVQLT GLP GI  MI  EAHS S S LT T  836
      . | | | : | | | | | |   | | | | | | | | | | | | | | | . | | | | | | |   . : | | | | | | | |   | . 
 776  T T T CVP MHGGT LCAAWDANGCAT RQGI  AT T VQLT GLP KT F I  EAHS S S ETI   825

837  F S VEDP LT QS T VCLS GS EHS F GRI  GI  LKI  CCLNVLNAP QAAT QS VS VNVW  886
      :  | . : .   . | | . : | | | | | | | | | | | : | | | | | | | | | . | | | | . . | | |   | . | | | |
 826  I VVKNS NI  QS AI  CLS GS EHS F GRMGI  LKI  CCLNT LNAP KEAT QQVAVNVW   875

887  VKF DGVKF HF YS LKKQP VVS QML VDKLT NLGEMGCVVAT GT WS T T S S LNL       936
      :  | | | | | | | | .   | | | : | . | | | | | :    | . . | | : : | |  : : : | | | | | . | | | | | .   | |
 876  I KF DGVKF HVYS LRKNP VVS QLQVAS LT DI  GELS S VVAT GS WS T T S AT NL   925

937  LQLNVHP T ACF I  S DGL VT QT P LS VI  AHAF ARWRGS LKF T I  T F GAS MF T RG  986
      : : | | : | | | . |   |    : | | : | | | | | | | | : | | | | | | | | | | | | | | : . | . | | | | : | | | |
 926  MELNI  HP T S CAI  QNGLI  T QT P LS VLAHAF ARWRGS LKI  S I  I  F GAS LF T RG  975

987  RVLVAAI  P VAKRKET LT I  EEI  S GYHNVMCLLNGE RT S F ELEVP YHS VGED      1036
      | : | . | | : | | | | | | : | : . . : | | | | | | |   | | | |    : . | | | | : | | . | | | : |
 976  RI  LAAAVP VAKRKGT MS LDEI  S GYHNVCCLLNGQQT T F ELEI  P YYS VGQD      1025

1037  S YVCRDALF DVS S YAQNF MI  T RLHMVVI  DT LVMS S NAS NT I  S YCVMMGP G   1086
      | : | : | | | | | | | : | . . . . | | | | | | | | . | : : . | | | | . | | | | . | . . : |   : | | |
1026  S F VYRDALF DI  S AHDGNF MI  T RLHL VI  LDKLVMS ANAS NS I  NF S VT LGP G   1075

1087  KDLELRYLNGVHAQRNVRELKAQVS LGF S LQS GRNI  GVGF S DLLKRWAHL             1136
      . | | | | : | | . | | | | : | |   | | | | |   | | | | |   | : : . |     | |   | | . | | | . | | . | |
1076  S DLELKYLAGVHGQRI  VRELKMQVS LGRS F ENGVLI  GS GF DDLLQRWS HL          1125

1137  LT LHF DENNEKS EEKVGS YI  VT VAP S YRAF P QHNT LLS WF S QLF VQWQGS     1186
      : . : . | : . . . . : . |   | : | | | | | . | | . : |    | | | | | | | | | | | | | | . | :
1126  VS MP F NAKGDS DEI  QVF GYI  MT VAP AYRS LP VHCT LLS WF S QLF VQWKGG  1175

1187  LCYRLHVDS QE RRYGGYLRI  WHDP NGS LDEGVEF AMS T NLEP P P GAF VKY        1236
      :   | | | | : | | : | | | : | | : : : : | | | | | | | | | | |  | | | . . .    | . | | : | | : | : |
1176  I KYRLHI  DS EERRWGGF I  KVWHDP NGS LDEGKEF AKADI  LS P P AGAMVRY     1225

1237  WNYNEQS EF EF VVP YT ART P RLF VP KAMI  P T DS KS WI  LNYNGT LNF DYRG  1286
      | | |     . : : . | | . | | : . | | .  | | | | | | | | | | | . | | | | | | | | | | | | | | | . |
1226  WNY. LNGDLEF T VP F CART S T LF I  P KAMI  AT DS KS WI  LNYNGT LNF AYQG   1274

1287  VDDF NVT VDI  S AGDNF EF S VRT VAP KAGKVNES F T KLS YS NELVDI  KKP L   1336
      | | | | . : | | : . | | : | : | | |   | | | | | | : | | | | | | | . | | . |  . . . : |   | | | . . |
1275  VDDF T I  T VET S AADDF EF HVRT VAP RAGKVNEAF AKLEYAS DLKDI  KES L     1324

1337  T AAGRLKGP .  F NLNT LKT AVP KET P KES S DDKDKS NQKRKGAMDS LLNAV      1385
      |  . . . | | | | |   : .        | |     | . . . | | |   : | |         . |  . . . : : . | | | |
1325  T S S T RLKGP HYKT KI  T S I  EP NKI  DENES S RGKD. . .  NKS NS KF EDLLNAT   1371

1386  AQMET I  NS DANGCF S LGGLKS T AKML DS RKT CEKF ADI  MDF T HDT LGVKD   1435
      | | | :    . . . | | . .     : :     . | | | : | . . | . | | . | : | | : : | | | | . .   | . : . .
1372  AQMDF DRAT ANVGCVP F S I  AKT AKVLS ERET CKKMADVLDF T HS CLNLDS      1421
```

TABLE 2-continued

Comparison of MCDV-Tn and MCDV-T amino acid sequences

```
1436  G P A A Q R L A A A V A Q I  A P I I  E S V S R T T E S  V E S K L T C L D K Y K D G I  L G I  L Q S L C   1485
      . | | | . | | | | | : . | | | | | : | | : : | | | : | | | . | | . : | . : : |   | : : : :   . . :
1422  Q P A A A R L A A A I  S Q I  A P I  M E S I  G R T T Q S  V E E K L A S  V D T F R D K I  M A L I  S N V L   1471

1486  K E T I  P G L A I  V D F K K G K Y M W A T L L T L I  A G A A L F W A C K S  Q K S  F L K R F  S V V V M   1535
      : | : | | | | | . | | | | | | | : | | . : | | : | | : . . :   | | . . | . | | | | | | | | . | | . |
1472  G D T L P G L A I  A D F K K G K Y V W A S  F L T M I  A A C V V A W A A T S  K K S  F L K R F  A V V A M   1521

1536  I I  W S P F L A G K V W S  L G Q W I  V Q K W C H L W P  K S  D S  C R Q H S  L A G L F E S  A K T K V R G   1585
      | | | | | | | | : | . | .  | |   . . | : .  | | | | | | | | | | | | | |   | | .   | . : : :
1522  I I  W S P F L A S  K I  W A L G T W I  R K S  W S  K L W P  K S  D S  C R Q H S  L A G L C E S  V F T S  F K D   1571

1586  F P D W F R S  G G M N I  V T Q V C S  V L L T I  V S L I  T L G T I  P S  A K K S  K S  L A D R F I  E F G N   1635
      | | | | | : | | | : . | | | | | | . | | | | | | | | | | | | | | . | . .   . : | | : |   | | | |
1572  F P D W F K S  G G I  T I  V T Q V C T  V L L T I  V S L I  T L G T I  P S  T K Q N A T  F A D K F  K E F G N   1621

1636  M N R A A T S I  A A G Y K S I  S E L C S  K F T H F  V A T H F L G A T  V D D N V F  K D L  V T F N V K D   1685
      | . | | . | | | | | | | | | | | . | | | | | | | : : :   . | | |   | | | . | | | | . | | | | |
1622  M S  R A T T S I  A A G Y K T I  S E L C S  K F T N Y L A V T F F G A Q V D D D A F  K G L  V A F N V K E   1671

1686  W V E Q V K V A S  L E E N K F K S  F G S  P E Q L T R V R H M Y D K S  L E I  T N K L L D R N K V P  V A   1735
      |  :   : | |       | | | | | | | | . : | | : . | : | . : | | | | | | | | : | | |    | | | : : | : | | : |
1672  W I  L E V K N L S  L E E N K F S  G F G G D E H L V K V R H L Y D K S  V E I  T Y K L L Q K N R V P I  A   1721

1736  M L P  V I  R D T C K K C E E L L N D S  Y S  Y K G M K T P R I  D P  F Y I  C L T G P P  G V G K S T V A S   1785
      | | | : | | | | | | | | | : | | | : | | . | | | | | | | | | | | |   | : | | | | | | | |
1722  M L P I I  R D T C K K C E D L L N E S  Y T  Y K G M K T P R V D P  F Y I  C L F G A P  G V G K S T V A S   1771

1786  I I I  N D L L D Y M G E P  K T D R I  Y T R C C A D S  Y W S  N Y H H E P  V I I  Y D D L G A I  S K V A S   1835
      : | : : | | | |    | | | | | . | | | | | | | | | . |   | | | | | | | | | | | | . | | | | | | | | : . | |
1772  M I  V D D L L D A M G E P  K V D R I  Y T R C C S  D Q Y W S  N Y H H E P  V I  C Y D D L G A I  S R P A S   1821

1836  L S  D Y A E I  M G I  K S  N R P  Y S  L P  M A A V E E K G R H C L S  K Y L  V A C T N L  T H L D D T G D V   1885
      | | | | : | | | | | | | | | | | | | | | | | | | :   | | | | | | | |    : | | :  | | | | | | | | | | |
1822  L S  D Y G E I  M G I  K S  N R P  Y S  L P  M A A V D E K G R H C L S  R Y L I  A C T N L  T H L D D T G D V   1871

1886  K T K E A Y Y R R I  N L P  V T V E R D L A M P  M S  P E D P  A S  G L L F T I  G D I  H E N G R N V S  V V   1935
      | | | : | | | | | | | : | | | | . | : : .    | . | | | | . . | |   | | : : : :   : . | |    : . | .
1872  K T K D A Y Y R R I  N V P  V T V T R E V T A M M N P E D P  T D G L R F T  V E Q V L D G G R W I  N V T   1921

1936  E S  R L L N G R V P  F R A G D L  R N M S  Y N Y F  M E F  V R I  Y A T I  Y M E N Q Q Q L  V A K L S  G D D   1985
      | | | | | | | | : | | | | : | | . | | . | | | | |  | | : : | | . : | | | | | |    | | | | | . | . :
1922  E S  R L L N G R M P  F R A E D L  M N M N Y S  Y F  M E F  L K M Y A A L  Y M E N Q N M L  V A K L R G T E   1971

1986  Y E S  S S S S  F P  E N E E L E F D F L A Q A H N G V Y L T I  E E V V A K F E S  M K F S  G K Q L N A E   2035
      . . . | . | |     | | | | | | | | | | : |     | | :     : | : : | : | . | | | : |    | : . | | | | |
1972  I P E S  R S S  . . E N E E L E F D Y L A T A Q M D H T  V T F G E L V T K F N S  Y K L T  G K Q W N K R   2019

2036  I  E K F E R I  G V D G W R T N K A L S  F N D L  V K R F C G C C L G D D C N F  D F  H Y R T L F K V L I   2085
      :   . : : : . . : | | | . | | |    : . | : | | |      | | | | |    . . : | | | | | |  . . .    |    . |
2020  L C E L G W T S  L D G W N T N K I  M R F D D L  V A G F C G C S  R N E N C N F  D F  Y H Q R L Q A C L N   2069

2086  E N K Q I  P A Y K C M V L H K V N P  D R M K T Q I  K M V N G Y T L E T M F  K T L N P L T I  F L Y L V   2135
      . .    | | |  : . | | : |  .   | | |  : | : |   : | |    : .   | : | | |  . : | |    | |
2070  K K G F A P  A Y Q Y F N L H K L N S  D T Q K T E L K L K C G T T  A E D L F R Q A D L M V I  F S  Y L L   2119

2136  F V L K C G I  S A D N V C L S  Y Q L F A M N D A E Q V E F E I  E D S  L R L D E Q V Q I  G Q Y S  C Y V   2185
      | |    : . | : | . . | | | | | . : : . : . | . . . : | :    | : |   |   | .   . . . | : .   . | | :
2120  F V A R I  G V S  G S  H V C L S  Y N M L N V K D V K D F E I  C R E N V L D L S  R K T T I  D G E E C Y I   2169

2186  W P  S  V G K F  Y P  E I  L A K R G C I  A V N D G T T F Y I  F V S S S Q I  D K I  H P  E A A W S  D M L Q G   2235
      |     : : . : |    | : | |    . | : . . | | | | | . | | | | . . . . : |  | : . | | | | | : : .  |
2170  W N F I  S  D I  F P R I  V A K Y N C V V L N D G E K R Y I  F V T D S  A P  T R I  F P D L A W S  D L I  S  G   2219

2236  V G R R G V D I  L S I  A G P  T K T K F L I  K H V E S  C Y E T L K S  P E D W K A K C K E  Y Y E S I  S L   2285
      .    : . : | | : . . | | . | | . |     : :    . : : . | . . : | . . |    . : | |    . . . : .
2220  K Q V V S  P N I  I  K V A G E T K S  K T I  A P  L L A D S  Y K V F  K D P  K A W L E R N K E L K A A L E T   2269
```

TABLE 2-continued

Comparison of MCDV-Tn and MCDV-T amino acid sequences

```
2286  YEYI LLLMAVGS RAGI ETQRMS KYQARKNKI RMP EVLEKYI EVEKATI GK  2335
      |||  ||:||::  ||    ||  :.|  ..|.:  :.|..: |||  |||  ||:
2270  EEYI ALLFAVACEAGRFTQI LDKPPS RRKI LNMS ERYNAYI EQEKGLI GR  2319

2336  LSKP AKTCLAI GAGVAI FGVLAGLGVGLYKLI THFS KTDS EDNDI EI DDL  2385
      ||||||.||||||.||||||.|||:|||:|||.||.|.:.| ::||:| |
2320  LSKP AKI CLAI GTGVAI FGALAGI GVGLFKLI AHFNKDEEEVDEI EFDI L  2369

2386  VPEMS GAHAS DENVTTYAVRRQVP KVRLAKQFKV................  2419
      ||||| .|.|:::.|  |..:.||..   :|.
2370  SPEMS GS HES GQHT TRYVTKERVPS KPARRQHEF DL MFDNL PTPQVEELK  2419

2420  ..RSS PS PS DNEQP............KVDI LVPEMTGCHAS DEHLTKHFT  2455
       ..::|:||:...      :|   |:|:.|.||||:|  |..:.
2420  SEMTCAS AS DEHKTQYVKRRVGP VS KRKDAS VAEI SGAHAS DQHHTEYLK  2469

2456  KRRVTMKRVGAVKES HI VTY. DENTPHVRLI RNLRRTRLARAI KQMAQLG  2504
      |.. |||  :.|||.||| |||  ..|.:|.:|||||||||||  |:
2470  ARVPLMKRI . ATKES YVVTYDDEPS SHI SLVRRI RRTRLARAI KQMAVLE  2518

2505  ELPDTLS EI QVWQQYVVDKGI RPAEHTTDFRLFS AI ADQEQEDPEEI NMA  2554
      ::|.||.||..:|.|  ..:||: .:...|.  ::||::  |:|:|:|:::||
2519  DFPSTLEEI RLWRQNAANKGVI VPKYS TSGKFFS GLLDDEEEEPQNVNML  2568

2555  SGETMKFDENKYNEI VQVVKGI S PTKS DI VTMTTKGAHHTAI KQVRI GYK  2604
      .:|.:..|..::.| :|:..| | |.:: |...|..:||.|:. |
2569  NEEDI EVDKRMFEKI S EVI S VI QPRKNELERMI EEGVHHKVVKQARVNDK  2618

2605  SLDKDPNMVSI LSNQLTKI SCVI LNVTPGRTAYLNVMRLCGTFVVCPAHY  2654
      :|.|||||||.||.:.|..||.||:|:||.| ||:||:||.||:|||||||
2619  GLAKDPNMVTI LTDKLI NI SAVI VNLTPTRRAYMNVRLI GTI VVCPAHY  2668

2655  LEALEEDDTI YFI SFS VCI KLRFQPDRVTLVNTHQDLVVWDLGNS VPPAI  2704
      ||||||:|.:|||:||:.|||  |:|.||||||.:|||:|||||| |||.|
2669  LEALEEGDELYFI CFS LVI KLTFDPS RVTLVNS QQDLMVWDLGNMVPPSI  2718

2705  DVLS MI PTVADWDKFQDGP GAFGVTKYNARYPTNYI NTLDMI ERI RADTQ  2754
      |.|.|||:.|||.||||||||||:|||||||.:.:|||||||.||||||:||
2719  DTLKMI PTLEDWDHFQDGP GAFAVTKYNS KFPTNYI NTLTMI ERI RANTQ  2768

2755  NPTGI YKMLNS DHTI TTGLRYQMYS LEGFCGGLI LRACTRMVRKI VGLHV  2804
      ||||.|.|:.:|:||||||||||:|||||||||||||:|.||||:||:||:||
2769  NPTGCYS MMGS QHTI TTGLRYQMFS LDGFCGGLI LRAS TNMVRKVVGI HV  2818

2805  AAS ANHAMGYAECLVQEDLKHAI NKLS PDARS LI I GHLNPKVETATKQCG  2854
      |:|.||||||||||:|.|||:.|:|||.|:..:.|||.||.||||
2819  AGS QNHAMGYAECLI AEDLRAAVARLALDPRS TI QAS LKGRI DAVS KQCG  2868

2855  I VRSLGSLGCHGKVTS EDVAMTATKTTI RKS RI YGLVGDI KTEPSI LHAH  2904
      : |.||.:|||||||.|||:. ||||.||||||.||||:|.||||||||||||
2869  LDRALGTI GCHGKVAS EDI TS AATKTSI RKS RI HGLVGEI RTEPSI LHAH  2918

2905  DPRLPEDQI GKWDPVFEAALKYGTRI EPFPI EEI LEVEDHLSI I LKGMDN  2954
      |||||.|.|.|||||.||:|||.|.||.||| |:::.|||||||.|||.  :|
2919  DPRLPKDKI GKWDPVI EAS MKYGS RI TPFPVDQI LEVEDHLS KMLANCEN  2968

2955  TLKKRNVNNLEVGI NGI DQSDYWLQI ETNTS PGWPYTKRKPKGAEGKKWL  3004
      ..||.||||:|||||||||||||||  :||.||||.||||  ||.|||||
2969  SKNKRQVNNLEI GI NGI DQS DYWQQI EMDTSSGWP YAKRKP VGAAGKKWL  3018

3005  FKEVGNYPSGKPI LEMEDSGLI ES YNKMLRDAKQGVAPI VVTVECPKDER  3054
      |..: |.||||||   ::.|.||||||.|| :||||:.|.|||.||:||||
3019  FEQDGTYPSGKPRYVFGDAGLI ES YNS MLGEAKQGI SPTVVTI ECAKDER  3068

3055  RKLSKI YEQPATRTFTI LPPEI NI LFRQYFGDFAAMI MTNRS KLFCQVGI  3104
      |||.|||.|||||||||||||||||||||||||||||||:||  |.||||||||
3069  RKLNKI YEKPATRTFTI LPPEI NI LFRQYFGDFAAMVMTCRAKLFCQVGI  3118
```

TABLE 2-continued

Comparison of MCDV-Tn and MCDV-T amino acid sequences

```
3105  N P E N M E W S D L M H E F L H K S T H G F A G D Y S K F D G I G D P Q I Y H S I T Q V V N N W Y D  3154
      | | | . | | | : | | |   : :   . | | | . | | | | | | | | | | | | | | | | | | | | | | | | | | | | | :
3119  N P E S M E W G D L M L G L K E K S T K G F A G D Y S K F D G I G D P Q I Y H S I T Q V V N N W Y N  3168

3155  D G E E N A R T R H A L I S S I I H R E G I V K E Y L F Q Y C Q G M P S G F A M T V I F N S F V N Y  3204
      | | | | | |   . | | | | | | | | | | |   | | | | | | | | | | | | | | | | | | | | | | | | | | | : | |
3169  D G E E N A T I R H A L I S S I I H R R G I V K E Y L F Q Y C Q G M P S G F A M T V I F N S F M N Y  3218

3205  Y Y L A M A W M N L I S H S P L S P Q S T V R D F D N Y C K V V V Y G D D N I V S V D L N F L E Y Y  3254
      | | | . : | | | | | | | |   | | | | |   . . : |   | | : | | | | : | | | | | | | | . | :   : | | | | |
3219  Y Y L S L A W M N L I S A S P L S P Q A S L R Y F D E Y C K V I V Y G D D N I V A V N E E F L E Y Y  3268

3255  N L R T V A A Y L S Q F G V T Y T D D A K N P I E K S V P F V E I T S V S F L K R R W V P L G G R L  3304
      | | |   | | : | | | | | | | | . | | | | | | | | | | |   . : | . | . . | . | | | | | | | . | | | |
3269  N L R L V A G Y L S Q F G V S Y T D D A K N P I E K S E R Y V K I E D V T F L K R R W V S L G G R A  3318

3305  S T I Y K A P L D K T S I E E R L H W I R E C D N D I E A L N Q N I E S A L Y E A S I H G K I Y F G  3354
      |   : | | | | | | | . | | | | | | : | | | | | | : :     | |   | | | | | | | | | | | | | | . . | | |
3319  S M L Y K A P L D K V S I E E R L N W I R E C D D G E L A L V Q N I E S A L Y E A S I H G H T Y F G  3368

3355  D L L Q R I R I A C D A V M I P V P S V T F K D C H K R W W A S M T G G A L D P A S L S R L Y L A A  3404
      : |   : : |       | | | | | | | . : | . :   :   | | : : | | | . | | | | |   | : | . . . : : |
3369  E L K D K I A K A C D A V M I T M P N I R Y I D C Q R R W W T S M T G G Y L E P S D V T K L V R L V  3418

3405  E N Q L V D T R K V W K D R F L G E D R S L I D M L K S A R A V P L A A Y H V *    3444
      | . . | : | . . : | | | | | . : .     . : :     | : | : | : . . : | . | | | | : |
3419  E K G L L D P K S V W K D P L Y R T N K L L F D L L R E V K A A P L A A F V V.    3457
```

As can be seen from this comparison, the entire genome of these viruses exhibit only 59% identity at the nucleotide and amino acid level. The lack of significant homology between these viral genomes provides conclusive evidence that they are indeed distinct viruses.

Comparison of the MCDV-Tn sequence with 3' terminal sequences reported for the only other putative MCDV strain, MCDV-M1 (SEQ ID NO: 11; Ngazimbi, C. M., "Maize chlorotic dwarf virus strain M1, a distinct member of the machlovirus group", PhD thesis dissertation for Ohio State University, Columbus (1993) reveals an even greater lack of homology with this strain. This comparison is shown in Table 3 below.

TABLE 3

Comparison of MCDV-Tn and MCDV-M1 genomic nucleotide sequences

```
11000 ATGATACACGAGTACTCTCATTAGAGAGAACCGGATTCCACATTGTGGAA 11049 (SEQ ID NO:1)
       | |         | | | | | |     | |       | |                 | |
    1 ......ttgaactctcacgagtcgagaaggcagtggtagttccatagaac  44    (SEQ ID NO:11)

11050 TCTCCCAGGAATTGACCTGGGTTCCTCACGAAAGTGAGGCGACAACTTGG 11099
       | |       | |         |       | | |     | |     |         | |
   45 gacccttt gt ggt gt gact aggcatt gacct agt t ggt ggt gt gat gagc  94

11100 TCGAAAAACAAGTTCAGTTTAGTTGAGACTGAAGTACAAACTCAACATTT 11149
       | | |                 | | | | | |   |       | |       | | | | | |     |       |
   95 cat aaat cat cagct agtt aaggt acat ct agt t t acaaagt accccca 144

11150 CATAGTGTGTGATTTTTCCGATCCCCATTTGGTGTAACCCATATGTGCCA 11199
       | |         | |   | | |       | | | |       | | |   | | |     | | |       | |
  145 ct cacaaagt t t t t gt gat ggt ct ct ggt t gaagt caagc .tact ggcat 193

11200 CCTCATAATCCTTTTAAGGGTTAAATTTGGTAAGTGTTGTGGGGAGCCAA 11249
       |         |   | | | |     | | | | |     | |     | | | |   | | |     | |     | | |     |
  194 t cgt t cat cct t t t at aggat t t gagt cagt acgggt ct t gat ggggaac 243

11250 GAG . GGGTAGGGTCTTTTTGTTACGTACTTTCTCATGTCAACATGGTGTT 11298
       | |         | | |   | | | | | | | | | |       | |     | | | | | | |   | | | | | |   | | | | | |
  244 cagaacctagcgt ct t t t t gt t t t gt gt t t t ct cacgt caact t ggt gt t 293

11299 GAGATGGGCGCTTGGT . . . CAGCGGAAGAATAAAGCGAGACGTACATTAT 11345
       | | |   | | | | | | | | | | | |       | | | | | |   | |     | | | |   | | | | | | | | | | | |
  294 gaggt gggcgct t ggt cagcagcgggaaat aaaagt gt gacgt acat tat 343
```

TABLE 3-continued

Comparison of MCDV-Tn and MCDV-M1 genomic nucleotide sequences

```
11346 TATCTCGTAGACTACGGCAGGTGAGACACACCGTCGTCCCTTGAGGGGGA 11395
       | || |  ||||||||||||| |||||||  || ||||| | ||||||||||
  344  t gt cac a ca ga ct a cgg ca gg cga ga ca cgcc .t cgt ct cct ga gg gg ga  392

11396 AAGTAGCTCCAGGCATTTAATCCTGAAGTGTTCAG . ATAAGTCTCTGATC 11444
       ||||||||||||||||||| ||||||||||||||||| |     ||||||||||
  393  a a gt a gct cc a gg ca tt ga a t cct ga a gt gtt ca gt a gt t a t ct ct ga t c  442

11445 CTCCTCCGGGGGAAAAAGGGGACTTAATCTGTTAAGCCGTATCAACGACT 11494
       || |||||||||||||||| ||||    |||||||| | | |||
  443  ct .ct cc gg gg ga a a a a t ggga t act a t ct gt tt ggt cat a t tt cat t gg  491

11495 TGATGAAACAACCACCTGTTCTGGTGTAAACCCAGGATAATCACATAGGT 11544
       | |    |    |   |   | ||          |    ||||            | |
  492  ca gagt a gat a ga a a gcgact tt gtt ggt ct t ct t t a t a t a gcggct gct  541

11545 AGCTGTGTGGTGTTTCAACCATTTGGATTCATCCGAGCACGGATTACCTT 11594
       ||              | ||              ||| |||             | ||
  542  t gc .........gagagat ca gcga a gact a t ct ga gat gt a ggcgcgtt  582

11595 GTGGTCAGAGTCTCCGAATGTCCTGTACGATGTGGGTAACTCCCTTTGGC 11644
       ||    | |        |||| | |       | | || |  ||||||   || |     |
  583  gtt cga a a at ct cat ga a a ggct ca ca t ggt gcga gta a cat ccgt aca c  632

11645 CAGGGCTAGGCACACTTCTCTACGGGTTGGTGTCGCTAGATATGTTAATA 11694
       ||  |||||||||||||||| |||||||| ||||||||     ||| ||||||
  633  t gt gggt a gg ca ca ct t ct cc a cggg ttt gt gt cgct t a gt a t a tt a a t a  682

11695 CTAGTGCCATATCGGAAATAGTTGTAAATCGTTGAACCAAGTGACGATGG 11744
       | ||||| ||||||||| | ||||||||| ||||||||| || || ||||||
  683  c ga gt gct a t a t cgga ga ca gtt gt a a gacgtt ga act a a a t gt cgat gg  732

11745 GGTCCATTGTACACCCGACTTGGTTACGTTTTCTATTTTCCGTGTCAATA 11794
       || ||| ||  |||||||  || ||||||| |||||  |||| ||||||||||
  733  ggcc ca gt gagca ccggt tt a gtt a cgct tt ct .gt t t ct gt gt caa t a  781

11795 TGGATAATAGTGGGGTAGTAAAAAAAAAAAAAAAAAAAAA 11832
       |||||  ||||||||||
  782  ga gat a a a a gt gggg t a a c ..................... 800
```

The polyprotein encoded by the MCDV-Tn genome includes 3 distinct coat proteins designated CP1, CP2, and CP3 whose coding sequences are set forth in SEQ ID Nos: 5, 7, and 9, respectively, and whose amino acid sequences are set forth in SEQ ID Nos: 6, 8, and 10, respectively. This polyprotein is also contemplated to include a replicase protein, a protease, a helper component, proteins involved in viral movement in the host plant (both cell to cell and long distance transport), a helicase protein and a VPg protein.

MCDV-Tn is contemplated to contain a cysteine protease analogous to cystein proteases that have been identified in related plant viruses which encode polyproteins. These cysteine proteases have a characteristic catalytic domain of three amino acids consisting of a histidine at position 1 of the domain, a glutamine or an asparagine at the second position, and a cysteine at the third (see Gorbalenya, A. E. et al., FEBS Letters 243 (2): 103–114 (1989)). These amino acids are separated in the primary amino acid sequence in a region spanning approximately 150 amino acids. The intervening sequences between each of the catalytic domain sequences exhibits additional limited homology among the known proteases (see Gorbalenya, A. E. et al., supra). Based upon comparison with the known protease sequences, the MCDV-Tn protease catalytic domain is contemplated to span a 131 amino acid sequence from position 2653 to 2784 of SEQ ID No: 2 with the three catalytic residues occuring at 2653, 2690 (asparagine) and 2784.

The isolated MCDV-Tn genomic sequences taught by the present invention may be manipulated according to standard genetic engineering techniques to suit any desired purpose. For example, the complement to the entire MCDV-Tn genomic RNA sequence or portions thereof may be used as probes capable of specifically hybridizing to the MCDV-Tn genomic RNA. To achieve specific hybridization under a variety of conditions, such probes are based upon sequences that are unique among the known MCDV genomic sequences or putative sequences (see Tables 1 and 3 above) and are preferably at least 10 nucleotides in length, and most preferably at least 20 nucleotides in length. The specificity of such probes may be confirmed simply by assaying them for hybridisation to purified preparations of individual MCDV isolates (see, e.g Hunt, R. E. et al., Phytopatholog 78: 499–504 (1988). Such probes may be used to amplify and analyze MCDV-Tn sequences from a chosen organism via the well known process of polymerase chain reaction (PCR). This technique is contemplated to be particularly useful as a diagnostic assay to determine the presence or absence of MCDV-Tn in a plant and to distinguish between the presence of this strain and other MCDV strains, particularly the known strain MCDV-T and putative strain MCDV-M1. MCDV-Tn specific hybridization probes may also be used to quantitate levels of MCDV-Tn genomic RNA in a plant using standard techniques such as Northern blot analysis. Alternatively, probes corresponding to the MCDV-Tn genomic sequence may be used to detect and quantitate MCDV-Tn viral gene transcripts.

The isolated MCDV-Tn genomic sequences taught by the present invention are particularly useful for the development of viral resistance in susceptible host plants. With the information provided by the present invention, several approaches for inhibiting plant virus infection in suceptible plant hosts which involve expressing in such hosts various inhibitory transcripts or proteins derived from the target virus genome in may now be applied to MCDV-Tn.

One general approach which has been used to confer plant virus resistance is the expression of antisense genes or ribozymes. This involves the expression of antisense genes or ribozymes designed to hybridise to the target virus genome, or to target virus transcripts, in the host plant (e.g. U.S. Pat. No. 5,316,930 issued May 31, 1994; WO 93/14218 pub. Jan. 13, 1992; WO 92/13090 pub. Jan. 17, 1991; EP 558,944 pub. Feb. 6, 1992; said references herein incorporated by reference in their entirety).

Antisense genes or ribozymes targeting MCDV-Tn may be constructed based upon the MCDV-Tn RNA genomic sequence provided by the present invention. Such an antisense gene or ribozyme will produce transcripts which include nucleotide sequences complementary to a portion of the MCDV-Tn RNA genome. When expressed in a host plant, such an antisense gene or ribozyme is contemplated to inhibit MCDV-Tn infection via hybridisation to MCDV-Tn genomic RNA.

Another general approach which has been used to confer plant virus resistance is to express one or more of the coat proteins of the target virus in the host plant (e.g. WO 9416550 pub. Aug. 4, 1994 for Tomato Spotted Wilt Virus; U.S. Pat. No. 5,349,128 issued Sep. 20, 1994 for Cucumber Mosaic Virus; EP 0 240 331 pub. Apr. 2, 1986 for Alfalfa Mosaic Virus; US 4,970, 168 pub. Nov. 13, 1990 for PVX and PVY potato viruses; said references herein incorporated by reference in their entirety). This approach may be applied to MCDV-Tn using the information provided by the present invention. Using standard techniques, the coding sequences for coat proteins CP1 (SEQ ID No: 5), CP2 (SEQ ID No: 7), and CP3 (SEQ ID No: 9), of MCDV-Tn may be engineered for recombinant expression in a host plant which is normally susceptible to infection by MCDV-Tn. Recombinant expression of these coding sequences, either individually or in any combination, in such a host plant is contemplated to confer resistance to (i.e. inhibit) MCDV-Tn infection.

Yet another approach which may be used to confer plant virus resistance is to express the replicase gene of the target virus in the host plant (e.g. international patent application pub. nos. WO94/18336 pub. Aug. 18, 1994 to Tumer et al. for potato leaf roll virus and WO 91/13542 pub. Sep. 19, 1991 to Zaitlin et al. for tobacco mosaic virus; herein incorporated by reference in their entirety). This approach may also be applied to MCDV-Tn using the information provided by the present invention.

The coding sequence for the replicase gene of MCDV-Tn may be determined by the location of conserved motifs common to viral replicase genes and by identification of putative viral proteinase cleavage sites bordering the replicase coding sequence. Conserved motifs have been found in other viral replicases. In particular, the conserved amino acid motif GDD (known as domain C) is the hallmark consensus sequence for all RNA- dependent replicases (Poch et al. EMBO 8: 3867–3874 (1989). This conserved motif is found at amino acids 3239–3241 in the MCDV-Tn open reading frame (SEQ ID No: 2). Two additional conserved motifs characteristic of a plant viral replicase have been identified and designated as domain A and B (Poch et al., supra). Domain A is a 17 amino acid sequence with two centrally conserved amino acids which are present in the MCDV-Tn genome at amino acids 3129 and 3134 of SEQ ID No: 2. Domain B is a 10 amino acid sequence consisting of 5 conserved amino acids which are present in the MCDV-Tn genome at 3190, 3191, 3195, 3199 and 3200 of SEQ ID No: 2. For resistance strategies which depend upon expression of a viral replicase coding sequence in a transgenic plant, a cDNA clone encompassing nucleotides 9790 to 10180 of SEQ ID No: 1 contemplated to include the active domains of the MCDV replicase can be used for plant transformation. More preferably, such strategies may be employed by transforming a plant with larger expressible fragments of the MCDV-Tn genome contemplated to encompass the entire replicase protein. In this case, the MCDV-Tn replicase would be cleaved from the encoded polypeptide when exposed to MCDV-Tn viral proteinase in the plant cell.

The MCDV-Tn replicase coding sequence may either be used in unmodified form or modified in the Gly-Asp-Asp motif shared by many plant viruses as described in international patent publication no. WO 93/21329, published Oct. 28, 1993 to Baulcombe et al. (PCT/GB93/00829; herein incorporated by reference in its entirety). As with the coat protein coding sequences, either form of the MCDV-Tn replicase coding sequence may be engineered for recombinant expression in a host plant which is normally susceptible to infection by MCDV-Tn. Expression of unmodified or modified MCDV-Tn replicase in such a host plant is contemplated to confer resistance to (i.e. inhibit) MCDV-Tn infection.

Suitable host plants which may benefit from application of any of the resistance approaches described above include any species which are susceptible to infection by MCDV-Tn. In particular, suitable host plants are contemplated to include maize, Sorghum and wheat.

To express inhibitory transcripts or proteins derived from the MCDV-Tn genome in a host plant cell, the corresponding coding sequence is operably linked to regulatory sequences which cause its expression in the chosen host plant cell. Examples of promoters capable of functioning in plants or plant cells, i.e., those capable of driving expression of the associated coding sequences such as MCDV-Tn CP1 in plant cells, include the cauliflower mosaic virus (CaMV) 19S or 35S promoters and CaMV double promoters; nopaline synthase promoters; pathogenesis-related (PR) protein promoters; small subunit of ribulose bisphosphate carboxylase (ssuRUBISCO) promoters, and the like. Preferred are the rice actin promoter (McElroy et al., *Mol. Gen. Genet.* 231: 150 (1991)), maize ubiquitin promoter (EP 0 342 926; Taylor et al., *Plant Cell Rep*.12: 491 (1993); Toki et al., *Plant Phys*. 100:1503–1507 (1992)), a maize pith-preferred promoter (international patent application no. PCT/US92/08476 published Apr. 15, 1993 as WO 93/07278, incorporated by reference herein in its entirety; in particular see FIG. 24 and pages 27–28), and the Pr-1 promoter from tobacco, Arabidopsis, or maize (see European Patent Application publication No. 332,104 published Sep. 13, 1989). Also preferred are the 35S promoter and an enhanced or double 35S promoter such as that described in Kay et al., *Science* 236: 1299–1302 (1987) and the double 35S promoter cloned into pCGN2113, deposited as ATCC 40587. The promoters themselves may be modified to manipulate promoter strength to increase expression of MCDV-Tn coding sequences in accordance with art-recognized procedures.

The coding sequences for MCDV-Tn viral proteins provided by the invention may also be engineered for recombinant expression in any desired host organism. Generally, the coding sequence is operably linked to regulatory sequences which cause its expression in the chosen host. The choice of specific regulatory sequences to be used such as promoter, signal sequence, 5' and 3' untranslated sequences, and enhancer, is within the level of skill of the routineer in the art. The resultant molecule, containing the individual elements linked in proper reading frame, may be inserted into a vector capable of being transformed into the host cell. Suitable expression vectors and methods for recombinant production of proteins are well known for host organisms such as *E. coli* (see, e.g. Studier and Moffatt, *J. Mol. Biol.* 189: 113 (1986); Brosius, DNA 8: 759 (1989)), yeast (see, e.g. Schneider and Guarente, *Meth. Enzymol.* 194: 373 (1991)) and insect cells (see, e.g. Luckow and Summers, *Bio/Technol.* 6: 47 (1988)). Specific examples include plasmids such as pBluescript (Stratagene, La Jolla, Calif.), pFLAG (International Biotechnologies, Inc., New Haven, Conn.), pTrcHis (Invitrogen, La Jolla, Calif.), and baculovirus expression vectors, e.g., those derived from the genome of *Autographica californica* nuclear polyhedrosis virus (AcMNPV). A preferred baculovirus/insect system is pVl11392/Sf21 cells (Invitrogen, La Jolla, Calif.).

Recombinantly produced MCDV-Tn viral proteins can be isolated and purified using a variety of standard techniques. The actual techniques which may be used will vary depending upon the host organism used, whether the ADSS enzyme is designed for secretion, and other such factors familiar to the skilled artisan (see, e.g. chapter 16 of Ausubel, F. et al., "Current Protocols in Molecular Biology", pub. by John Wiley & Sons, Inc. (1994).

Recombinantly produced MCDV-Tn coat proteins are useful for a variety of purposes. For example, they may be used to further elucidate and study the structure of the individual coat proteins and the MCDV-Tn viral particle. MCDV-Tn coat proteins may also be used as antigens for producing antibodies which can bind to MCDV-Tn viral particles. Such antibodies may be used in a standard assay such as an ELISA assay to detect the presence of MCDV-Tn in a plant (e.g. Clark, M. F. and Adams, A. N., *J. Gen. Virol.* 34: 475–483 (1977); Matthews, R. E. F., "Plant Virology", 3rd Edition, Academic Press, New York (1991)). Single chain antibodies may also be constructed from such antibodies. Chimeric genes designed to express such single chain antibodies are contemplated to be useful for inhibiting MCDV-Tn infection in plants in the same manner that the expression of specific single chain antibodies to artichoke mottled crinkle virus coat protein in plants has been reported to inhibit this virus (see Tavladoraki et al., *Nature* 366: 469–472 (1993)).

The chimeric DNA construct(s) of the invention may contain multiple copies of a promoter or multiple copies of a particular coding sequence. In addition, the construct(s) may include coding sequences for markers and coding sequences for other peptides such as signal or transit peptides, each in proper reading frame with the other functional elements in the DNA molecule. The preparation of such constructs are within the ordinary level of skill in the art.

Useful markers include peptides providing herbicide, antibiotic or drug resistance, such as, for example, resistance to hygromycin, kanamycin, G418, gentamycin, lincomycin, methotrexate, glyphosate, phosphinothricin, or the like. These markers can be used to select cells transformed with the chimeric DNA constructs of the invention from untransformed cells. Other useful markers are peptidic enzymes which can be easily detected by a visible reaction, for example a color reaction, for example luciferase, β-glucuronidase, or β-galactosidase.

EXAMPLES

Standard recombinant DNA and molecular cloning techniques used here are well known in the art and are described by T. Maniatis, E. F. Fritsch and J. Sambrook, *Molecular Cloning. A Laboratory Manual*, Cold Spring Harbor laboratory, Cold Spring Harbor, N.Y. (1982) and by T. J. Silhavy, M. L. Berman, and L. W. Enquist, *Experiments with Gene Fusions*, Cold Spring Harbor Laboratory, Cold Spring Harbor, N.Y. (1984).

Example 1

Construction of Plant Transformation Vectors

Numerous transformation vectors are available for plant transformation, and the genes of this invention can be used in conjunction with any such vectors. The selection of vector for use will depend upon the preferred transformation technique and the target species for transformation. For certain target species, different antibiotic or herbicide selection markers may be preferred. Selection markers used routinely in transformation include the nptII gene which confers resistance to kanamycin and related antibiotics (Messing & Vierra, *Gene* 19: 259–268 (1982); Bevan et al., *Nature* 304:184–187 (1983)), the bar gene which confers resistance to the herbicide phosphinothricin (White et al., *Nucl Acids Res* 18: 1062 (1990), Spencer et al. Theor Appl Genet 79: 625–631(1990)), the hph gene which confers resistance to the antibiotic hygromycin (Blochinger & Diggelmann, *Mol Cell Biol* 4: 2929–2931), and the dhfr gene, which confers resistance to methotrexate (Bourouis et al., *EMBO J*. 2(7): 1099–1104 (1983)).

(1) Construction of vectors suitable for Agrobacterium transformation.

Many vectors are available for transformation using *Agrobacterium tumefaciens.* These typically carry at least one T-DNA border sequence and include vectors such as pBIN19 (Bevan, *Nucl. Acids Res.* (1984)) and pXYZ. Below the construction of two typical vectors is described.

Construction of pCIB200 and pCIB2001. The binary vectors pCIB200 and pCIB2001 are used for the construction of recombinant vectors for use with Agrobacterium and was constructed in the following manner. pTJS75kan was created by NarI digestion of pTJS75 (Schmidhauser & Helinski, *J Bacteriol.* 164: 446–455 (1985)) allowing excision of the tetracycline-resistance gene, followed by insertion of an AccI fragment from pUC4K carrying an NPTII (Messing & Vierra, *Gene* 19: 259–268 (1982); Bevan et al., *Nature* 304: 184–187 (1983); McBride et al., *Plant Molecular Biology* 14: 266–276 (1990)). XhoI linkers were ligated to the EcoRV fragment of pCIB7 which contains the left and right T-DNA borders, a plant selectable nos/nptII chimeric gene and the pUC polylinker (Rothstein et al., *Gene* 53: 153–161 (1987)), and the XhoI-digested fragment was cloned into SalI-digested pTJS75kan to create pCIB200 (see also EP 0 332 104, example 19 [1338]). pCIB200 contains the following unique polylinker restriction sites: EcoRI, SstI, KpnI, BglII, XbaI, and SalI pCIB2001 is a derivative of pCIB200 which created by the insertion into the polylinker of additional restriction sites. Unique restriction sites in the polylinker of pCIB2001 are EcoRI, SstI, KpnI, BglII, XbaI, SalI, MluI, BclI, AvrII, ApaI, HpaI, and StuI. pCIB2001, in addition to containing these unique restriction sites also has plant and bacterial kanamycin selection, left and right T-DNA borders for Agrobacterium-mediated transformation, the RK2-derived trfA function for mobilization between *E. coli* and other hosts, and the OriT and OriV functions also from RK2. The pCIB2001 polylinker is suitable for the cloning of plant expression cassettes containing their own regulatory signals.

Construction of pCIB10 and Hygromycin Selection Derivatives thereof. The binary vector pCIB10 contains a gene encoding kanamycin resistance for selection in plants, T-DNA right and left border sequences and incorporates sequences from the wide host-range plasmid pRK252 allowing it to replicate in both *E. coli* and Agrobacterium. Its construction is described by Rothstein et al., *Gene* 53: 153–161 (1987). Various derivatives of pCIB10 have been constructed which incorporate the gene for hygromycin B phosphotransferase described by Gritz et al., *Gene* 25: 179–188 (1983)). These derivatives enable selection of transgenic plant cells on hygromycin only (pCIB743), or hygromycin and kanamycin (pCIB715, pCIB717).

(2) Construction of Vectors Suitable for non-Agrobacterium Transformation.

Transformation without the use of *Agrobacterium tumefaciens* circumvents the requirement for T-DNA sequences in the chosen transformation vector and consequently vectors lacking these sequences can be utilized in addition to vectors such as the ones described above which contain T-DNA sequences. Transformation techniques which do not rely on Agrobacterium include transformation via particle bombardment, protoplast uptake (e.g. PEG and electroporation) and microinjection. The choice of vector depends largely on the preferred selection for the species being transformed. Below, the construction of some typical vectors is described.

Construction of pCIB3064. pCIB3064 is a pUC-derived vector suitable for direct gene transfer techniques in combination with selection by the herbicide basta (or phosphinothricin). The plasmid pCIB246 comprises the CaMV 35S promoter in operational fusion to the *E. coli* GUS gene and the CaMV 35S transcriptional terminator and is described in the PCT published application WO 93/07278. The 35S promoter of this vector contains two ATG sequences 5' of the start site. These sites were mutated using standard PCR techniques in such a way as to remove the ATGs and generate the restriction sites SspI and PvuII. The new restriction sites were 96 and 37 bp away from the unique SalI site and 101 and 42 bp away from the actual start site. The resultant derivative of pCIB246 was designated pCIB3025. The GUS gene was then excised from pCIB3025 by digestion with SalI and SacI, the termini rendered blunt and religated to generate plasmid pCIB3060. The plasmid pJIT82 was obtained from the John Innes Centre, Norwich and the 400 bp SmaI fragment containing the bar gene from *Streptomyces viridochromogenes* was excised and inserted into the HpaI site of pCIB3060 (Thompson et al. EMBO J 6: 2519–2523 (1987)). This generated pCIB3064 which comprises the bar gene under the control of the CaMV 35S promoter and terminator for herbicide selection, a gene from ampicillin resistance (for selection in *E. coli*) and a polylinker with the unique sites SphI, PstI, HindIII, and BamHI. This vector is suitable for the cloning of plant expression cassettes containing their own regulatory signals.

Construction of pSOG19 and pSOG35. pSOG35 is a transformation vector which utilizes the *E. coli* gene dihydrofolate reductase (DHFR) as a selectable marker conferring resistance to methotrexate. PCR was used to amplify the 35S promoter (~800 bp), intron 6 from the maize Adh1 gene (~550 bp) and 18 bp of the GUS untranslated leader sequence from pSOG10. A 250 bp fragment encoding the *E. coli* dihydrofolate reductase type II gene was also amplified by PCR and these two PCR fragments were assembled with a SacI-PstI fragment from pBI221 (Clontech) which comprised the pUC19 vector backbone and the nopaline synthase terminator. Assembly of these fragments generated pSOG19 which contains the 35S promoter in fusion with the intron 6 sequence, the GUS leader, the DHFR gene and the nopaline synthase terminator. Replacement of the GUS leader in pSOG19 with the leader sequence from Maize Chlorotic Mottle Virus (MCMV) generated the vector pSOG35. pSOG19 and pSOG35 carry the pUC gene for ampicillin resistance and have HindIII, SphI, PstI and EcoRI sites available for the cloning of foreign sequences.

Example 2

Construction of Plant Expression Cassettes

Gene sequences intended for expression in transgenic plants are firstly assembled in expression cassettes behind a suitable promoter and upstream of a suitable transcription terminator to create a chimeric gene. These expression cassettes can then be easily transferred to the plant transformation vectors described above in Example 1.

Promoter selection. The selection of a promoter used in expression cassettes will determine the spatial and temporal expression pattern of the transgene in the transgenic plant. Selected promoters will express transgenes in specific cell types (such as leaf epidermal cells, mesophyll cells, root cortex cells) or in specific tissues or organs (roots, leaves or flowers, for example) and this selection will reflect the desired location of expression of the transgene. Alternatively, the selected promoter may drive expression of the gene under a light-induced or other temporally regulated promoter. A further alternative is that the selected promoter be chemically regulated. This would provide the possibility of inducing expression of the transgene only when desired and caused by treatment with a chemical inducer.

Transcriptional terminators. A variety of transcriptional terminators are available for use in expression cassettes. These are responsible for the termination of transcription beyond the transgene and its correct polyadenylation. Appropriate transcriptional terminators and those which are known to function in plants and include the CaMV 35S terminator, the tml terminator, the nopaline synthase terminator, the pea rbcS E9 terminator. These can be used in both monocotyledons and dicotyledons.

Sequences for the enhancement or regulation of expression. Numerous sequences have been found to enhance gene expression from within the transcriptional unit and these sequences can be used in conjunction with the genes of this invention to increase their expression in transgenic plants.

Various intron sequences have been shown to enhance expression, particularly in monocotyledonous cells. For example, the introns of the maize Adh1 gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis et al., *Genes Develop.* 1: 1183–1200 (1987)). In the same experimental system, the intron from the maize bronze1 gene had a similar effect in enhancing expression (Callis et al., supra). Intron sequences have been routinely incorporated into plant transformation vectors, typically within the non-translated leader.

A number of non-translated leader sequences derived from viruses are also known to enhance expression. Specifically, leader sequences from Tobacco Mosaic Virus (TMV, the "W-sequence"), Maize Chlorotic Mottle Virus (MCMV), and Alfalfa Mosaic Virus (AMV) have been shown to be effective in enhancing expression (e.g. Gallie et al. *Nucl. Acids Res.* 15: 8693–8711 (1987); Skuzeski et al. *Plant Molec. Biol.* 15: 65–79 (1990))

Example 3

Transformation of Monocotyledons

Transformation of most monocotyledon species has become routine. Preferred techniques include direct gene transfer into protoplasts using PEG or electroporation techniques, and particle bombardment into callus tissue. Transformations can be undertaken with a single DNA species or multiple DNA species (i.e. co-transformation) and both these techniques are suitable for use with this invention. Co-transformation may have the advantage of avoiding complex vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al. *Biotechnology* 4: 1093–1096 (1986)).

Patent Applications EP 0 292 435 (to Ciba-Geigy), EP 0 392 225 (to Ciba-Geigy) and WO 93/07278 (to Ciba-Geigy) describe techniques for the preparation of callus and protoplasts from an elite inbred line of maize, transformation of protoplasts using PEG or electroporation, and the regeneration of maize plants from transformed protoplasts. Gordon-Kamm et al., *Plant Cell* 2: 603–618 (1990)) and Fromm et al., *Biotechnology* 8: 833–839 (1990)) have published techniques for transformation of A188-derived maize line using particle bombardment. Furthermore, WO 93/07278 (to Ciba-Geigy) and Koziel et al., *Biotechnology* 11: 194–200 (1993)) describe techniques for the transformation of elite inbred lines of maize by particle bombardment. This technique utilizes immature maize embryos of 1.5–2.5 mm length excised from a maize ear 14–15 days after pollination and a PDS-1000He Biolistics device for bombardment.

Transformation of rice can also be undertaken by direct gene transfer techniques utilizing protoplasts or particle bombardment. Protoplast-mediated transformation has been described for Japonica-types and Indica-types (Zhang et al., *Plant Cell Rep* 7: 379–384 (1988); Shimamoto et al. *Nature* 338: 274–277 (1989); Datta et al. *Biotechnology* 8: 736–740 (1990)). Both types are also routinely transformable using particle bombardment (Christou et al. *Biotechnology* 9: 957–962 (1991)).

Patent Application EP 0 332 581 (to Ciba-Geigy) describes techniques for the generation, transformation and regeneration of Pooideae protoplasts. These techniques allow the transformation of Dactylis and wheat. Furthermore, wheat transformation was been described by Vasil et al., *Biotechnology* 10: 667–674 (1992)) using particle bombardment into cells of type C long-term regenerable callus, and also by Vasil et al., *Biotechnology* 11: 1553–1558 (1993)) and Weeks et al., *Plant Physiol.* 102: 1077–1084 (1993) using particle bombardment of immature embryos and immature embryo-derived callus. A preferred technique for wheat transformation, however, involves the transformation of wheat by particle bombardment of immature embryos and includes either a high sucrose or a high maltose step prior to gene delivery. Prior to bombardment, any number of embryos (0.75–1 mm in length) are plated onto MS medium with 3% sucrose (Murashige & Skoog, *Physiologia Plantarum* 15: 473–497 (1962)) and 3 mg/l 2,4-D for induction of somatic embryos which is allowed to proceed in the dark. On the chosen day of bombardment, embryos are removed from the induction medium and placed onto the osmoticum (i.e. induction medium with sucrose or maltose added at the desired concentration, typically 15%). The embryos are allowed to plasmolyze for 2–3 h and are then bombarded. Twenty embryos per target plate is typical, although not critical. An appropriate gene-carrying plasmid (such as pCIB3064 or pSG35) is precipitated onto micrometer size gold particles using standard procedures. Each plate of embryos is shot with the DuPont Biolistics' helium device using a burst pressure of ~1000 psi using a standard 80 mesh screen. After bombardment, the embryos are placed back into the dark to recover for about 24 h (still on osmoticum). After 24 hrs, the embryos are removed from the osmoticum and placed back onto induction medium where they stay for about a month before regeneration. Approximately one month later the embryo explants with developing embryogenic callus are transferred to regeneration medium (MS+1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" which contained half-strength MS, 2% sucrose, and the same concentration of selection agent.

Example 4

Diagnostic Assay for MCDV-Tn Infected Plants Using MCDV-Tn Specific Oligomer Probes Oligomers can be designed from the MCDV genome using computer algorithms such as the Prime program which is a part of the University of Wisconsin Genetic Computer Group programs (GCG; see Devereux et al., *Nucleic Acids Res*.1: 387–395 (1984)).

Any oligomer of 20 contiguous nucleotides would be capable of differentiating MCDV-Tn from MCDV-T. Smaller oligomers capable of differentiating MCDV-Tn from MCDV-T are also possible if taken from particularly distinct regions apparent from the sequence comparison. Preferably, the oligomer represents those MCDV-Tn genomic regions which are most distinctive (i.e. show the least similarity to MCDV-T genomic sequence) and does not include those regions with a relatively high degree of similarity such as the regions between nucleotides 1151 and 1172, nucleotides 5124 and 5160, nucleotides 5242 and 5269, nucleotides 8859 and 8881, and nucleotides 11440 and 11459 of the MCDV-Tn genome.

Although oligomers could be designed to any part of the MCDV genome, optimal primers would be designed from between nucleotides 1 and 1000 and between nucleotides 10600 and 11813. These areas are preferred due to the low sequence identity (less than 50%) in these regions. Pairs of oligomers would be designed representing both the viral sense and anti-sense orientation. Preferably, these primers would not be separated by less than 250 nucleotides nor greater than 800 nucleotides. The oligomers would then be used for RT-PCR (Tan, S. S. and Weis, J. H., PCR *Methods Appl.* 2:137–143 (1992); Robertson et al., *Journal of General Virology* 72:1473–1477 (1991); Henson, J. M. and French, R., *Ann. Rev. Phytopath.* 31:81–109 (1993)). The template for the RT-PCR would be either total RNA isolated from plants or purified MCDV preparations (e.g. Hunt et al., *Phytopathology* 78:499–504 (1988)). These specific oligomers will result in amplification of only MCDV-Tn sequences.

Example 5

MCDV-Tn Resistance Conferred by Expression of Viral Coat Protein

MCDV-Tn encodes three distinct coat proteins. These proteins designated CP2 (nucleotide 2524 to 3153), CP3 (nucleotide 3154 to 3759), and CP1 (nucleotide 3760 to 4593) could be cloned either individually or in combination into a plasmid vector suitable for transformation as described above in Examples 1–2. These proteins would be under the control of a plant promoter, preferably a ubiquitin, PEPC or actin gene promoter or pith preferred promoter derived from the target plant species.

Since the coat protein open reading frames do not have a translation initiation codon, an in-frame methionine codon is inserted immediately preceding the first amino acid codon of the protein. The methionine codon can be created by mutagenesis or by introduction on primers during the polymerase chain reaction. Transformation of maize with the constructs described above will be by standard procedures. Expression of the viral coat protein in the transformed plants can then be detected through standard techniques such as a northern blot assay for the presence of coat protein transcripts, a western or ELISA assay using antibodies against the coat protein, and an infectivity assay to detect inhibition of (i.e. resistance to) MCDV-Tn infection.

Example 6

MCDV-Tn Resistance Conferred by Expression of Antisense Genes Targeting the Viral Genomic Rna Sequences corresponding to the complementary sense (antisense) of MCDV-Tn can also be used in transgenic plants to provide resistance. Antisense constructs can be prepared to any region of the viral genome. However, it would be preferred to use regions complementary to the 5' and 3' non-coding regions. These viral regions are thought to be involved in virus replication which could be inhibited by the binding of an antisense construct. The 5' region would be composed of nucleotides 1 through 434 and the 3' region would be composed of nucleotides 10766 through 11813.

Example 7

Diagnostic Assay for MCDV-Tn Infected Plants Using an Antibody to an MCDV-Tn Coat Protein Polyclonal antibodies have been prepared to purified preparations of MCDV-Tn coat protein using standard techniques (see chapter 18 of Sambrook, J., Fritsch, E. F., and Maniatis, T., *Molecular Cloning* 2nd Edition, Cold Spring Harbour Press, (1989)). These antibodies or monoclonal antibodies can be used to detect MCDV-Tn within crude protein preparations by standard immunological techniques. These techniques would include enzyme linked immunosorbent assay (ELISA), western blot analsyis, and dot blot analysis.

Example 8

MCDV-Tn Resistance Conferred by Expression of Single Chain Antibodies

Single chain antibodies (SCA) are small recombinant antibody fragments which retain antigen binding affinity (see Bird et al., *Science* 242:423–426, 1988). SCAs are composed of the variable light and heavy chains of an antibody covalently linked by a peptide linker. The isolation of these variable regions from antibody genes can be performed by two distinct methods. In the first, a random phage library of antibody genes can be screened for the expression of antibodies with specificity for the desired target protein. The variable regions are then sub-cloned using the polymerase chain reaction (see generally, Mullis et al., *Meth. Enzymol.*, 155:335–350 (1987); Erlich, (ed.), *PCR Technology*, Stockton Press (New York, 1989)) from clones expressing the desired antibody. Alternatively, antibody genes can be directly cloned from a monoclonal cell line developed to the target protein.

When cloned genes encoding an antibody with the desired specificity are identified, they may be recombined with an appropriate linker coding sequence and regulatory sequence to construct a SCA coding sequence.

Any of the proteins encoded by the MCDV-Tn genome taught in the present invention can be used as a target antigen in this standard method to generate monoclonal antibodies and corresponding genes and construct a SCA coding sequence therefrom. When expressed in a plant, such a SCA is contemplated to confer resistance to MCDV-Tn infection. Preferably, the target protein is a protein involved in replication of the MCDV-Tn, particularly including the MCDV-Tn replicase protein, helicase protein, Vpg, or proteinase.

Various modifications of the invention described herein will become apparent to those skilled in the art. Such modifications are intended to fall within the scope of the appended claims.

---

We claim:

1. An isolated DNA molecule comprising a contiguous sequence of the MCDV-Tn genome of SEQ ID NO. 1 said contiguous sequence being at least 20 nucleotides in length, wherein said sequence encodes a protein, and wherein said sequence is not present in the genome of MCDV-T.

2. The isolated DNA molecule of claim 1, wherein said sequence is selected from the group consisting of CP1 (SEQ ID NO: 5), CP2 (SEQ ID NO: 7), and CP3 (SEQ ID NO: 9).

3. A chimeric gene capable of expressing an MCDV-Tn viral protein in a host cell comprising the DNA molecule of claim 1.

4. The chimeric gene of claim 3, wherein said host cell is selected from the group consisting of a bacterial cell, an insect cell and a yeast cell.

5. A chimeric gene comprising a plant-operable promoter linked to a DNA molecule according to claim 1, wherein expression of said chimeric gene in a plant inhibits MCDV-Tn infection in said plant.

6. The chimeric gene of claim 5 wherein said MCDV-Tn viral protein is selected from the group consisting of a CP1 (SEQ ID NO: 6), CP2 (SEQ ID NO: 8), and CP3 (SEQ ID NO: 10).

7. The chimeric gene of claim 5 wherein said MCDV-Tn viral protein is a replicase.

8. The chimeric gene of claim 5 wherein said plant-operable promoter is selected from the group consisting of a plant ubiquitin gene promoter, a plant actin gene promoter, and a plant pith-preferred promoter.

9. A method for producing a plant with an inheritable trait of resistance to infection by MCDV-Tn comprising transforming said plant with the chimeric gene of claim 5.

10. A plant comprising the chimeric gene of claim 5.

* * * * *

UNITED STATES PATENT AND TRADEMARK OFFICE
CERTIFICATE OF CORRECTION

PATENT NO. : 5,866,780
DATED : Feb. 2, 1999
INVENTOR(S) : Marcus Law, et al

It is certified that error appears in the above-identified patent and that said Letters Patent is hereby corrected as shown below:

Column 1, line 63: "genormic" should read --genomic--.

Column 42, line 46: "Phytopatholog" should read --Phytopathology--.

Column 143, line 38: "No 1 said" should read --No. 1, said--.

Signed and Sealed this

Tenth Day of August, 1999

Attest:

Q. TODD DICKINSON

*Attesting Officer*     Acting Commissioner of Patents and Trademarks